(12) United States Patent
Su et al.

(10) Patent No.: US 9,512,380 B2
(45) Date of Patent: Dec. 6, 2016

(54) HINDERED PHENOL COMPOUND, PREPARATION THEREOF AND USE THEREOF AS AN ANTIOXIDANT

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Shuo Su, Beijing (CN); Jun Long, Beijing (CN); Qinghua Duan, Beijing (CN); Han Zhou, Beijing (CN); Zhiqiang Wu, Beijing (CN); Xinhua Li, Beijing (CN); Yi Zhao, Beijing (CN); Xiaoguang Zhao, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 141 days.

(21) Appl. No.: 14/296,763

(22) Filed: Jun. 5, 2014

(65) Prior Publication Data
US 2015/0353858 A1 Dec. 10, 2015

(51) Int. Cl.
| | |
|---|---|
| *C10M 135/36* | (2006.01) |
| *C10M 135/28* | (2006.01) |
| *C07C 319/14* | (2006.01) |
| *C07D 219/08* | (2006.01) |
| *C07D 279/20* | (2006.01) |
| *C07D 513/04* | (2006.01) |
| *C07C 313/04* | (2006.01) |
| *C07C 323/20* | (2006.01) |
| *C07C 323/25* | (2006.01) |
| *C07C 323/32* | (2006.01) |
| *C07C 323/52* | (2006.01) |
| *C07C 323/60* | (2006.01) |

(52) U.S. Cl.
CPC .......... *C10M 135/36* (2013.01); *C07C 313/04* (2013.01); *C07C 319/14* (2013.01); *C07C 323/20* (2013.01); *C07C 323/25* (2013.01); *C07C 323/32* (2013.01); *C07C 323/52* (2013.01); *C07C 323/60* (2013.01); *C07D 219/08* (2013.01); *C07D 279/20* (2013.01); *C07D 513/04* (2013.01); *C10M 135/28* (2013.01); *C10M 2219/086* (2013.01); *C10M 2219/104* (2013.01); *C10N 2230/10* (2013.01)

(58) Field of Classification Search
CPC .............. C10M 135/36; C10M 135/28; C10M 2219/086; C10M 2219/104; C10N 2230/04; C07C 313/04; C07C 319/14; C07C 323/20; C07C 323/25; C07C 323/32; C07C 323/52; C07C 323/60; C07D 219/08; C07D 279/20; C07D 513/04
USPC .................................. 508/251, 569; 564/367
See application file for complete search history.

(56) References Cited

U.S. PATENT DOCUMENTS

| | | | |
|---|---|---|---|
| 4,551,259 A | 11/1985 | Braid | |
| 4,772,405 A | 9/1988 | Wirth | |
| 5,207,939 A * | 5/1993 | Farng | C10L 1/221 252/390 |
| 5,304,314 A | 4/1994 | Hsu et al. | |
| 2006/0189824 A1* | 8/2006 | Kumar | C07C 215/50 562/442 |
| 2006/0217274 A1 | 9/2006 | Brown et al. | |

FOREIGN PATENT DOCUMENTS

| | | |
|---|---|---|
| CA | 1219584 A1 | 3/1987 |
| EP | 0811631 B1 | 2/2003 |

OTHER PUBLICATIONS

Database Registry (Online). Chemical Abstracts Service, Columbus, Ohio, US, Aug. 12, 2012, XP002732884, retrieved from STN Database accession No. 1389055-22-4.*
Database Registry (Online). Chemical Abstracts Service, Columbus, Ohio, US; Aug. 12, 2012, XP002732884, retrieved from STN Database accession No. 1389055-22-4.
Database Chemcats (Online). Chemical Abstracts Service, Columbus, Ohio, US; Oct. 24, 2013, XP002732885, retrieved from STN Database accession No. 1946301708.

* cited by examiner

*Primary Examiner* — James Goloboy
(74) *Attorney, Agent, or Firm* — Novick, Kim & Lee, PLLC; Allen Xue

(57) ABSTRACT

This invention relates to a novel hindered phenol compound of Formula (I) (wherein the groups R and R' are as defined in the specification), preparation thereof and use thereof as an antioxidant. By using the hindered phenol compound of this invention as an antioxidant, it is possible to produce a lubricant oil composition exhibiting excellent oxidation resistance at elevated temperatures.

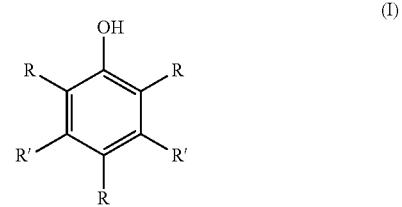

18 Claims, No Drawings

HINDERED PHENOL COMPOUND, PREPARATION THEREOF AND USE THEREOF AS AN ANTIOXIDANT

TECHNICAL FIELD

This invention relates to a novel hindered phenol compound. Specifically, this invention relates to a hindered phenol compound containing sulfur and an aromatic amine moiety, preparation thereof and use thereof as an antioxidant.

BACKGROUND ART

Oxidation stability has been identified as a very important performance for an oil product. For example, to nearly all types of lubricant oil products, an antioxidant is added as an essential component, so as to elongate its serve life. Further, with the rapid development of the modern automobile industry and machinery industry, the power output from engines and that input into mechanical machines have been dramatically increased, and as a result, the temperature at which lubricant oils work has been significantly increased, which exacerbates the oxidation problem. At the same time, as the quality grade of lubricant oils improves, it is needed to further lengthen the change-oil cycle, which sets an even higher demand on the oxidation stability (at elevated temperatures) of lubricant oil products.

In order to met these requirements set by the prior art, the technicians have been working on developing novel compounds having improved performance in oxidation resistance, so as to improve the oxidation stability of oil products. U.S. Pat. No. 5,304,314 discloses a phenol compound containing S and an aromatic amine moiety to be used as an antioxidant. US patent application No. 2006/0189824A1 discloses a hindered phenol compound containing a secondary aromatic amine moiety to be used as an antioxidant. Canada patent No. 1219584 discloses a hindered phenol compound containing S and a tertiary aromatic amine moiety to be used as an antioxidant. However, there still remains much room for the prior art compounds to be improved in oxidation resistance at elevated temperatures.

Therefore, there still remains a need for a novel compound, which exhibits significantly improved oxidation resistance at elevated temperatures as compared with prior art ones.

INVENTION SUMMARY

The present inventors, on the basis of the prior art, found a novel hindered phenol compound, and further found that, by using the hindered phenol compound as an antioxidant, the aforesaid problems encountered by the prior art can be solved, and then this invention is achieved.

Specifically, this invention relates to the following aspects.

1. A hindered phenol compound represented by Formula (I),

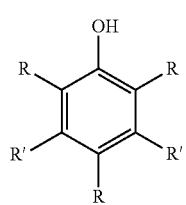

(I)

In Formula (I), the plural Rs may be identical to or different from each other, each independently selected from the group consisting of hydrogen, a $C_{1-300}$ linear or branched alkyl (preferably a $C_{1-10}$ linear or branched alkyl or a polyolefin group having a number-average molecular weight (Mn) of from 300 to 3000), a group represented by Formula (II) and a group represented by Formula (III), with the proviso that at least one R is a group represented by Formula (II); the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl),

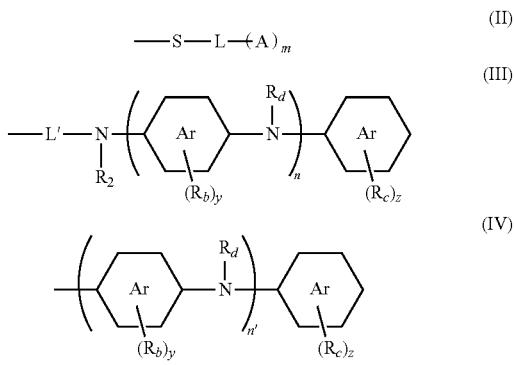

In each Formula, the group L is selected from the group consisting of a m+1 valent $C_{1-20}$ linear or branched alkyl optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a m+1 valent $C_{3-20}$ linear or branched hetero-alkyl optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl; the group L' is a group represented by

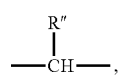

wherein the group R" is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl; the plural As may be identical to or different from each other, each independently selected from the group consisting of

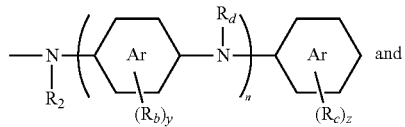 and

-continued

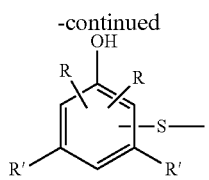

(wherein, the plural Rs may be identical to or different from each other, each independently selected from the group consisting of hydrogen, a $C_{1-300}$ linear or branched alkyl (preferably a $C_{1-10}$ linear or branched alkyl or a polyolefin group having a number-average molecular weight (Mn) of from 300 to 3000), a group represented by Formula (II) and a group represented by Formula (III) (preferably each independently selected from the group consisting of hydrogen and a $C_{1-300}$ linear or branched alkyl); the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl); two Rs and one group —S— occupy the rest three positions on the benzene ring respectively), with the proviso that at least one A is

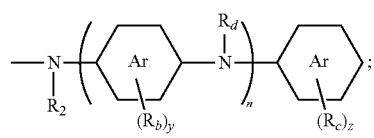

m is an integer in the range of from 1 to 4 (preferably 1); the plural $R_2$s may be identical to or different from each other, each independently selected from the group consisting of hydrogen, a $C_{1-20}$ linear or branched alkyl, a group represented by Formula (IV) and a group represented by Formula (V) (preferably each independently selected from the group consisting of hydrogen, a $C_{1-10}$ linear or branched alkyl and a group represented by Formula (IV)); the plural $R_b$s may be identical to or different from each other, each independently selected from the group consisting of hydrogen and a $C_{1-20}$ linear or branched alkyl (preferably each independently selected from the group consisting of hydrogen and a $C_{1-10}$ linear or branched alkyl); the plural $R_c$s may be identical to or different from each other, each independently selected from the group consisting of hydrogen, a $C_{1-20}$ linear or branched alkyl and a $C_{1-20}$ linear or branched alkyloxy (preferably each independently selected from the group consisting of hydrogen, a $C_{1-10}$ linear or branched alkyl and a $C_{1-10}$ linear or branched alkyloxy, more preferably locates at the position opposite to a N atom on the ring

y is an integer in the range of from 0 to 3 (preferably 0 or 1); z is an integer in the range of from 0 to 3 (preferably 0 or 1); n is an integer in the range of from 1 to 8 (preferably 1 or 2); n' is an integer in the range of from 0 to 7 (preferably 0, 1 or 2), with the proviso that n'+n≤8 (preferably n'+n=1 or n'+n=2); the plural $R_d$s may be identical to or different from each other, each independently selected from the group consisting of hydrogen and a group represented by Formula (V) (preferably hydrogen); the plural rings

may be identical to or different from each other, each independently selected from the group consisting of benzene ring and naphthalene ring (preferably benzene ring), wherein two adjacent rings

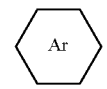

may optionally form a phenothiazine ring with the N atom bridging these two rings and an additional S atom, and/or, two adjacent rings

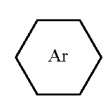

may optionally form a 9,10-dihydroacridine ring with the N atom bridging these two rings and an additional group

(wherein the group R" is selected from the group consisting of hydrogen, a $C_{1-20}$ hydrocarbyl (preferably a $C_{1-20}$ linear or branched alkyl) and a $C_{3-20}$ linear or branched heteroalkyl, preferably selected from the group consisting of hydrogen and a $C_{1-10}$ linear or branched alkyl) a 9,10-dihydroacridine ring, $$—L—(A)_m \qquad (V)$$

In Formula (V), the plural As may be identical to or different from each other, each independently selected from the group consisting of

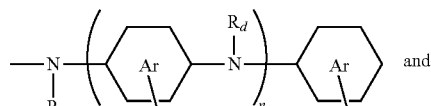 and

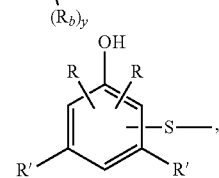

wherein the plural Rs may be identical to or different from each other, each independently selected from the group consisting of hydrogen, a $C_{1-300}$ linear or branched alkyl (preferably a $C_{1-10}$ linear or branched alkyl or a polyolefin group having a number-average molecular weight (Mn) of from 300 to 3000), a group represented by Formula (II) and a group represented by Formula (III) (preferably each independently selected from the group consisting of hydrogen and a $C_{1-300}$ linear or branched alkyl); the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl); two Rs and one group —S— occupy the rest three positions on the benzene ring respectively; the group L, the group $R_2$, the group $R_b$, the group $R_c$, the group $R_d$, the ring

and y, n, z and m are as defined in Formula (II) respectively, wherein the linear or branched hetero-alkyl is selected from the group consisting of a group obtained by directly replacing one or more group —$CH_2$— locating inside of a linear or branched alkyl by a corresponding number of replacing group selected from —O—, —S— and —NR'— (R' is H or a $C_{1-4}$ linear or branched alkyl) and a group obtained by directly replacing one or more group —CH< locating inside of a linear or branched alkyl by a corresponding number of replacing group —N<, wherein throughout the molecular structure of the hindered phenol compound, at least one $R_d$ is hydrogen.

2. The hindered phenol compound according to any one of the preceding aspects, wherein the group L is selected from the group consisting of a group

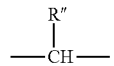

(herein m=1), a m+1 valent $C_{2-20}$ linear or branched alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl, a m+1 valent $C_{3-20}$ linear or branched hetero-alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a group

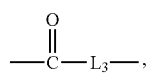

wherein the group R" is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl, the group $L_3$ is selected from the group consisting of a m+1 valent $C_{2-19}$ linear or branched alkyl optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a m+1 valent $C_{3-19}$ linear or branched hetero-alkyl optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl. 3. The hindered phenol compound according to any one of the preceding aspects, wherein the Formula (II) is selected from one of the following Formula ($II_X$), Formula ($II_{XX}$) and Formula ($II_{XXX}$),

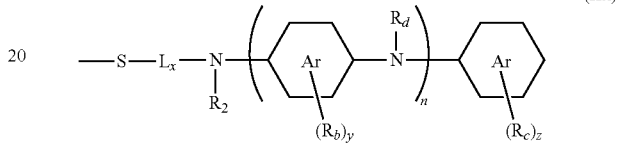

In Formula ($II_X$), the group $L_X$ is a group represented by

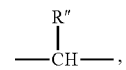

wherein the group R" is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl,

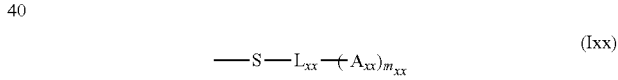

In Formula ($II_{XX}$), the group $L_X$ is selected from the group consisting of a $m_{XX+}1$ valent $C_{2-20}$ linear or branched alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a $m_{XX+}1$ valent $C_{3-20}$ linear or branched hetero-alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl; the plural $A_{XX}$s may be identical to or different from each other, each independently selected from the group consisting of

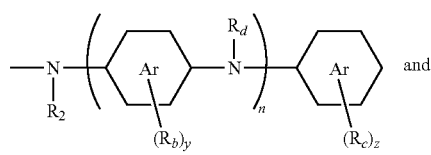 and

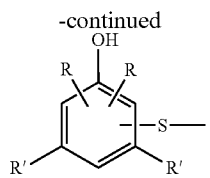

(wherein, the plural Rs may be identical to or different from each other, each independently selected from the group consisting of hydrogen, a $C_{1-300}$ linear or branched alkyl (preferably a $C_{1-10}$ linear or branched alkyl or a polyolefin group having a number-average molecular weight (Mn) of from 300 to 3000), a group represented by Formula ($II_{xx}$) and a group represented by Formula (III) (preferably each independently selected from the group consisting of hydrogen and a $C_{1-300}$ linear or branched alkyl); the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl); two Rs and one group —S— occupy the rest three positions on the benzene ring respectively), with the proviso that at least one $A_{xx}$ is

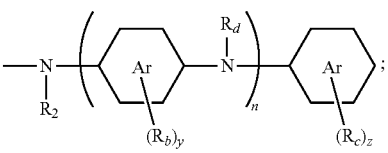

$m_{xx}$ is an integer in the range of from 1 to 4 (preferably 1),

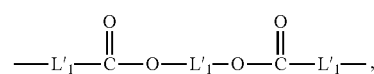
($II_{xxx}$)

In Formula ($II_{xxx}$), the group $L_{xxx}$ is selected from the group consisting of a $m_{xxx+}1$ valent $C_2$ to $C19\text{-}m_{xxx}$ linear or branched alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl, a $m_{xxx+}1$ valent $C_3$ to $C19\text{-}m_{xxx}$ linear or branched hetero-alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a group represented by

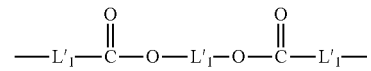

wherein the plural $L'_1$s may be identical to or different from each other, each independently selected from the group consisting of a $C_{1-10}$ linear or branched alkyl and a $C_{3-10}$ linear or branched hetero-alkyl, with the proviso that (1) the plural $L'_1$s each independently represents a 2 valent to $m_{xxx+}1$ valent group, so as to make the group

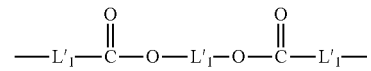

to present as, as a whole, $m_{xxx+}1$ valent, and (2) the total atom number of all groups $L'_1$ is no more than 14, wherein the plural $L'_1$ may each independently be optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl; the plural $A_{xxx}$s may be identical to or different from each other, each independently selected from the group consisting of

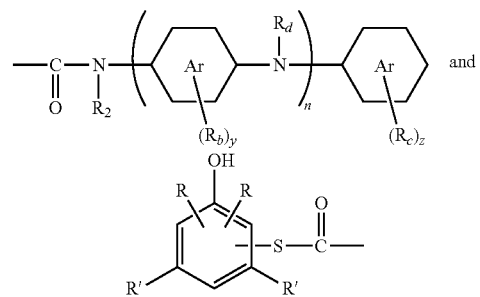

and (wherein, the plural Rs may be identical to or different from each other, each independently selected from the group consisting of hydrogen, a $C_{1-300}$ linear or branched alkyl (preferably a $C_{1-10}$ linear or branched alkyl or a polyolefin group having a number-average molecular weight (Mn) of from 300 to 3000), a group represented by Formula ($II_{xxx}$) and a group represented by Formula (III) (preferably each independently selected from the group consisting of hydrogen and a $C_{1-300}$ linear or branched alkyl); the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl); two Rs and one group

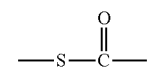

occupy the rest three positions on the benzene ring respectively), with the proviso that at least one $A_{xxx}$ is

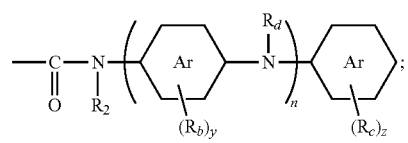

$m_{xxx}$ is an integer in the range of from 1 to 4 (preferably 1), and/or, the Formula (V) is selected from one of the following Formula ($V_x$), Formula ($V_{xx}$) and Formula ($V_{xxx}$),

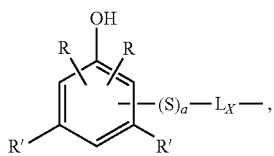
(V$_X$)

In Formula (V$_X$), the plural Rs may be identical to or different from each other, each independently selected from the group consisting of hydrogen, a C$_{1-300}$ linear or branched alkyl (preferably a C$_{1-10}$ linear or branched alkyl or a polyolefin group having a number-average molecular weight (Mn) of from 300 to 3000), a group represented by Formula (II$_X$) and a group represented by Formula (III) (preferably each independently selected from the group consisting of hydrogen and a C$_{1-300}$ linear or branched alkyl); the plural R's may be identical to or different from each other, each independently selected from the group consisting of hydrogen and a C$_{1-20}$ linear or branched alkyl (preferably each independently selected from the group consisting of hydrogen and a C$_{1-4}$ linear or branched alkyl); the group L$_X$ is a group represented by $$-\underset{\underset{\text{CH}}{|}}{\overset{R''}{|}}-,$$

wherein the group R" is selected from the group consisting of hydrogen, a C$_{1-20}$ hydrocarbyl (preferably a C$_{1-20}$ linear or branched alkyl) and a C$_{3-20}$ linear or branched hetero-alkyl, preferably selected from the group consisting of hydrogen, a C$_{1-10}$ linear or branched alkyl and a C$_{3-10}$ linear or branched hetero-alkyl; a is 1, and two Rs and one group —(S)$_a$-L$_X$- occupy the rest three positions on the benzene ring respectively,

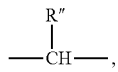
(V$_{XX}$)

In Formula (V$_{XX}$), the plural A$_{XX}$s may be identical to or different from each other, each independently selected from the group consisting of

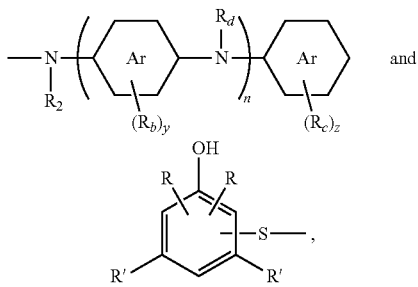

wherein the plural Rs may be identical to or different from each other, each independently selected from the group consisting of hydrogen, a C$_{1-300}$ linear or branched alkyl (preferably a C$_{1-10}$ linear or branched alkyl or a polyolefin group having a number-average molecular weight (Mn) of from 300 to 3000), a group represented by Formula (II$_{XX}$) and a group represented by Formula (III) (preferably each independently selected from the group consisting of hydrogen and a C$_{1-300}$ linear or branched alkyl); the plural R's may be identical to or different from each other, each independently selected from the group consisting of hydrogen and a C$_{1-20}$ linear or branched alkyl (preferably each independently selected from the group consisting of hydrogen and a C$_{1-4}$ linear or branched alkyl); two Rs and one group —S— occupy the rest three positions on the benzene ring respectively; the group L$_{XX}$ and m$_{XX}$ are as defined in Formula (II$_{XX}$) respectively,

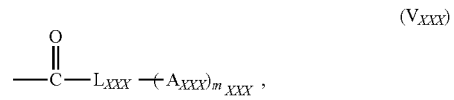
(V$_{XXX}$)

In Formula (V$_{XXX}$), the plural A$_{XXX}$s may be identical to or different from each other, each independently selected from the group consisting of

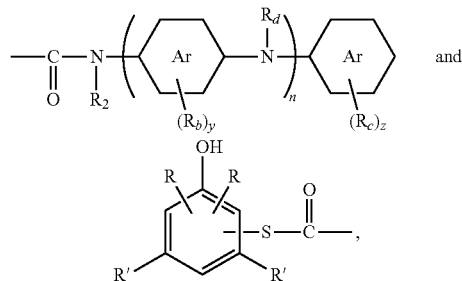

wherein the plural Rs may be identical to or different from each other, each independently selected from the group consisting of hydrogen, a C$_{1-300}$ linear or branched alkyl (preferably a C$_{1-10}$ linear or branched alkyl or a polyolefin group having a number-average molecular weight (Mn) of from 300 to 3000), a group represented by Formula (II$_{XXX}$) and a group represented by Formula (III) (preferably each independently selected from the group consisting of hydrogen and a C$_{1-300}$ linear or branched alkyl); the plural R's may be identical to or different from each other, each independently selected from the group consisting of hydrogen and a C$_{1-20}$ linear or branched alkyl (preferably each independently selected from the group consisting of hydrogen and a C$_{1-4}$ linear or branched alkyl); two Rs and one group

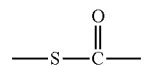

occupy the rest three positions on the benzene ring respectively; the group L$_{XXX}$ and m$_{XXX}$ are as defined in Formula (II$_{XXX}$) respectively, other groups and numerical values are as defined in aspect 1.

4. The hindered phenol compound according to any one of the preceding aspects, selected from the group consisting of the following specific compounds or their mixture at any ratio therebetween:

11
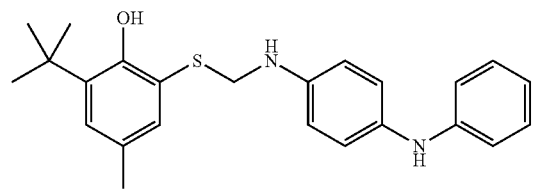
12
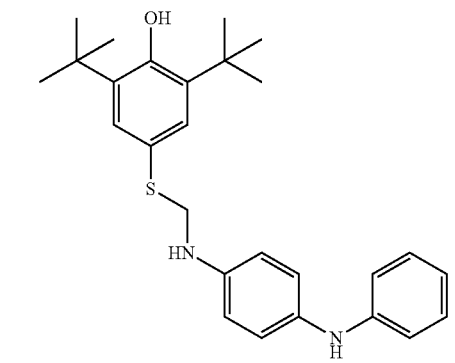
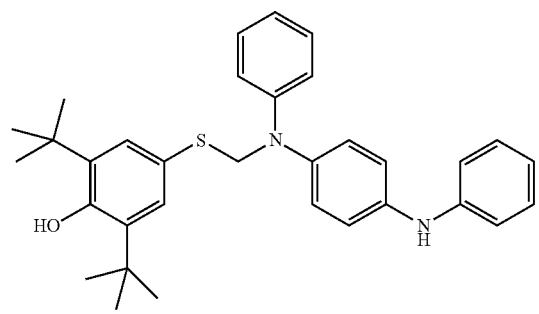
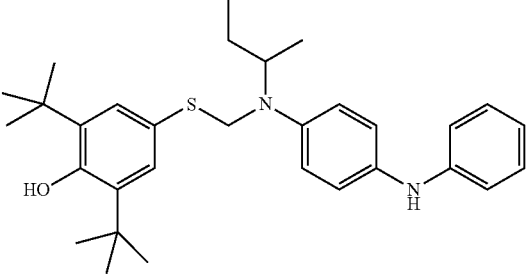
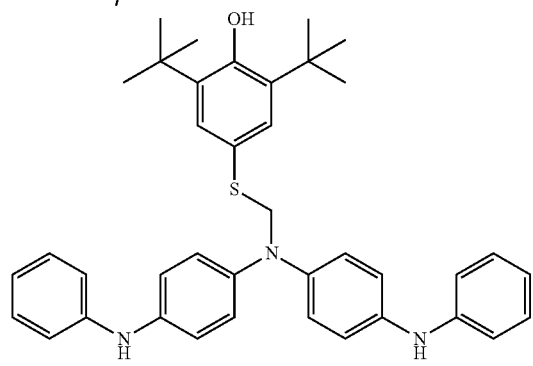
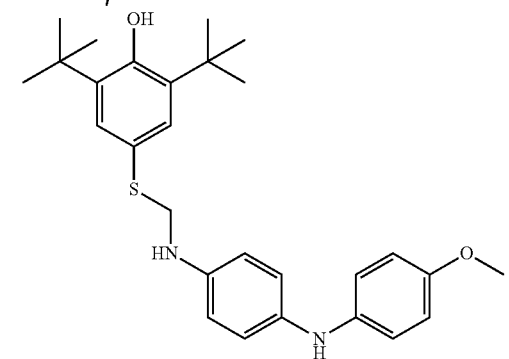
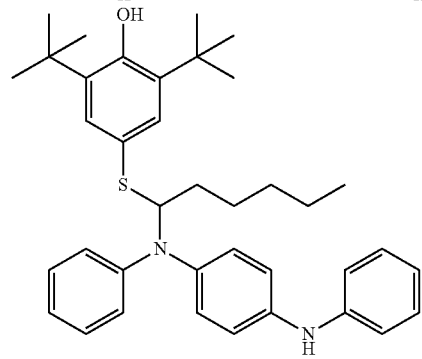
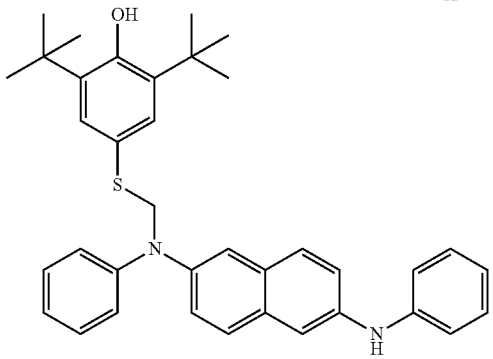
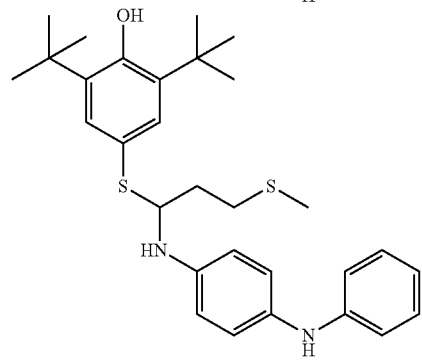
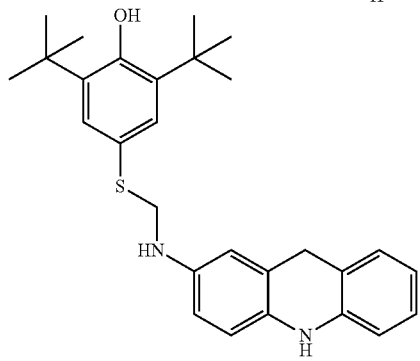

-continued
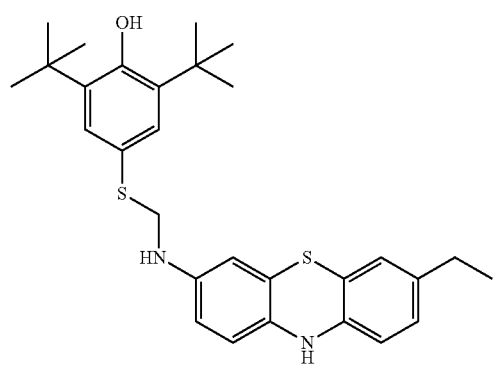
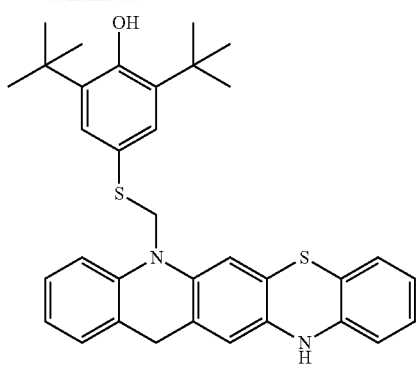
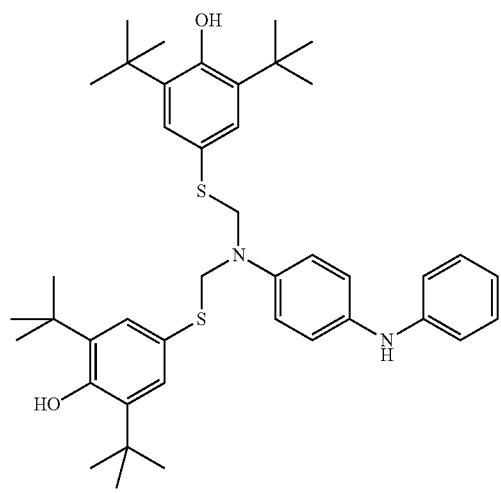
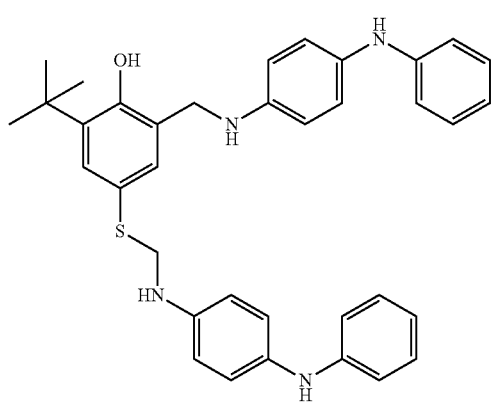
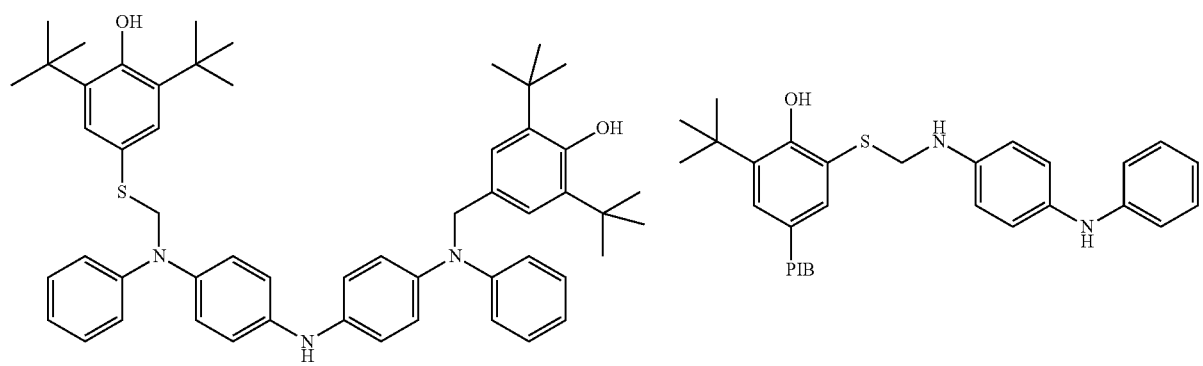
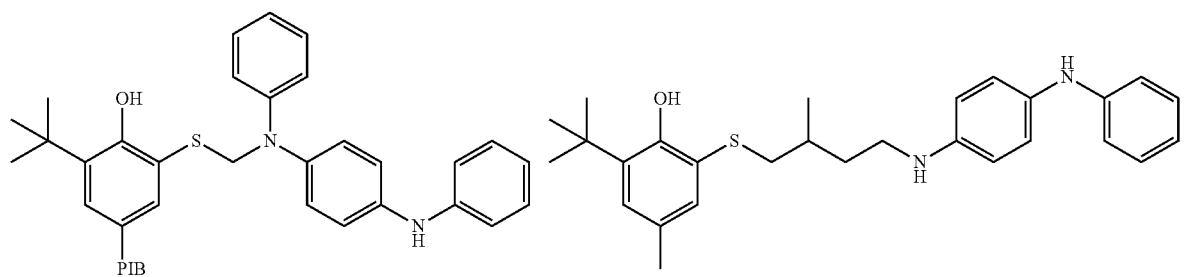

15
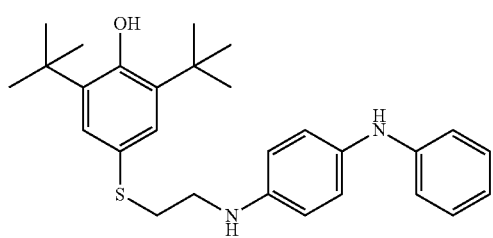
-continued
16
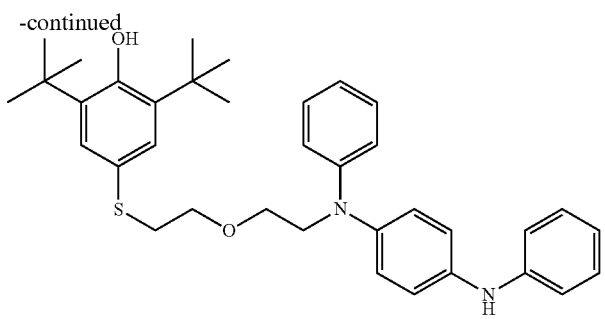
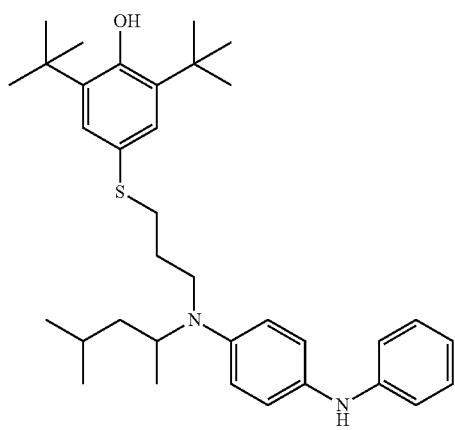
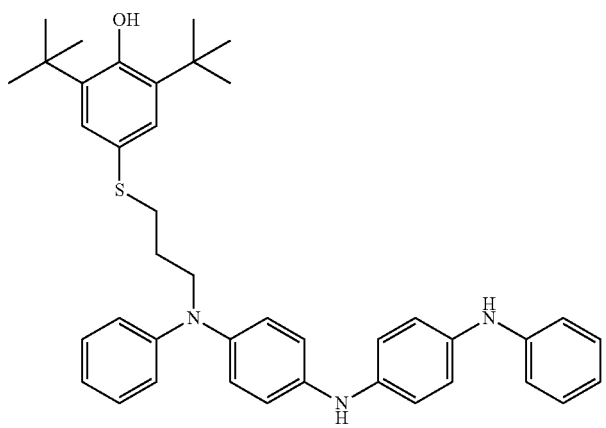
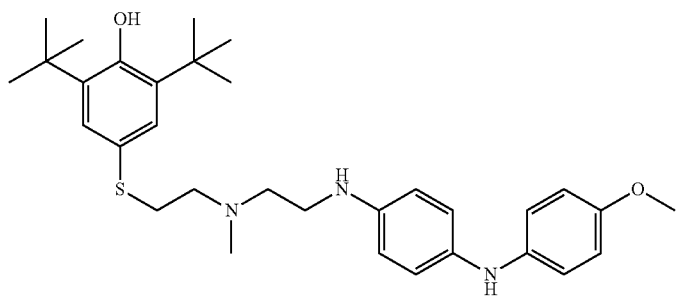
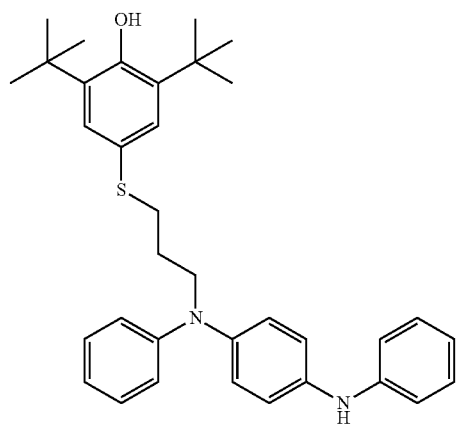
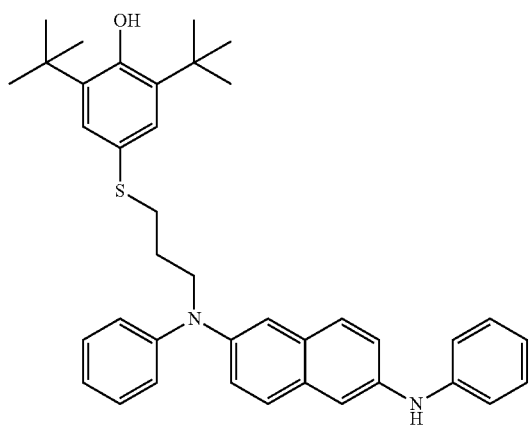
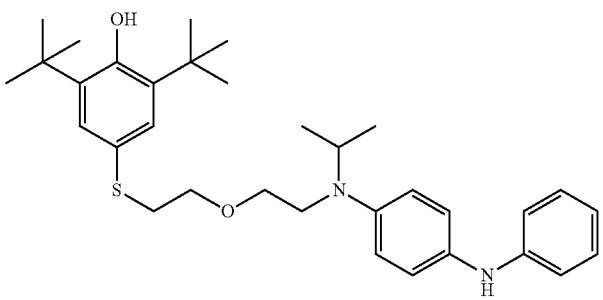

-continued
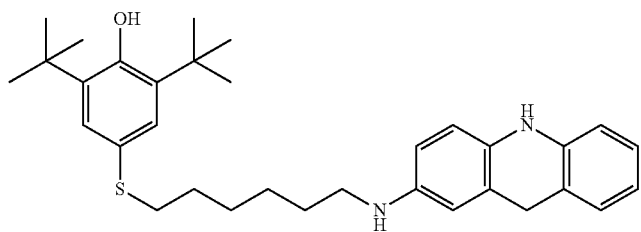
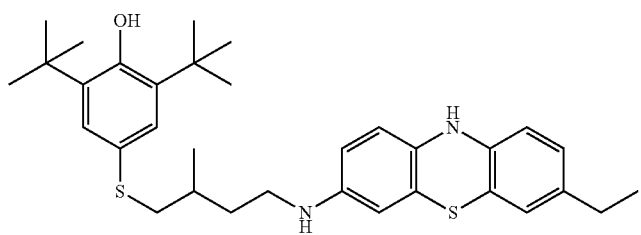
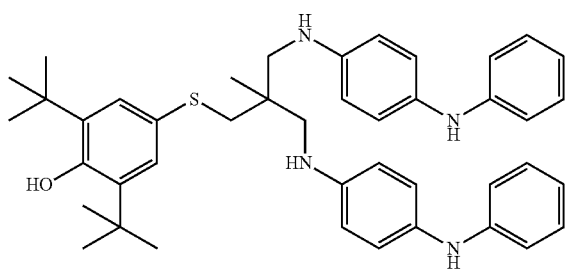
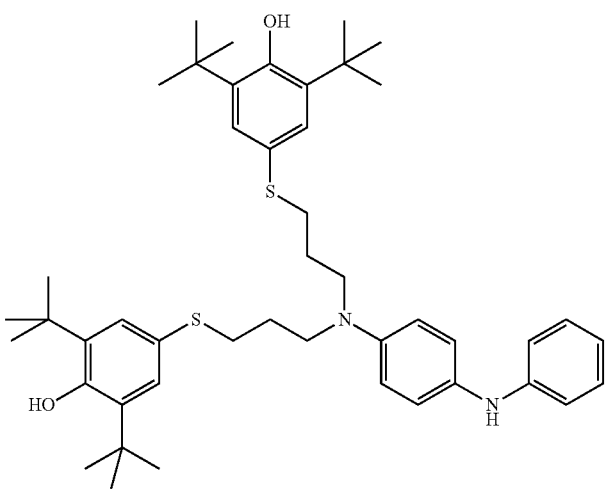
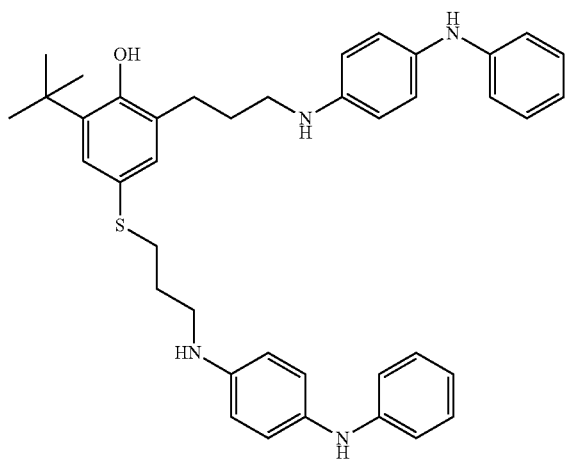

-continued
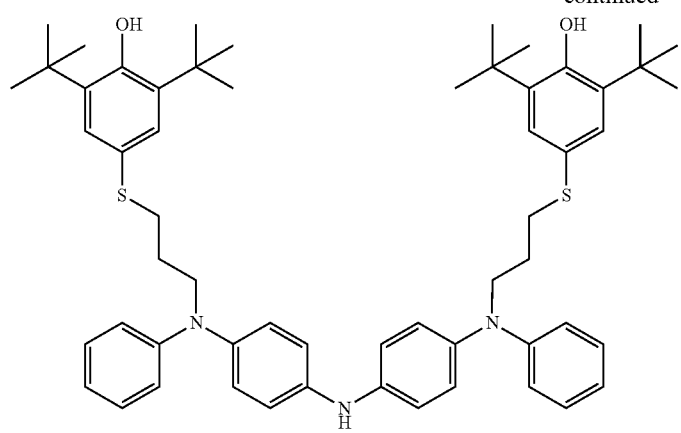
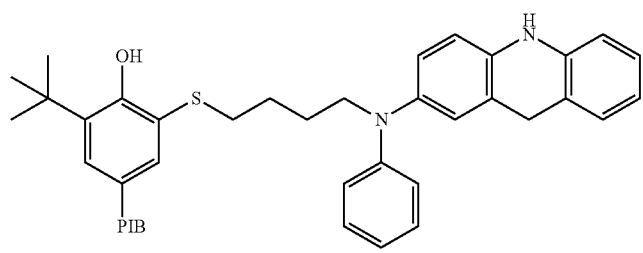
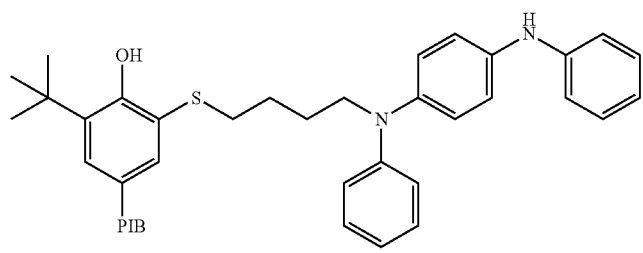
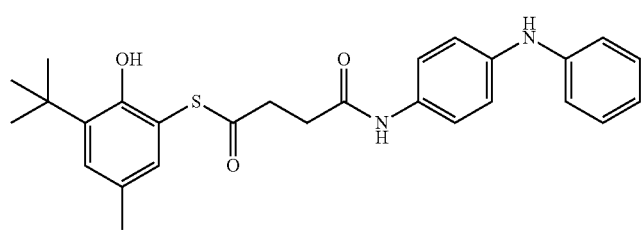
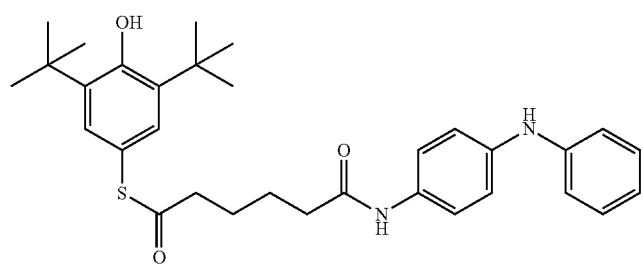

-continued
| 21 | 22 |
|---|---|
| 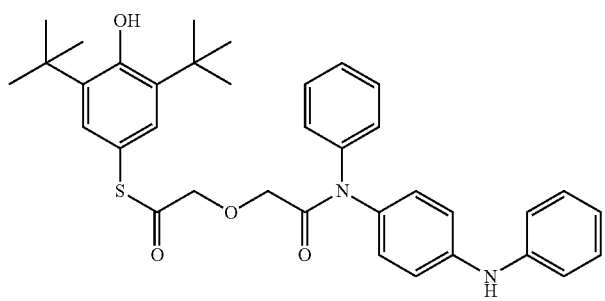 | 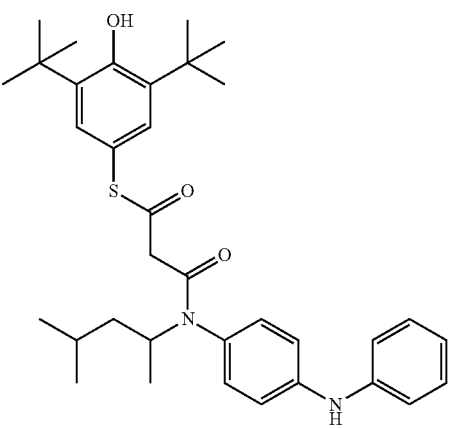 |
| 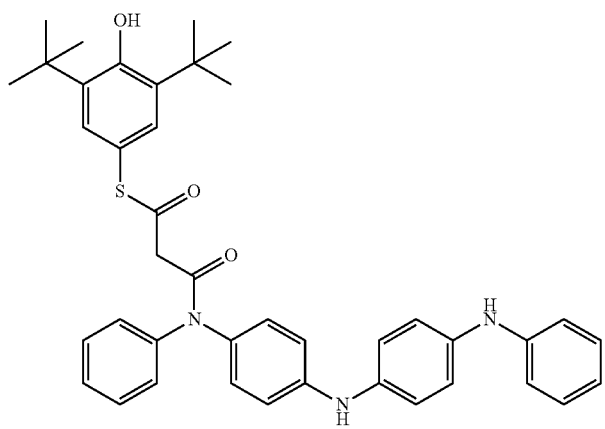 | 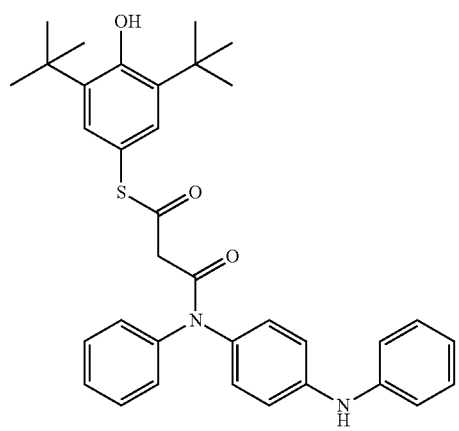 |
| 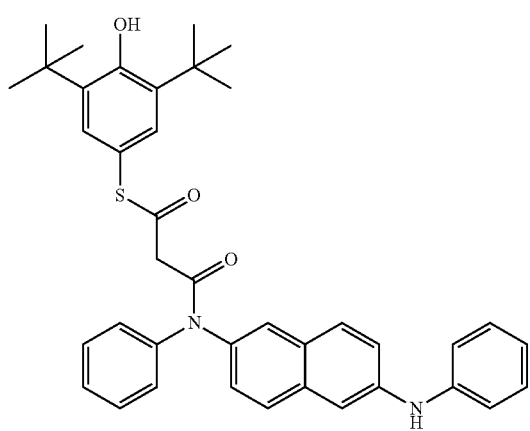 | 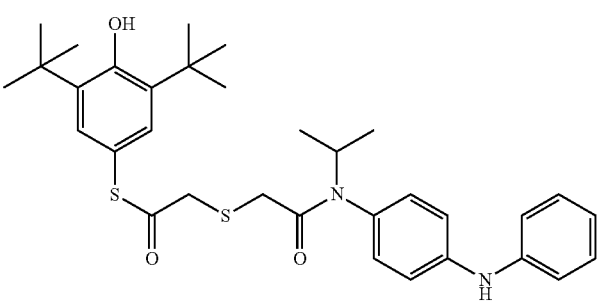 |

-continued
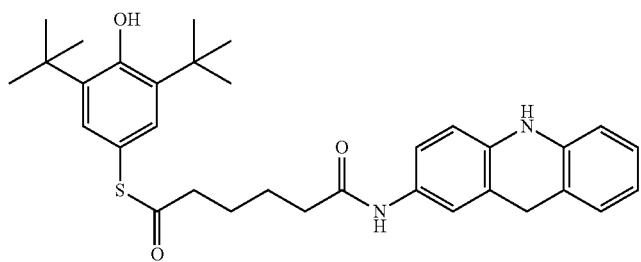
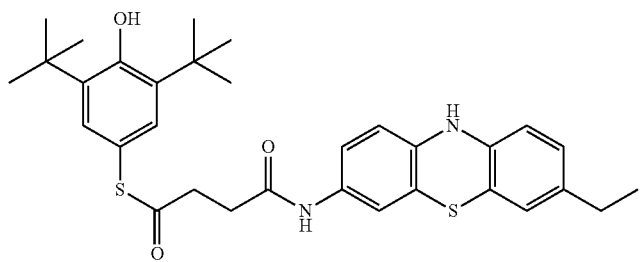
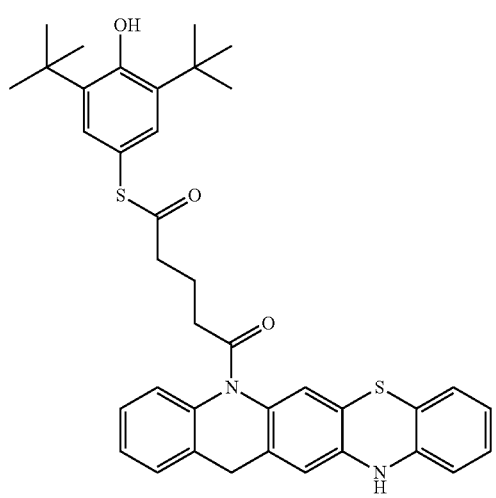
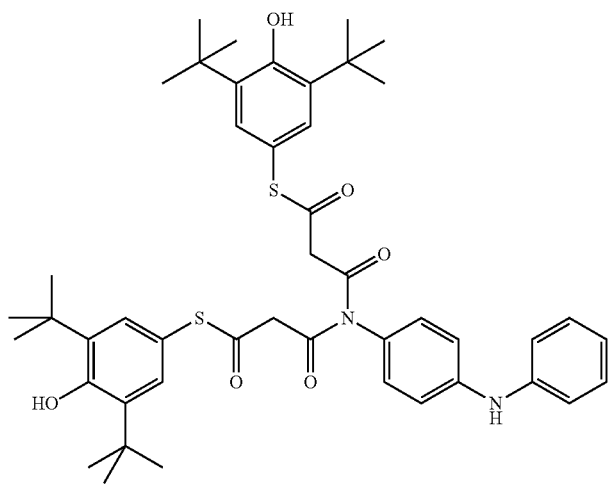
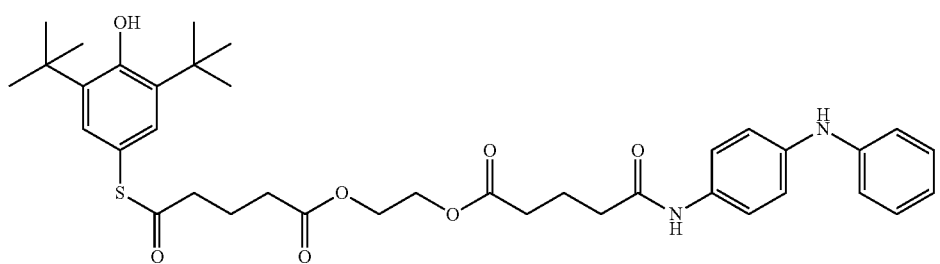

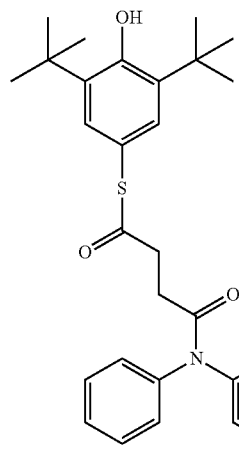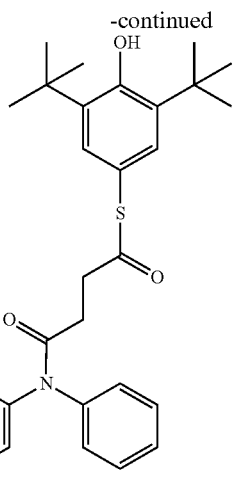
-continued
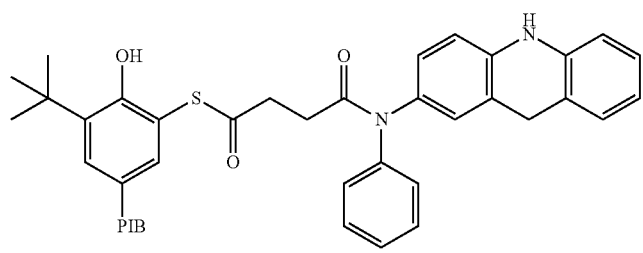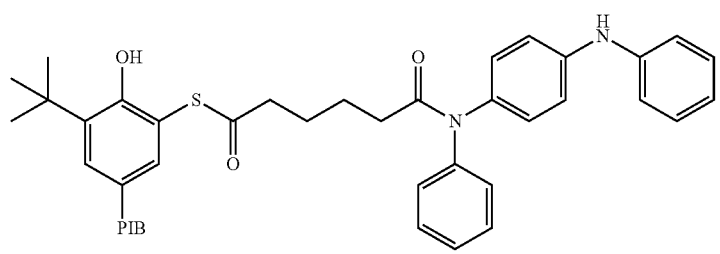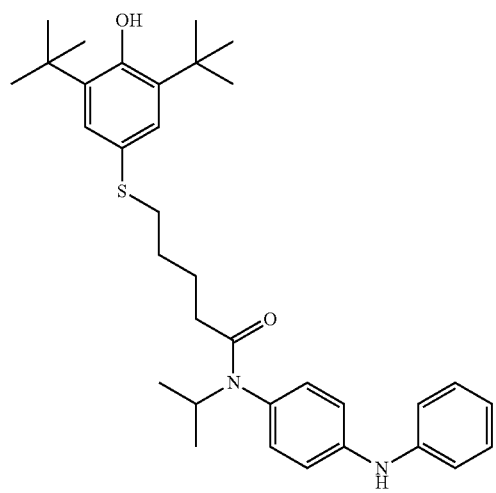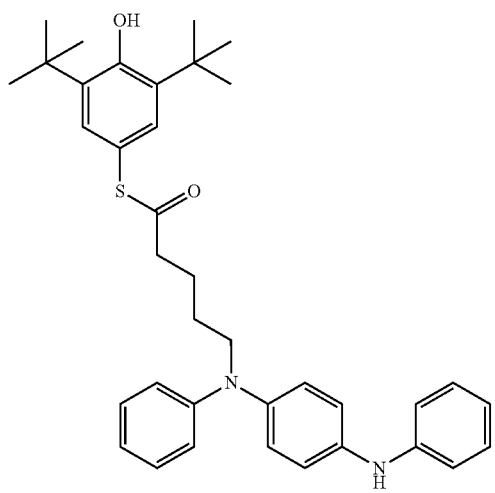

-continued

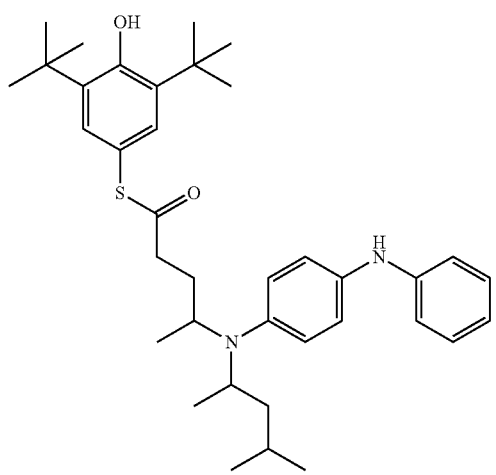
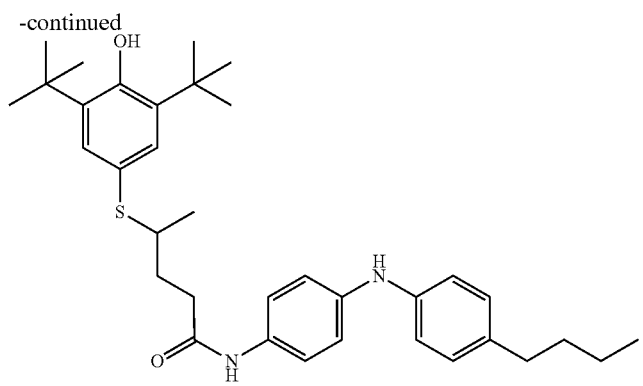
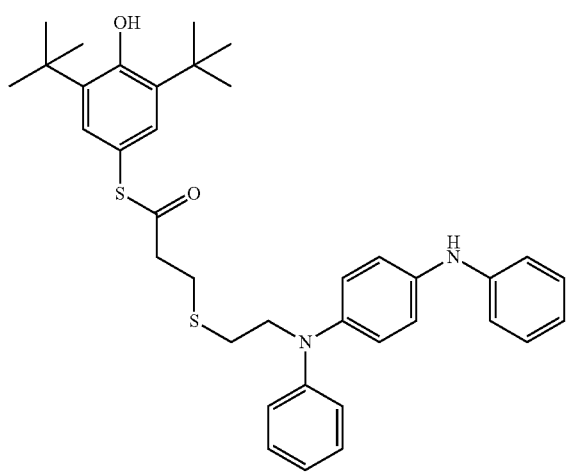
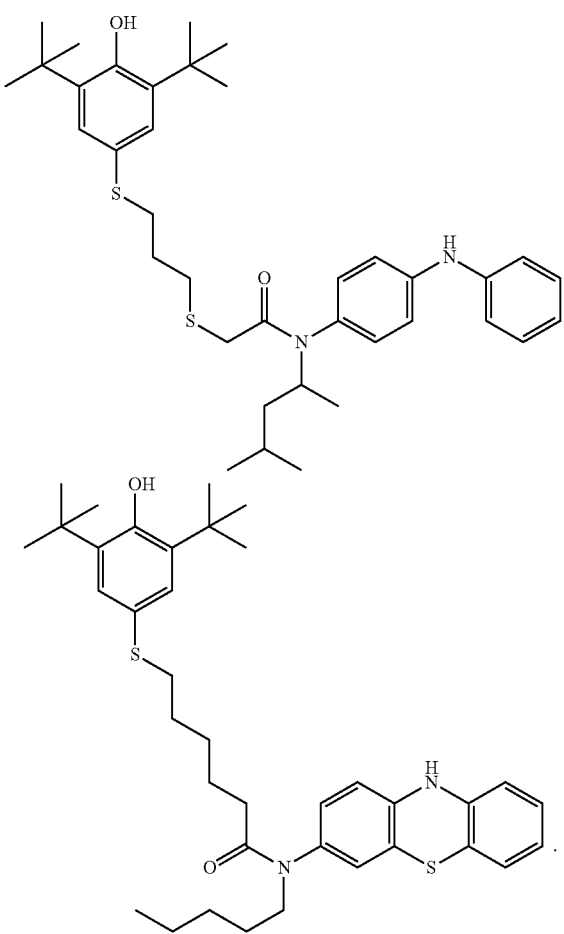
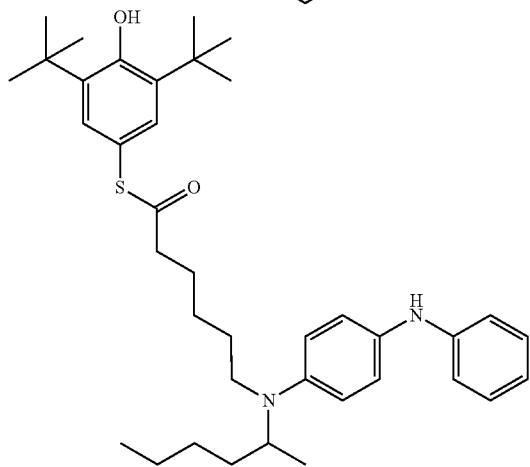

5. A process for producing a hindered phenol compound, including a first step of having a phenol compound represented by Formula (X) to react with an amine compound represented by Formula (Y) in the presence of at least one bridging compound selected from the group consisting of a compound represented by Formula (A) and formaldehyde, optionally further including an additional step of having the resultant of the first step to react with a sulfuring agent (preferably sulfur) and/or to react with an aldehyde compound represented by Formula (Z) (preferably formaldehyde),

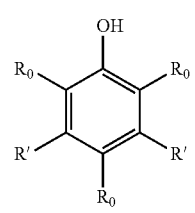

In Formula (X), the plural $R_0$s may be identical to or different from each other, each independently selected from the group consisting of hydrogen, —SH and a $C_{1-300}$ linear or branched alkyl (preferably a $C_{1-10}$ linear or branched alkyl or a polyolefin group having a number-average molecular weight (Mn) of from 300 to 3000), with the proviso that at least one $R_0$ is a group represented by —SH; the plural R's may be identical to or different from each other, each independently selected from the group consisting of hydrogen and a $C_{1-20}$ linear or branched alkyl (preferably each independently selected from the group consisting of hydrogen and a $C_{1-4}$ linear or branched alkyl),

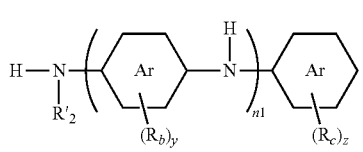
(Y)

In Formula (Y), the group $R_2$ is selected from the group consisting of hydrogen, a $C_{1-20}$ linear or branched alkyl and a group represented by

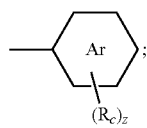

the plural $R_b$s may be identical to or different from each other, each independently selected from the group consisting of hydrogen and a $C_{1-20}$ linear or branched alkyl (preferably each independently selected from the group consisting of hydrogen and a $C_{1-10}$ linear or branched alkyl); the plural $R_c$s may be identical to or different from each other, each independently selected from the group consisting of hydrogen, a $C_{1-20}$ linear or branched alkyl and a $C_{1-20}$ linear or branched alkyloxy (preferably each independently selected from the group consisting of hydrogen, a $C_{1-10}$ linear or branched alkyl and a $C_{1-10}$ linear or branched alkyloxy, more preferably locates at the position opposite to a N atom on the ring

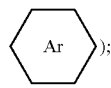

y is an integer in the range of from 0 to 3 (preferably 0 or 1); z is an integer in the range of from 0 to 3 (preferably 0 or 1); n1 is an integer in the range of from 1 to 8 (preferably 1 or 2); the plural rings

may be identical to or different from each other, each independently selected from the group consisting of benzene ring and naphthalene ring (preferably benzene ring),

(A)

In Formula (A), the group $R_f$ is selected from the group consisting of a m1 valent $C_{1-20}$ hydrocarbyl (preferably $C_{1-20}$ linear or branched alkyl) optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a m1 valent $C_{3-20}$ linear or branched hetero-alkyl optionally substituted by one or more substituent selected from the group consisting of oxo, a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl; m1 is an integer in the range of from 2 to 5 (preferably 2), the plural Funs may be identical to or different from each other, each independently selected from the group consisting of a halogen atom, a carboxylic acid residue group, an anhydride residue group and an aldehyde residue group, while in case that m1 is 1, the group Fun is an aldehyde residue group, wherein by "carboxylic acid residue group" it refers to a group obtained by removing one carbonyl

from carboxyl (i.e. —COOH), with the proviso that it is necessary for the carbon atom directly bonding to the group to take the form of carbonyl

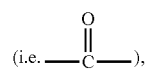

by "anhydride residue group" it refers to a group obtained by removing two carbonyls

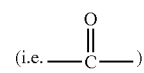

from anhydride

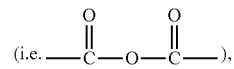

with the proviso that it is necessary for the two carbon atoms directly bonding to the group to take the form of carbonyl

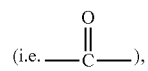

by "aldehyde residue group" it refers to a group obtained by removing one carbonyl from formyl

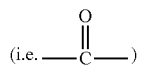

with the proviso that it is necessary for the carbon atom directly bonding to the group to take the form of carbonyl

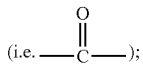

In Formula (Z), the group R″ is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl, wherein, the linear or branched hetero-alkyl is selected from the group consisting of a group obtained by directly replacing one or more group —CH$_2$— locating inside of a linear or branched alkyl by a corresponding number of replacing group selected from —O—, —S— or —NR'— (R' is H or a $C_{1-4}$ linear or branched alkyl) and a group obtained by directly replacing one or more group —CH< locating inside of a linear or branched alkyl by a corresponding number of replacing group —N<.

6. The process according to any one of the preceding aspects, wherein the bridging compound is one or more selected from the group consisting of an aldehyde compound represented by Formula ($A_Y$), a polyhalo-compound represented by Formula ($A_{YY}$) and a polybasic carboxylic acid represented by Formula ($A_{YYY}$) or derivatives thereof (selected from the group consisting of an anhydride of the polybasic carboxylic acid and an acyl halide of the polybasic carboxylic acid),

In Formula ($A_Y$), the group $R_Y$ is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl,

In Formula ($A_{YY}$), the group $R_{halo}$ is selected from the group consisting of a $m_{YY}$ valent $C_{2-20}$ linear or branched alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a $m_{YY}$ valent $C_{3-20}$ linear or branched hetero-alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl, the group Halo is a halogen atom, $m_{YY}$ is an integer in the range of from 2 to 5 (preferably 2),

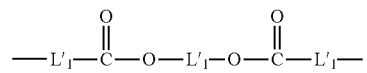

In Formula ($A_{YYY}$), the group $R_L$ is selected from the group consisting of a $m_{YYY}$ valent $C_2$ to $C_{20-m_{YYY}}$ linear or branched alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl, a $m_{YYY}$ valent $C_3$ to $C_{20-m_{YYY}}$ linear or branched hetero-alkyl optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl and a group represented by

(wherein, the plural $L'_1$s may be identical to or different from each other, each independently selected from the group consisting of a $C_{1-10}$ linear or branched alkyl and a $C_{3-10}$ linear or branched hetero-alkyl, with the proviso that (1) the plural $L'_1$s each independently represents a 2 valent to $m_{YYY}$ valent group, so as to make the group

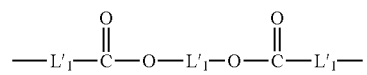

to present as, as a whole, $m_{YYY}$ valent, and (2) the total atom number of all groups $L'_1$ is no more than 14, wherein the plural $L'_1$ may each independently be optionally substituted by one or more substituent selected from the group consisting of a $C_{1-20}$ hydrocarbyl (preferably a $C_{1-20}$ linear or branched alkyl, a $C_{6-20}$ aryl or a combination group thereof) and a $C_{3-20}$ linear or branched hetero-alkyl), $m_{YYY}$ is an integer in the range of from 2 to 5 (preferably 2).

7. The process according to any one of the preceding aspects, wherein in the first step, molar ratio of the phenol compound represented by Formula (X) to the amine compound represented by Formula (Y) is 1:0.1-10, preferably 1:0.5-5.0, more preferably 1:0.8-2.0, molar ratio of the phenol compound represented by Formula (X) to the bridging compound is 1:0.1-10, preferably 1:0.2-5.0, more preferably 1:0.3-3.0, in the additional step, molar ratio of the amine compound represented by Formula (Y) to the sulfuring agent is 1:1-10, preferably 1:1.2-6.0, more preferably 1:1.5-3.0, molar ratio of the amine compound represented by Formula (Y) to the aldehyde compound represented by Formula (Z) is 1:0.1-10, preferably 1:0.5-5.0, more preferably 1:0.8-2.0.

8. Use of the hindered phenol compound according to any one of the preceding aspects or the hindered phenol compound produced in line with the process according to any one of the preceding aspects as an antioxidant.

9. A lubricant oil composition, comprising a lubricant base oil and a hindered phenol compound according to any one of the preceding aspects or the hindered phenol compound produced in line with the process according to any one of the preceding aspects as an antioxidant, wherein the antioxidant represents 0.001-30 wt %, preferably 0.1-10 wt %, of the total weight of the lubricant oil composition.

10. The lubricant oil composition according to any one of the preceding aspects, produced by mixing the hindered phenol compound with the lubricant base oil.

TECHNICAL EFFECTS

The hindered phenol compound according to this invention, contains no phosphorus and metals, generates little ash, and is thus identified as an environment friendly antioxidant. The hindered phenol compound according to this invention, as compared with a prior art compound, exhibits significantly improved oxidation resistance at elevated temperatures (thermal stability), and is thus capable of effectively improving the oxidation stability (at elevated temperatures) of e.g. a lubricant oil.

The hindered phenol compound according to this invention, in a preferred embodiment, in addition to the excellent oxidation resistance at elevated temperatures, further exhibits excellent anticorrosion performance. This performance is hardly found with a prior art compound.

The hindered phenol compound according to this invention, in a preferred embodiment, in addition to the excellent oxidation resistance at elevated temperatures, further exhibits excellent cleansing performance (i.e. deposit formation inhibition performance). This performance is hardly found with a prior art compound.

The hindered phenol compound according to this invention, in a preferred embodiment, in addition to the excellent oxidation resistance at elevated temperatures, further exhibits excellent performance of inhibiting increase in viscosity. This performance is hardly found with a prior art compound.

The hindered phenol compound according to this invention, in a preferred embodiment, in addition to the excellent oxidation resistance at elevated temperatures, further exhibits excellent performance of inhibiting increase in acid value. This performance is hardly found with a prior art compound.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this specification, the term "halo" or the like refers to fluoro, chloro, bromo or iodo.

In the context of this specification, the term "hydrocarbyl" should be interpreted as commonly known in this field, and intends to include a linear or branched alkyl, a linear or branched alkenyl, a linear or branched alkynyl, a cycloalkyl, a cycloalkenyl, a cycloalkynyl, an aryl or a combination group thereof, preferably a linear or branched alkyl, a linear or branched alkenyl, an aryl or a combination group thereof. As the hydrocarbyl, further exemplified could be a $C_{1-20}$ hydrocarbyl, including a $C_{1-20}$ linear or branched alkyl, a $C_{2-20}$ linear or branched alkenyl, a $C_{2-20}$ linear or branched alkynyl, a $C_{3-20}$ cycloalkyl, a $C_{3-20}$ cycloalkenyl, a $C_{3-20}$ cycloalkynyl, a $C_{6-20}$ aryl or a combination group thereof, preferably a $C_{1-20}$ linear or branched alkyl, a $C_{6-20}$ aryl or a combination group thereof. As the combination group, exemplified could be a group obtained by directly bonding one or more $C_{1-20}$ linear or branched alkyl (preferably one or more $C_{1-10}$ linear or branched alkyl) with one or more $C_{6-20}$ aryl (preferably one or more phenyl or naphthyl). As the combination group, for example, further exemplified could be (one or more) $C_{1-10}$ linear or branched alkyl phenyl, phenyl $C_{1-10}$ linear or branched alkyl or (one or more) $C_{1-10}$ linear or branched alkyl phenyl $C_{1-10}$ linear or branched alkyl etc., more preferably $C_{1-10}$ linear or branched alkyl phenyl (for example, tert-butyl phenyl), phenyl $C_{1-10}$ linear or branched alkyl (for example, benzyl) or $C_{1-10}$ linear or branched alkyl phenyl $C_{1-10}$ linear or branched alkyl (for example, tert-butyl benzyl).

In the context of this specification, by "linear or branched hetero-alkyl", it refers to a group obtained by directly replacing one or more (for example, from 1 to 4, from 1 to 3, from 1 to 2, or 1) group —$CH_2$— locating inside (not including that at the terminal of the main chain or any side chain in the molecular structure) of a linear or branched alkyl by a corresponding number of replacing group selected from —O—, —S— or —NR'— (R' is H or a $C_{1-4}$ linear or branched alkyl), and a group obtained by directly replacing one or more (for example, from 1 to 3, from 1 to 2, or 1) group —CH< locating inside (not including that at the terminal of the main chain or any side chain in the molecular structure) of a linear or branched alkyl by a corresponding number of replacing group —N<. As the replacing group, preferably —O— or —S—, more preferably —S—. It is obvious that, from the standpoint of structure stability, when plural exist, these replacing groups do not directly bond to each other. Further, the carbon atom number of the linear or branched alkyl is reduced accordingly due to the replacement of the group —$CH_2$— or —CH< by the replacing group, however, to simplify the description, the carbon atom number of the linear or branched alkyl before the replacement is still used to refer to the carbon atom number of the linear or branched hetero-alkyl (obtained by the replacement). As the linear or branched hetero-alkyl, if specifically exemplified, a $C_4$ linear alkyl, for example,

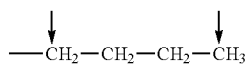

(In this figure, the groups indicated by the arrow marks do not locate inside of the linear alkyl, but rather at the terminal of the main chain) if directly replaced by one replacing group —O—,

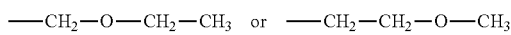

will be obtained, called as a $C_4$ linear hetero-alkyl. Or, a $C_4$ branched alkyl, for example,

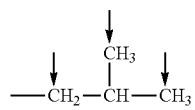

(In this figure, the groups indicated by the arrow marks do not locate inside of the branched alkyl, but rather at the terminal of the main chain and that of the side chain) if directly replaced by one replacing group —N<,

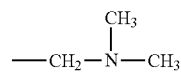

will be obtained, called as a $C_4$ branched hetero-alkyl. According to this invention, as the linear or branched hetero-alkyl, exemplified could be a $C_{3-20}$ linear or branched hetero-alkyl, preferably a $C_{3-10}$ linear or branched hetero-alkyl or a $C_{3-6}$ linear or branched hetero-alkyl. The term "linear or branched hetero-alkane" or the like can be interpreted similarly.

In the context of this specification, if a group is defined or described in the form of "numerical value+valent+group" or the like, it refers to a group obtained by removing a number of hydrogen atom (wherein the number of the hydrogen atom corresponds to the numerical value) from the corresponding basic structure (for example, a chain, a ring or a combination thereof) of the group, preferably refers to a group obtained by removing a number of hydrogen atom (wherein the number of the hydrogen atom corresponds to the numerical value) from a carbon atom (preferably from a saturated carbon atom and/or if the numerical value is two or more, from different carbon atoms) in the basic structure. For example, "3 valent linear or branched alkyl" refers to a group obtained by removing 3 (three) hydrogen atoms from a linear or branched alkane (i.e. the corresponding basic structure (chain) of the linear or branched alkyl), while "2 valent linear or branched hetero-alkyl" refers to a group obtained by removing 2 (two) hydrogen atoms from a linear or branched hetero-alkane (preferably from a carbon atom of the hetero-alkane, or, from two different carbon atoms in the hetero-alkane).

Unless otherwise specified, percents, parts or ratios or the like mentioned in this specification are all on a weight basis.

In the context of this specification, unless otherwise specified, the number-average molecular weight (Mn) is determined by gel permeation chromatography (GPC).

In the context of this specification, unless otherwise specified, the gel permeation chromatography is performed on Waters 2695 Gel Permeation Chromatograph (from Waters, USA), with a mobile phase of tetrafuran, a flow rate of 1 mL/min, a column temperature of 35 degrees Celsius, an elution time of 40 min, and a mass fraction of the sample of from 0.16% to 0.20%.

According to this invention, concerned is a hindered phenol compound represented by Formula (I).

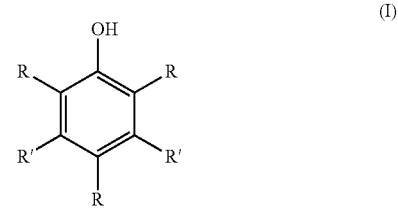

(I)

According to this invention, in Formula (I), when plural exist, the plural Rs may be identical or different from each other, each independently selected from the group consisting of hydrogen, a $C_{1-300}$ linear or branched alkyl, a group represented by Formula (II) and a group represented by Formula (III), with the proviso that at least one R is a group represented by Formula (II).

According to this invention, in Formula (I), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula (I), there exist plural Rs, wherein one of the Rs is a group represented by Formula (II), one of the other two Rs is the polyolefin group, the rest one is selected from the group consisting of hydrogen, a $C_{1-20}$ linear or branched alkyl (preferably a $C_{1-10}$ linear or branched alkyl) or a group represented by Formula (III).

According to an embodiment of this invention, in Formula (I), when the group R is the polyolefin group, the polyolefin group preferably locates at the position opposite to the phenol hydroxyl in Formula (I)

According to this invention, in Formula (I), when plural exist, the plural R's may be identical to or different from each other, each independently selected from the group consisting of hydrogen and a $C_{1-20}$ linear or branched alkyl.

According to an embodiment of this invention, in Formula (I), when plural exist, the plural R's may be identical to or different from each other, each independently selected from the group consisting of hydrogen and a $C_{1-4}$ linear or branched alkyl.

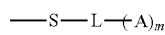 (II)

According to this invention, in Formula (II), the group L is selected from the group consisting of an optionally substituted m+1 valent $C_{1-20}$ linear or branched alkyl and an optionally substituted m+1 valent $C_{3-20}$ linear or branched hetero-alkyl, preferably selected from the group consisting of an optionally substituted m+1 valent $C_{1-10}$ linear or branched alkyl and an optionally substituted m+1 valent $C_{3-10}$ linear or branched hetero-alkyl, more preferably selected from the group consisting of an optionally substituted m+1 valent $C_{1-6}$ linear or branched alkyl and an optionally substituted m+1 valent $C_{3-6}$ linear or branched hetero-alkyl.

According to an embodiment of this invention, in Formula (II), m=1, the group L is a group represented by

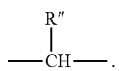

In the definition of the group L, the group R'' is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl, preferably selected from the group consisting of hydrogen and a $C_{1-10}$ linear or branched alkyl.

According to an embodiment of this invention, in Formula (II), the group L is selected from the group consisting of an optionally substituted m+1 valent $C_{2-20}$ linear or branched alkyl and an optionally substituted m+1 valent $C_{3-20}$ linear or branched hetero-alkyl, preferably selected from the group consisting of an optionally substituted m+1 valent $C_{2-10}$ linear or branched alkyl and an optionally substituted m+1 valent $C_{3-10}$ linear or branched hetero-alkyl, more preferably selected from the group consisting of an optionally substituted m+1 valent $C_{2-6}$ linear or branched alkyl and an optionally substituted m+1 valent $C_{3-6}$ linear or branched hetero-alkyl.

According to an embodiment of this invention, in Formula (II), the group L is a group represented by

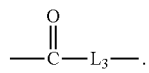

In the definition of the group L, the group $L_3$ is selected from the group consisting of an optionally substituted m+1 valent $C_{2-19}$ linear or branched alkyl and an optionally substituted m+1 valent $C_{3-19}$ linear or branched hetero-alkyl, preferably selected from the group consisting of an optionally substituted m+1 valent $C_{2-9}$ linear or branched alkyl and an optionally substituted m+1 valent $C_{3-9}$ linear or branched hetero-alkyl, more preferably selected from the group consisting of an optionally substituted m+1 valent $C_{2-6}$ linear or branched alkyl and an optionally substituted m+1 valent $C_{3-6}$ linear or branched hetero-alkyl. Preferably, the group

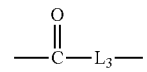

directly bonds to the S atom through its carbonyl.

According to this invention, in Formula (II), in the definitions of the group L and the group $L_3$, by "optionally substituted", it refers to optionally substituted by one or more (for example, from 1 to 5, from 1 to 4, from 1 to 3, from 1 to 2, or 1) substituent selected from the group consisting of oxo

a $C_{1-20}$ hydrocarbyl and a $C_{3-20}$ linear or branched hetero-alkyl. As the substituent, preferably oxo, a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula (II), in the definitions of the group L and the group $L_3$, when oxo exists as the substituent, preferably at least one oxo exists on the carbon atom directly bonding to the S atom or to the group A as the substituent, or in the group L or the group $L_3$, at least one or m+1 of the carbon atoms directly bonding to the S atom and to the group A has oxo as the substituent, so as to render the carbon atom present in the form of carbonyl

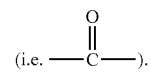

If specifically exemplified, the group L is assumed to be $CH_2$—$CH_2$—$CH_2$ (m is 1) substituted by two oxo as the substituent, if the two oxo exist on the carbon atoms directly bonding to the S atom and to the group A, the group L would be in the form of

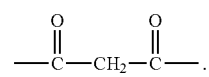

According to this invention, in Formula (II), m is an integer in the range of from 1 to 4, preferably 1.

According to this invention, in Formula (II), the plural As may be identical to or different from each other, each independently selected from the group consisting of a group represented by Formula (II-1) and a group represented by Formula (II-2), with the proviso that at least one A is a group represented by Formula (II-1).

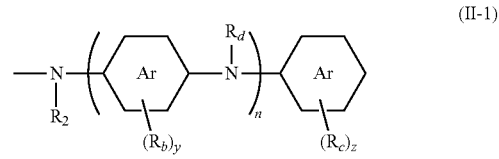 (II-1)

According to this invention, in Formula (II-1), the group $R_2$ is selected from the group consisting of hydrogen, a $C_{1-20}$ linear or branched alkyl, a group represented by Formula (IV) and a group represented by Formula (V).

According to an embodiment of this invention, in Formula (II-1), the group $R_2$ is selected from the group consisting of hydrogen, a $C_{1-10}$ linear or branched alkyl and a group represented by Formula (IV).

According to this invention, in Formula (II-1), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula (II-1), when plural exist, the plural $R_b$s may be identical to or different from each other, each independently selected from the group consisting of hydrogen and a $C_{1-6}$ linear or branched alkyl, preferably hydrogen.

According to this invention, in Formula (II-1), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula (II-1), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula (II-1), preferably one of the $R_c$ locates at the position opposite to a N atom (i.e. the N atom bonding to the group $R_d$) on the ring

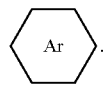.

According to this invention, in Formula (II-1), y is an integer in the range of from 0 to 3, preferably 0 or 1.

According to this invention, in Formula (II-1), z is an integer in the range of from 0 to 3, preferably 0 or 1.

According to this invention, in Formula (II-1), n is an integer in the range of from 1 to 8, preferably 1 or 2.

According to this invention, in Formula (II-1), when plural exist, the plural $R_d$s may be identical to or different from each other, each independently selected from the group consisting of hydrogen and a group represented by Formula (V), preferably hydrogen.

According to this invention, in Formula (II-1), when plural exist, the plural rings

(as a bivalent group when locating inside of Formula (II-1)) may be identical to or different from each other, each independently selected from the group consisting of benzene ring (preferably in Formula (II-1) as 1,4-phenylene when locating inside thereof) and naphthalene ring (preferably in Formula (II-1) as 1,4- or 2,6-naphthylene when locating inside thereof), preferably benzene ring.

According to an embodiment of this invention, in Formula (II-1), two adjacent rings

may optionally with an additional S atom (not shown in the formula) and the N atom bridging these two rings (i.e. the N atom bonding to the group $R_d$) to form a phenothiazine ring, i.e.

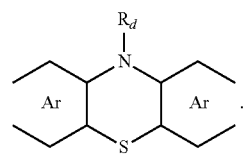.

According to this embodiment of this invention, in Formula (II-1), when exist two or more rings

, it is acceptable as long as at least two (adjacent) rings

to form the phenothiazine ring, it is not necessary for each of the rings

to form the phenothiazine ring with its adjacent ring

.

According to an embodiment of this invention, in Formula (II-1), two adjacent rings

may optionally with an additional group represented by

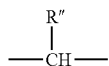

(not shown in the formula) and the N atom bridging these two rings (i.e. the N atom bonding to the group $R_d$) to form a 9,10-dihydroacridine ring, i.e.

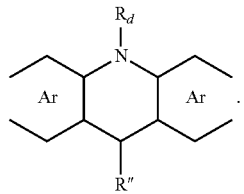

According to this invention, in the definition of the group

the group R″ is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

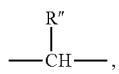

the group R″ is selected from the group consisting of hydrogen and a $C_{1-10}$ linear or branched alkyl.

According to this embodiment of this invention, in Formula (II-1), when exist two or more rings

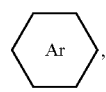

it is acceptable as long as at least two (adjacent) rings

form the 9,10-dihydroacridine ring, it is not necessary for each of the rings

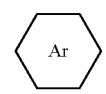

to form the 9,10-dihydroacridine ring with its adjacent ring

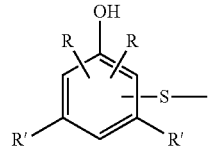

According to this invention, in Formula (II-2), when plural exist, the plural Rs may be identical to or different from each other, each independently selected from the group consisting of hydrogen, a $C_{1-300}$ linear or branched alkyl, a group represented by Formula (II) and a group represented by Formula (III).

According to this invention, in Formula (II-2), two Rs and one group —S— occupy the rest three positions on the benzene ring respectively.

According to an embodiment of this invention, in Formula (II-2), when plural exist, the plural Rs may be identical to or different from each other, each independently selected from the group consisting of hydrogen and a $C_{1-300}$ linear or branched alkyl.

According to this invention, in Formula (II-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula (II-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula (II-2), when the group R is the polyolefin group, the polyolefin group preferably locates at the position opposite to the phenol hydroxyl in Formula (II-2).

According to this invention, in Formula (II-2), when plural exist, the plural R's may be identical to or different from each other, each independently selected from the group consisting of hydrogen and a $C_{1-20}$ linear or branched alkyl.

According to an embodiment of this invention, in Formula (II-2), when plural exist, the plural R's may be identical to or different from each other, each independently selected from the group consisting of hydrogen and a $C_{1-4}$ linear or branched alkyl.

According to an embodiment of this invention, the Formula (II) is selected from one of the following Formula ($II_X$), Formula ($II_{XX}$) and Formula ($II_{XXX}$). In this embodiment, unless otherwise specified, any group or numerical value is as defined in Formula (II).

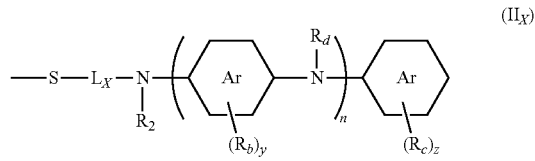

According to this invention, in Formula ($II_X$), the group $L_X$ is a group represented by

According to this invention, in Formula ($II_X$), in the definition of the group $L_X$, the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in Formula ($II_X$), in the definition of the group $L_X$, the group R" is selected from the group consisting of hydrogen, a $C_{1-10}$ linear or branched alkyl and a $C_{3-10}$ linear or branched hetero-alkyl.

According to this invention, in Formula ($II_X$), the group $R_2$ is selected from the group consisting of hydrogen, a $C_{1-20}$ linear or branched alkyl, a group represented by Formula (IV) and a group represented by Formula (V) (especially a group represented by Formula ($V_X$)).

According to an embodiment of this invention, in Formula ($II_X$), the group $R_2$ is selected from the group consisting of hydrogen, a $C_{1-10}$ linear or branched alkyl and a group represented by Formula (IV).

According to this invention, in Formula ($II_X$), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula ($II_X$), when plural exist, the plural $R_b$s may be identical to or different from each other, each independently selected from the group consisting of hydrogen and a $C_{1-6}$ linear or branched alkyl, preferably hydrogen.

According to this invention, in Formula ($II_X$), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula ($II_X$), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula ($II_X$), preferably one of the $R_c$ locates at the position opposite to a N atom (i.e. the N atom bonding to the group $R_d$) on the ring

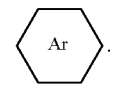

According to this invention, in Formula ($II_X$), y is an integer in the range of from 0 to 3, preferably 0 or 1.

According to this invention, in Formula ($II_X$), z is an integer in the range of from 0 to 3, preferably 0 or 1.

According to this invention, in Formula ($II_X$), n is an integer in the range of from 1 to 8, preferably 1 or 2.

According to this invention, in Formula ($II_X$), when plural exist, the plural $R_d$s may be identical to or different from each other, each independently selected from the group consisting of hydrogen and a group represented by Formula (V) (especially a group represented by Formula ($V_X$)), preferably hydrogen.

According to this invention, in Formula ($II_X$), when plural exist, the plural rings

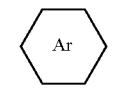

(in Formula ($II_X$) as a bivalent group when locating inside thereof) may be identical to or different from each other, each independently selected from the group consisting of benzene ring (preferably in Formula ($II_X$) as 1,4-phenylene when locating inside thereof) and naphthalene ring (preferably in Formula ($II_X$) as 1,4- or 2,6-naphthylene when locating inside thereof), preferably benzene ring.

According to an embodiment of this invention, in Formula ($II_X$), two adjacent rings

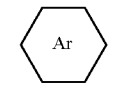

may optionally with an additional S atom (not shown in the formula) and the N atom bridging these two rings (i.e. the N atom bonding to the group $R_d$) to form a phenothiazine ring, i.e.

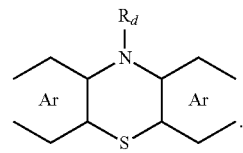

According to this embodiment of this invention, in Formula (II$_x$), when exist two or more rings

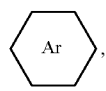

it is acceptable as long as at least two (adjacent) rings

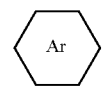

to form the phenothiazine ring, it is not necessary for each of the rings

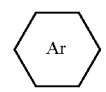

to form the phenothiazine ring with its adjacent ring

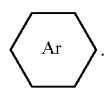

According to an embodiment of this invention, in Formula (II$_x$), two adjacent rings

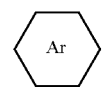

may optionally with an additional group represented by

(not shown in the formula) and the N atom bridging these two rings (i.e. the N atom bonding to the group R$_d$) to form a 9,10-dihydroacridine ring, i.e.

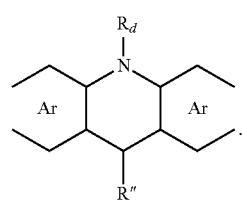

According to this invention, in the definition of the group

the group R″ is selected from the group consisting of hydrogen, a C$_{1-20}$ hydrocarbyl (preferably a C$_{1-20}$ linear or branched alkyl) and a C$_{3-20}$ linear or branched hetero-alkyl.

According to an embodiment of this invention, in the definition of the group

the group R″ is selected from the group consisting of hydrogen and a C$_{1-10}$ linear or branched alkyl.

According to this embodiment of this invention, in Formula (II$_x$), when exist two or more rings

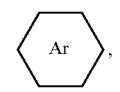

it is acceptable as long as at least two (adjacent) rings

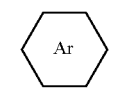

form the 9,10-dihydroacridine ring, it is not necessary for each of the rings

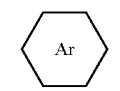

to form the 9,10-dihydroacridine ring with its adjacent ring

$$—S—L_{XX}—(A_{XX})_{m_{XX}} \quad (II_{XX})$$

According to this invention, in Formula (II$_{XX}$), the group L$_{XX}$ is selected from the group consisting of an optionally substituted m$_{XX+}$1 valent C$_{2-20}$ linear or branched alkyl and an optionally substituted m$_{XX+}$1 valent C$_{3-20}$ linear or branched hetero-alkyl, preferably selected from the group consisting of an optionally substituted m$_{XX+}$1 valent C$_{2-10}$ linear or branched alkyl and an optionally substituted m$_{XX+}$1 valent C$_{3-10}$ linear or branched hetero-alkyl, more preferably selected from the group consisting of an optionally substituted m$_{XX+}$1 valent C$_{2-6}$ linear or branched alkyl and an optionally substituted m$_{XX+}$1 valent C$_{3-6}$ linear or branched hetero-alkyl, more preferably selected from the group consisting of an optionally substituted m$_{XX+}$1 valent C$_{2-6}$ linear or branched alkyl.

According to this invention, in Formula (II$_{XX}$), in the definition of the group L$_{XX}$, by "optionally substituted", it refers to optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($II_{XX}$), $m_{XX}$ is an integer in the range of from 1 to 4, preferably 1.

According to this invention, in Formula ($II_{XX}$), the plural $A_{XX}$s may be identical to or different from each other, each independently selected from the group consisting of a group represented by Formula ($II_{XX}$-1) and a group represented by Formula ($II_{XX}$-2), with the proviso that at least one $A_{XX}$ is a group represented by Formula ($II_{XX}$-1).

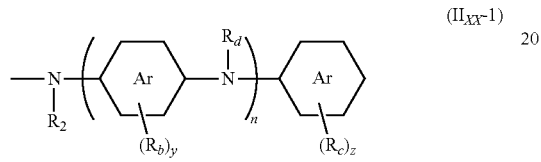
($II_{XX}$-1)

According to this invention, in Formula ($II_{XX}$-1), the group $R_2$ is selected from the group consisting of hydrogen, a $C_{1-20}$ linear or branched alkyl, a group represented by Formula (IV) and a group represented by Formula (V) (especially a group represented by Formula ($V_{XX}$)).

According to an embodiment of this invention, in Formula ($II_{XX}$-1), the group $R_2$ is selected from the group consisting of hydrogen, a $C_{1-10}$ linear or branched alkyl and a group represented by Formula (IV).

According to this invention, in Formula ($II_{XX}$-1), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula ($II_{XX}$-1), when plural exist, the plural $R_b$s may be identical to or different from each other, each independently selected from the group consisting of hydrogen and a $C_{1-6}$ linear or branched alkyl, preferably hydrogen.

According to this invention, in Formula ($II_{XX}$-1), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula ($II_{XX}$-1), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula ($II_{XX}$-1), preferably one of the $R_c$ locates at the position opposite to a N atom (i.e. the N atom bonding to the group $R_d$) on the ring

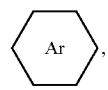.

According to this invention, in Formula ($II_{XX}$-1), y is an integer in the range of from 0 to 3, preferably 0 or 1.

According to this invention, in Formula ($II_{XX}$-1), z is an integer in the range of from 0 to 3, preferably 0 or 1.

According to this invention, in Formula ($II_{XX}$-1), n is an integer in the range of from 1 to 8, preferably 1 or 2.

According to this invention, in Formula ($II_{XX}$-1), when plural exist, the plural $R_d$s may be identical to or different from each other, each independently selected from the group consisting of hydrogen and a group represented by Formula (V) (especially a group represented by Formula ($V_{XX}$)), preferably hydrogen.

According to this invention, in Formula ($II_{XX}$-1), when plural exist, the plural rings

(in Formula ($II_{XX}$-1) as a bivalent group when locating inside thereof) may be identical to or different from each other, each independently selected from the group consisting of benzene ring (preferably in Formula ($II_{XX}$-1) as 1,4-phenylene when locating inside thereof) and naphthalene ring (preferably in Formula ($II_{XX}$-1) as 1,4- or 2,6-naphthylene when locating inside thereof), preferably benzene ring.

According to an embodiment of this invention, in Formula ($II_{XX}$-1), two adjacent rings

may optionally with an additional S atom (not shown in the formula) and the N atom bridging these two rings (i.e. the N atom bonding to the group $R_d$) to form a phenothiazine ring, i.e.

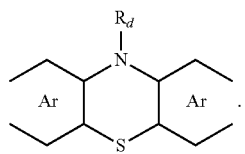

According to this embodiment of this invention, in Formula ($II_{XX}$-1), when exist two or more rings

, it is acceptable as long as at least two (adjacent) rings to form the phenothiazine ring, it is not necessary for each of the rings

to form the phenothiazine ring with its adjacent ring

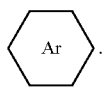.

According to an embodiment of this invention, in Formula ($II_{XX}$-1), two adjacent rings

may optionally with an additional group represented by

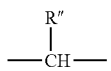

(not shown in the formula) and the N atom bridging these two rings (i.e. the N atom bonding to the group $R_d$) to form a 9,10-dihydroacridine ring, i.e.

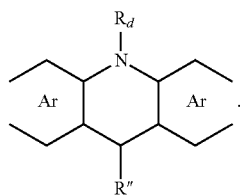

According to this invention, in the definition of the group

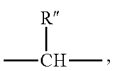

the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

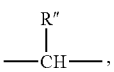

the group R" is selected from the group consisting of hydrogen and a $C_{1-10}$ linear or branched alkyl.

According to this embodiment of this invention, in Formula ($II_{XX}$-1), when exist two or more rings

it is acceptable as long as at least two (adjacent) rings

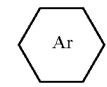

form the 9,10-dihydroacridine ring, it is not necessary for each of the rings

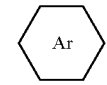

to form the 9,10-dihydroacridine ring with its adjacent ring

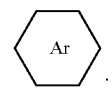.

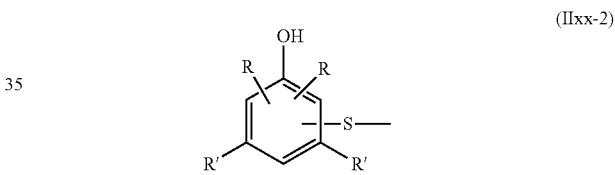 (IIxx-2)

According to this invention, in Formula ($II_{XX}$-2), when plural exist, the plural Rs may be identical to or different from each other, each independently selected from the group consisting of hydrogen, a $C_{1-300}$ linear or branched alkyl, a group represented by Formula (II) (especially a group represented by Formula ($II_{XX}$)) and a group represented by Formula (III).

According to this invention, in Formula ($II_{XX}$-2), two Rs and one group —S— occupy the rest three positions on the benzene ring respectively.

According to an embodiment of this invention, in Formula ($II_{XX}$-2), when plural exist, the plural Rs may be identical to or different from each other, each independently selected from the group consisting of hydrogen and a $C_{1-300}$ linear or branched alkyl.

According to this invention, in Formula ($II_{XX}$-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula ($II_{xx}$-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula ($II_{xx}$-2), when the group R is the polyolefin group, the polyolefin group preferably locates at the position opposite to the phenol hydroxyl in Formula ($II_{xx}$-2).

According to this invention, in Formula ($II_{xx}$-2), when plural exist, the plural R's may be identical to or different from each other, each independently selected from the group consisting of hydrogen and a $C_{1-20}$ linear or branched alkyl.

According to an embodiment of this invention, in Formula ($II_{xx}$-2), when plural exist, the plural R's may be identical to or different from each other, each independently selected from the group consisting of hydrogen and a $C_{1-4}$ linear or branched alkyl.

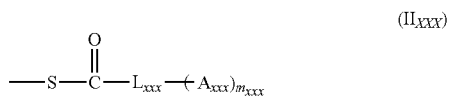

($II_{XXX}$)

According to this invention, in Formula ($II_{XXX}$), $m_{xxx}$ is an integer in the range of from 1 to 4, preferably 1.

According to this invention, in Formula ($II_{XXX}$), the group $L_{XXX}$ is selected from the group consisting of an optionally substituted $m_{XXX+}1$ valent $C_2$ to $C19$-$m_{XXX}$ linear or branched alkyl, an optionally substituted $m_{XXX+}1$ valent $C_3$ to $C19$-$m_{XXX}$ linear or branched hetero-alkyl and a group represented by

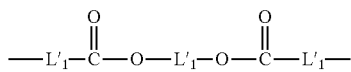

(hereinafter referred to as Formula ($II_{XXX}$-A)), preferably selected from the group consisting of an optionally substituted $m_{XXX+}1$ valent $C_2$ to $C19$-$m_{XXX}$ linear or branched alkyl and a group represented by Formula ($II_{XXX}$-A), more preferably selected from the group consisting of an optionally substituted $m_{XXX+}1$ valent $C_2$ to $C19$-$m_{XXX}$ linear or branched alkyl.

According to this invention, in Formula ($II_{XXX}$), in the definition of the group $L_{XXX}$, as the optionally substituted $m_{XXX+}1$ valent $C_2$ to $C19$-$m_{XXX}$ linear or branched alkyl, preferably an optionally substituted $m_{XXX+}1$ valent $C_2$ to $C9$-$m_{XXX}$ linear or branched alkyl, more preferably an optionally substituted $m_{XXX+}1$ valent $C_{2-6}$ linear or branched alkyl.

According to this invention, in Formula ($II_{XXX}$), in the definition of the group $L_{XXX}$, as the optionally substituted $m_{XXX+}1$ valent $C_3$ to $C19$-$m_{XXX}$ linear or branched hetero-alkyl, preferably an optionally substituted $m_{XXX+}1$ valent $C_3$ to $C9$-$m_{XXX}$ linear or branched hetero-alkyl, more preferably an optionally substituted $m_{XXX+}1$ valent $C_{3-6}$ linear or branched hetero-alkyl.

According to this invention, in Formula ($II_{XXX}$), in the definition of the group $L_{XXX}$, by "optionally substituted", it refers to optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($II_{XXX}$), in the group represented by Formula ($II_{XXX}$-A), the plural $L'_1$s may be identical to or different from each other, each independently selected from the group consisting of a $C_{1-10}$ linear or branched alkyl and a $C_{3-10}$ linear or branched hetero-alkyl, preferably each independently selected from the group consisting of a $C_{1-6}$ linear or branched alkyl.

According to this invention, in Formula ($II_{XXX}$), as for the group represented by Formula ($II_{XXX}$-A), the requirement (1) is that: the plural $L'_1$s each independently represents a 2 valent to $m_{XXX+}1$ valent group, so as to make the group represented by Formula ($II_{XXX}$-A) to present as $m_{XXX+}1$ valent, as a whole. In this context, in the group represented by Formula ($II_{XXX}$-A), the valency between different $L'_1$ may vary and may be different from each other. In view of this, in the group represented by Formula ($II_{XXX}$-A), the group $L'_1$ is not specified for its valency. In fact, the valency of each $L'_1$ could be determined by the requirement (1). Specifically, assuming that each $L'_1$ is ethyl (with no valency specified), $m_{XXX}$ is 2, then, the group represented by Formula ($II_{XXX}$-A) could be any one of the followings.

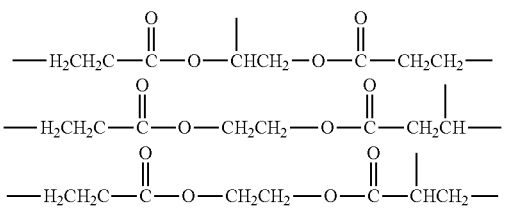

According to this invention, in Formula ($II_{XXX}$), in the group represented by Formula ($II_{XXX}$-A), the requirement (2) is that: the total atom number of all groups $L'_1$ (not figuring in any atom of the substituent that may exist on the group $L'_1$ as specified hereafter) is not more than 14, so as to make the group represented by Formula ($II_{XXX}$-A) to have a total atom number (not figuring in any atom of the substituent that may exist on the group $L'_1$ as specified hereafter) of no more than 18.

According to this invention, in Formula ($II_{XXX}$), in the group represented by Formula ($II_{XXX}$-A), after the aforesaid two requirements are met, the plural $L'_1$ may be each independently further optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($II_{xxx}$), the plural $A_{xxx}$s may be identical to or different from each other, each independently selected from the group consisting of a group represented by Formula ($II_{xxx}$-1) and a group represented by Formula ($II_{xxx}$-2), with the proviso that at least one $A_{xxx}$ is a group represented by Formula ($II_{xxx}$-1).

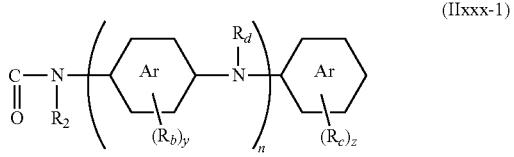

(IIxxx-1)

According to this invention, in Formula ($II_{xxx}$-1), the group $R_2$ is selected from the group consisting of hydrogen, a $C_{1-20}$ linear or branched alkyl, a group represented by Formula (IV) and a group represented by Formula (V) (especially a group represented by Formula ($V_{xxx}$)).

According to an embodiment of this invention, in Formula ($II_{xxx}$-1), the group $R_2$ is selected from the group consisting of hydrogen, a $C_{1-10}$ linear or branched alkyl and a group represented by Formula (IV).

According to this invention, in Formula ($II_{xxx}$-1), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula ($II_{xxx}$-1), when plural exist, the plural $R_b$s may be identical to or different from each other, each independently selected from the group consisting of hydrogen and a $C_{1-6}$ linear or branched alkyl, preferably hydrogen.

According to this invention, in Formula ($II_{xxx}$-1), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula ($II_{xxx}$-1), when plural exist, the plural $R_b$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula ($II_{xxx}$-1), preferably one of the $R_c$ locates at the position opposite to a N atom (i.e. the N atom bonding to the group $R_d$) on the ring

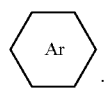

According to this invention, in Formula ($II_{xxx}$-1), y is an integer in the range of from 0 to 3, preferably 0 or 1.

According to this invention, in Formula ($II_{xxx}$-1), z is an integer in the range of from 0 to 3, preferably 0 or 1.

According to this invention, in Formula ($II_{xxx}$-1), n is an integer in the range of from 1 to 8, preferably 1 or 2.

According to this invention, in Formula ($II_{xxx}$-1), when plural exist, the plural $R_d$s may be identical to or different from each other, each independently selected from the group consisting of hydrogen and a group represented by Formula (V) (especially a group represented by Formula ($V_{xxx}$)), preferably hydrogen.

According to this invention, in Formula ($II_{xxx}$-1), when plural exist, the plural rings

(in Formula ($II_{xxx}$-1) as a bivalent group when locating inside thereof) may be identical to or different from each other, each independently selected from the group consisting of benzene ring (preferably in Formula ($II_{xxx}$-1) as 1,4-phenylene when locating inside thereof) and naphthalene ring (preferably in Formula ($II_{xxx}$-1) as 1,4- or 2,6-naphthylene when locating inside thereof), preferably benzene ring.

According to an embodiment of this invention, in Formula ($II_{xxx}$-1), two adjacent rings

may optionally with an additional S atom (not shown in the formula) and the N atom bridging these two rings (i.e. the N atom bonding to the group $R_d$) to form a phenothiazine ring, i.e.

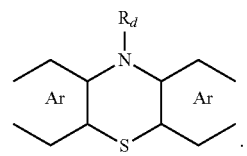

According to this embodiment of this invention, in Formula ($II_{xxx}$-1), when exist two or more rings

it is acceptable as long as at least two (adjacent) rings

to form the phenothiazine ring, it is not necessary for each of the rings

to form the phenothiazine ring with its adjacent ring

According to an embodiment of this invention, in Formula ($II_{xxx}$-1), two adjacent rings

may optionally with an additional group represented by

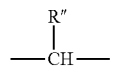

(not shown in the formula) and the N atom bridging these two rings (i.e. the N atom bonding to the group $R_d$) to form a 9,10-dihydroacridine ring, i.e.

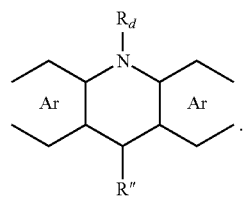

According to this invention, in the definition of the group

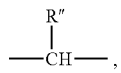

the group R″ is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

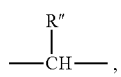

the group R″ is selected from the group consisting of hydrogen and a $C_{1-10}$ linear or branched alkyl.

According to this embodiment of this invention, in Formula ($II_{xxx}$-1), when exist two or more rings

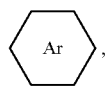

it is acceptable as long as at least two (adjacent) rings

form the 9,10-dihydroacridine ring, it is not necessary for each of the rings

to form the 9,10-dihydroacridine ring with its adjacent ring

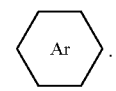

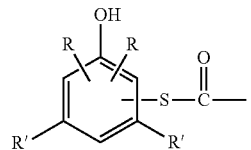

($II_{xxx}$-2)

According to this invention, in Formula ($II_{xxx}$-2), when plural exist, the plural Rs may be identical to or different from each other, each independently selected from the group consisting of hydrogen, a $C_{1-300}$ linear or branched alkyl, a group represented by Formula (II) (especially a group represented by Formula ($II_{xxx}$)) and a group represented by Formula (III).

According to this invention, in Formula ($II_{xxx}$-2), two Rs and one group

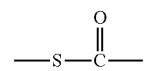

occupy the rest three positions on the benzene ring respectively.

According to an embodiment of this invention, in Formula ($II_{xxx}$-2), when plural exist, the plural Rs may be identical to or different from each other, each independently selected from the group consisting of hydrogen and a $C_{1-300}$ linear or branched alkyl.

According to this invention, in Formula ($II_{xxx}$-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula ($II_{XXX}$-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula ($II_{XXX}$-2), when the group R is the polyolefin group, the polyolefin group preferably locates at the position opposite to the phenol hydroxyl in Formula ($II_{XXX}$-2)

According to this invention, in Formula ($II_{XXX}$-2), when plural exist, the plural R's may be identical to or different from each other, each independently selected from the group consisting of hydrogen and a $C_{1-20}$ linear or branched alkyl.

According to an embodiment of this invention, in Formula ($II_{XXX}$-2), when plural exist, the plural R's may be identical to or different from each other, each independently selected from the group consisting of hydrogen and a $C_{1-4}$ linear or branched alkyl.

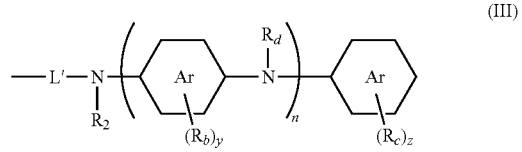

(III)

According to this invention, in Formula (III), the group L' is a group represented by

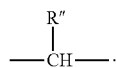

According to this invention, in Formula (III), in the definition of the group L', the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in Formula (III), in the definition of the group L', the group R" is selected from the group consisting of hydrogen, a $C_{1-10}$ linear or branched alkyl and a $C_{3-10}$ linear or branched hetero-alkyl, preferably selected from the group consisting of hydrogen and a $C_{1-10}$ linear or branched alkyl.

According to this invention, in Formula (III), the group $R_2$ is selected from the group consisting of hydrogen, a $C_{1-20}$ linear or branched alkyl, a group represented by Formula (IV) and a group represented by Formula (V).

According to an embodiment of this invention, in Formula (III), the group $R_2$ is selected from the group consisting of hydrogen, a $C_{1-10}$ linear or branched alkyl and a group represented by Formula (IV).

According to this invention, in Formula (III), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula (III), when plural exist, the plural $R_b$s may be identical to or different from each other, each independently selected from the group consisting of hydrogen and a $C_{1-6}$ linear or branched alkyl, preferably hydrogen.

According to this invention, in Formula (III), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula (III), when plural exist, the plural $R_b$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula (III), preferably one of the $R_c$ locates at the position opposite to a N atom (i.e. the N atom bonding to the group $R_d$) on the ring

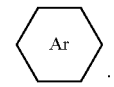

According to this invention, in Formula (III), y is an integer in the range of from 0 to 3, preferably 0 or 1.

According to this invention, in Formula (III), z is an integer in the range of from 0 to 3, preferably 0 or 1.

According to this invention, in Formula (III), n is an integer in the range of from 1 to 8, preferably 1 or 2.

According to this invention, in Formula (III), when plural exist, the plural $R_d$s may be identical to or different from each other, each independently selected from the group consisting of hydrogen and a group represented by Formula (V), preferably hydrogen.

According to this invention, in Formula (III), when plural exist, the plural rings

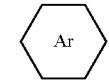

(in Formula (III) as a bivalent group when locating inside thereof) may be identical to or different from each other, each independently selected from the group consisting of benzene ring (preferably in Formula (III) as 1,4-phenylene when locating inside thereof) and naphthalene ring (preferably in Formula (III) as 1,4- or 2,6-naphthylene when locating inside thereof), preferably benzene ring.

According to an embodiment of this invention, in Formula (III), two adjacent rings

may optionally with an additional S atom (not shown in the formula) and the

N atom bridging these two rings (i.e. the N atom bonding to the group $R_d$) to form a phenothiazine ring, i.e.

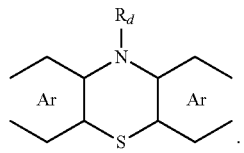

According to this embodiment of this invention, in Formula (III), when exist two or more rings

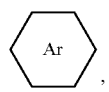

it is acceptable as long as at least two (adjacent) rings

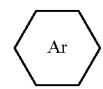

to form the phenothiazine ring, it is not necessary for each of the rings

to form the phenothiazine ring with its adjacent ring

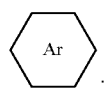

According to an embodiment of this invention, in Formula (III), two adjacent rings

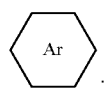

may optionally with an additional group represented by

(not shown in the formula) and the N atom bridging these two rings (i.e. the N atom bonding to the group $R_d$) to form a 9,10-dihydroacridine ring, i.e.

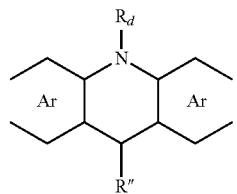

According to this invention, in the definition of the group

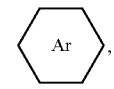

the group R″ is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

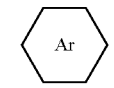

the group R″ is selected from the group consisting of hydrogen and a $C_{1-10}$ linear or branched alkyl.

According to this embodiment of this invention, in Formula (III), when exist two or more rings

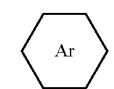

it is acceptable as long as at least two (adjacent) rings

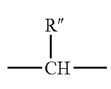

form the 9,10-dihydroacridine ring, it is not necessary for each of the rings

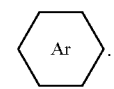

to form the 9,10-dihydroacridine ring with its adjacent ring

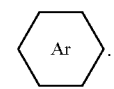

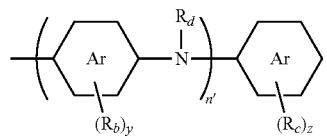 (IV)

According to this invention, in Formula (IV), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula (IV), when plural exist, the plural $R_b$s may be identical to or different from each other, each independently selected from the group consisting of hydrogen and a $C_{1-6}$ linear or branched alkyl, preferably hydrogen.

According to this invention, in Formula (IV), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula (IV), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula (IV), preferably one of the $R_c$ locates at the position opposite to a N atom (i.e. the N atom bonding to the group $R_d$) on the ring

.

According to this invention, in Formula (IV), y is an integer in the range of from 0 to 3, preferably 0 or 1.

According to this invention, in Formula (IV), z is an integer in the range of from 0 to 3, preferably 0 or 1.

According to this invention, in Formula (IV), n' is an integer in the range of from 0 to 7, preferably 0, 1 or 2, with the proviso that n'+n≤8. According to an embodiment of this invention, n'+n=1 or n'+n=2. Herein, n is as defined in the aforesaid Formula (II-1).

According to this invention, in Formula (IV), when plural exist, the plural $R_d$s may be identical to or different from each other, each independently selected from the group consisting of hydrogen and a group represented by Formula (V), preferably hydrogen.

According to this invention, in Formula (IV), when plural exist, the plural rings

(in Formula (IV) as a bivalent group when locating inside thereof) may be identical to or different from each other, each independently selected from the group consisting of benzene ring (preferably in Formula (IV) as 1,4-phenylene when locating inside thereof) and naphthalene ring (preferably in Formula (IV) as 1,4- or 2,6-naphthylene when locating inside thereof), preferably benzene ring.

According to an embodiment of this invention, in Formula (IV), two adjacent rings

may optionally with an additional S atom (not shown in the formula) and the N atom bridging these two rings (i.e. the N atom bonding to the group $R_d$) to form a phenothiazine ring, i.e.

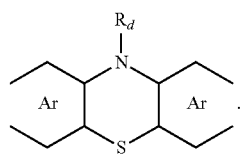.

According to this embodiment of this invention, in Formula (IV), when exist two or more rings

, it is acceptable as long as at least two (adjacent) rings

to form the phenothiazine ring, it is not necessary for each of the rings

to form the phenothiazine ring with its adjacent ring

.

According to an embodiment of this invention, in Formula (IV), two adjacent rings

may optionally with an additional group represented by

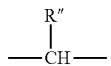

(not shown in the formula) and the N atom bridging these two rings (i.e. the N atom bonding to the group $R_d$) to form a 9,10-dihydroacridine ring, i.e.

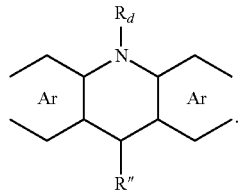

According to this invention, in the definition of the group

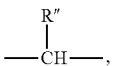

the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

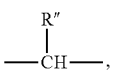

the group R" is selected from the group consisting of hydrogen and a $C_{1-10}$ linear or branched alkyl.

According to this embodiment of this invention, in Formula (IV), when exist two or more rings

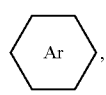

it is acceptable as long as at least two (adjacent) rings

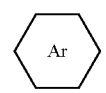

form the 9,10-dihydroacridine ring, it is not necessary for each of the rings

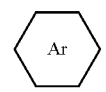

to form the 9,10-dihydroacridine ring with its adjacent ring

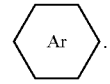

$$—L—(A)_m \quad (V)$$

According to this invention, in Formula (V), the plural As may be identical to or different from each other, each independently selected from the group consisting of a group represented by Formula (V-1) and a group represented by Formula (V-2).

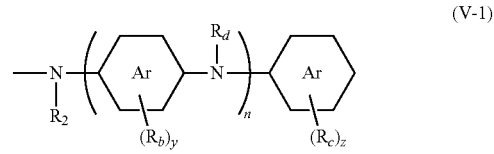

According to this invention, in Formula (V-1), the group $R_2$ is selected from the group consisting of hydrogen, a $C_{1-20}$ linear or branched alkyl, a group represented by Formula (IV) and a group represented by Formula (V).

According to an embodiment of this invention, in Formula (V-1), the group $R_2$ is selected from the group consisting of hydrogen, a $C_{1-10}$ linear or branched alkyl and a group represented by Formula (IV).

According to this invention, in Formula (V-1), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula (V-1), when plural exist, the plural $R_b$s may be identical to or different from each other, each independently selected from the group consisting of hydrogen and a $C_{1-6}$ linear or branched alkyl, preferably hydrogen.

According to this invention, in Formula (V-1), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula (V-1), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula (V-1), preferably one of the $R_c$ locates at the position opposite to a N atom (i.e. the N atom bonding to the group $R_d$) on the ring

According to this invention, in Formula (V-1), y is an integer in the range of from 0 to 3, preferably 0 or 1.

According to this invention, in Formula (V-1), z is an integer in the range of from 0 to 3, preferably 0 or 1.

According to this invention, in Formula (V-1), n is an integer in the range of from 1 to 8, preferably 1 or 2.

According to this invention, in Formula (V-1), when plural exist, the plural $R_d$s may be identical to or different from each other, each independently selected from the group consisting of hydrogen and a group represented by Formula (V), preferably hydrogen.

According to this invention, in Formula (V-1), when plural exist, the plural rings

(in Formula (V-1) as a bivalent group when locating inside thereof) may be identical to or different from each other, each independently selected from the group consisting of benzene ring (preferably in Formula (V-1) as 1,4-phenylene when locating inside thereof) and naphthalene ring (preferably in Formula (V-1) as 1,4- or 2,6-naphthylene when locating inside thereof), preferably benzene ring.

According to an embodiment of this invention, in Formula (V-1), two adjacent rings

may optionally with an additional S atom (not shown in the formula) and the N atom bridging these two rings (i.e. the N atom bonding to the group $R_d$) to form a phenothiazine ring, i.e.

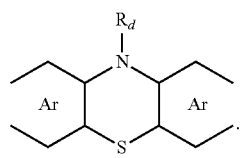

According to this embodiment of this invention, in Formula (V-1), when exist two or more rings

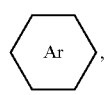

it is acceptable as long as at least two (adjacent) rings

to form the phenothiazine ring, it is not necessary for each of the rings

to form the phenothiazine ring with its adjacent ring

.

According to an embodiment of this invention, in Formula (V-1), two adjacent rings

may optionally with an additional group represented by $$-\underset{\mid}{\overset{R''}{C}}H-$$

(not shown in the formula) and the N atom bridging these two rings (i.e. the N atom bonding to the group $R_d$) to form a 9,10-dihydroacridine ring, i.e.

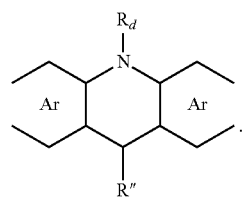

According to this invention, in the definition of the group $$-\underset{\mid}{\overset{R''}{C}}H-,$$

the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group $$-\underset{\mid}{\overset{R''}{C}}H-,$$

the group R" is selected from the group consisting of hydrogen and a $C_{1-10}$ linear or branched alkyl.

According to this embodiment of this invention, in Formula (V-1), when exist two or more rings

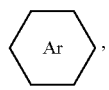

it is acceptable as long as at least two (adjacent) rings

form the 9,10-dihydroacridine ring, it is not necessary for each of the rings

to form the 9,10-dihydroacridine ring with its adjacent ring

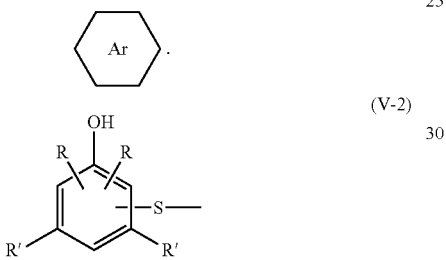

According to this invention, in Formula (V-2), when plural exist, the plural Rs may be identical to or different from each other, each independently selected from the group consisting of hydrogen, a $C_{1-300}$ linear or branched alkyl, a group represented by Formula (II) and a group represented by Formula (III).

According to this invention, in Formula (V-2), two Rs and one group —S— occupy the rest three positions on the benzene ring respectively.

According to an embodiment of this invention, in Formula (V-2), when plural exist, the plural Rs may be identical to or different from each other, each independently selected from the group consisting of hydrogen and a $C_{1-300}$ linear or branched alkyl.

According to this invention, in Formula (V-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula (V-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula (V-2), when the group R is the polyolefin group, the polyolefin group preferably locates at the position opposite to the phenol hydroxyl in Formula (V-2)

According to this invention, in Formula (V-2), when plural exist, the plural R's may be identical to or different from each other, each independently selected from the group consisting of hydrogen and a $C_{1-20}$ linear or branched alkyl.

According to an embodiment of this invention, in Formula (V-2), when plural exist, the plural R's may be identical to or different from each other, each independently selected from the group consisting of hydrogen and a $C_{1-4}$ linear or branched alkyl.

According to this invention, in Formula (V), other groups including the group L, the group $R_2$, the group $R_b$, the group $R_c$, the group $R_d$ and the ring

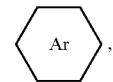

and other numerical values including y, n, z and m, are as defined in Formula (II) respectively.

According to an embodiment of this invention, the Formula (V) is selected from one of the following Formula $(V_X)$, Formula $(V_{XX})$ and Formula $(V_{XXX})$. In this embodiment, unless otherwise specified, any group or numerical value is as defined in Formula (V).

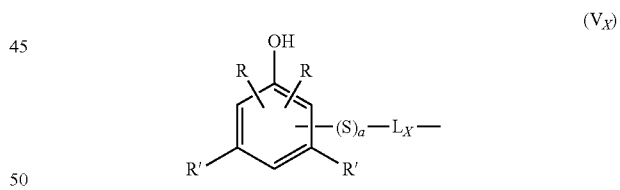

According to this invention, in Formula $(V_X)$, when plural exist, the plural Rs may be identical to or different from each other, each independently selected from the group consisting of hydrogen, a $C_{1-300}$ linear or branched alkyl, a group represented by Formula (II) (especially a group represented by Formula $(II_X)$) and a group represented by Formula (III)

According to an embodiment of this invention, in Formula $(V_X)$, when plural exist, the plural Rs may be identical to or different from each other, each independently selected from the group consisting of hydrogen and a $C_{1-300}$ linear or branched alkyl.

According to this invention, in Formula $(V_X)$, as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula ($V_X$), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula ($V_X$), when the group R is the polyolefin group, the polyolefin group preferably locates at the position opposite to the phenol hydroxyl in Formula ($V_X$)

According to this invention, in Formula ($V_X$), when plural exist, the plural R's may be identical to or different from each other, each independently selected from the group consisting of hydrogen and a $C_{1-20}$ linear or branched alkyl.

According to an embodiment of this invention, in Formula ($V_X$), when plural exist, the plural R's may be identical to or different from each other, each independently selected from the group consisting of hydrogen and a $C_{1-4}$ linear or branched alkyl.

According to this invention, in Formula ($V_X$), the group $L_X$ is a group represented by

According to this invention, in Formula ($V_X$), in the definition of the group $L_X$, the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in Formula ($V_X$), in the definition of the group $L_X$, the group R" is selected from the group consisting of hydrogen, a $C_{1-10}$ linear or branched alkyl and a $C_{3-10}$ linear or branched hetero-alkyl.

According to a preferred embodiment of this invention, in Formula ($V_X$), in the definition of the group $L_X$, the group R" is selected from the group consisting of hydrogen and a $C_{1-10}$ linear or branched alkyl.

According to this invention, in Formula ($V_X$), two Rs and one group —(S)$_a$-L- occupy the rest three positions on the benzene ring in Formula ($V_X$) respectively.

According to this invention, in Formula ($V_X$), a is 1.

 ($V_{XX}$)

According to this invention, in Formula ($V_{XX}$), the group $L_{XX}$ is selected from the group consisting of an optionally substituted $m_{XX+}1$ valent $C_{2-20}$ linear or branched alkyl and an optionally substituted $m_{XX+}1$ valent $C_{3-20}$ linear or branched hetero-alkyl, preferably selected from the group consisting of an optionally substituted $m_{XX+}1$ valent $C_{2-10}$ linear or branched alkyl and an optionally substituted $m_{XX+}1$ valent $C_{3-10}$ linear or branched hetero-alkyl, more preferably selected from the group consisting of an optionally substituted $m_{XX+}1$ valent $C_{2-6}$ linear or branched alkyl and an optionally substituted $m_{XX+}1$ valent $C_{3-6}$ linear or branched hetero-alkyl, more preferably selected from the group consisting of an optionally substituted $m_{XX+}1$ valent $C_{2-6}$ linear or branched alkyl.

According to this invention, in Formula ($V_{XX}$), in the definition of the group $L_{XX}$, by optionally substituted, it refers to optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($V_{XX}$), $m_{XX}$ is an integer in the range of from 1 to 4, preferably 1.

According to this invention, in Formula ($V_{XX}$), the plural $A_{XX}$s may be identical to or different from each other, each independently selected from the group consisting of a group represented by Formula ($V_{XX}$-1) and a group represented by Formula ($V_{XX}$-2).

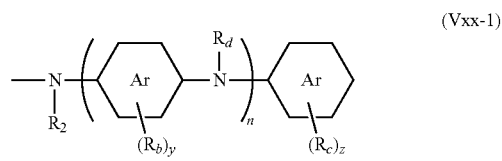

(Vxx-1)

According to this invention, in Formula ($V_{XX}$-1), the group $R_2$ is selected from the group consisting of hydrogen, a $C_{1-20}$ linear or branched alkyl, a group represented by Formula (IV) and a group represented by Formula (V) (especially a group represented by Formula ($V_{XX}$)).

According to an embodiment of this invention, in Formula ($V_{XX}$-1), the group $R_2$ is selected from the group consisting of hydrogen, a $C_{1-10}$ linear or branched alkyl and a group represented by Formula (IV).

According to this invention, in Formula ($V_{XX}$-1), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula ($V_{XX}$-1), when plural exist, the plural $R_b$s may be identical to or different from each other, each independently selected from the group consisting of hydrogen and a $C_{1-6}$ linear or branched alkyl, preferably hydrogen.

According to this invention, in Formula ($V_{XX}$-1), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula ($V_{xx}$-1), when plural exist, the plural $R_c$s may be identical to or different from each other, each independently selected from the group consisting of hydrogen, a $C_{1\text{-}10}$ linear or branched alkyl and a $C_{1\text{-}10}$ linear or branched alkyloxy.

According to an embodiment of this invention, in Formula ($V_{xx}$-1), preferably one of the $R_c$ locates at the position opposite to a N atom (i.e. the N atom bonding to the group $R_d$) on the ring

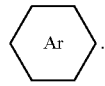.

According to this invention, in Formula ($V_{xx}$-1), y is an integer in the range of from 0 to 3, preferably 0 or 1.

According to this invention, in Formula ($V_{xx}$-1), z is an integer in the range of from 0 to 3, preferably 0 or 1.

According to this invention, in Formula ($V_{xx}$-1), n is an integer in the range of from 1 to 8, preferably 1 or 2.

According to this invention, in Formula ($V_{xx}$-1), when plural exist, the plural $R_d$s may be identical to or different from each other, each independently selected from the group consisting of hydrogen and a group represented by Formula (V) (especially a group represented by Formula ($V_{xx}$)), preferably hydrogen.

According to this invention, in Formula ($V_{xx}$-1), when plural exist, the plural rings

(in Formula ($V_{xx}$-1) as a bivalent group when locating inside thereof) may be identical to or different from each other, each independently selected from the group consisting of benzene ring (preferably in Formula ($V_{xx}$-1) as 1,4-phenylene when locating inside thereof) and naphthalene ring (preferably in Formula ($V_{xx}$-1) as 1,4- or 2,6-naphthylene when locating inside thereof), preferably benzene ring.

According to an embodiment of this invention, in Formula ($V_{xx}$-1), two adjacent rings

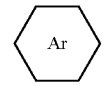

may optionally with an additional S atom (not shown in the formula) and the N atom bridging these two rings (i.e. the N atom bonding to the group $R_d$) to form a phenothiazine ring, i.e.

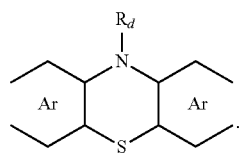

According to this embodiment of this invention, in Formula ($V_{xx}$-1), when exist two or more rings

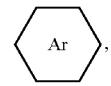, it is acceptable as long as at least two (adjacent) rings

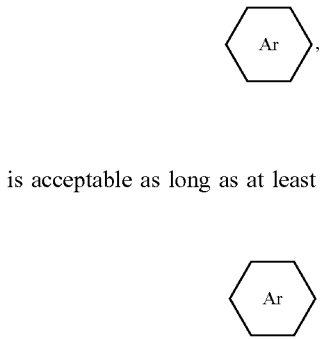

to form the phenothiazine ring, it is not necessary for each of the rings

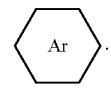

to form the phenothiazine ring with its adjacent ring

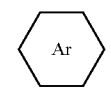.

According to an embodiment of this invention, in Formula ($V_{xx}$-1), two adjacent rings

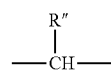

may optionally with an additional group represented by $$-\underset{\underset{\text{CH}}{|}}{R''}-$$

(not shown in the formula) and the N atom bridging these two rings (i.e. the N atom bonding to

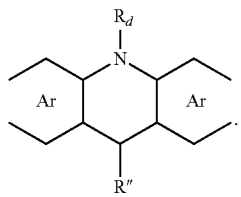

the group $R_d$) to form a 9,10-dihydroacridine ring, i.e.

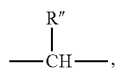

According to this invention, in the definition of the group the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

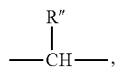

According to an embodiment of this invention, in the definition of the group the group R" is selected from the group consisting of hydrogen and a $C_{1-10}$ linear or branched alkyl.

According to this embodiment of this invention, in Formula ($V_{xx}$-1), when exist two or more rings

it is acceptable as long as at least two (adjacent) rings

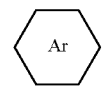

form the 9,10-dihydroacridine ring, it is not necessary for each of the rings

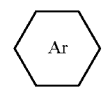

to form the 9,10-dihydroacridine ring with its adjacent ring

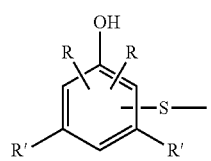

According to this invention, in Formula ($V_{xx}$-2), when plural exist, the plural Rs may be identical to or different from each other, each independently selected from the group consisting of hydrogen, a $C_{1-300}$ linear or branched alkyl, a group represented by Formula (II) (especially a group represented by Formula ($II_{xx}$)) and a group represented by Formula (III).

According to this invention, in Formula ($V_{xx}$-2), two Rs and one group —S— occupy the rest three positions on the benzene ring respectively.

According to an embodiment of this invention, in Formula ($V_{xx}$-2), when plural exist, the plural Rs may be identical to or different from each other, each independently selected from the group consisting of hydrogen and a $C_{1-300}$ linear or branched alkyl.

According to this invention, in Formula ($V_{xx}$-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula ($V_{xx}$-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula ($V_{xx}$-2), when the group R is the polyolefin group, the polyolefin group preferably locates at the position opposite to the phenol hydroxyl in Formula ($V_{xx}$-2)

According to this invention, in Formula ($V_{xx}$-2), when plural exist, the plural R's may be identical to or different from each other, each independently selected from the group consisting of hydrogen and a $C_{1-20}$ linear or branched alkyl.

According to an embodiment of this invention, in Formula ($V_{xx}$-2), when plural exist, the plural R's may be identical to or different from each other, each independently selected from the group consisting of hydrogen and a $C_{1-4}$ linear or branched alkyl.

$$-\overset{O}{\underset{\|}{C}}-L_{xxx}-(A_{xxx})_{m_{xxx}} \quad (V_{xxx})$$

According to this invention, in Formula ($V_{xxx}$), $m_{xxx}$ is an integer in the range of from 1 to 4, preferably 1.

According to this invention, in Formula ($V_{xxx}$), the group $L_{xxx}$ is selected from the group consisting of an optionally substituted $m_{xxx}+1$ valent $C_2$ to $C19-m_{xxx}$ linear or branched alkyl, an optionally substituted $m_{xxx}+1$ valent $C_3$ to $C19-m_{xxx}$ linear or branched hetero-alkyl and a group represented by

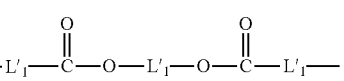

(hereinafter referred to as Formula ($V_{xxx}$-A)), preferably selected from the group consisting of an optionally substituted $m_{xxx+}1$ valent $C_2$ to $C19\text{-}m_{xxx}$ linear or branched alkyl and a group represented by Formula ($V_{xxx}$-A), more preferably selected from the group consisting of an optionally substituted $m_{xxx+}1$ valent $C_2$ to $C19\text{-}m_{xxx}$ linear or branched alkyl.

According to this invention, in Formula ($V_{xxx}$), in the definition of the group $L_{xxx}$, as the optionally substituted $m_{xxx+}1$ valent $C_2$ to $C19\text{-}m_{xxx}$ linear or branched alkyl, preferably an optionally substituted $m_{xxx+}1$ valent $C_2$ to $C9\text{-}m_{xxx}$ linear or branched alkyl, more preferably an optionally substituted $m_{xxx+}1$ valent $C_{2\text{-}6}$ linear or branched alkyl.

According to this invention, in Formula ($V_{xxx}$), in the definition of the group $L_{xxx}$, as the optionally substituted $m_{xxx+}1$ valent $C_3$ to $C19\text{-}m_{xxx}$ linear or branched hetero-alkyl, preferably an optionally substituted $m_{xxx+}1$ valent $C_3$ to $C9\text{-}m_{xxx}$ linear or branched hetero-alkyl, more preferably an optionally substituted $m_{xxx+}1$ valent $C_{3\text{-}6}$ linear or branched hetero-alkyl.

According to this invention, in Formula ($V_{xxx}$), in the definition of the group $L_{xxx}$, by "optionally substituted", it refers to optionally substituted by one or more (for example, from 1 to 4, from 1 to 3, from 1 to 2, or 1) substituent selected from the group consisting of a $C_{1\text{-}20}$ hydrocarbyl and a $C_{3\text{-}20}$ linear or branched hetero-alkyl. As the substituent, preferably a $C_{1\text{-}20}$ linear or branched alkyl, a $C_{6\text{-}20}$ aryl or a combination group thereof. As the $C_{1\text{-}20}$ linear or branched alkyl, preferably a $C_{1\text{-}10}$ linear or branched alkyl, more preferably a $C_{1\text{-}6}$ linear or branched alkyl, for example, methyl or ethyl.

According to this invention, in Formula ($V_{xxx}$), in the group represented by Formula ($V_{xxx}$-A), the plural $L'_1$s may be identical to or different from each other, each independently selected from the group consisting of a $C_{1\text{-}10}$ linear or branched alkyl and a $C_{3\text{-}10}$ linear or branched hetero-alkyl, preferably each independently selected from the group consisting of a $C_{1\text{-}6}$ linear or branched alkyl.

According to this invention, in Formula ($V_{xxx}$), as for the group represented by Formula ($V_{xxx}$-A), the requirement (1) is that: the plural $L'_1$s each independently represents a 2 valent to $m_{xxx+}1$ valent group, so as to make the group represented by Formula ($V_{xxx}$-A) to present as $m_{xxx+}1$ valent, as a whole. In this context, in the group represented by Formula ($V_{xxx}$-A), the valency between different $L'_1$ may vary and may be different from each other. In view of this, in the group represented by Formula ($V_{xxx}$-A), the group $L'_1$ is not specified for its valency. In fact, the valency of each $L'_1$ could be determined by the requirement (1). Specifically, assuming that each $L'_1$ is ethyl (with no valency specified), $m_{xxx}$ is 2, then, the group represented by Formula ($V_{xxx}$-A) could be any one of the followings.

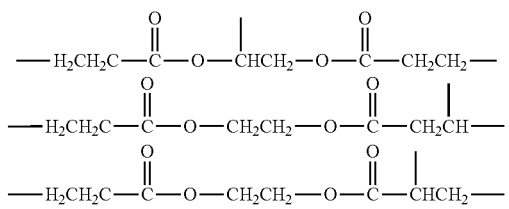

According to this invention, in Formula ($V_{xxx}$), in the group represented by Formula ($V_{xxx}$-A), the requirement (2) is that: the total atom number of all groups $L'_1$ (not figuring in any atom of the substituent that may exist on the group $L'_1$ as specified hereafter) is not more than 14, so as to make the group represented by Formula ($V_{xxx}$-A) to have a total atom number (not figuring in any atom of the substituent that may exist on the group $L'_1$ as specified hereafter) of no more than 18.

According to this invention, in Formula ($V_{xxx}$), in the group represented by Formula ($V_{xxx}$-A), after the aforesaid two requirements are met, the plural $L'_1$ may be each independently further optionally substituted by one or more (for example, from 1 to 4, from 1 to 3, from 1 to 2, or 1) substituent selected from the group consisting of a $C_{1\text{-}20}$ hydrocarbyl and a $C_{3\text{-}20}$ linear or branched hetero-alkyl. As the substituent, preferably a $C_{1\text{-}20}$ linear or branched alkyl, a $C_{6\text{-}20}$ aryl or a combination group thereof. As the $C_{1\text{-}20}$ linear or branched alkyl, preferably a $C_{1\text{-}10}$ linear or branched alkyl, more preferably a $C_{1\text{-}6}$ linear or branched alkyl, for example, methyl or ethyl.

According to this invention, in Formula ($V_{xxx}$), the plural $A_{xxx}$s may be identical to or different from each other, each independently selected from the group consisting of a group represented by Formula ($V_{xxx}$-1) and a group represented by Formula ($V_{xxx}$-2).

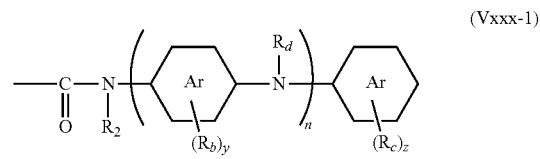

(Vxxx-1)

According to this invention, in Formula ($V_{xxx}$-1), the group $R_2$ is selected from the group consisting of hydrogen, a $C_{1\text{-}20}$ linear or branched alkyl, a group represented by Formula (IV) and a group represented by Formula (V) (especially a group represented by Formula ($V_{xxx}$)).

According to an embodiment of this invention, in Formula ($V_{xxx}$-1), the group $R_2$ is selected from the group consisting of hydrogen, a $C_{1\text{-}10}$ linear or branched alkyl and a group represented by Formula (IV).

According to this invention, in Formula ($V_{xxx}$-1), when plural exist, the plural $R_b$s may be identical to or different from each other, each independently selected from the group consisting of hydrogen and a $C_{1\text{-}20}$ linear or branched alkyl, preferably each independently selected from the group consisting of hydrogen and a $C_{1\text{-}10}$ linear or branched alkyl.

According to an embodiment of this invention, in Formula ($V_{xxx}$-1), when plural exist, the plural $R_b$s may be identical to or different from each other, each independently selected from the group consisting of hydrogen and a $C_{1\text{-}6}$ linear or branched alkyl, preferably hydrogen.

According to this invention, in Formula ($V_{xxx}$-1), when plural exist, the plural $R_c$s may be identical to or different from each other, each independently selected from the group consisting of hydrogen, a $C_{1\text{-}20}$ linear or branched alkyl and a $C_{1\text{-}20}$ linear or branched alkyloxy.

According to an embodiment of this invention, in Formula ($V_{xxx}$-1), when plural exist, the plural $R_b$s may be identical to or different from each other, each independently selected from the group consisting of hydrogen, a $C_{1\text{-}10}$ linear or branched alkyl and a $C_{1\text{-}10}$ linear or branched alkyloxy.

According to an embodiment of this invention, in Formula ($V_{xxx}$-1), preferably one of the $R_c$ locates at the position opposite to a N atom (i.e. the N atom bonding to the group $R_d$) on the ring

According to this invention, in Formula ($V_{xxx}$-1), y is an integer in the range of from 0 to 3, preferably 0 or 1.

According to this invention, in Formula ($V_{xxx}$-1), z is an integer in the range of from 0 to 3, preferably 0 or 1.

According to this invention, in Formula ($V_{xxx}$-1), n is an integer in the range of from 1 to 8, preferably 1 or 2.

According to this invention, in Formula ($V_{xxx}$-1), when plural exist, the plural $R_d$s may be identical to or different from each other, each independently selected from the group consisting of hydrogen and a group represented by Formula (V) (especially a group represented by Formula ($V_{xxx}$)), preferably hydrogen.

According to this invention, in Formula ($V_{xxx}$-1), when plural exist, the plural rings

(in Formula ($V_{xxx}$-1) as a bivalent group when locating inside thereof) may be identical to or different from each other, each independently selected from the group consisting of benzene ring (preferably in Formula ($V_{xxx}$-1) as 1,4-phenylene when locating inside thereof) and naphthalene ring (preferably in Formula ($V_{xxx}$-1) as 1,4- or 2,6-naphthylene when locating inside thereof), preferably benzene ring.

According to an embodiment of this invention, in Formula ($V_{xxx}$-1), two adjacent rings

may optionally with an additional S atom (not shown in the formula) and the N atom bridging these two rings (i.e. the N atom bonding to the group $R_d$) to form a phenothiazine ring, i.e.

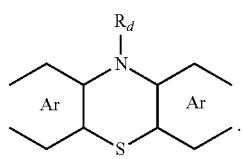

According to this embodiment of this invention, in Formula ($V_{xxx}$-1), when exist two or more rings

it is acceptable as long as at least two (adjacent) rings

to form the phenothiazine ring, it is not necessary for each of the rings

to form the phenothiazine ring with its adjacent ring

According to an embodiment of this invention, in Formula ($V_{xxx}$-1), two adjacent rings

may optionally with an additional group represented by $$-\overset{R''}{\underset{|}{C}H}-$$

(not shown in the formula) and the N atom bridging these two rings (i.e. the N atom bonding to the group $R_d$) to form a 9,10-dihydroacridine ring, i.e.

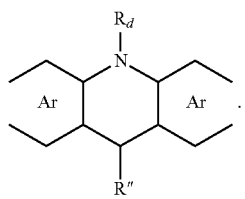

According to this invention, in the definition of the group

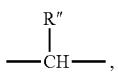

the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in the definition of the group

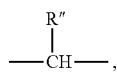

the group R" is selected from the group consisting of hydrogen and a $C_{1-10}$ linear or branched alkyl.

According to this embodiment of this invention, in Formula ($V_{xxx}$-1), when exist two or more rings

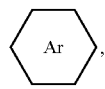

it is acceptable as long as at least two (adjacent) rings

form the 9,10-dihydroacridine ring, it is not necessary for each of the rings

to form the 9,10-dihydroacridine ring with its adjacent ring

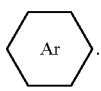

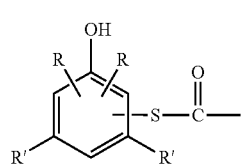

(V$_{xxx}$-2)

According to this invention, in Formula ($V_{xxx}$-2), when plural exist, the plural Rs may be identical to or different from each other, each independently selected from the group consisting of hydrogen, a $C_{1-300}$ linear or branched alkyl, a group represented by Formula (II) (especially a group represented by Formula (II$_{xxx}$)) and a group represented by Formula (III).

According to this invention, in Formula ($V_{xxx}$-2), two Rs and one group

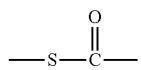

occupy the rest three positions on the benzene ring respectively.

According to an embodiment of this invention, in Formula ($V_{xxx}$-2), when plural exist, the plural Rs may be identical to or different from each other, each independently selected from the group consisting of hydrogen and a $C_{1-300}$ linear or branched alkyl.

According to this invention, in Formula ($V_{xxx}$-2), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula ($V_{xxx}$-2), there exist plural Rs, wherein one of the Rs is the polyolefin group, the rest one is selected from the group consisting of hydrogen or a $C_{1-20}$ linear or branched alkyl (preferably a $C_{1-10}$ linear or branched alkyl, more preferably a $C_{1-4}$ linear or branched alkyl).

According to an embodiment of this invention, in Formula ($V_{xxx}$-2), when the group R is the polyolefin group, the polyolefin group preferably locates at the position opposite to the phenol hydroxyl in Formula ($V_{xxx}$-2)

According to this invention, in Formula ($V_{xxx}$-2), when plural exist, the plural R's may be identical to or different from each other, each independently selected from the group consisting of hydrogen and a $C_{1-20}$ linear or branched alkyl.

According to an embodiment of this invention, in Formula ($V_{xxx}$-2), when plural exist, the plural R's may be identical to or different from each other, each independently selected from the group consisting of hydrogen and a $C_{1-4}$ linear or branched alkyl.

According to this invention, the hindered phenol compound, as aforesaid defined (for example, illustrated by Formula (I) or further by Formula (II-2) or further by Formula (V-2) etc.), necessarily comprises the structure

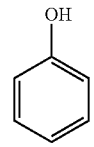

as the phenol unit. According to a preferred embodiment of this invention, the hindered phenol compound, throughout its molecular structure, comprises at most 5, at most 3, at most 2 or at most 1 of the phenol unit.

According to this invention, the hindered phenol compound, as aforesaid defined (for example, illustrated by Formula (II-1) or further by Formula (III), Formula (IV) or Formula (V-1) etc.), necessarily comprises the structure

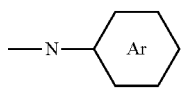

as the amine unit.

According to a preferred embodiment of this invention, the hindered phenol compound, throughout its molecular structure, comprises at most 15, at most 10, at most 8, at most 6, at most 4, at most 3 or at most 2 of the amine unit.

According to this invention, the hindered phenol compound, throughout its molecular structure, preferably at least one (preferably 2, 3 or 4 or more) group $R_d$ is hydrogen. Specifically, the hindered phenol compound preferably, throughout its molecular structure, comprise at least one selected from the group consisting of the following hydroamine unit (1), the following hydroamine unit (2) and the following hydroamine unit (3).

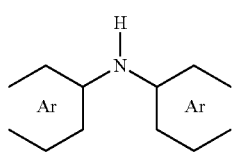

(1)

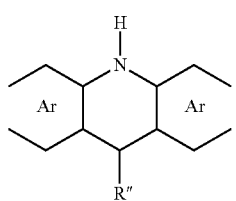

(2)

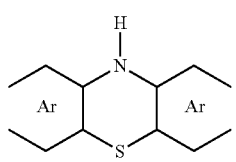

(3)

According to this invention, in these hydroamine units, as aforesaid, the group R" is selected from the group consisting of hydrogen, a $C_{1-20}$ hydrocarbyl (preferably a $C_{1-20}$ linear or branched alkyl) and a $C_{3-20}$ linear or branched hetero-alkyl, preferably selected from the group consisting of hydrogen, a $C_{1-10}$ linear or branched alkyl and a $C_{3-10}$ linear or branched hetero-alkyl, more preferably selected from the group consisting of hydrogen and a $C_{1-10}$ linear or branched alkyl, while the ring

is selected from the group consisting of benzene ring and naphthalene ring, preferably benzene ring.

According to a preferred embodiment of this invention, the hindered phenol compound, throughout its molecular structure, comprises at least one hydroamine unit (1).

Specifically, taking the hindered phenol compound

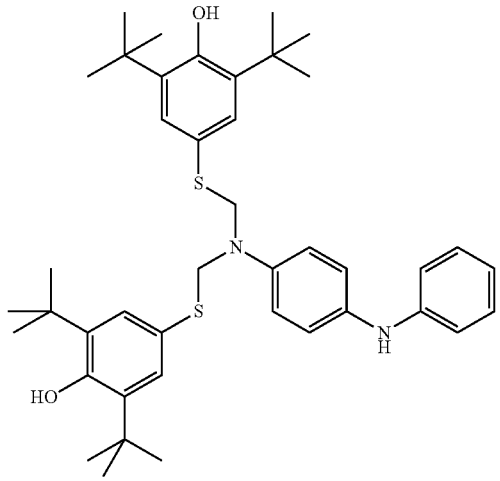 [SMILES: CC(C)(C)c1cc(SCN(CSc2cc(C(C)(C)C)c(O)c(C(C)(C)C)c2)c2ccc(Nc3ccccc3)cc2)cc(C(C)(C)C)c1O]

as an example, this compound, throughout its molecular structure, comprises 2 phenol units and 2 amine units, and at the same time, comprises one hydroamine unit (1). Or, taking the hindered phenol compound

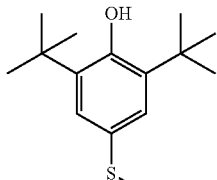

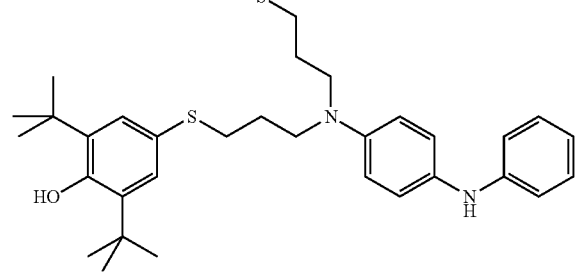

as an example, this compound, throughout its molecular structure, comprises 2 phenol units and 2 amine units, and at the same time, comprises one hydroamine unit (1). Or, taking the hindered phenol compound

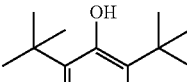

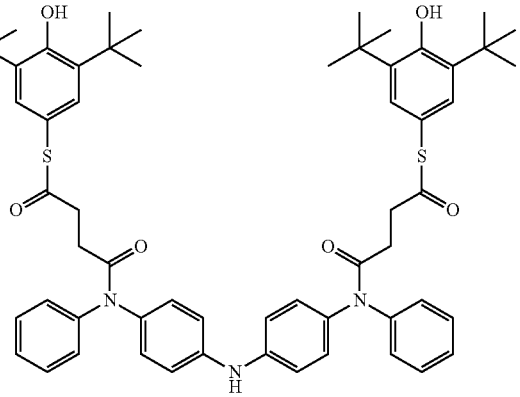

as an example, this compound, throughout its molecular structure, comprises 2 phenol units and 3 amine units, and at the same time, comprises one hydroamine unit (1).

According to this invention, as the hindered phenol compound, exemplified could be any of the following specific compounds or their mixture at any ratio therebetween, but this invention is not limited thereto.

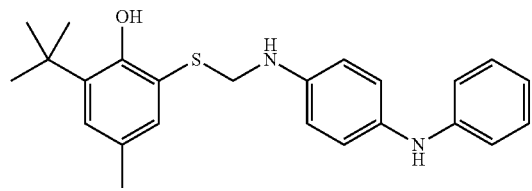
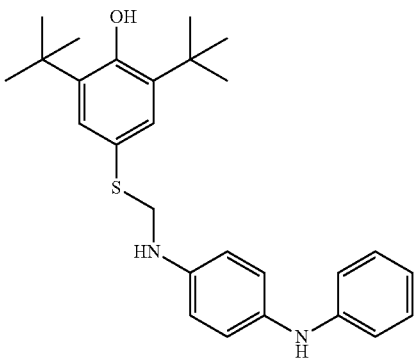
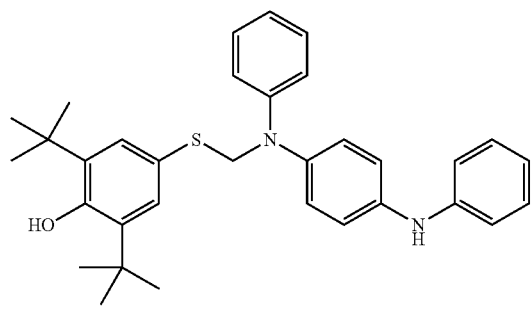
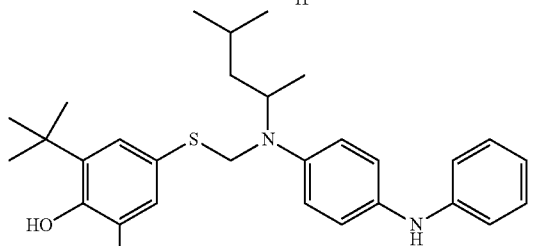
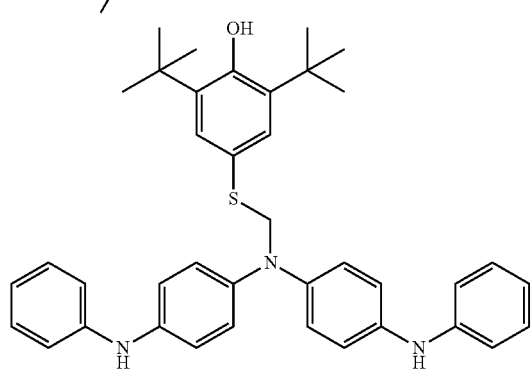
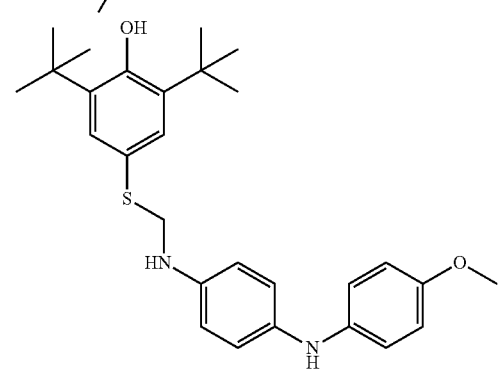
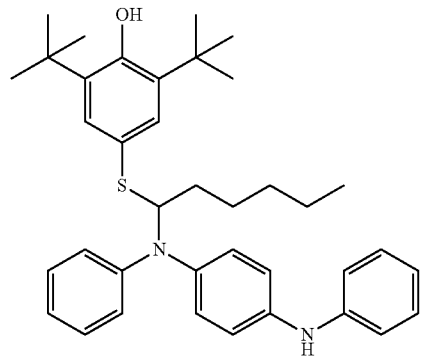
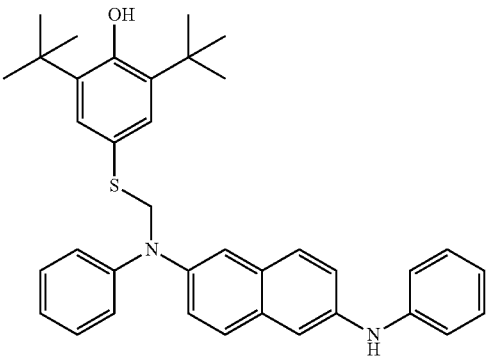
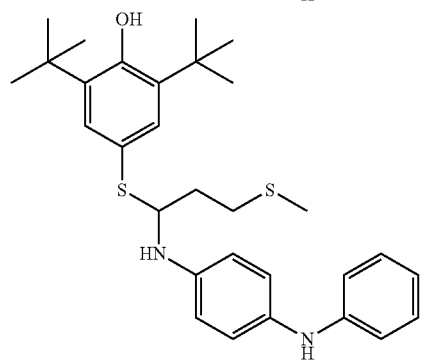
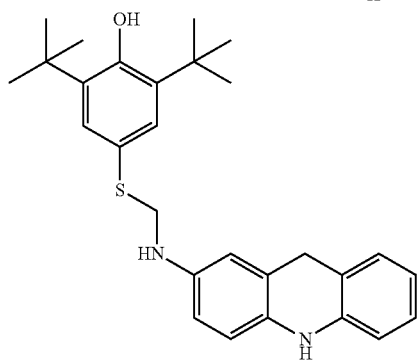

-continued
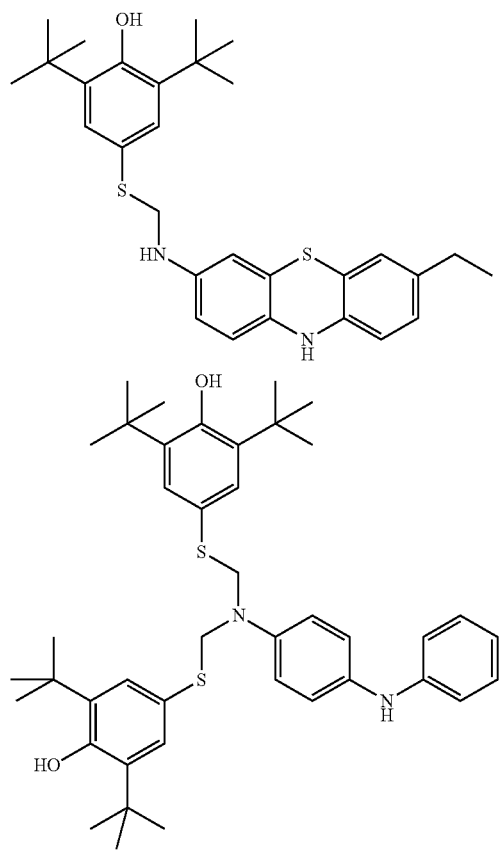
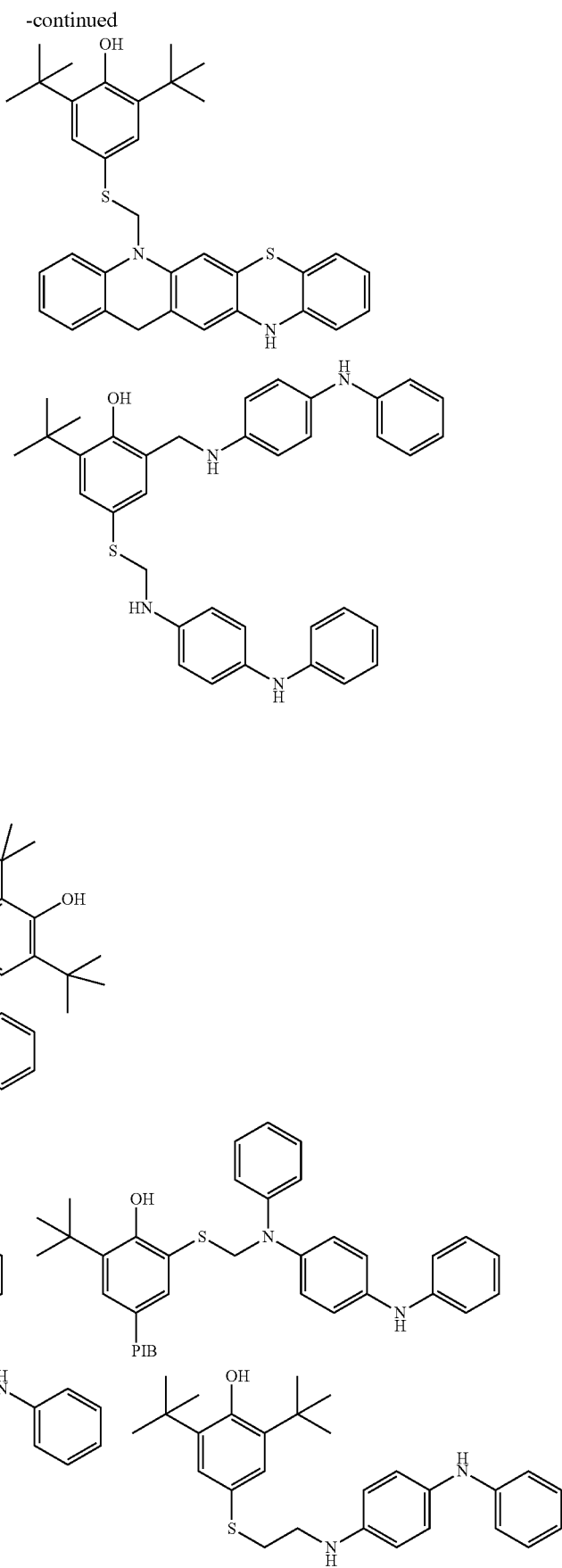

87
88
-continued
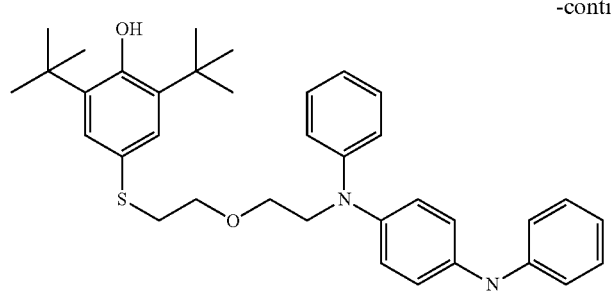
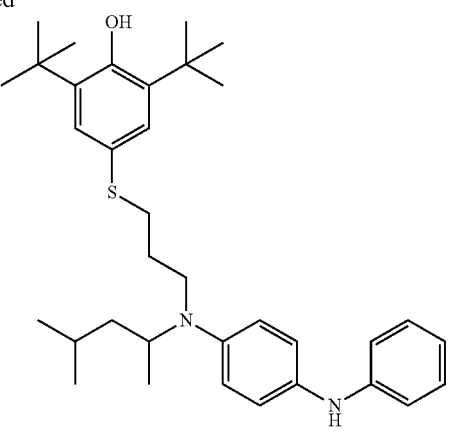
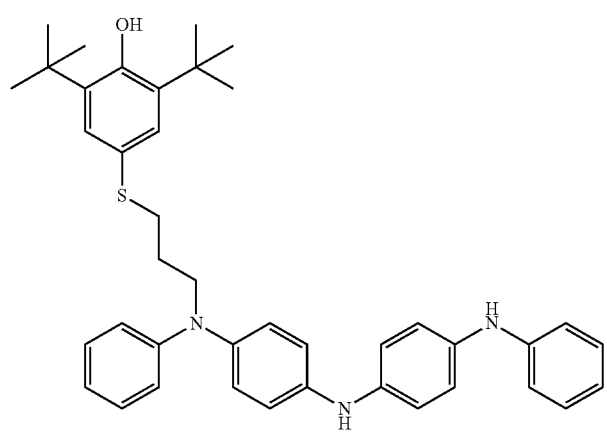
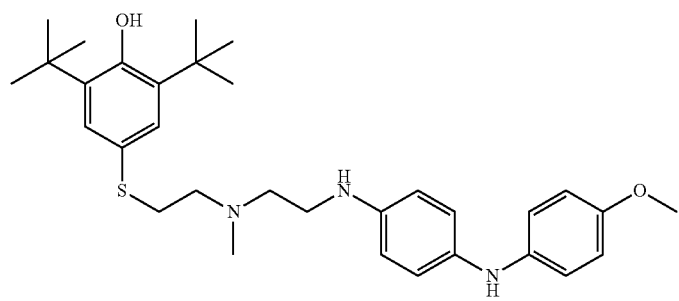
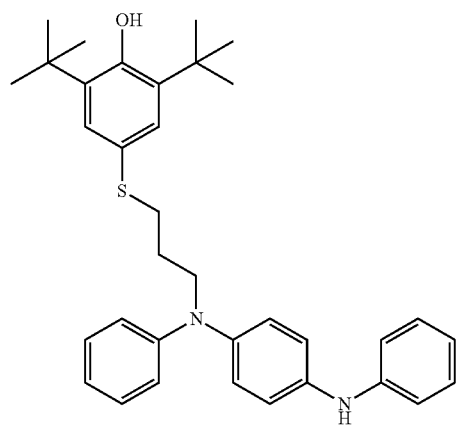
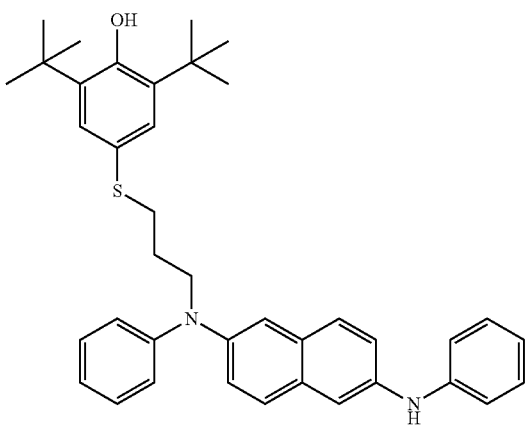

-continued
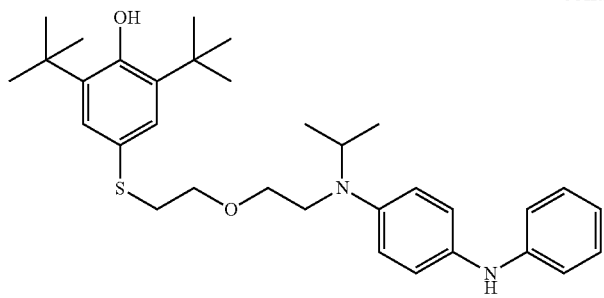
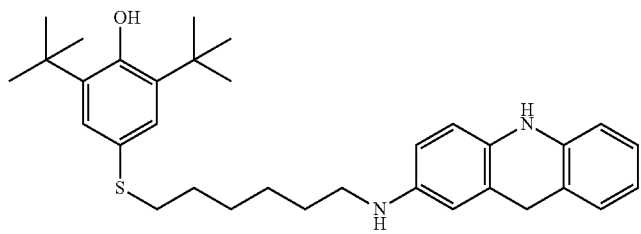
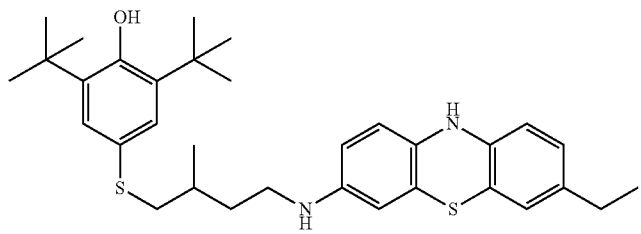
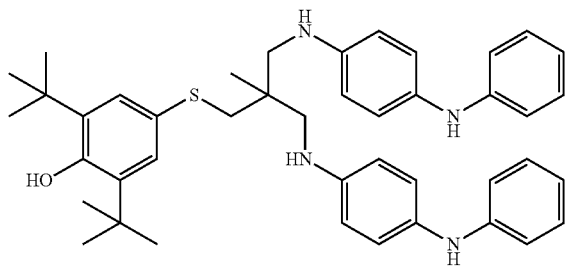
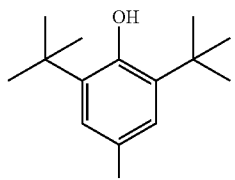
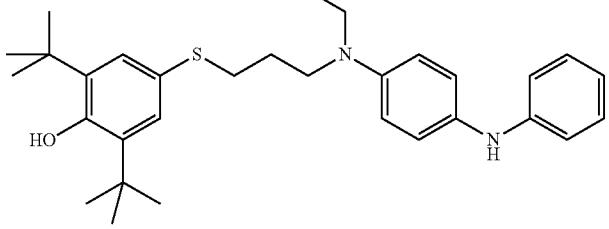
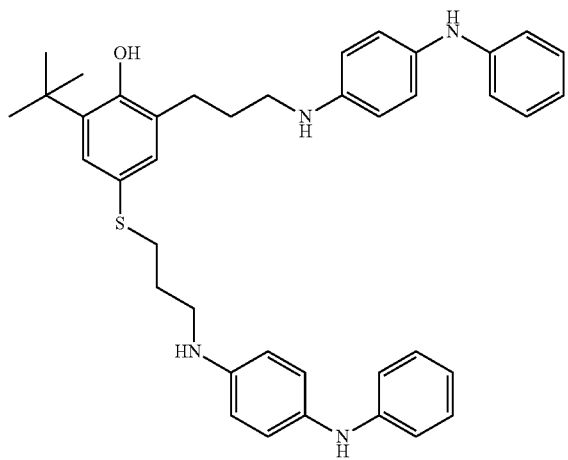

-continued
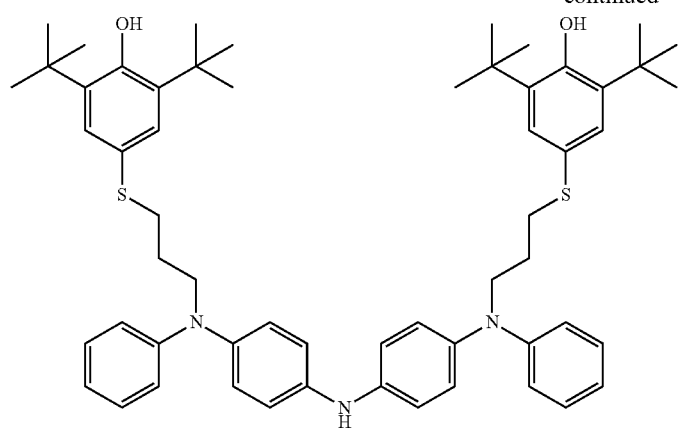
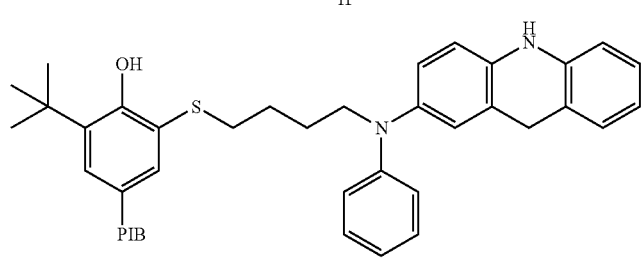
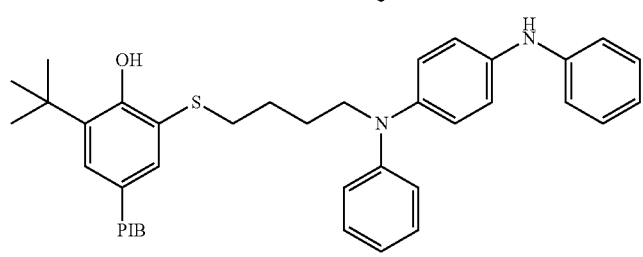
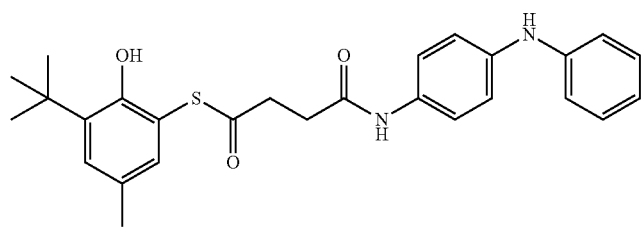
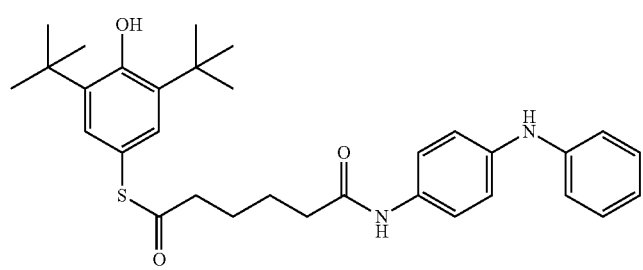
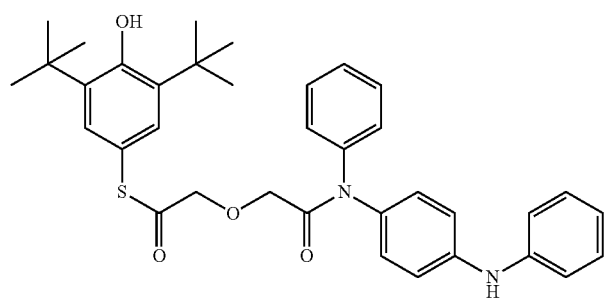

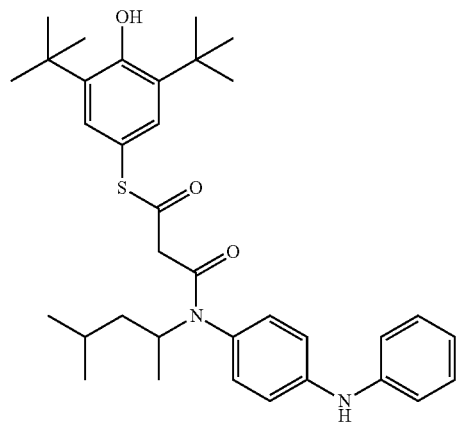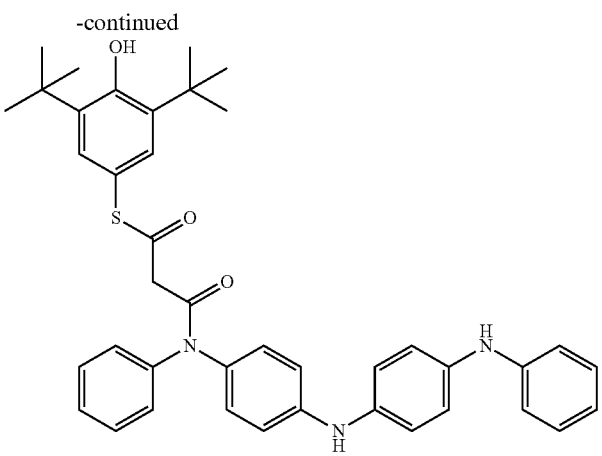
-continued
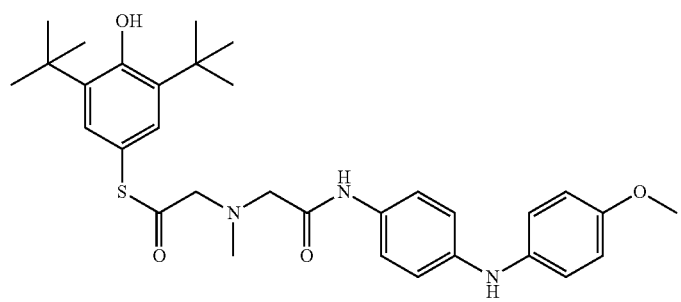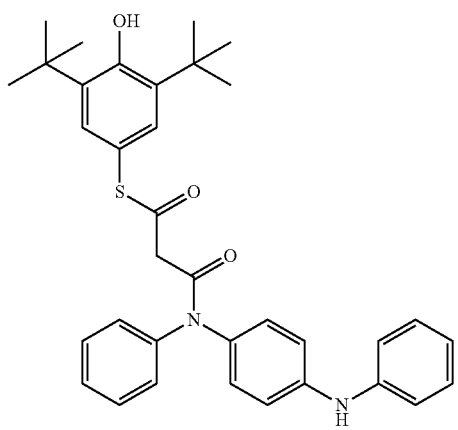
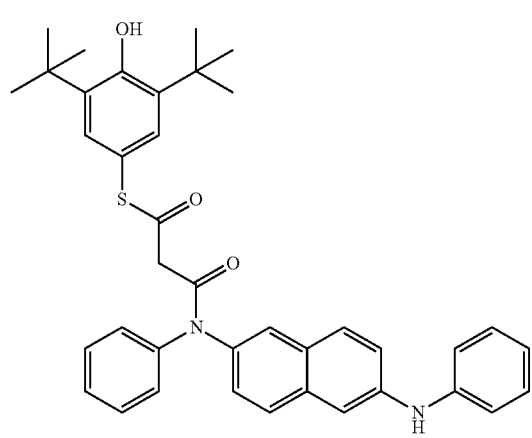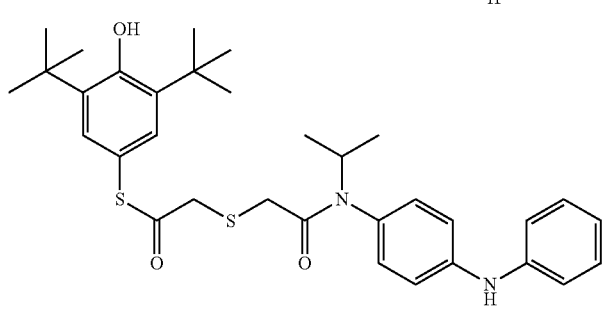
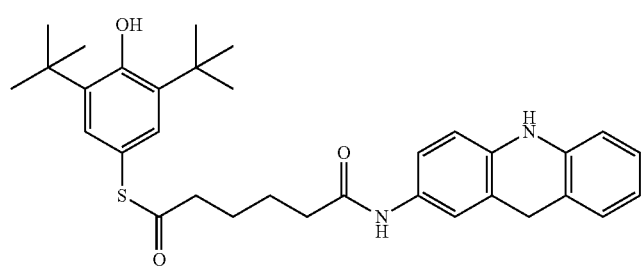

95
96
-continued
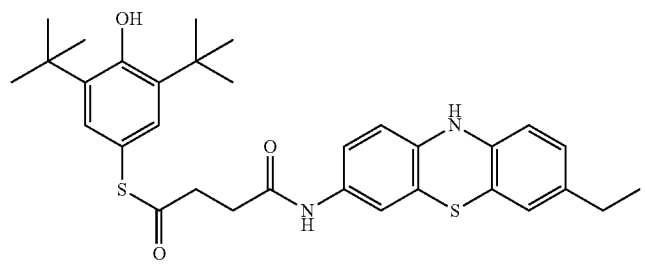
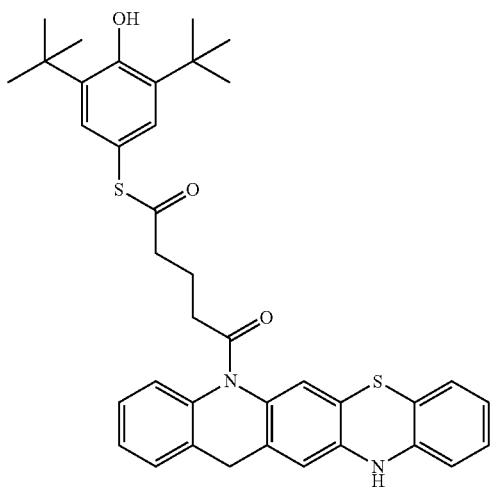
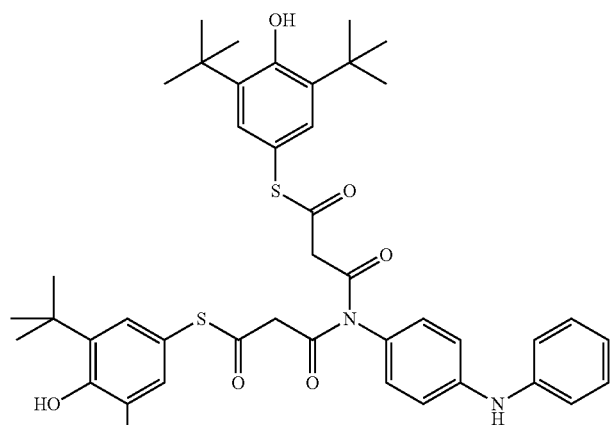
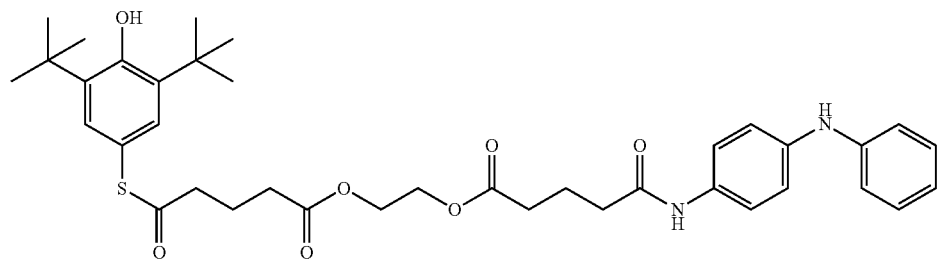
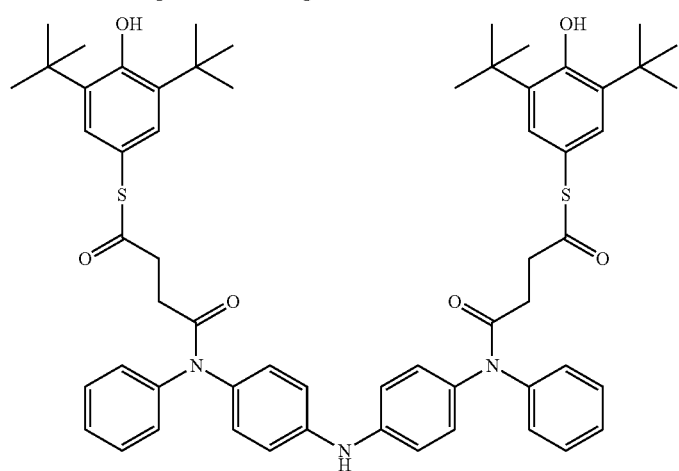

-continued
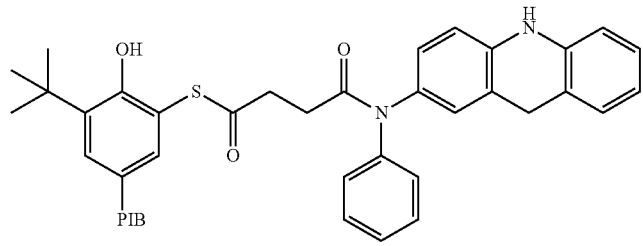
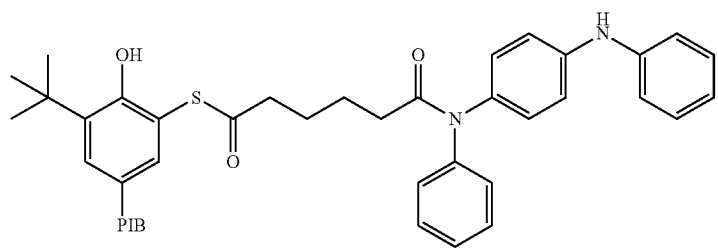
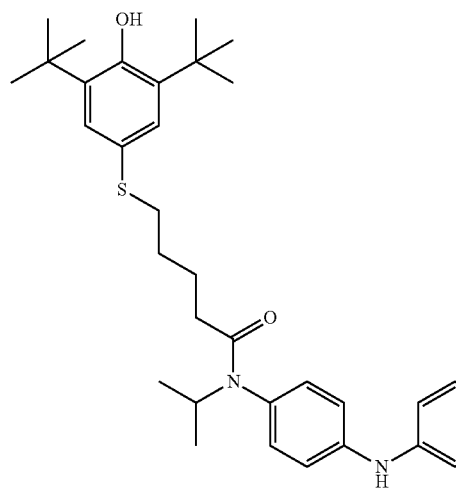
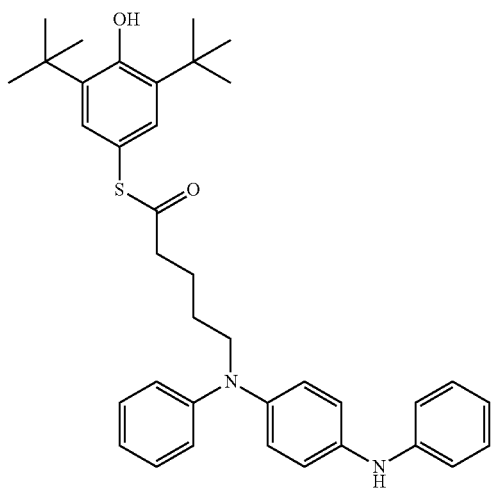
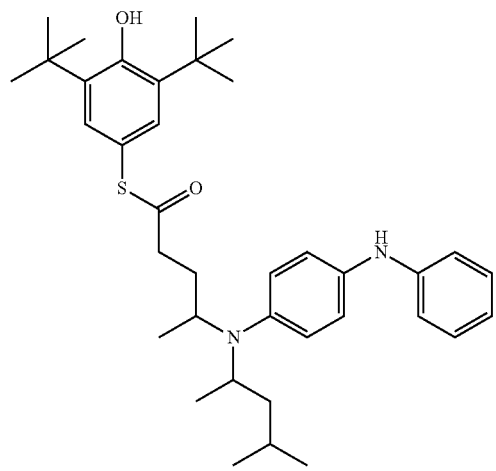
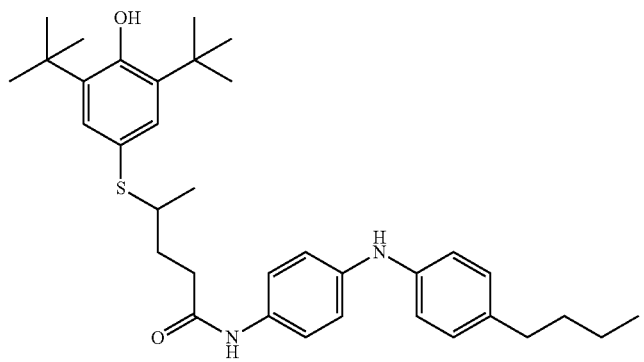

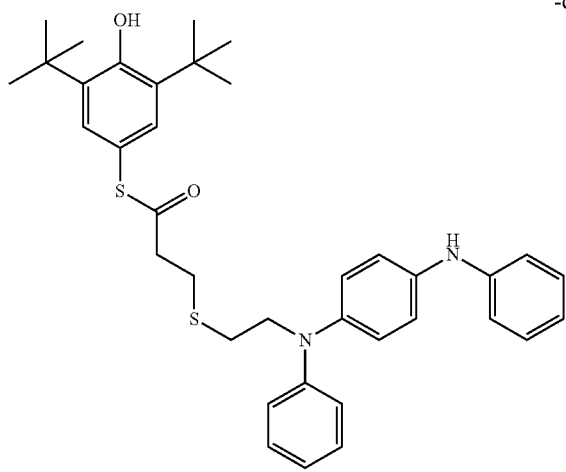

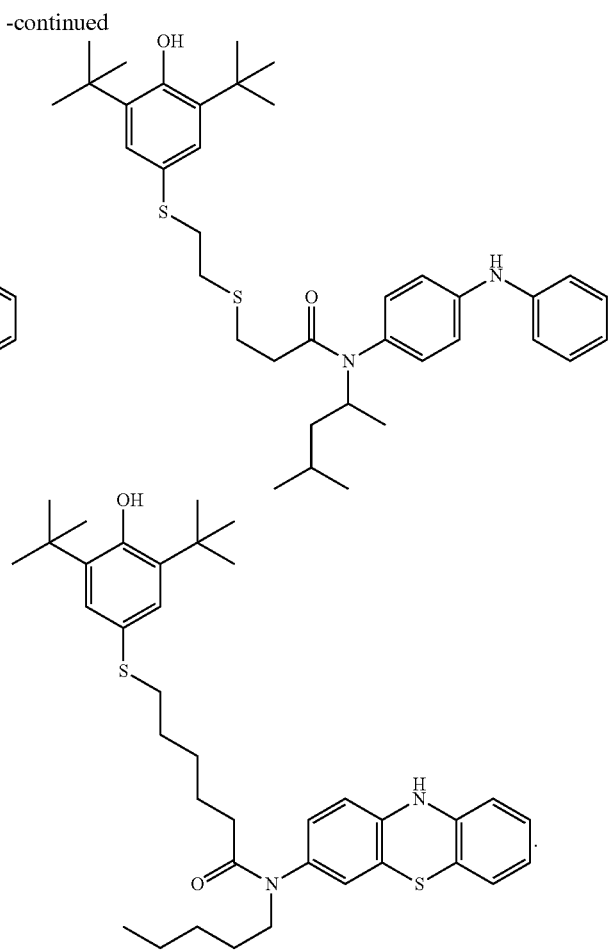

According to this invention, the aforesaid hindered phenol compound represented by Formula (I) could be present, produced or used as individual (pure) compounds, or as a mixture (at any ratio therebetween) thereof.

According to this invention, the hindered phenol compound represented by Formula (I) could be produced by the following process, but not limited thereto.

According to this invention, the process includes a first step of having a phenol compound represented by Formula (X) to react with an amine compound represented by Formula (Y) in the presence of at least one bridging compound selected from the group consisting of a compound represented by Formula (A) and formaldehyde, hereinafter referred to as bridging reaction.

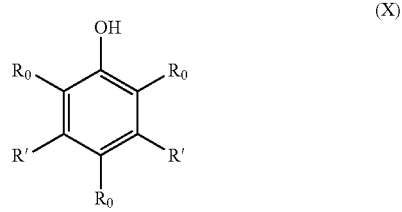

(X)

According to this invention, in Formula (X), when plural exist, the plural $R_0$s may be identical to or different from each other, each independently selected from the group consisting of hydrogen, —SH and a $C_{1-300}$ linear or branched alkyl, with the proviso that at least one $R_0$ is —SH.

According to this invention, in Formula (X), as the $C_{1-300}$ linear or branched alkyl, exemplified could be a $C_{1-20}$ linear or branched alkyl (preferably a $C_{1-10}$ linear or branched alkyl, more preferably a $C_{1-4}$ linear or branched alkyl) or a polyolefin group. As the polyolefin group, further exemplified could be a polyolefin group having a number-average molecular weight (Mn) of from 300 to 3000. Herein, the number-average molecular weight (Mn) of the polyolefin group is preferably in the range of from 500 to 2000, more preferably in the range of from 500 to 1500. According to this invention, the polyolefin group has a (substantially) saturated structure (in the form of a linear long-chain alkyl), however, depending on the nature of the starting polyolefin or the process for producing the starting polyolefin, there may exist some (only a small amount of) ethylenic double bond (for example, remained from or introduced during production of the polyolefin) along the molecular chain of the polyolefin group, which will not adversely interfere with the effects anticipated by this invention. For this reason, this invention does not intend to specify at what level this amount of ethylenic double bond could be, but rather, still identifies a polyolefin group of this kind as an "alkyl".

According to an embodiment of this invention, in Formula (X), there exist plural $R_0$s, wherein one of the $R_0$s is —SH, one of the other two $R_0$s is the polyolefin group, the rest one is hydrogen or a $C_{1-20}$ linear or branched alkyl (preferably a $C_{1-10}$ linear or branched alkyl).

According to an embodiment of this invention, in Formula (X), the group $R_0$ is the polyolefin group, and the polyolefin group preferably locates at the position opposite to the phenol hydroxyl in Formula (X).

According to this invention, in Formula (X), when plural exist, the plural R's may be identical to or different from each other, each independently selected from the group consisting of hydrogen and a $C_{1-20}$ linear or branched alkyl.

According to an embodiment of this invention, in Formula (X), when plural exist, the plural R's may be identical to or different from each other, each independently selected from the group consisting of hydrogen and a $C_{1-4}$ linear or branched alkyl.

According to this invention, the phenol compound represented by Formula (X) could be commercially available, or could be produced in line with any process known in this field, without any specific limitation thereto. Further, as the phenol compound represented by Formula (X), one kind or a mixture of two or more kinds at any ratio therebetween could be used According to this invention, as a process for producing the phenol compound represented by Formula (X), exemplified could be a process including a step of in the presence of an alkylation catalyst, reacting a phenol compound represented by Formula (X') with a polyolefin (having a number-average molecular weight (Mn) in the range of from 300 to 3000, preferably in the range of from 500 to 2000, more preferably in the range of from 500 to 1500), hereinafter referred to as alkylation reaction.

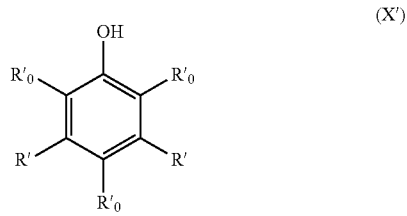

According to this invention, in Formula (X'), the group R' is as defined in Formula (X).

According to this invention, there are three $R'_0$s in Formula (X'), wherein one of the $R'_0$ is a group represented by —SH, another one of the $R'_0$ is H, the rest one $R'_0$ is hydrogen, —SH or a $C_{1-20}$ linear or branched alkyl (preferably a $C_{1-10}$ linear or branched alkyl).

According to an embodiment of this invention, in Formula (X'), at least one $R'_0$ is H, and the group $R'_0$ preferably locates at the position opposite to the group OH in Formula (X')

According to this invention, the polyolefin may be a polyolefin obtained by the homopolymerization of ethylene, propylene or a $C_4$-$C_{10}$ α-olefin or that obtained by the copolymerization between two or more of these olefins. As the $C_4$-$C_{10}$ α-olefin, exemplified could be n-butene, isobutene, n-pentene, n-hexene, n-octene and n-decene.

According to this invention, in the polyolefin, at least 20 wt % (preferably at least 50 wt %, more preferably at least 70 wt %) of the polymer chain have an ethylenic double bond at its terminal. The ethylenic double bond generally takes the form of (highly reactive) vinylidene or vinyl.

According to this invention, as the polyolefin, more preferably polybutene. Unless otherwise specified, the term "polybutene" herein includes any polymer obtained by the homopolymerization of 1-butene or isobutene, or that obtained by the copolymerization of two or more selected from the group consisting of 1-butene, 2-butene, and isobutene. The commercial available polymer of this kind may further contain some amount of other olefin units, which is acceptable to this invention.

According to this invention, as the polyolefin, more preferably polyisobutene (FIB), also referred to as highly reactive polyisobutene. In the polyisobutene of this kind, at least 20 wt % (preferably at least 50 wt %, more preferably at least 70 wt %) of the total terminal ethylenic double bond is provided by methyl vinylidene.

According to this invention, as the alkylation catalyst, exemplified could be a Lewis acid catalyst, for example, one or more selected from the group consisting of aluminum trichloride, boron trifluoride, tin tetrachloride, titanium tetrabromide, boron trifluoride.phenol, boron trifluoride.alcohol complex and boron trifluoride.ether complex, preferably boron trifluoride.diethyl ether complex and/or boron trifluoride.methanol complex. These alkylation catalysts are commercially available.

According to this invention, in the alkylation reaction, molar ratio between the polyolefin, the phenol compound represented by Formula (X') and the alkylation catalyst could be for example, 1:1-3:0.1-0.5, preferably 1:1.5-3:0.1-0.4, more preferably 1:1.5-3:0.2-0.4, but not limited thereto.

According to this invention, the duration of the alkylation reaction could be for example, 0.5 h-10 h, preferably 1 h-8 h, more preferably 3 h-5 h, but not limited thereto.

According to this invention, the reaction temperature of the alkylation reaction could be for example, 0 degrees Celsius to 200 degrees Celsius, preferably 10 degrees Celsius to 150 degrees Celsius, more preferably 20 degrees Celsius to 100 degrees Celsius, but not limited thereto.

According to this invention, the alkylation reaction could be carried out in the presence of a solvent. As the solvent, exemplified could be a $C_{6-10}$ alkane (for example, hexane, heptane, octane, nonane or decane), preferably hexane and heptane, more preferably hexane.

According to this invention, upon completion of the alkylation reaction, after removing the alkylation catalyst, unreacted reactants and any solvent by a conventional way from the resultant reaction mixture, a phenol compound represented by Formula (X) will be obtained.

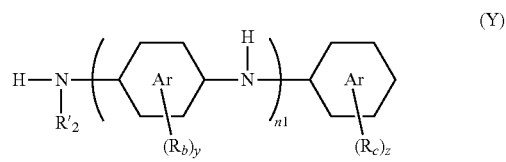

According to this invention, in Formula (Y), the group $R_2$ is selected from the group consisting of hydrogen, a $C_{1-20}$ linear or branched alkyl and a group represented by

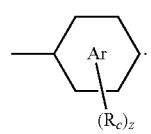

According to this invention, in Formula (Y), when plural exist, the plural $R_b$s may be identical to or different from each other, each independently selected from the group consisting of hydrogen and a $C_{1-20}$ linear or branched alkyl, preferably each independently selected from the group consisting of hydrogen and a $C_{1-10}$ linear or branched alkyl.

According to an embodiment of this invention, in Formula (Y), when plural exist, the plural $R_c$s may be identical to or different from each other, each independently selected from the group consisting of hydrogen and a $C_{1-6}$ linear or branched alkyl, preferably hydrogen.

According to this invention, in Formula (Y), when plural exist, the plural $R_c$s may be identical to or different from each other, each independently selected from the group consisting of hydrogen, a $C_{1-20}$ linear or branched alkyl and a $C_{1-20}$ linear or branched alkyloxy.

According to an embodiment of this invention, in Formula (Y), when plural exist, the plural $R_c$s may be identical to or different from each other, each independently selected from the group consisting of hydrogen, a $C_{1-10}$ linear or branched alkyl and a $C_{1-10}$ linear or branched alkyloxy.

According to an embodiment of this invention, in Formula (Y), preferably one of the $R_c$ locates at the position opposite to a N atom (i.e. the N atom bonding to the group $R_d$) on the ring

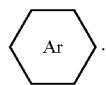

According to this invention, in Formula (Y), y is an integer in the range of from 0 to 3, preferably 0 or 1.

According to this invention, in Formula (Y), z is an integer in the range of from 0 to 3, preferably 0 or 1.

According to this invention, in Formula (Y), n1 is an integer in the range of from 1 to 8, preferably 1 or 2.

According to this invention, in Formula (Y), when plural exist, the plural rings

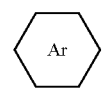

(in Formula (Y) as a bivalent group when locating inside thereof) may be identical to or different from each other, each independently selected from the group consisting of benzene ring (preferably in Formula (Y) as 1,4-phenylene when locating inside thereof) and naphthalene ring (preferably in Formula (Y) as 1,4- or 2,6-naphthylene when locating inside thereof), preferably benzene ring.

According to this invention, as the amine compound represented by Formula (Y), any commercial available one could be used, without any specific limitation thereto. Further, as the amine compound represented by Formula (Y), one kind or a mixture of two or more kinds at any ratio therebetween could be used.

According to an embodiment of this invention, a compound represented by Formula (A) is used as the bridging compound.

$$R_f \!-\!\!\!-\!\!\!\left(Fun\right)_{m1} \quad (A)$$

According to an embodiment of this invention, in Formula (A), when m1 is an integer in the range of from 2 to 5 (preferably 2), the plural Funs may be identical to or different from each other, each independently selected from the group consisting of a halogen atom, a carboxylic acid residue group, an anhydride residue group and an aldehyde residue group.

According to an embodiment of this invention, in Formula (A), when m1 is 1, the group Fun is an aldehyde residue group.

According to this invention, in Formula (A), the group $R_f$ is selected from the group consisting of an optionally substituted m1 valent $C_{1-20}$ hydrocarbyl (preferably a $C_{1-20}$ linear or branched alkyl) and an optionally substituted m1 valent $C_{3-20}$ linear or branched hetero-alkyl.

According to this invention, in Formula (A), in the definition of the group $R_f$, by optionally substituted, it refers to optionally substituted by one or more (for example, from 1 to 5, from 1 to 4, from 1 to 3, from 1 to 2, or 1) substituent selected from the group consisting of oxo

(i.e. $\overset{O}{\|}$), a $C_{1-20}$ hydrocarbyl and a $C_{3-20}$ linear or branched hetero-alkyl. As the substituent, preferably oxo, a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula (A), in the definition of the group $R_f$, when oxo exists as the substituent, it is preferred that at least one oxo exists on the carbon atom directly bonding to the group Fun, or, in the definition of the group $R_f$, at least one or m1 carbon atom(s) directly bonding to the group Fun has oxo as the substituent, whereby making the carbon atom present in the form of carbonyl

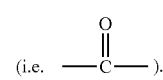

(i.e. $-\overset{O}{\underset{\|}{C}}-$).

For example, assuming that $R_f$ is $-CH_2-CH_2-CH_2-$ (m1=2), both groups Fun are Cl, when one oxo exists as the substituent, the compound represented by Formula (A) could be

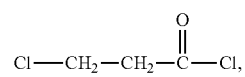

$Cl-CH_2-CH_2-\overset{O}{\underset{\|}{C}}-Cl,$ when two oxo exist as the substituent, the compound represented by Formula (A) could be

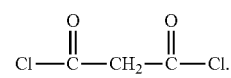

$Cl-\overset{O}{\underset{\|}{C}}-CH_2-\overset{O}{\underset{\|}{C}}-Cl.$

In the context of this specification, by "carboxylic acid residue group" it refers to a group (i.e. —OH) obtained by removing one carbonyl (i.e. 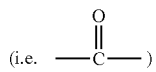)

from carboxyl (i.e. —COOH), with the proviso that it is necessary for the carbon atom directly bonding to the group to take the form of carbonyl (i.e. 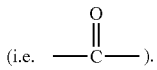).

Specifically, assuming that $R_f$ is —$CH_2$—$CH_2$—$CH_2$— (m1=2), one Fun is Cl, one Fun is a carboxylic acid residue group, the compound represented by Formula (A) could be

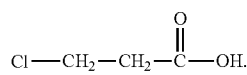

In the context of this specification, by "aldehyde residue group" it refers to a group (i.e. —H) obtained by removing one carbonyl (i.e. 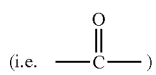)

from formyl (i.e. 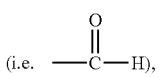), with the proviso that it is necessary for the carbon atom directly bonding to the group to take the form of carbonyl (i.e. 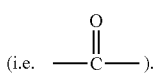).

Specifically, assuming that $R_f$ is —$CH_2$—$CH_2$—$CH_2$— (m1=2), one Fun is Cl, one Fun is an aldehyde residue group, the compound represented by Formula (A) could be

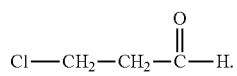

In the context of this specification, by "anhydride residue group" it refers to a group (i.e. —O—) obtained by removing two carbonyls (i.e. 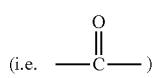)

from anhydride (i.e. 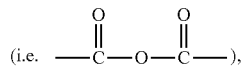), with the proviso that it is necessary for the two carbon atoms directly bonding to the group to take the form of carbonyl (i.e. 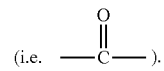).

Herein, the two carbon atoms could originate from one single compound, or from different compounds. Specifically, assuming that $R_f$ is —$CH_2$—$CH_2$—$CH_2$— (m1=2), one Fun is Cl, one Fun is an anhydride residue group, the compound represented by Formula (A) could be

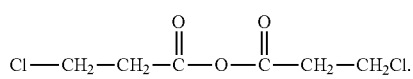

According to an embodiment of this invention, formaldehyde is used as the bridging compound. As the formaldehyde, for example, an aqueous solution thereof could be used, or in the form of paraformaldehyde or polyformaldehyde, without any specific limitation thereto.

According to this invention, as the bridging compound, any commercial available one could be used, without any specific limitation thereto. Further, as the bridging compound, one kind or a mixture of two or more kinds at any ratio therebetween could be used.

According to an embodiment of this invention, the bridging compound is selected from the group consisting of an aldehyde compound represented by Formula ($A_Y$), a polyhalo-compound represented by Formula ($A_{YY}$) and a polybasic carboxylic acid represented by Formula ($A_{YYY}$) or derivatives thereof (selected from the group consisting of an anhydride of the polybasic carboxylic acid and an acyl halide of the polybasic carboxylic acid). As the bridging compound, any commercial available one could be used, without any specific limitation thereto. Further, as the bridging compound, one kind or a mixture of two or more kinds at any ratio therebetween could be used.

($A_Y$)

According to this invention, in Formula ($A_Y$), the group $R_Y$ is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in Formula ($A_Y$), the group $R_Y$ is selected from the group consisting of hydrogen, a $C_{1-10}$ linear or branched alkyl and a $C_{3-10}$ linear or branched hetero-alkyl.

According to a preferred embodiment of this invention, in Formula ($A_Y$), the group $R_Y$ is selected from the group consisting of hydrogen and a $C_{1-10}$ linear or branched alkyl.

According to this invention, as the aldehyde compound represented by Formula ($A_Y$), exemplified could be a $C_{1-6}$ aliphatic aldehyde and benzaldehyde.

According to an embodiment of this invention, as the $C_{1-6}$ aliphatic aldehyde, exemplified could be a $C_{1-6}$ linear or branched saturated aliphatic aldehyde, specifically, acetaldehyde or formaldehyde, more preferably formaldehyde. As the formaldehyde, for example, an aqueous solution thereof could be used, or in the form of paraformaldehyde or polyformaldehyde, without any specific limitation thereto.

According to this invention, as the aldehyde compound represented by Formula ($A_Y$), one kind or a mixture of two or more kinds at any ratio therebetween could be used.

($A_{YY}$)

According to this invention, in Formula ($A_{YY}$), the group $R_{halo}$ is selected from the group consisting of an optionally substituted $m_{YY}$ valent $C_{2-20}$ linear or branched alkyl and an optionally substituted $m_{YY}$ valent $C_{3-20}$ linear or branched hetero-alkyl, preferably selected from the group consisting of an optionally substituted $m_{YY}$ valent $C_{2-10}$ linear or branched alkyl and an optionally substituted $m_{YY}$ valent $C_{3-10}$ linear or branched hetero-alkyl, more preferably selected from the group consisting of an optionally substituted $m_{YY}$ valent $C_{2-6}$ linear or branched alkyl and an optionally substituted $m_{YY}$ valent $C_{3-6}$ linear or branched hetero-alkyl, more preferably selected from the group consisting of an optionally substituted $m_{YY}$ valent $C_{2-6}$ linear or branched alkyl.

According to this invention, in Formula ($A_{YY}$), in the definition of the group $R_{halo}$, by optionally substituted, it refers to optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($A_{YY}$), the group Halo is halo, including fluoro, chloro, bromo and iodo, preferably chloro.

According to this invention, in Formula ($A_{YY}$), $m_{YY}$ is an integer in the range of from 2 to 5, preferably 2.

According to this invention, as the polyhalo-compound represented by Formula ($A_{YY}$), one kind or a mixture of two or more kinds at any ratio therebetween could be used.

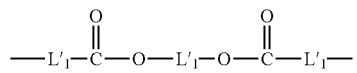
($A_{YYY}$)

According to this invention, in Formula ($A_{YYY}$), $m_{YYY}$ is an integer in the range of from 2 to 5, preferably 2.

According to this invention, in Formula ($A_{YYY}$), the group $R_L$ is selected from the group consisting of an optionally substituted $m_{YYY}$ valent $C_2$ to $C20$-$m_{YYY}$ linear or branched alkyl, an optionally substituted $m_{YYY}$ valent $C_3$ to $C20$-$m_{YYY}$ linear or branched hetero-alkyl and a group represented by

(hereinafter referred to as Formula ($A_{YYY}$-A)), preferably selected from the group consisting of an optionally substituted $m_{YYY}$ valent $C_2$ to $C20$-$m_{YYY}$ linear or branched alkyl and a group represented by Formula ($A_{YYY}$-A), more preferably selected from the group consisting of an optionally substituted $m_{YYY}$ valent $C_2$ to $C20$-$m_{YYY}$ linear or branched alkyl.

According to this invention, in Formula ($A_{YYY}$), in the definition of the group $R_L$, as the optionally substituted $m_{YYY}$ valent $C_2$ to $C20$-$m_{YYY}$ linear or branched alkyl, preferably an optionally substituted $m_{YYY}$ valent $C_2$ to $C10$-$m_{YYY}$ linear or branched alkyl, more preferably an optionally substituted $m_{YYY}$ valent $C_{2-6}$ linear or branched alkyl.

According to this invention, in Formula ($A_{YYY}$), in the definition of the group $R_L$, as the optionally substituted $m_{YYY}$ valent $C_3$ to $C20$-$m_{YYY}$ linear or branched hetero-alkyl, preferably an optionally substituted $m_{YYY}$ valent $C_3$ to $C10$-$m_{YYY}$ linear or branched hetero-alkyl, more preferably an optionally substituted $m_{YYY}$ valent $C_{3-6}$ linear or branched hetero-alkyl.

According to this invention, in Formula ($A_{YYY}$), in the definition of the group $R_L$, by "optionally substituted", it refers to optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, in Formula ($A_{YYY}$), in the group represented by Formula ($A_{YYY}$-A), the plural $L'_1$s may be identical to or different from each other, each independently selected from the group consisting of a $C_{1-10}$ linear or branched alkyl and a $C_{3-10}$ linear or branched hetero-alkyl, preferably each independently selected from the group consisting of a $C_{1-6}$ linear or branched alkyl.

According to this invention, in Formula ($A_{YYY}$), as for the group represented by Formula ($A_{YYY}$-A), the requirement (1) is that: the plural $L'_1$s each independently represents a 2 valent to $m_{YYY}$ valent group, so as to make the group represented by Formula ($A_{YYY}$-A) to present as $m_{YYY}$ valent, as a whole. In this context, in the group represented by Formula ($A_{YYY}$-A), the valency between different $L'_1$ may vary and may be different from each other. In view of this, in the group represented by Formula ($A_{YYY}$-A), the group $L'_1$ is not specified for its valency. In fact, the valency of each $L'_1$ could be determined by the requirement (1). Specifically, assuming that each $L'_1$ is ethyl (with no valency specified), $m_{YYY}$ is 3, then, the group represented by Formula ($A_{YYY}$-A) could be any one of the followings.

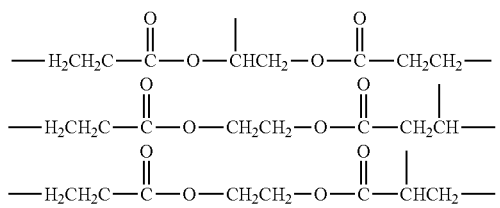

According to this invention, in Formula ($A_{YYY}$), in the group represented by Formula ($A_{YYY}$-A), the requirement (2) is that: the total atom number of all groups $L'_1$ (not figuring in any atom of the substituent that may exist on the group $L'_1$ as specified hereafter) is not more than 14, so as to make the group represented by Formula ($A_{YYY}$-A) to have a total atom number (not figuring in any atom of the substituent that may exist on the group $L'_1$ as specified hereafter) of no more than 18.

According to this invention, in Formula ($A_{YYY}$), in the group represented by Formula ($A_{YYY}$-A), after the aforesaid two requirements are met, the plural $L'_1$ may be each independently further optionally substituted by one or more (for example, from 1 to 4, from 1 to 3, from 1 to 2, or 1) substituent selected from the group consisting of a $C_{1-20}$ hydrocarbyl and a $C_{3-20}$ linear or branched hetero-alkyl. As the substituent, preferably a $C_{1-20}$ linear or branched alkyl, a $C_{6-20}$ aryl or a combination group thereof. As the $C_{1-20}$ linear or branched alkyl, preferably a $C_{1-10}$ linear or branched alkyl, more preferably a $C_{1-6}$ linear or branched alkyl, for example, methyl or ethyl.

According to this invention, as the derivative of the polybasic carboxylic acid represented by Formula ($A_{YYY}$), exemplified could be an anhydride or acyl halide of the polybasic carboxylic acid. As the acyl halide, exemplified could be acyl fluorides, acyl chlorides and acyl bromides, preferably acyl chlorides.

According to this invention, as the polybasic carboxylic acid represented by Formula ($A_{YYY}$) or derivatives thereof, one kind or a mixture of two or more kinds at any ratio therebetween could be used. Further, as the polybasic carboxylic acid represented by Formula ($A_{YYY}$) or derivatives thereof, any commercial available one could be used, without any specific limitation thereto.

According to this invention, in the process for producing the hindered phenol compound, in the first step, molar ratio of the phenol compound represented by Formula (X) to the amine compound represented by Formula (Y) is generally 1:0.1-10, preferably 1:0.5-5.0, more preferably 1:0.8-2.0.

According to this invention, in the process for producing the hindered phenol compound, in the first step, as a whole, molar ratio of the phenol compound represented by Formula (X) to the bridging compound is generally 1:0.1-10, preferably 1:0.2-5.0, more preferably 1:0.3-3.0.

According to this invention, there is no specific limitation as to how to conduct the bridging reaction in the first step, as long as the reaction between the phenol compound represented by Formula (X), the amine compound represented by Formula (Y) and the bridging compound will occur. To simplify description, in this specification, the aldehyde compound represented by Formula ($A_Y$) (First embodiment), the polyhalo-compound represented by Formula ($A_{YY}$) (Second embodiment) and the polybasic carboxylic acid represented by Formula ($A_{YYY}$) or derivatives thereof (Third embodiment) are exemplified as the bridging compound, to illustrate how to conduct the bridging reaction, however, this invention is not limited thereto. It is easy for a person skilled in the art to learn how to conduct the bridging reaction when using other compounds represented by Formula (A) as the bridging compound if enlightened by the various reaction procedures illustrated in the following embodiments, for example, by combining the reaction procedures specified in the following embodiments or the reaction steps involved therein in a suitable order.

First Embodiment

According to the first embodiment, to conduct the first step, a phenol compound represented by Formula (X) reacts with an amine compound represented by Formula (Y) in the presence of an aldehyde compound represented by Formula ($A_Y$) (hereinafter referred to as bridging reaction).

According to this invention, in the process for producing the hindered phenol compound, in the first step, molar ratio of the phenol compound represented by Formula (X) to the aldehyde compound represented by Formula ($A_Y$) is generally 1:0.1-10, preferably 1:0.5-5.0, more preferably 1:0.8-2.0.

According to this invention, in the process for producing the hindered phenol compound, the first step could be conducted in the presence of a solvent. As the solvent, exemplified could be a $C_{2-10}$ aliphatic nitrile (for example, acetonitrile, etc.), a $C_{6-20}$ aromatic hydrocarbon (for example, benzene, toluene, xylene and cumene), a $C_{6-10}$ alkane (for example, n-hexane, cyclohexane and petroleum ether), a $C_{1-6}$ aliphatic alcohol (for example, methanol, ethanol, n-propanol, isopropanol, n-butanol and ethylene glycol), a $C_{2-20}$ halogenated hydrocarbon (for example, dichloromethane, carbon tetrachloride, chlorobenzene and 1,2-dichlorobenzene), a $C_{3-10}$ ketone (for example, acetone, butanone and methyl isobutyl ketone) or a $C_{3-10}$ amide (for example, dimethylfomamide, dimethylacetamide and N-methyl pyrrolidone), etc. As the solvent, one kind or a mixture of two or more kinds at any ratio therebetween could be used.

According to this invention, in the process for producing the hindered phenol compound, in the first step, a catalyst could be used, if needed. As the catalyst, exemplified could be an inorganic acid catalyst and an organic acid catalyst. As the inorganic acid catalyst, exemplified could be hydrochloric acid, sulphuric acid and phosphoric acid, etc. As the organic acid catalyst, exemplified could be methyl sulfonic acid, ethyl sulfonic acid, aminosulfonic acid and p-toluene sulfonic acid, etc.

As the amount of the catalyst to be used, any amount that conventionally used is acceptable, without any specific limitation thereto.

According to this invention, in the process for producing the hindered phenol compound, there is no specific limitation as to the reaction duration of the first step, but generally in the range of 0.1 h-24 h, preferably 0.2 h-12 h, more preferably 0.5 h-6 h.

According to this invention, in the process for producing the hindered phenol compound, there is no specific limitation as to the reaction temperature of the first step, but generally in the range of 0 degrees Celsius to 250 degrees Celsius, preferably 20 degrees Celsius to 180 degrees Celsius, more preferably 60 degrees Celsius to 120 degrees Celsius.

According to this invention, in the process for producing the hindered phenol compound, upon completion of the first step, by a separation method commonly known (for example, by evaporation, etc.), any volatile like solvent that may exist is removed from the reaction mixture obtained from the first step (hereinafter referred to as reaction mixture of the first step), then the resultant of the first step can be obtained.

Second Embodiment

According to the Second embodiment, to conduct the first step, a phenol compound represented by Formula (X) reacts with an amine compound represented by Formula (Y) in the presence of the polyhalo-compound represented by Formula ($A_{YY}$) (hereinafter referred to as bridging reaction).

According to this invention, in the process for producing the hindered phenol compound, in the first step, molar ratio of the phenol compound represented by Formula (X) to the polyhalo-compound represented by Formula ($A_{YY}$) is generally 1:0.1-10, preferably 1:0.2-5.0, more preferably 1:0.3-3.0.

According to this invention, in the process for producing the hindered phenol compound, the first step could be conducted in the presence of a solvent. As the solvent, exemplified could be a $C_{2-10}$ aliphatic nitrile (for example, acetonitrile, etc.), a $C_{6-20}$ aromatic hydrocarbon (for example, benzene, toluene, xylene and cumene), a $C_{6-10}$ alkane (for example, n-hexane, cyclohexane and petroleum ether), a $C_{1-6}$ aliphatic alcohol (for example, methanol, ethanol, n-propanol, isopropanol, n-butanol and ethylene glycol), a $C_{2-20}$ halogenated hydrocarbon (for example, dichloromethane, carbon tetrachloride, chlorobenzene and 1,2-dichlorobenzene), a $C_{3-10}$ ketone (for example, acetone, butanone and methyl isobutyl ketone) or a $C_{3-10}$ amide (for example, dimethylfomamide, dimethylacetamide and N-methyl pyrrolidone), etc. As the solvent, preferably a $C_{6-20}$ aromatic hydrocarbon (for example, benzene, toluene, xylene and cumene), a $C_{3-10}$ ketone (for example, acetone, butanone and methyl isobutyl ketone) or a $C_{3-10}$ amide (for example, dimethylfomamide, dimethylacetamide and N-methyl pyrrolidone), etc. As the solvent, one kind or a mixture of two or more kinds at any ratio therebetween could be used.

According to this invention, in the process for producing the hindered phenol compound, in the first step, a catalyst could be used, if needed. As the catalyst, exemplified could be an alkaline catalyst. As the alkaline catalyst, exemplified could be a hydroxide of alkali metal, for example, NaOH and KOH, etc., or an alkali metal salt of weak acid, for example, sodium acetate, potassium acetate, sodium carbonate, potassium carbonate, sodium hydrogen carbonate and potassium hydrogen carbonate, etc. As the catalyst, one kind or a mixture of two or more kinds at any ratio therebetween could be used. As the amount of the catalyst to be used, any amount that conventionally used is acceptable, without any specific limitation thereto.

According to this invention, in the process for producing the hindered phenol compound, there is no specific limitation as to the reaction duration of the first step, but generally in the range of 0.1 h-48 h, preferably 0.2-12 h, more preferably 0.5-6 h.

According to this invention, in the process for producing the hindered phenol compound, there is no specific limitation as to the reaction temperature of the first step, but generally in the range of 0-200 degrees Celsius, preferably 20-180 degrees Celsius, more preferably 60-120 degrees Celsius.

According to this invention, in the process for producing the hindered phenol compound, upon completion of the first step, by a separation method commonly known (for example, by evaporation, etc.), any volatile like solvent that may exist is removed from the reaction mixture obtained from the first step (hereinafter referred to as reaction mixture of the first step), then the resultant of the first step can be obtained.

Third Embodiment

According to the Third embodiment, to conduct the first step, a phenol compound represented by Formula (X) reacts with an amine compound represented by Formula (Y) in the presence of a polybasic carboxylic acid represented by Formula ($A_{YYY}$) or derivatives thereof (hereinafter referred to as bridging reaction).

According to this invention, in the process for producing the hindered phenol compound, in the first step, molar ratio of the phenol compound represented by Formula (X) to the polybasic carboxylic acid represented by Formula ($A_{YYY}$) or derivatives thereof is generally 1:0.1-10, preferably 1:0.2-5.0, more preferably 1:0.3-3.0.

According to this invention, in the process for producing the hindered phenol compound, the first step could be conducted in the presence of a solvent. As the solvent, exemplified could be a $C_{2-10}$ aliphatic nitrile (for example, acetonitrile, etc.) and a $C_{6-20}$ aromatic hydrocarbon (for example, benzene, toluene, xylene and cumene), etc. As the solvent, one kind or a mixture of two or more kinds at any ratio therebetween could be used.

According to this invention, in the process for producing the hindered phenol compound, in the first step, a catalyst could be used, if needed. Specifically, for a polybasic carboxylic acid represented by Formula ($A_{YYY}$), as the catalyst, exemplified could be an alkaline catalyst. As the alkaline catalyst, exemplified could be a hydroxide of alkali metal, for example, NaOH and KOH, etc., or an alkali metal salt of weak acid, for example, sodium acetate, potassium acetate, sodium carbonate, potassium carbonate, sodium hydrogen carbonate and potassium hydrogen carbonate, etc. As the catalyst, one kind or a mixture of two or more kinds at any ratio therebetween could be used. As the amount of the catalyst to be used, any amount that conventionally used is acceptable, without any specific limitation thereto. Further, for an anhydride of the polybasic carboxylic acid represented by Formula ($A_{YYY}$), as the catalyst, exemplified could be a transition metal salt, further exemplified could be cobalt dichloride and ruthenium trichloride, etc. As the catalyst, one kind or a mixture of two or more kinds at any ratio therebetween could be used. As the amount of the catalyst to be used, any amount that conventionally used is acceptable, without any specific limitation thereto.

According to this invention, in the process for producing the hindered phenol compound, there is no specific limitation as to the reaction duration of the first step, but generally in the range of 0.2 h-12 h, preferably 0.2-12 h, more preferably 0.5-6 h.

According to this invention, in the process for producing the hindered phenol compound, there is no specific limitation as to the reaction temperature of the first step, but generally in the range of 0-200 degrees Celsius, preferably 10-150 degrees Celsius, more preferably 20-120 degrees Celsius.

According to this invention, in the process for producing the hindered phenol compound, upon completion of the first step, by a separation method commonly known (for example, by evaporation, etc.), any volatile like solvent that may exist is removed from the reaction mixture obtained from the first step (hereinafter referred to as reaction mixture of the first step), then the resultant of the first step can be obtained.

According to an embodiment of this invention, the process for producing the hindered phenol compound optionally further includes an additional step of having the resultant of the first step to react with a sulfuring agent (to form a phenothiazine ring) (hereinafter referred to as additional step A).

According to an embodiment of this invention, the process for producing the hindered phenol compound optionally further includes an additional step of having the resultant of the first step to react with an aldehyde compound represented by Formula (Z) (to form a 9,10-dihydroacridine ring) (hereinafter referred to as additional step B).

(Z)

According to this invention, in Formula (Z), the group R" is selected from the group consisting of hydrogen, a $C_{1-20}$ hydrocarbyl (preferably a $C_{1-20}$ linear or branched alkyl) and a $C_{3-20}$ linear or branched hetero-alkyl.

According to an embodiment of this invention, in Formula (Z), the group R" is selected from the group consisting of hydrogen, a $C_{1-10}$ linear or branched alkyl and a $C_{3-10}$ linear or branched hetero-alkyl.

According to a preferred embodiment of this invention, in Formula (Z), the group R" is selected from the group consisting of hydrogen and a $C_{1-10}$ linear or branched alkyl.

According to this invention, as the aldehyde compound represented by Formula (Z), exemplified could be a $C_{1-6}$ aliphatic aldehyde and benzaldehyde.

According to an embodiment of this invention, as the $C_{1-6}$ aliphatic aldehyde, exemplified could be a $C_{1-6}$ linear or branched saturated aliphatic aldehyde, specifically, acetaldehyde or formaldehyde, more preferably formaldehyde. As the formaldehyde, for example, an aqueous solution thereof could be used, or in the form of paraformaldehyde or polyformaldehyde, without any specific limitation thereto.

According to this invention, in the process for producing the hindered phenol compound, it is acceptable to conduct only the additional step A, or to conduct only the additional step B, or to conduct both the additional step A and the additional step B. In case that both the additional step A and the additional step B are conducted, there is no specific limitation as to the sequence or order in which the additional step A and the additional step B are conducted. It is acceptable to firstly conduct the additional step A, and after completion of the additional step A, to conduct the additional step B, or to firstly conduct the additional step B, and after completion of the additional step B, to conduct the additional step A. Further, there may be, or may not be, a product (i.e. the resultant obtained from the preceding additional step) isolation operation between two additional steps, without any specific limitation thereto.

According to an embodiment of this invention, in the process for producing the hindered phenol compound, the additional step A could be conducted after completion of the first step. When the additional step A is conducted after completion of the first step, it is acceptable for the resultant of the first step to have been isolated out of the reaction mixture of the first step as herein described, or without any isolation, to be directly used to conduct the additional step A in the form of the reaction mixture of the first step. And/or, the additional step A could be conducted after completion of the additional step B. When the additional step A is conducted after completion of the additional step B, it is acceptable for the resultant of the additional step B to have been isolated out of the reaction mixture of the additional step B as herein described, or without any isolation, to be directly used to conduct the additional step A in the form of the reaction mixture of the additional step B.

According to an embodiment of this invention, in the process for producing the hindered phenol compound, in the additional step A, as the sulfuring agent, exemplified could be sulfur and sulfur dichloride, etc., preferably sulfur. As the sulfur, exemplified could be powdered sulfur or sublimed sulfur.

According to this invention, in the process for producing the hindered phenol compound, in the additional step A, molar ratio of the amine compound represented by Formula (Y) to the sulfuring agent is generally 1:1-10, preferably 1:1.2-6.0, more preferably 1:1.5-3.0.

According to this invention, in the process for producing the hindered phenol compound, the additional step A could be conducted in the presence of a solvent. As the solvent, exemplified could be a $C_{2-10}$ aliphatic nitrile (for example, acetonitrile, etc.), a $C_{6-20}$ aromatic hydrocarbon (for example, benzene, toluene, xylene and cumene), a $C_{6-10}$ alkane (for example, n- hexane, cyclohexane and petroleum ether), a $C_{1-6}$ aliphatic alcohol (for example, methanol, ethanol, n-propanol, isopropanol, n-butanol and ethylene glycol), a $C_{2-20}$ halogenated hydrocarbon (for example, dichloromethane, carbon tetrachloride, chlorobenzene and 1,2-dichlorobenzene), a $C_{3-10}$ ketone (for example, acetone, butanone and methyl isobutyl ketone) or a $C_{3-10}$ amide (for example, dimethylfomamide, dimethylacetamide and N-methyl pyrrolidone), etc. As the solvent, one kind or a mixture of two or more kinds at any ratio therebetween could be used.

According to this invention, in the process for producing the hindered phenol compound, the additional step A may be conducted in the presence of a catalyst. As the catalyst, exemplified could be a catalyst commonly known for this purpose, specifically, iodine. As the amount of the catalyst to be used, any amount that conventionally used is acceptable, without any specific limitation thereto.

According to this invention, in the process for producing the hindered phenol compound, there is no specific limitation as to the reaction duration of the additional step A, but generally in the range of 0.1 h-24 h, preferably 0.2 h-12 h, more preferably 0.5 h-4 h.

According to this invention, in the process for producing the hindered phenol compound, there is no specific limitation as to the reaction temperature of the additional step A, but generally in the range of 60 degrees Celsius to 300 degrees Celsius, preferably 120 degrees Celsius to 240 degrees Celsius, more preferably 150 degrees Celsius to 200 degrees Celsius.

According to this invention, in the process for producing the hindered phenol compound, upon completion of the additional step A, by a separation method commonly known (for example, by evaporation, etc.), any volatile like solvent that may exist is removed from the reaction mixture obtained from the additional step A, so as to obtain a resultant of the additional step A, or alternatively, without any separation, this reaction mixture is directly used as the resultant of the additional step A to conduct the subsequent reaction step (for example, the additional step B).

According to an embodiment of this invention, in the process for producing the hindered phenol compound, the additional step B could be conducted after completion of the first step. When the additional step B is conducted after completion of the first step, it is acceptable for the resultant of the first step to have been isolated out of the reaction mixture of the first step as herein described, or without any isolation, to be directly used to conduct the additional step B in the form of the reaction mixture of the first step. And/or, the additional step B could be conducted after completion of the additional step A. When the additional step B is conducted after completion of the additional step A, it is acceptable for the resultant of the additional step A to have been isolated out of the reaction mixture of the additional step A as herein described, or without any isolation, to be directly used to conduct the additional step B in the form of the reaction mixture of the additional step A.

According to this invention, in the process for producing the hindered phenol compound, in the additional step B, molar ratio of the amine compound represented by Formula (Y) to the aldehyde compound represented by Formula (Z) is generally 1:0.1-10, preferably 1:0.5-5.0, more preferably 1:0.8-2.0.

According to this invention, in the process for producing the hindered phenol compound, the additional step B could be conducted in the presence of a solvent. As the solvent, exemplified could be a $C_{2-10}$ aliphatic nitrile (for example, acetonitrile, etc.), a $C_{6-20}$ aromatic hydrocarbon (for example, benzene, toluene, xylene and cumene), a $C_{6-10}$ alkane (for example, n- hexane, cyclohexane and petroleum ether), a $C_{1-6}$ aliphatic alcohol (for example, methanol, ethanol, n-propanol, isopropanol, n-butanol and ethylene glycol), a $C_{2-20}$ halogenated hydrocarbon (for example, dichloromethane, carbon tetrachloride, chlorobenzene and 1,2-dichlorobenzene), a $C_{3-10}$ ketone (for example, acetone, butanone and methyl isobutyl ketone) or a $C_{3-10}$ amide (for example, dimethylfomamide, dimethylacetamide and N-methyl pyrrolidone), etc. As the solvent, one kind or a mixture of two or more kinds at any ratio therebetween could be used.

According to this invention, in the process for producing the hindered phenol compound, in the additional step B, a catalyst could be used, if needed. As the catalyst, exemplified could be an inorganic acid catalyst and an organic acid catalyst. As the inorganic acid catalyst, exemplified could be a hydrochloric acid, sulphuric acid and phosphoric acid, etc. As the organic acid catalyst, exemplified could be a methyl sulfonic acid, ethyl sulfonic acid, aminosulfonic acid and p-toluene sulfonic acid, etc. As the amount of the catalyst to be used, any amount that conventionally used is acceptable, without any specific limitation thereto.

According to this invention, in the process for producing the hindered phenol compound, at the beginning of or during the additional step B, if needed, it is acceptable to further add an amine compound represented by Formula (Y), whereby forming both the 9,10-dihydroacridine ring and the group represented by Formula (III) in a single step.

Herein, molar ratio of the amine compound represented by Formula (Y) to the aldehyde compound represented by Formula (Z) is generally 1:0.1-10, preferably 1:0.5-5.0, more preferably 1:0.8-2.0.

According to this invention, in the process for producing the hindered phenol compound, there is no specific limitation as to the reaction duration of the additional step B, but generally in the range of 0.1 h-24 h, preferably 0.2 h-12 h, more preferably 0.5 h-6 h.

According to this invention, in the process for producing the hindered phenol compound, there is no specific limitation as to the reaction temperature of the additional step B, but generally in the range of 0 degrees Celsius to 250 degrees Celsius, preferably 20 degrees Celsius to 180 degrees Celsius, more preferably 60 degrees Celsius to 120 degrees Celsius.

According to this invention, in the process for producing the hindered phenol compound, after completion of the additional step B, by a separation method commonly known (for example, by evaporation, etc.), any volatile like solvent that may exist is removed from the reaction mixture obtained from the additional step B, so as to obtain a resultant of the additional step B, or alternatively, without any separation, this reaction mixture is directly used as the resultant of the additional step B to conduct the subsequent reaction step (for example, the additional step A).

According to this invention, obviously, each of the aforesaid reactions or steps (including the first step, the additional step A and the additional step B) is generally conducted under the protection of an inert gas atmosphere. As the inert gas, exemplified could be $N_2$ gas and Ar gas, etc., without any specific limitation thereto.

According to this invention, in the process for producing the hindered phenol compound, the resultant of the first step, the resultant of the additional step A or the resultant of the additional step B, could be isolated into individual hindered phenol compound(s) (for example, one single hindered phenol compound represented by Formula (I)), or could be produced as a mixture of two or more hindered phenol compounds. All these resultants are covered by this invention and identified as being effective and desirable in this invention. In view of this, in the context of this specification, these resultants are all accepted or referred to as the hindered phenol compound of this invention without any discrimination therebetween. In this context, according to this invention, it is not absolutely necessary to further purify these resultants, or to further isolate one or more specific hindered phenol compound(s) from these resultants. Of course, this purification or isolation may be preferred in some cases by this invention, however, is not absolutely necessary to this invention. Nevertheless, as the purification or isolation method, exemplified could be column chromatography or preparative chromatography, etc.

According to an embodiment of this invention, further related to is a hindered phenol compound produced in line with the aforesaid process.

According to this invention, the hindered phenol compound exhibits excellent performance in oxidation resistance at elevated temperatures, and therefore is especially suitable to be used as an antioxidant, especially in a lubricant oil composition for which improved oxidation stability (at elevated temperatures) is anticipated. In view of this, according to an embodiment of this invention, related to is a lubricant oil composition, which comprises a lubricant base oil and any aforesaid hindered phenol compound (or their mixture at any ratio therebetween) of this invention as an antioxidant.

According to this invention, any lubricant base oil commonly used in this field could be used. As the lubricant base oil, exemplified could be one or more selected from mineral base oils, animal oils, vegetable oils, synthetic base oils and etc. As the mineral base oil, exemplified could be one having a viscosity index of above 80, or one having a saturated hydrocarbon content of above 90 wt % and a sulfur content of less than 0.03 wt %. As the synthetic base oil, exemplified could be one or more selected from polyolefins, synthetic esters, silicone oils and polyethers, etc. As the lubricant base oil, one kind or a mixture of two or more kinds at any ratio therebetween could be used.

According to an embodiment of this invention, in the lubricant oil composition, the antioxidant represents 0.001-30 wt %, preferably 0.1-10 wt %, of the total weight of the lubricant oil composition.

According to this invention, the lubricant oil composition optionally further comprises other lubricant oil additive selected from the group consisting of metal cleansing agents, ashless dispersants, antifriction agents, anti-scuff agents, extreme pressure agents, viscosity index modifiers, metal corrosion inhibitors, antirust additives, pour-point depressants and anti-foaming agents. As the other lubricant oil additive, one kind or a mixture of two or more kinds at any ratio therebetween, at an amount commonly used in this field, could be used, without any specific limitation thereto.

According to this invention, the aforesaid hindered phenol compound (or their mixture at any ratio therebetween) and the lubricant base oil (and other lubricant oil additive, if any) are mixed together till homogenous (under heat if needed) at a predetermined ratio or respective amount, so as to produce the lubricant oil composition.

In a preferred aspect of this invention, the lubricant oil composition comprises the hindered phenol compound of this invention as an antioxidant, and therefore exhibits excellent performance in oxidation resistance at elevated temperatures, and at the same time, in at least one performance selected from anticorrosion, cleansing (deposite formation inhibition), inhibiting increase in viscosity and inhibiting increase in acid value. These performances can not be found at the same time with a prior art antioxidant. Further, the hindered phenol compound according to this invention, contains no phosphorus and metals, generates little ash when burning, leading to less particulate emission of engines (which is greatly responsible for smog), and is thus identified as an environment friendly antioxidant.

EXAMPLE

The present invention is further illustrated by using the following examples, but not limiting to same.

Performances mentioned in Examples and Comparative Examples are determined as follows.

(1) Oxidation Resistance at Elevated Temperatures

The lubricant oil composition produced in Example or Comparative Example was taken as the test sample, evaluated for its oxidation resistance by Pressured differential Scanning Calorimetry (PDSC), with a PDSC temperature of 210 degrees Celsius, a pressure of 0.5 MPa and an oxygen flow rate of 100 mL/min, expressed as oxidative induction period (unit: min).

(2) Deposite Formation Inhibition

The lubricant oil composition produced in Example or Comparative Example was taken as the test sample to conduct the engine crankcase coking simulation test, which simulates depositing on the piston. During this test, 300 ml of the test sample was added to a coke-forming plate simulator, heated up to 150 degrees Celsius, continuously splashed onto an aluminium plate having a temperature of 310 degrees Celsius. After 6 hours, coke deposited on the aluminium plate was weighted, expressed as the deposit amount (unit: mg). The more the deposit amount is, the worse the piston cleansing performance of the test sample exhibits.

(3) Anticorrosion

The lubricant oil composition produced in Example or Comparative Example was taken as the test sample to conduct the ball rust test (BRT). Throughout the bench scale test lasting for 18 hours, a metal ball protected by the test sample was made to continuously contact an acid liquid and air, with an acid liquid injection speed of 0.19 ml/h, an air flow rate of 40 ml/min and an oil temperature of 48 degrees Celsius. Upon completion of the test, the spherical reflection intensity of the metal ball was determined to obtain a gray value, which was used to evaluate the corrosion degree. The greater the gray value is, the more serious the corrosion degree is. The acid liquid was an acetic acid/HBr/hydrochloric acid/deionized water solution.

(4) Inhibiting Increase in Viscosity

The lubricant oil composition produced in Example or Comparative Example was taken as the test sample to conduct the IIIE simulation experiment (VIT) at a temperature of 180 degrees Celsius, with a duration of 72 h and an oxygen flow rate of 5 L/h, expressed as the increase (by %) in viscosity of the test sample after and before the experiment.

(5) Inhibiting Increase in Acid Value

The lubricant oil composition produced in Example or Comparative Example was taken as the test sample to conduct the IIIE simulation experiment (VIT) at a temperature of 180 degrees Celsius, with a duration of 72 h and an oxygen flow rate of 5 L/h, expressed as the increase (by $mgKOH \cdot g^{-1}$) in acid value of the test sample after and before the experiment.

Example I-1

To a 500 ml four-necked flask equipped with a stirrer, a thermometer, a condensing tube and a dropping funnel, there were added 58.79 g (0.323 mol) 2-tert-butyl-6-mercapto-phenol, 6.88 g (0.048 mol) boron trifluoride.diethyl ether (as the alkylation catalyst), 100 ml n-hexane (as the solvent) and 161.61 g (0.162 mol) polyisobutene (Mn=1000, from Jilin Chemical Group Fine Chemicals Co., Ltd.), reacted at 80 degrees Celsius for 2 h. Upon completion of the reaction, the reaction mixture was washed once with a 5 wt % KOH aqueous solution, and then washed with hot water till neutral to remove any catalyst, and then vacuum distillated to remove any solvent and unreacted phenols, to obtain a polyisobutenyl thiophenol, having a hydroxyl value of 53.49 mgKOH/g. The hydroxyl value was determined by referring to the acetic anhydride method in GB/T7383-2007.

The reaction procedure can be illustrated as follows.

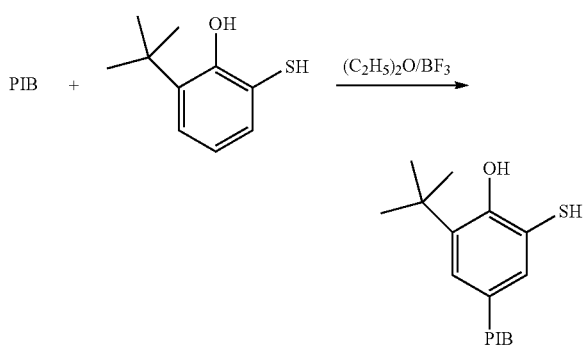

On the $^1$H-NMR spectra of the produced polyisobutenyl thiophenol, the peak at the chemical shift of 1.40 was identified as the characteristic peak of the hydrogen of the tert-butyl on the benzene ring; the single peak at the chemical shift of 3.58 was identified as the characteristic peak of the hydrogen of the mercapto on the benzene ring; the single peak at the chemical shift of 4.84 was identified as the characteristic peak of the hydrogen of the hydroxyl on the benzene ring; the single peak at the chemical shift of 7.12 and that at 7.20 were respectively identified as the characteristic peak of the two hydrogens on the benzene ring. If the integral of the hydrogen of the hydroxyl on the benzene ring is defined as 1, the value of the integral ratio between the hydrogen on the benzene ring, the hydrogen of the mercapto and the hydrogen of the hydroxyl were calculated as 0.95: 0.97:1.05:0.94, approximating to the theoretical value of 1:1:1:1:1. As can be seen from this NMR spectra analysis, the polyisobutenyl thiophenol was obtained as anticipated.

Example I-2

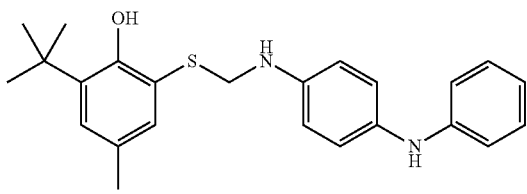 [SMILES: Cc1cc(SCNc2ccc(Nc3ccccc3)cc2)c(O)c(C(C)(C)C)c1]

Under the protective atmosphere of nitrogen gas, to a 250 ml four-necked flask equipped with a stirrer, a thermometer, a condensing tube and a dropping funnel, there were added 30.58 g (156 mmol) 2-mercapto-4-methyl-6-methyl phenol, 9.29 g (112 mmol) formaldehyde, 32.38 g (176 mmol) N-phenyl p-phenylene diamine and 100 mL toluene, rapidly stirred, reacted at 100 degrees Celsius for 2 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ1.40 (9H), 2.37 (3H), 4.02 (1H), 4.83 (2H), 6.95-7.00 (12H), 7.26 (2H), 7.55 (1H);
$^{13}$C NMR (75 MHz, CDCl$_3$): δ21.2, 30.1, 34.1, 49.9, 114.3, 118.9, 119.4, 121.8, 122.2, 125.8, 126.5, 129.5, 131.8, 132.3, 133.5, 143.3, 150.8;
C$_{24}$H$_{28}$N$_2$OS (calculated): C, 73.43; H, 7.19; N, 7.14; O, 4.08; S, 8.17. (measured): C, 73.31; H, 7.23; N, 7.21; O, 3.99; S, 8.28.

Example I-3

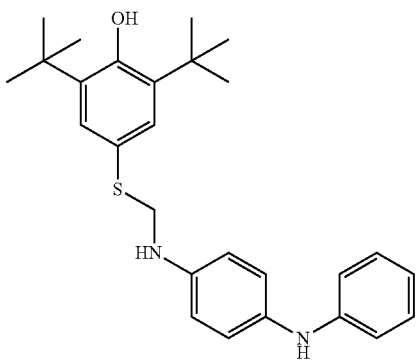 [SMILES: CC(C)(C)c1cc(SCNc2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 31.65 g (133 mmol) 2,6-di-tert-butyl-4-mercaptophenol, 1.86 g (62 mmol) formaldehyde, 28.15 g (153 mmol) N-phenyl p-phenylene diamine, 0.75 g (7.5 mmol) hydrochloric acid and 150 mL isopropanol, rapidly stirred, reacted at 25 degrees Celsius for 24 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ1.36-1.54 (18H), 3.75 (1H), 4.80 (2H), 5.32 (1H), 6.80 (2H), 6.97 (5H), 7.17 (2H), 7.26 (2H), 7.55 (1H);
$^{13}$C NMR (75 MHz, CDCl$_3$): δ29.6, 34.6, 51.2, 119.4, 121.8, 126.5, 129.5, 131.4, 136.6, 144.5, 153.4;
C$_{27}$H$_{34}$N$_2$OS (calculated): C, 74.61; H, 7.88; N, 6.45; O, 3.68; S, 7.38. (measured): C, 74.52; H, 7.84; N, 6.51; O, 3.73; S, 7.40.

Example I-4

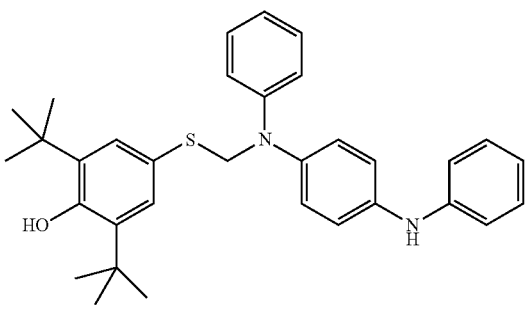 [SMILES: CC(C)(C)c1cc(SCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 8.57 g (36 mmol) 2,6-di-tert-butyl-4-mercaptophenol, 1.24 g (15 mmol) formaldehyde, 10.14 g (39 mmol) N,N'-diphenyl-1,4-phenylene diamine and 150 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 1.36 (18H), 5.23 (2H), 6.80-7.02 (10H), 7.17 (2H), 7.26 (4H), 7.55 (1H);
$^{13}$C NMR (75 MHz, CDCl$_3$): δ 29.6, 34.6, 55.2, 117.1, 121.8, 126.2, 129.5, 136.6, 143.6, 153.4;
C$_{33}$H$_{38}$N$_2$OS (calculated): C, 77.60; H, 7.50; N, 5.48; O, 3.13; S, 6.28. (measured): C, 77.71; H, 7.52; N, 5.53; O, 3.10; S, 6.23.

Example I-5

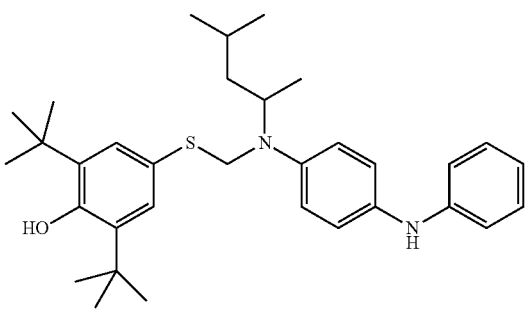 [SMILES: CC(C)CC(C)N(CSc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 9.54 g (115 mmol) formaldehyde, 18.49 g (69 mmol) N-(1,3-dimethylbutyl)-N'-phenyl p-phenylene diamine and 150 mL benzene, rapidly stirred, reacted at 85 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11-1.21 (4H), 1.36 (18H), 1.67 (2H), 3.47 (1H), 4.80 (2H), 5.32 (1H), 6.80 (2H), 6.97 (5H), 7.17 (2H), 7.26 (2H), 7.55 (1H);

$^{13}$C NMR (75 MHz, CDCl$_3$): δ 17.9, 22.4, 29.6, 34.6, 45.2, 52.7, 58.6, 119.4, 121.8, 126.2, 129.5, 131.2, 136.6, 144.1, 146.1, 153.4;

C$_{33}$H$_{46}$N$_2$OS (calculated): C, 76.40; H, 8.94; N, 5.40; O, 3.08; S, 6.18. (measured): C, 76.48; H, 8.96; N, 5.35; O, 3.09; S, 6.12.

Example I-6

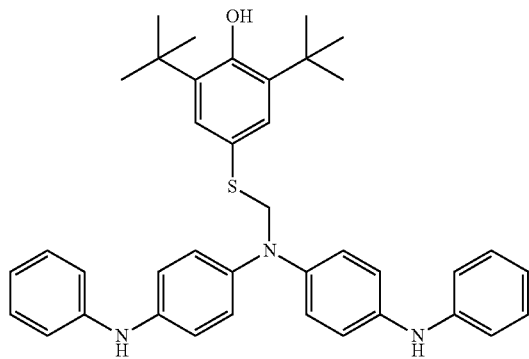 [SMILES: CC(C)(C)c1cc(SCN(c2ccc(Nc3ccccc3)cc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 3.57 g (15 mmol) 2,6-di-tert-butyl-4-mercaptophenol, 5.14 g (62 mmol) formaldehyde, 21.76 g (103 mmol) N-phenyl-N'-[4-(phenylamino) phenyl]-1,4-phenylene diamine and 150 mL toluene, rapidly stirred, reacted at 110 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 5.20 (2H), 5.32 (1H), 6.80-7.02 (14H), 7.17 (2H), 7.20 (1H), 7.26 (4H), 7.55 (1H);

$^{13}$C NMR (75 MHz, CDCl$_3$): δ 29.6, 34.6, 55.5, 117.1, 120.4, 126.2, 129.5, 132.3, 136.6, 142.8, 146.1, 153.4;

C$_{36}$H$_{43}$N$_3$OS (calculated): C, 77.83; H, 7.20; N, 6.98; O, 2.66; S, 5.33. (measured): C, 77.69; H, 7.19; N, 7.08; O, 2.65; S, 5.38.

Example I-7

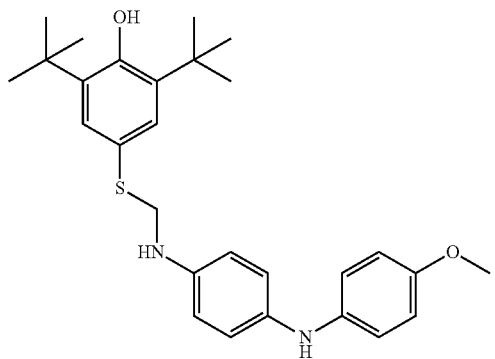 [SMILES: COc1ccc(Nc2ccc(NCSc3cc(C(C)(C)C)c(O)c(C(C)(C)C)c3)cc2)cc1]

Under the protective atmosphere of nitrogen gas, to a 250 ml four-necked flask equipped with a stirrer, a thermometer, a condensing tube and a dropping funnel, there were added 34.51 g (145 mmol) 2,6-di-tert-butyl-4-mercaptophenol, 2.91 g (35 mmol) formaldehyde, 4.49 g (21 mmol) 4-amino-4'-methoxy diphenyl amine, 0.26 g (2.61 mmol) hydrochloric acid and 150 mL benzene, rapidly stirred, reacted at 90 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 3.72-3.76 (4H), 4.80 (2H), 5.32 (1H), 6.97-7.06 (8H), 7.17 (2H), 7.20 (1H);

$^{13}$C NMR (75 MHz, CDCl$_3$): δ 29.6, 34.6, 51.1, 55.5, 114.6, 118.9, 121.8, 124.7, 126.5, 132.3, 136.6, 144.5, 153.4, 154.5;

C$_{28}$H$_{36}$N$_2$O$_2$S (calculated): C, 72.38; H, 7.81; N, 6.03; O, 6.89; S, 6.90. (measured): C, 72.37; H, 7.69; N, 6.12; O, 6.80; S, 6.83.

Example I-8

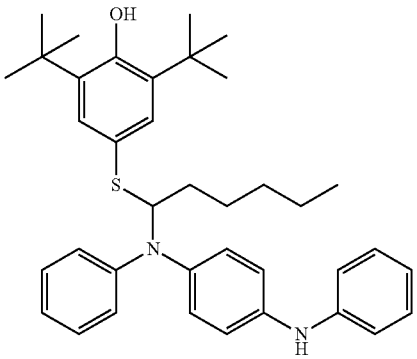 [SMILES: CCCCCC(Sc1cc(C(C)(C)C)c(O)c(C(C)(C)C)c1)N(c1ccccc1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 1.35 g (9.51 mmol) nonanal, 6.51 g (25 mmol) N,N'-diphenyl-1,4-phenylene diamine and 150 mL benzene, rapidly stirred, reacted at 70 degrees Celsius for 6 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.88 (3H), 1.08-1.85 (24H), 5.23 (1H), 5.32 (1H), 6.80 (1H), 6.97 (8H), 7.17 (2H), 7.26 (4H), 7.55 (1H);

$^{13}$C NMR (75 MHz, CDCl$_3$): δ 14.1, 22.6, 29.6, 31.7, 34.6, 41.6, 60.8, 116.6, 119.4, 121.8, 126.5, 129.5, 131.4, 136.6, 142.8, 144.5, 146.1, 153.4;

C$_{38}$H$_{48}$N$_2$OS (calculated): C, 78.57; H, 8.33; N, 4.82; O, 2.75; S, 5.52. (measured): C, 78.62; H, 8.25; N, 4.75; O, 2.81; S, 5.42.

Example I-9

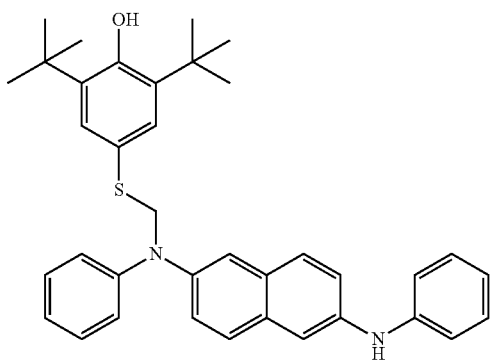 [SMILES: CC(C)(C)c1cc(SCN(c2ccccc2)c2ccc3cc(Nc4ccccc4)ccc3c2)cc(C(C)(C)C)c1O]

Under the protective atmosphere of nitrogen gas, to a 250 ml four-necked flask equipped with a stirrer, a thermometer, a condensing tube and a dropping funnel, there were added 8.33 g (35 mmol) 2,6-di-tert-butyl-4-mercaptophenol, 4.23 g (51 mmol) formaldehyde, 9.61 g (31 mmol) N,N'-diphenyl-2,6-naphthalene diamine and 150 mL toluene, rapidly stirred, reacted at 110 degrees Celsius for 4 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 1.36 (18H), 5.25 (2H), 5.32 (1H), 5.80 (1H), 6.99-7.06 (7H), 7.17 (3H), 7.26 (4H), 7.40 (2H), 7.84 (2H);
$^{13}$C NMR (75 MHz, CDCl$_3$): δ 29.6, 34.6, 54.8, 106.9, 118.6, 123.3, 126.2, 129.2, 136.6, 142.8, 148.3, 153.5;
$C_{37}H_{41}N_2OS$ (calculated): C, 79.24; H, 7.19; N, 5.00; O, 2.85; S, 5.72. (measured): C, 79.20; H, 7.23; N, 5.14; O, 2.72; S, 5.65.

Example I-10

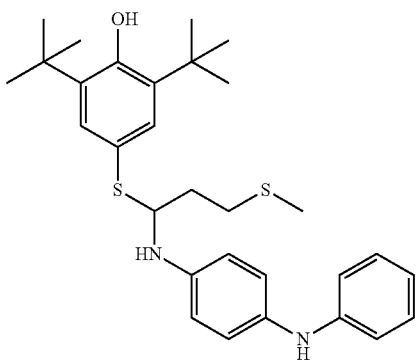 [SMILES: CSCCC(Nc1ccc(Nc2ccccc2)cc1)Sc1cc(C(C)(C)C)c(O)c(C(C)(C)C)c1]

Under the protective atmosphere of nitrogen gas, to a 250 ml four-necked flask equipped with a stirrer, a thermometer, a condensing tube and a dropping funnel, there were added 6.19 g (26 mmol) 2,6-di-tert-butyl-4-mercaptophenol, 9.57 g (92 mmol) 3-methylthiopropionic aldehyde, 3.13 g (17 mmol) N-phenyl p-phenylene diamine and 150 mL toluene, rapidly stirred, reacted at 80 degrees Celsius for 2 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ1.36-1.54 (18H), 2.12-2.80 (7H), 3.47 (1H), 4.97 (1H), 5.32 (1H), 6.97 (7H), 7.17 (2H), 7.26 (2H), 7.55 (1H);
$^{13}$C NMR (75 MHz, CDCl$_3$): δ 15.2, 29.6, 31.9, 34.6, 41.7, 60.2, 114.3, 119.4, 121.8, 126.2, 129.5, 132.4, 136.6, 144.5, 146.1, 153.5;
$C_{30}H_{40}N_2OS_2$ (calculated): C, 70.82; H, 7.92; N, 5.51; O, 3.14; S, 12.60. (measured): C, 70.75; H, 7.83; N, 5.46; O, 3.20; S, 12.71.

Example I-11

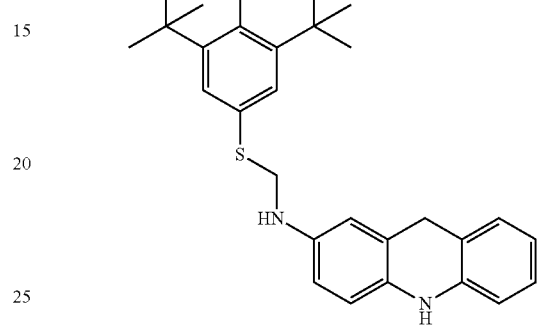

Under the protective atmosphere of nitrogen gas, to a 250 ml four-necked flask equipped with a stirrer, a thermometer, a condensing tube and a dropping funnel, there were added 4.99 g (21 mmol) 2,6-di-tert-butyl-4-mercaptophenol, 4.4 g (53 mmol) formaldehyde, 5.70 g (31 mmol) N-phenyl p-phenylene diamine and 150 mL ethanol, rapidly stirred, after reacted at 60 degrees Celsius for 2.5 h, cooled to the room temperature, there were added 7.05 g (85 mmol) formaldehyde, heated to 85 degrees Celsius and reacted for 2.5 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ1.36 (18H), 3.74 (1H), 4.12 (2H), 4.59 (1H), 4.83 (2H), 5.32 (1H), 6.97-7.11 (5H), 7.17 (2H), 7.24 (2H);
$^{13}$C NMR (75 MHz, CDCl$_3$): δ 29.6, 33.1, 34.6, 50.6, 119.4, 123.3, 126.2, 126.7, 127.9, 136.6, 140.5, 142.9, 153.4; $C_{26}H_{34}N_2OS$ (calculated): C, 75.29; H, 7.67; N, 6.27; O, 3.58; S, 7.18. (measured): C, 75.20; H, 7.59; N, 6.29; O, 3.65; S, 7.22.

Example I-12

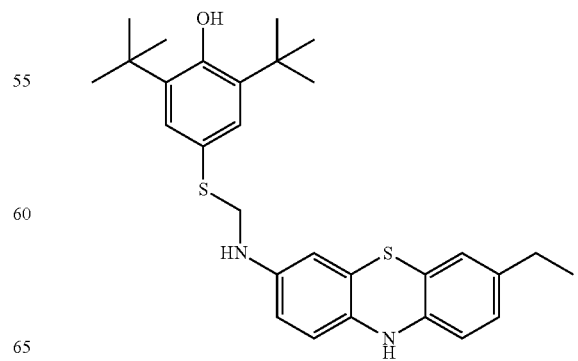

Under the protective atmosphere of nitrogen gas, to a 250 ml four-necked flask equipped with a stirrer, a thermometer, a condensing tube and a dropping funnel, there were added 19.52 g (82 mmol) 2,6-di-tert-butyl-4-mercaptophenol, 10.04 g (121 mmol) formaldehyde, 19.93 g (94 mmol) 4-amino-4'-ethyl diphenyl amine and 150 mL xylene, rapidly stirred, after reacted at 90 degrees Celsius for 3 h, cooled to the room temperature, there were added 10.11 g (316 mmol) sulfur and 0.04 g (0.35 mmol) iodine, heated to 150 degrees Celsius and reacted for 8 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.23 (1H), 1.36 (18H), 2.61 (2H), 3.77 (1H), 4.84 (2H), 5.32 (1H), 5.70 (1H), 6.98 (5H), 7.17 (2H), 7.49 (1H);

$^{13}$C NMR (75 MHz, CDCl$_3$): δ 15.60, 29.6, 34.6, 50.7, 118.9, 121.8, 126.2, 129.7, 136.6, 141.2, 146.1, 153.4;

C$_{29}$H$_{36}$N$_2$OS$_2$ (calculated): C, 70.69; H, 7.36; N, 5.69; O, 3.25; S, 13.02. (measured): C, 70.77; H, 7.41; N, 5.67; O, 3.17; S, 12.93.

Example I-13

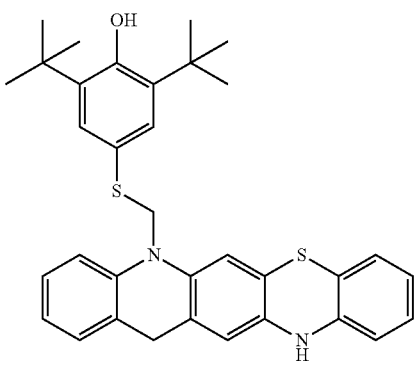 [SMILES: CC(C)(C)c1cc(SCN2c3ccccc3Cc3cc4c(cc32)Sc2ccccc2N4)cc(C(C)(C)C)c1O]

Under the protective atmosphere of nitrogen gas, to a 250 ml four-necked flask equipped with a stirrer, a thermometer, a condensing tube and a dropping funnel, there were added 10.95 g (46 mmol) 2,6-di-tert-butyl-4-mercaptophenol, 3.98 g (48 mmol) formaldehyde, 13.78 g (53 mmol) N,N'-diphenyl-1,4-phenylene diamine and 150 mL trimethylbenzene, rapidly stirred, after reacted at 85 degrees Celsius for 1 h, there were added 3.82 g (46 mmol) formaldehyde, after reacted at 85 degrees Celsius for 1 h, cooled to the room temperature, there were added 10.11 g (316 mmol) sulfur and 0.27 g (2.11 mmol) iodine, heated to 180 degrees Celsius and reacted for 1 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ1.36 (18H), 4.26 (2H), 5.18 (2H), 5.32 (1H), 6.40 (1H), 6.97 (8H), 7.17 (2H), 7.37 (2H);

$^{13}$C NMR (75 MHz, CDCl$_3$): δ 29.6, 33.6, 34.6, 54.3, 106.5, 114.4, 119.4, 121.8, 126.2, 129.5, 136.6, 141.9, 144.5, 153.4;

C$_{34}$H$_{36}$N$_2$OS$_2$ (calculated): C, 73.87; H, 6.56; N, 5.07; O, 2.89; S, 11.60. (measured): C, 73.91; H, 6.49; N, 5.02; O, 2.94; S, 11.49.

Example I-14

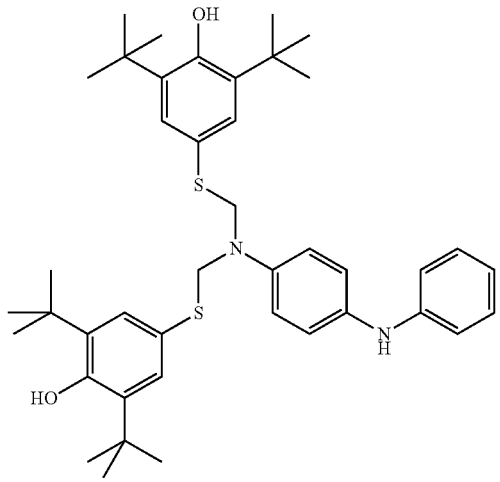 [SMILES: CC(C)(C)c1cc(SCN(CSc2cc(C(C)(C)C)c(O)c(C(C)(C)C)c2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 7.39 g (89 mmol) formaldehyde, 6.62 g (36 mmol) N-phenyl p-phenylene diamine, 0.45 g (4.51 mmol) NaOH and 150 mL isopropanol, rapidly stirred, reacted at 80 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ1.36-1.54 (36H), 4.82 (4H), 5.32 (2H), 6.97 (7H), 7.17 (4H), 7.26 (2H), 7.55 (1H);

$^{13}$C NMR (75 MHz, CDCl$_3$): δ 29.6, 34.6, 56.5, 106.5, 119.4, 121.8, 126.5, 129.5, 131.4, 136.6, 144.5, 146.1, 153.4;

C$_{42}$H$_{56}$N$_2$O$_2$S$_2$ (calculated): C, 73.64; H, 8.24; N, 4.09; O, 4.67; S, 9.36. (measured): C, 73.59; H, 8.21; N, 4.15; O, 4.62; S, 9.34.

Example I-15

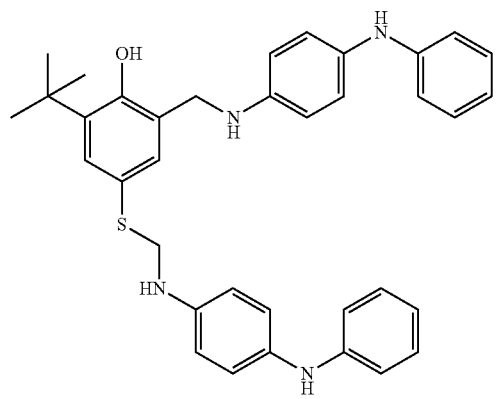 [SMILES: CC(C)(C)c1cc(SCNc2ccc(Nc3ccccc3)cc2)cc(CNc2ccc(Nc3ccccc3)cc2)c1O]

Under the protective atmosphere of nitrogen gas, to a 250 ml four-necked flask equipped with a stirrer, a thermometer, a condensing tube and a dropping funnel, there were added 6.55 g (36 mmol) 2-tert-butyl-4-mercaptophenol, 7.64 g (92 mmol) formaldehyde, 13.06 g (71 mmol) N-phenyl p-phenylene diamine and 150 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ1.36 (9H), 3.81 (1H), 4.38 (2H), 4.69 (2H), 5.29 (1H), 6.95-7.00 (15H), 7.17 (1H), 7.26 (4H), 7.55 (1H), 8.62 (1H);

$^{13}$C NMR (75 MHz, CDCl$_3$): δ 29.6, 34.6, 43.5, 50.8, 114.3, 119.4, 121.8, 125.4, 129.5, 132.3, 136.6, 145.2, 146.1, 149.0, 153.4;

$C_{36}H_{38}N_4OS$ (calculated): C, 75.23; H, 6.66; N, 9.75; O, 2.78; S, 5.58. (measured): C, 75.27; H, 6.69; N, 9.68; O, 2.79; S, 5.51.

Example I-16

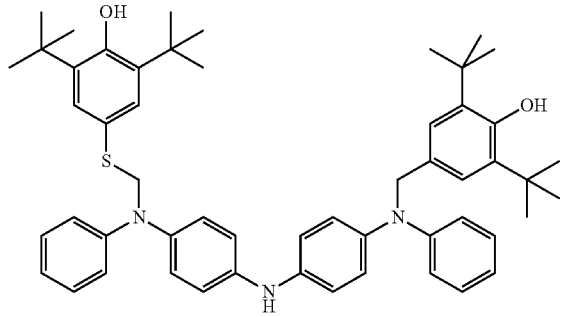 [SMILES: CC(C)(C)c1cc(CN(c2ccccc2)c2ccc(Nc3ccc(N(CSc4cc(C(C)(C)C)c(O)c(C(C)(C)C)c4)c4ccccc4)cc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 11.66 g (49 mmol) 2,6-di-tert-butyl-4-mercaptophenol, 10.92 g (53 mmol) 2,6-ditert-butyl phenol, 7.89 g (95 mmol) formaldehyde, 11.23 g (32 mmol) N-phenyl-N'-[4-(phenylamino)phenyl]-1,4-phenylene diamine and 150 mL toluene, rapidly stirred, reacted at 100 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ1.36-1.54 (36H), 4.91 (2H), 5.22 (2H), 5.32 (2H), 6.97-7.07 (16H), 7.17 (2H), 7.20 (1H), 7.27 (4H);

$^{13}$C NMR (75 MHz, CDCl$_3$): δ 29.6, 34.4, 55.6, 56.9, 93.6, 119.4, 123.3, 126.5, 129.2, 131.4, 136.6, 142.8, 146.1, 153.4;

$C_{54}H_{65}N_3O_2S$ (calculated): C, 79.08; H, 7.99; N, 5.12; O, 3.90; S, 3.91. (measured): C, 79.15; H, 8.03; N, 5.01; O, 3.87, 53.85.

Example I-17

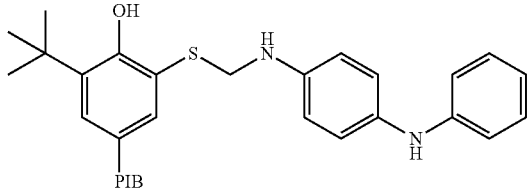

Under the protective atmosphere of nitrogen gas, to a 250 ml four-necked flask equipped with a stirrer, a thermometer, a condensing tube and a dropping funnel, there were added 47.16 g (45 mmol) polyisobutenyl thiophenol produced by Example I-1, 4.23 g (51 mmol) formaldehyde, 9.75 g (53 mmol) N-phenyl p-phenylene diamine and 150 mL benzene, rapidly stirred, reacted at 80 degrees Celsius for 2.5 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.88, 0.98, 1.02, 1.24, 1.40, 2.42, 4.86, 6.97, 7.02, 7.14, 7.26, 7.55;

$^{13}$C NMR (75 MHz, CDCl$_3$): δ 28.2, 30.1, 32.3, 34.5, 38.1, 49.8, 59.1, 114.3, 119.4, 121.8, 122.0, 127.3, 129.5, 132.3, 143.3, 146.1, 151.3.

Example I-18

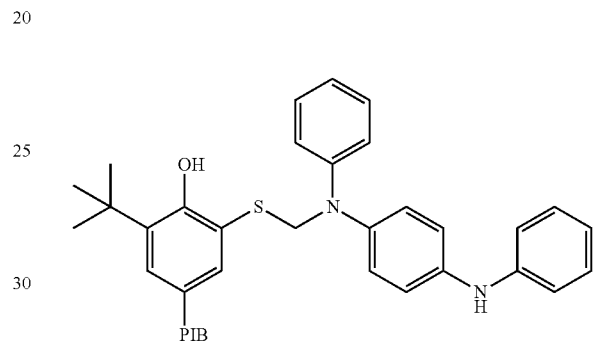

Under the protective atmosphere of nitrogen gas, to a 250 ml four-necked flask equipped with a stirrer, a thermometer, a condensing tube and a dropping funnel, there were added 29.34 g (28 mmol) polyisobutenyl thiophenol produced by Example I-1, 2.91 g (35 mmol) formaldehyde, 6.24 g (24 mmol) N,N'-diphenyl-1,4-phenylene diamine and 150 mL toluene, rapidly stirred, reacted at 90 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.88, 0.98, 1.02, 1.24, 1.40, 2.42, 4.00, 4.86, 5.56, 6.97, 7.02, 7.14, 7.26, 7.55;

$^{13}$C NMR (75 MHz, CDCl$_3$): δ 28.2, 30.1, 32.3, 33.1, 34.5, 38.1, 49.8, 59.1, 114.3, 119.4, 121.8, 125.2, 122.0, 127.3, 129.5, 132.3, 143.3, 146.1, 151.3.

Comparative Example I-1

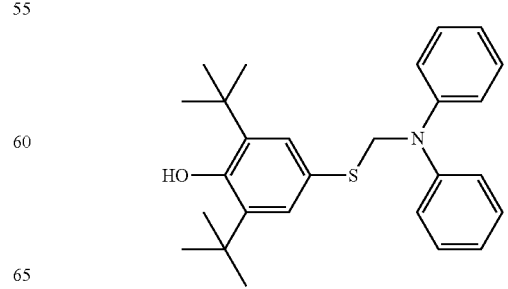

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 7.22 g (87 mmol) formaldehyde, 14.37 g (85 mmol) diphenyl amine and 150 mL methanol, rapidly stirred, reacted at 60 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ1.36 (18H), 5.21 (2H), 5.32 (1H), 6.99 (6H), 7.17 (2H), 7.27 (4H);

$^{13}$C NMR (75 MHz, CDCl$_3$): δ 29.6, 34.6, 55.2, 120.4, 123.3, 125.9, 126.2, 129.2, 136.6, 150.0, 153.5;

$C_{27}H_{33}NOS$ (calculated): C, 77.28; H, 7.93; N, 3.34; O, 3.81; S, 7.64. (measured): C, 77.22; H, 7.89; N, 3.31; O, 3.83; S, 7.67.

Comparative Example I-2

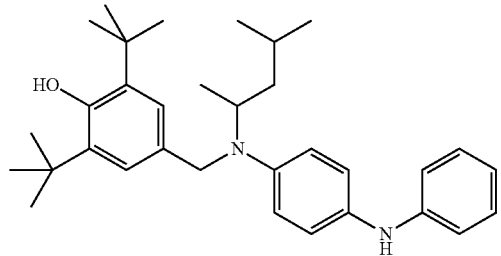 [SMILES: CC(C)CC(C)N(Cc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 10.71 g (52 mmol) 2,6-di-tert-butyl-4-mercaptophenol, 1.89 g (63 mmol) formaldehyde, 17.42 g (65 mmol) N-(1,3-dimethyl butyl)-N'-phenyl p-phenylene diamine and 150 mL methanol, rapidly stirred, reacted at 70 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11 (3H), 1.29 (1H), 1.36 (18H), 3.45 (1H), 4.53 (2H), 5.32 (2H), 6.97-7.07 (9H), 7.26 (2H), 7.55 (1H);

$^{13}$C NMR (75 MHz, CDCl$_3$): δ17.9, 22.40, 24.6, 30.4, 34.3, 45.7, 54.5, 56.7, 116.6, 120.4, 121.8, 125.9, 128.9, 129.5, 135.6, 146.1, 153.5, 154.8;

$C_{33}H_{46}N_2O$ (calculated): C, 81.43; H, 9.53; N, 5.76; O, 3.29. (measured): C, 81.38; H, 9.51; N, 5.79; O, 3.31.

Comparative Example I-3

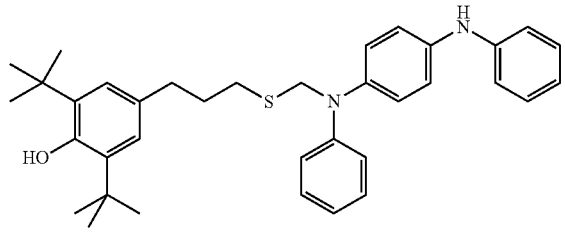 [SMILES: CC(C)(C)c1cc(CCCSCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 9.24 g (33 mmol) 2,6-ditert-butyl-4-(3-mercaptopropyl) phenol, 3.07 g (37 mmol) formaldehyde, 11.71 g (45 mmol) N,N'-diphenyl-1,4-phenylene diamine and 150 mL benzene, rapidly stirred, reacted at 80 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.40 (18H), 1.99 (1H), 2.61-2.80 (6H), 4.63 (2H), 5.32 (1H), 6.97-7.02 (12H), 7.26 (4H), 7.55 (1H);

$^{13}$C NMR (75 MHz, CDCl$_3$): δ 28.7, 31.1, 34.3, 35.7, 54.1, 117.1, 119.4, 123.3, 124.8, 129.2, 131.8, 136.0, 142.8, 144.9, 146.1, 151.9;

$C_{36}H_{44}N_2OS$ (calculated): C, 78.22; H, 8.02; N, 5.07; O, 2.89; S, 5.80. (measured): C, 78.27; H, 7.96; N, 4.98; O, 2.92; S, 5.83.

Example I-19 to Example I-35 and Comparative Example I-4 to Comparative Example I-8

Each of the hindered phenol compounds of Example I-2 to Example I-18 and Comparative Example I-1 to Comparative Example I-3 was respectively mixed with a lubricant base oil in line with the composition and ratio specified in Table I-1 at 40 degrees Celsius for 2 h, to obtain the lubricant oil compositions of Example I-19 to Example I-35 and the lubricant oil compositions of Comparative Example I-4 to Comparative Example I-6. Further, in line with the composition and ratio specified in Table I-2, the antioxidant was respectively mixed with a lubricant base oil at 40 degrees Celsius for 2 h, to obtain the lubricant oil compositions of Comparative Example I-7 to Comparative Example I-10. Herein, based on the total weight of each lubricant oil composition, the amount of the antioxidant to be used in each case was 0.5 wt %, the lubricant base oil used was a Group II hydrogenated base oil (produced by Sinopec Group, Gaoqiao Shanghai Branch). Further, the base oil without the antioxidant was taken as Control.

TABLE I-1

| lubricant oil composition | antioxidant | lubricant base oil | antioxidant amount |
|---|---|---|---|
| Example I-19 | Example I-2 | II | 0.50% |
| Example I-20 | Example I-3 | II | 0.50% |
| Example I-21 | Example I-4 | II | 0.50% |
| Example I-22 | Example I-5 | II | 0.50% |
| Example I-23 | Example I-6 | II | 0.50% |
| Example I-24 | Example I-7 | II | 0.50% |
| Example I-25 | Example I-8 | II | 0.50% |
| Example I-26 | Example I-9 | II | 0.50% |
| Example I-27 | Example I-10 | II | 0.50% |
| Example I-28 | Example I-11 | II | 0.50% |
| Example I-29 | Example I-12 | II | 0.50% |
| Example I-30 | Example I-13 | II | 0.50% |
| Example I-31 | Example I-14 | II | 0.50% |
| Example I-32 | Example I-15 | II | 0.50% |
| Example I-33 | Example I-16 | II | 0.50% |
| Example I-34 | Example I-17 | II | 0.50% |
| Example I-35 | Example I-18 | II | 0.50% |
| Comparative Example I-4 | Comparative Example I-1 | II | 0.50% |
| Comparative Example I-5 | Comparative Example I-2 | II | 0.50% |

TABLE I-1-continued

| lubricant oil composition | antioxidant | lubricant base oil | antioxidant amount |
|---|---|---|---|
| Comparative Example I-6 | Comparative Example I-3 | II | 0.50% |
| Control | — | II | — |

The lubricant oil compositions of Example I-19 to Example I-35, the lubricant oil compositions of Comparative Example I-4 to Comparative Example I-10 and the Control were taken as test samples, to evaluate the deposite formation inhibition performance, the results were shown in Table I-4.

TABLE I-2

| lubricant oil composition | hindered phenol compound | aromatic amine | hindered phenol compound amount | aromatic amine amount | lubricant base oil |
|---|---|---|---|---|---|
| Comparative Example I-7 | 2,2'-thiobis[3-(3,5-ditert-butyl-4-hydroxyl phenyl)propionic acid ethyl ester] | — | 0.50% | — | II |
| Comparative Example I-8 | — | N-(4-tert-octyl phenyl)-1-naphthylamine | — | 0.50% | II |
| Comparative Example I-9 | 2,6-ditert-butyl-4-amylthiophenol | 4,4'-ditert-octyl diphenyl amine | 0.25% | 0.25% | II |
| Comparative Example I-10 | 4,4'-[thiobismethylene]bis[2,6-ditert-butyl phenol] | 3,7-ditert-octyl phenothiazine | 0.30% | 0.20% | II |

The lubricant oil compositions of Example I-19 to Example I-35, the lubricant oil compositions of Comparative Example I-4 to Comparative Example I-10 and the Control were taken as test samples, to evaluate the oxidation resistance at elevated temperatures, with a PDSC temperature of 210 degrees Celsius, the results of were shown in Table I-3.

TABLE I-3

| lubricant oil composition | PDSC oxidative induction period (min) |
|---|---|
| Example I-19 | 18.5 |
| Example I-20 | 23.6 |
| Example I-21 | 21.1 |
| Example I-22 | 20.3 |
| Example I-23 | 28.6 |
| Example I-24 | 20.9 |
| Example I-25 | 21.5 |
| Example I-26 | 29.1 |
| Example I-27 | 23.2 |
| Example I-28 | 24.1 |
| Example I-29 | 26.4 |
| Example I-30 | 27.8 |
| Example I-31 | 24.3 |
| Example I-32 | 23.9 |
| Example I-33 | 27.1 |
| Example I-34 | 16.9 |
| Example I-35 | 18.3 |
| Comparative Example I-4 | 4.9 |
| Comparative Example I-5 | 7.5 |
| Comparative Example I-6 | 16.1 |
| Comparative Example I-7 | 8.6 |
| Comparative Example I-8 | 15.2 |
| Comparative Example I-9 | 5.3 |
| Comparative Example I-10 | 7.1 |
| Control | 0.2 |

TABLE I-4

| lubricant oil composition | deposit amount (mg) |
|---|---|
| Example I-22 | 15.5 |
| Example I-25 | 13.4 |
| Example I-29 | 10.5 |
| Example I-31 | 12.1 |
| Example I-34 | 4.2 |
| Example I-35 | 5.3 |
| Comparative Example I-4 | 19.5 |
| Comparative Example I-5 | 23.4 |
| Comparative Example I-6 | 20.8 |
| Comparative Example I-7 | 21.6 |
| Comparative Example I-8 | 25.6 |
| Comparative Example I-9 | 19.2 |
| Comparative Example I-10 | 18.5 |
| Control | 32.8 |

The lubricant oil compositions of Example I-19 to Example I-35, the lubricant oil compositions of Comparative Example I-4 to Comparative Example I-10 and the Control were taken as test samples, to evaluate the anticorrosion performance. The results of BRT (ball rust test) were shown in Table I-5.

TABLE I-5

| lubricant oil composition | corrosion degree |
|---|---|
| Example I-22 | slight |
| Example I-25 | slight |
| Example I-29 | slight |
| Example I-31 | moderate |
| Example I-34 | slight |
| Example I-35 | slight |
| Comparative Example I-4 | moderate |
| Comparative Example I-5 | moderate |
| Comparative Example I-6 | moderate |
| Comparative Example I-7 | moderate |
| Comparative Example I-8 | moderate |
| Comparative Example I-9 | moderate |
| Comparative Example I-10 | moderate |
| Control | severe |

The lubricant oil compositions of Example I-19 to Example I-35, the lubricant oil compositions of Comparative Example I-4 to Comparative Example I-10 and the Control were taken as test samples, to evaluate the performances of inhibiting increase in viscosity and inhibiting increase in acid value, the results of were shown in Table I-6.

TABLE I-6

| lubricant oil composition | increase in viscosity (%) | increase in acid value (mgKOH · g$^{-1}$) |
|---|---|---|
| Example I-19 | 24.1 | 2.811 |
| Example I-20 | 20.5 | 1.254 |
| Example I-21 | 21.3 | 1.139 |
| Example I-22 | 19.9 | 1.034 |
| Example I-23 | 17.3 | 0.810 |
| Example I-24 | 22.3 | 1.034 |
| Example I-25 | 20.9 | 0.937 |
| Example I-26 | 16.5 | 0.897 |
| Example I-27 | 18.4 | 2.138 |
| Example I-28 | 22.3 | 1.276 |
| Example I-29 | 17.2 | 1.531 |
| Example I-30 | 18.1 | 1.482 |
| Example I-31 | 19.7 | 1.734 |
| Example I-32 | 22.6 | 1.115 |
| Example I-33 | 19.8 | 1.065 |
| Example I-34 | 20.3 | 0.973 |
| Example I-35 | 18.5 | 1.341 |
| Comparative Example I-4 | 33.5 | 4.621 |
| Comparative Example I-5 | 27.5 | 3.482 |
| Comparative Example I-6 | 25.8 | 5.168 |
| Comparative Example I-7 | 27.6 | 2.953 |
| Comparative Example I-8 | 30.5 | 3.846 |
| Comparative Example I-9 | 28.1 | 5.429 |
| Comparative Example I-10 | 24.7 | 6.517 |
| Control | 67.2 | 24.525 |

Example II-1

To a 500 ml four-necked flask equipped with a stirrer, a thermometer, a condensing tube and a dropping funnel, there were added 58.79 g (0.323 mol) 2-tert-butyl-6-mercapto-phenol, 6.88 g (0.048 mol) boron trifluoride.diethyl ether (an alkylation catalyst), 100 ml n-hexane (as the solvent) and 161.61 g (0.162 mol) polyisobutene (Mn=1000, from Jilin Chemical Group Fine Chemicals Co., Ltd.), reacted at 80 degrees Celsius for 2 h. Upon completion of the reaction, the reaction mixture was washed once with a 5 wt % KOH aqueous solution, and then washed with hot water till neutral to remove any catalyst, and then vacuum distillated to remove any solvent and unreacted phenols, to obtain a polyisobutenyl thiophenol, having a hydroxyl value of 53.49 mgKOH/g. The hydroxyl value was determined by referring to the acetic anhydride method in GB/T7383-2007.

The reaction procedure can be illustrated as follows.

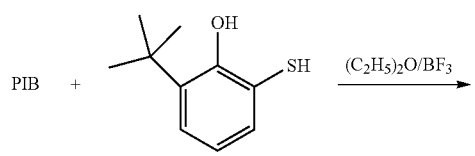

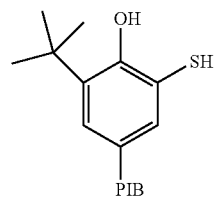

On the $^1$H-NMR spectra of the produced polyisobutenyl thiophenol, the peak at the chemical shift of 1.40 was identified as the characteristic peak of the hydrogen of the tert-butyl on the benzene ring; the single peak at the chemical shift of 3.58 was identified as the characteristic peak of the hydrogen of the mercapto on the benzene ring; the single peak at the chemical shift of 4.84 was identified as the characteristic peak of the hydrogen of the hydroxyl on the benzene ring; the single peak at the chemical shift of 7.12 and that at 7.20 were respectively identified as the characteristic peak of the two hydrogens on the benzene ring. If the integral of the hydrogen of the hydroxyl on the benzene ring is defined as 1, the value of the integral ratio between the hydrogen on the benzene ring, the hydrogen of the mercapto and the hydrogen of the hydroxyl were calculated as 0.95: 0.97:1.05:0.94, approximating to the theoretical value of 1:1:1:1:1. As can be seen from this NMR spectra analysis, the polyisobutenyl thiophenol was obtained as anticipated.

Example II-2

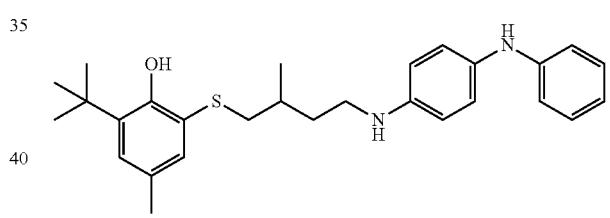

Under the protective atmosphere of nitrogen gas, to a 250 ml four-necked flask equipped with a stirrer, a thermometer, a condensing tube and a dropping funnel, there were added 30.58 g (156 mmol) 2-mercapto-4-methyl-6-methyl phenol, 15.79 g (112 mmol) 1,4-dichloro-2-methyl butane, 32.38 g (176 mmol) N-phenyl p-phenylene diamine, 3.45 g (25 mmol) potassium carbonate and 100 mL toluene, rapidly stirred, reacted at 90 degrees Celsius for 1 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.00 (3H), 1.31 (1H), 1.40 (9H), 1.78 (1H), 1.98 (1H), 2.37 (3H), 2.99 (2H), 3.33 (2H), 4.83 (1H), 6.95-7.26 (12H), 7.55 (1H);

$^{13}$C NMR (75 MHz, CDCl$_3$): δ 20.4, 21.2, 30.1, 33.7, 34.5, 43.8, 114.3, 118.9, 119.4, 121.8, 125.8, 129.5, 132.3, 133.5, 146.1, 149.0, 150.8;

C$_{28}$H$_{36}$N$_2$OS (calculated): C, 74.96; H, 8.09; N, 6.24; O, 3.57; S, 7.15. (measured): C, 74.88; H, 8.13; N, 6.21; O, 3.54; S, 7.09.

Example II-3

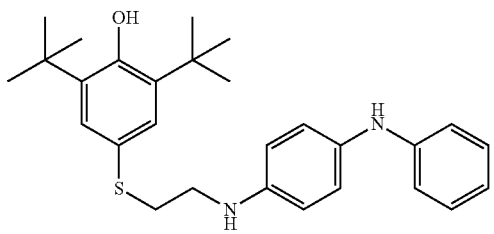 [SMILES: CC(C)(C)c1cc(SCCNc2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 31.65 g (133 mmol) 2,6-di-tert-butyl-4-mercaptophenol, 11.66 g (62 mmol) dibromoethane, 28.15 g (153 mmol) N-phenyl p-phenylene diamine, 0.79 g (7.5 mmol) sodium carbonate and 100 mL benzene, rapidly stirred, reacted at 25 degrees Celsius for 24 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 3.15 (2H), 3.63 (2H), 5.17 (1H), 5.32 (1H), 6.97-7.26 (11H), 7.55 (1H);

$^{13}$C NMR (75 MHz, CDCl$_3$): δ 29.6, 32.7, 34.6, 47.5, 114.3, 118.9, 119.4, 121.8, 126.2, 127.5, 129.5, 132.3, 136.5, 146.1, 149.0, 153.5;

C$_{28}$H$_{36}$N$_2$OS (calculated): C, 74.96; H, 8.09; N, 6.24; O, 3.57; S, 7.15. (measured): C, 75.06; H, 8.13; N, 6.11; O, 3.61; S, 7.09.

Example II-4

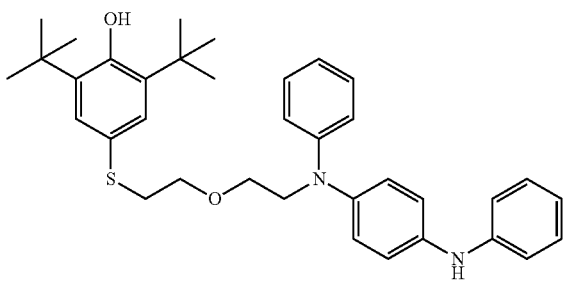 [SMILES: CC(C)(C)c1cc(SCCOCCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 8.57 g (36 mmol) 2,6-di-tert-butyl-4-mercaptophenol, 2.15 g (15 mmol) dichlorodiethyl ether, 10.14 g (39 mmol) N,N'-diphenyl-1,4-phenylene diamine, 0.55 g (5.1 mmol) sodium carbonate and 100 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 2.98 (2H), 3.34 (2H), 3.63 (2H), 3.76 (2H), 5.32 (1H), 6.80-7.27 (16H), 7.55 (1H);

$^{13}$C NMR (75 MHz, CDCl$_3$): δ 29.6, 32.1, 34.6, 46.9, 69.4, 69.6, 114.0, 116.6, 117.1, 119.3, 121.8, 126.2, 129.2, 136.5, 142.8, 146.1, 148.7, 153.5;

C$_{36}$H$_{44}$N$_2$O$_2$S (calculated): C, 76.02; H, 7.80; N, 4.92; O, 5.63; S, 5.64. (measured): C, 76.09; H, 7.85; N, 4.83; O, 5.65; S, 5.60.

Example II-5

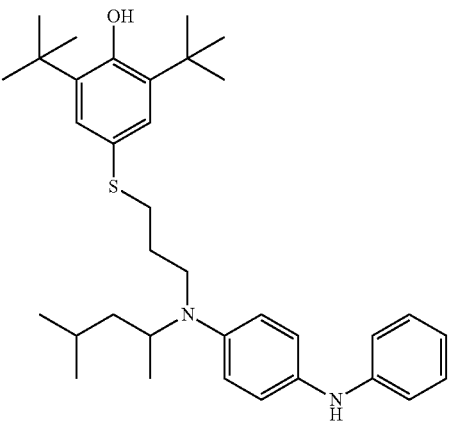 [SMILES: CC(C)CC(C)N(CCCSc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 12.99 g (115 mmol) 1,3-dichloropropane, 18.49 g (69 mmol) N-(1,3-dimethyl butyl)-N'-phenyl p-phenylene diamine, 0.76 g (7.2 mmol) sodium carbonate and 150 mL benzene, rapidly stirred, reacted at 85 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11-1.21 (5H), 1.36 (18H), 1.67 (1H), 2.16-3.47 (6H), 5.32 (1H), 6.80-7.17 (7H), 7.55 (1H);

$^{13}$C NMR (75 MHz, CDCl$_3$): δ 22.4, 24.6, 34.6, 45.2, 52.7, 58.6, 115.4, 116.6, 119.4, 121.8, 126.2, 129.5, 136.6, 144.1, 153.5;

C$_{35}$H$_{50}$N$_2$OS (calculated): C, 76.87; H, 9.22; N, 5.12; O, 2.93; S, 5.86. (measured): C, 76.95; H, 9.28; N, 5.08; O, 2.87; S, 5.80.

Example II-6

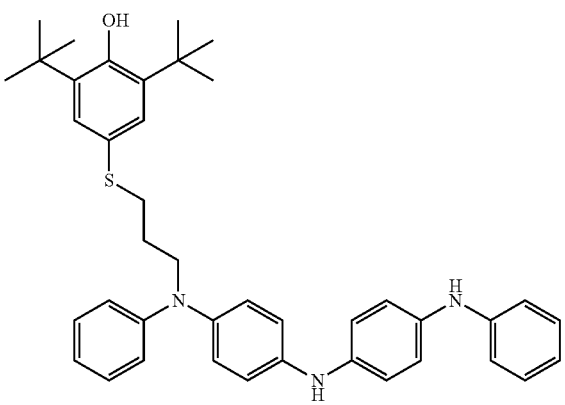 [SMILES: CC(C)(C)c1cc(SCCCN(c2ccccc2)c2ccc(Nc3ccc(Nc4ccccc4)cc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 3.57 g (15 mmol) 2,6-di-tert-butyl-4-mercaptophenol, 20.81 g (103 mmol) 1,3-dibromopropane, 21.76 g (103 mmol) N-phenyl-N'-[4-(phenylamino) phenyl]-1,4-phenylene diamine, 0.29 g (2.1 mmol) sodium carbonate and 150 mL benzene, rapidly stirred, reacted at 110 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 1.94 (2H), 2.95 (2H), 3.43 (2H), 5.32 (1H), 6.80-7.17 (16H), 7.20 (1H), 7.26 (4H), 7.55 (1H);

$^{13}$C NMR (75 MHz, CDCl$_3$): δ 28.5, 29.6, 29.9, 34.6, 47.2, 114.0, 116.6, 117.7, 118.4, 121.8, 126.2, 129.2, 132.3, 136.5, 142.8, 146.1, 148.7, 153.5;

C$_{41}$H$_{47}$N$_3$OS (calculated): C, 78.18; H, 7.52; N, 6.67; O, 2.54; S, 5.09. (measured): C, 78.29; H, 7.57; N, 6.55; O, 2.51; S, 5.10.

Example II-7

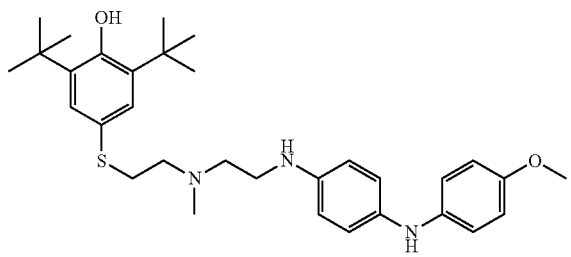

Under the protective atmosphere of nitrogen gas, to a 250 ml four-necked flask equipped with a stirrer, a thermometer, a condensing tube and a dropping funnel, there were added 34.51 g (145 mmol) 2,6-di-tert-butyl-4-mercaptophenol, 5.95 g (35 mmol) 2-chloroethyl-3-chloropropylmethylamine, 4.49 g (21 mmol) 4-amino-4'-methoxy diphenyl amine, 0.28 g (2.6 mmol) sodium carbonate and 150 mL benzene, rapidly stirred, reacted at 90 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 2.27 (3H), 2.65 (2H), 2.99 (2H), 3.09 (2H), 3.46 (2H), 3.76 (3H), 4.10 (1H), 5.32 (1H), 6.97-7.17 (10H), 7.20 (1H);

$^{13}$C NMR (75 MHz, CDCl$_3$): δ 29.6, 34.5, 35.1, 40.6, 45.2, 53.4, 54.3, 55.5, 114.3, 118.9, 120.1, 126.2, 132.3, 136.5, 149.0, 153.4, 154.5;

C$_{32}$H$_{45}$N$_3$O$_2$S (calculated): C, 71.73; H, 8.47; N, 7.84; O, 5.97; S, 5.98. (measured): C, 71.69; H, 8.43; N, 7.91; O, 5.92; S, 5.95.

Example II-8

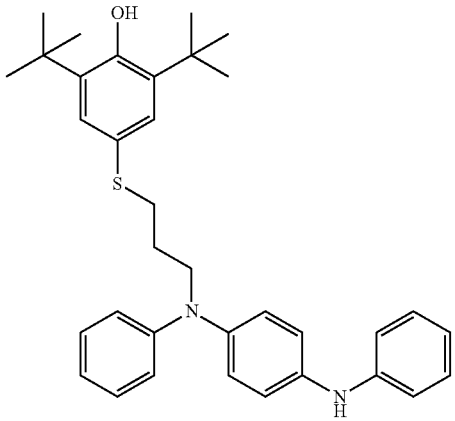 [SMILES: CC(C)(C)c1cc(SCCCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 1.07 g (9.51 mmol) 1,3-dichloropropane, 6.51 g (25 mmol) N,N'-diphenyl-1,4-phenylene diamine, 0.65 g (6.5 mmol) potassium hydrogen carbonate and 150 mL benzene, rapidly stirred, reacted at 70 degrees Celsius for 6 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 2.26 (2H), 3.05 (2H), 3.48 (2H), 5.32 (1H), 6.80-7.17 (12H), 7.27 (2H), 7.55 (1H);

$^{13}$C NMR (75 MHz, CDCl$_3$): δ 28.5, 29.6, 33.4, 34.6, 44.2, 81.5, 114.0, 117.1, 119.4, 121.8, 126.2, 129.5, 136.6, 142.8, 146.1, 148.7, 153.4;

C$_{35}$H$_{42}$N$_2$OS (calculated): C, 78.02; H, 7.86; N, 5.20; O, 2.97; S, 5.95. (measured): C, 78.09; H, 7.91; N, 5.15; O, 2.93; S, 5.87.

Example II-9

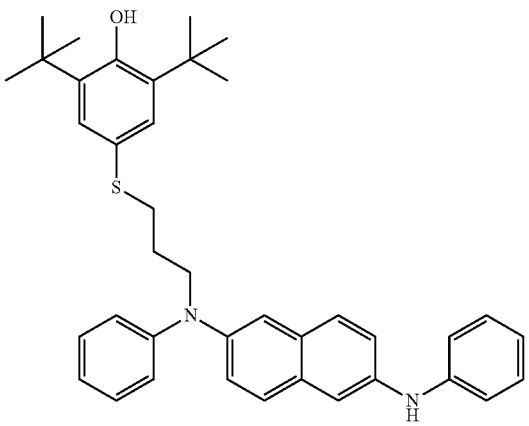 [SMILES: CC(C)(C)c1cc(SCCCN(c2ccccc2)c2ccc3cc(Nc4ccccc4)ccc3c2)cc(C(C)(C)C)c1O]

Under the protective atmosphere of nitrogen gas, to a 250 ml four-necked flask equipped with a stirrer, a thermometer, a condensing tube and a dropping funnel, there were added 8.33 g (35 mmol) 2,6-di-tert-butyl-4-mercaptophenol, 10.30 g (51 mmol) 1,3-dibromopropane, 9.61 g (31 mmol) N,N'-diphenyl-2,6-naphthalene diamine, 0.24 g (1.71 mmol) potassium carbonate and 150 mL toluene, rapidly stirred, reacted at 110 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 1.99 (2H), 3.06 (2H), 3.52 (2H), 5.32 (1H), 5.80 (1H), 6.99-7.27 (15H), 7.40 (1H), 7.84 (2H);

$^{13}$C NMR (75 MHz, CDCl$_3$): δ 28.5, 29.6, 29.9, 34.6, 43.0, 106.9, 111.1, 114.0, 116.5, 119.9, 121.4, 126.2, 128.9, 129.1, 129.4, 136.5, 140.7, 142.8, 147.5, 148.7, 153.5;

C$_{39}$H$_{44}$N$_2$OS (calculated): C, 79.55; H, 7.53; N, 4.76; O, 2.72; S, 5.45. (measured): C, 79.49; H, 7.51; N, 4.79; O, 2.70; S, 5.41.

Example II-10

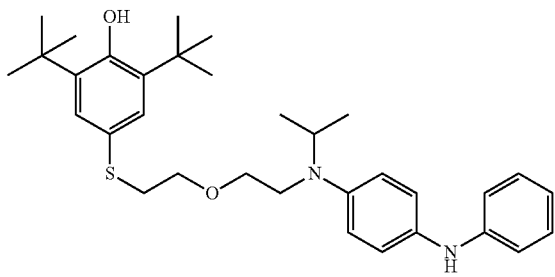

Under the protective atmosphere of nitrogen gas, to a 250 ml four-necked flask equipped with a stirrer, a thermometer, a condensing tube and a dropping funnel, there were added 6.19 g (26 mmol) 2,6-di-tert-butyl-4-mercaptophenol, 13.16 g (92 mmol) dichlorodiethyl ether, 3.84 g (17 mmol) N-isopropyl-N'-phenyl p-phenylene diamine, 0.43 g (3.1 mmol) potassium carbonate and 150 mL ethanol, rapidly stirred, reacted at 80 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.19 (6H), 1.36 (18H), 3.04 (2H), 3.25 (2H), 3.35 (2H), 3.43 (1H), 3.49 (2H), 5.32 (1H), 6.80-7.26 (11H), 7.55 (1H);

$^{13}$C NMR (75 MHz, CDCl$_3$): δ 19.9, 29.6, 31.9, 34.6, 44.5, 54.3, 69.24, 116.6, 117.2, 119.3, 121.8, 126.2, 129.5, 136.5, 142.8, 146.1, 153.4, 154.8;

C$_{33}$H$_{46}$N$_2$O$_2$S (calculated): C, 74.11; H, 8.67; N, 5.24; O, 5.98; S, 6.00. (measured): C, 74.05; H, 8.61; N, 5.29; O, 5.93; S, 6.07.

Example II-11

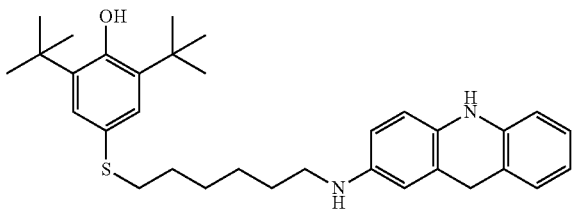

Under the protective atmosphere of nitrogen gas, to a 250 ml four-necked flask equipped with a stirrer, a thermometer, a condensing tube and a dropping funnel, there were added 4.99 g (21 mmol) 2,6-di-tert-butyl-4-mercaptophenol, 7.56 g (31 mmol) 1,6-dibromohexane, 5.70 g (31 mmol) N-phenyl p-phenylene diamine, 0.12 g (0.85 mmol) potassium carbonate and 150 mL ethanol, rapidly stirred, after reacted at 60 degrees Celsius for 2.5 h, cooled to the room temperature, there were added 7.05 g (85 mmol) formaldehyde, heated to 85 degrees Celsius and reacted for 2.5 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.32 (2H), 1.36 (18H), 1.41 (2H), 1.64-1.81 (4H), 2.93-3.28 (4H), 4.14 (2H), 4.43 (1H), 4.59 (1H), 5.32 (1H), 6.82-7.21 (9H);

$^{13}$C NMR (75 MHz, CDCl$_3$): δ 26.8, 28.3, 28.6, 29.6, 31.8, 33.1, 34.3, 44.56, 113.0, 118.9, 119.6, 122.4, 123.3, 125.1, 126.4, 127.9, 132.2, 140.5, 148.5, 153.4;

C$_{33}$H$_{44}$N$_2$OS (calculated): C, 76.70; H, 8.58; N, 5.42; O, 3.10; S, 6.20. (measured): C, 76.69; H, 8.51; N, 5.49; O, 3.12; S, 6.18.

Example II-12

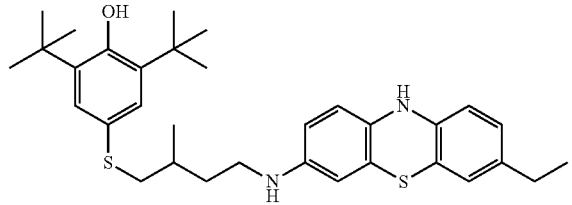

Under the protective atmosphere of nitrogen gas, to a 250 ml four-necked flask equipped with a stirrer, a thermometer, a condensing tube and a dropping funnel, there were added 19.52 g (82 mmol) 2,6-di-tert-butyl-4-mercaptophenol, 39.20 g (121 mmol) 1,4-diiodo-2-methyl butane, 19.93 g (94 mmol) 4-amino-4'-ethyl diphenyl amine, 2.22 g (16.1 mmol) potassium carbonate and 100 mL toluene, rapidly stirred, after reacted at 90 degrees Celsius for 3 h, cooled to the room temperature, to the toluene layer, there were added 10.11 g (316 mmol) sulfur and 0.04 g (0.35 mmol) iodine, heated to 150 degrees Celsius and reacted for 8 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.00 (3H), 1.23 (3H), 1.36 (18H), 1.87 (2H), 2.06 (1H), 2.65 (2H), 2.82 (2H), 3.29 (2H), 4.25 (1H), 5.32 (1H), 5.70 (1H), 6.72 (1H), 6.98-7.08 (4H), 7.17 (2H), 7.49 (1H);

$^{13}$C NMR (75 MHz, CDCl$_3$): δ 15.60, 20.3, 29.0, 29.6, 34.6, 44.2, 113.7, 116.1, 118.9, 126.2, 127.9, 129.7, 136.6, 141.2, 146.1, 153.4;

C$_{33}$H$_{44}$N$_2$OS$_2$ (calculated): C, 72.22; H, 8.08; N, 5.10; O, 2.92; S, 11.68. (measured): C, 72.29; H, 8.14; N, 5.08; O, 2.86; S, 11.57.

Example II-13

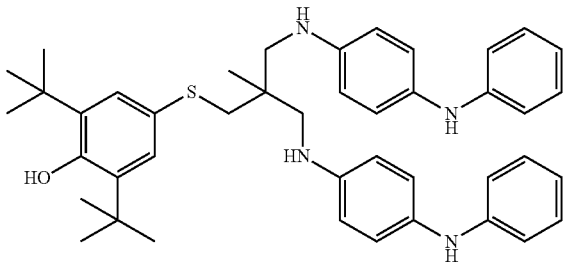 [SMILES: CC(CNc1ccc(Nc2ccccc2)cc1)(CNc1ccc(Nc2ccccc2)cc1)CSc1cc(C(C)(C)C)c(O)c(C(C)(C)C)c1]

Under the protective atmosphere of nitrogen gas, to a 250 ml four-necked flask equipped with a stirrer, a thermometer, a condensing tube and a dropping funnel, there were added 10.95 g (46 mmol) 2,6-di-tert-butyl-4-mercaptophenol, 8.42 g (48 mmol) 1,1,1-trichloromethyl ethane, 18.95 g (103 mmol) N-phenyl p-phenylene diamine, 0.71 g (5.12 mmol) potassium carbonate and 150 mL benzene, rapidly stirred, reacted at 85 degrees Celsius for 1 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.01 (3H), 1.36 (18H), 2.89 (2H), 3.03 (4H), 4.25 (2H), 5.32 (1H), 69.7-7.26 (20H), 7.55 (2H);

$^{13}$C NMR (75 MHz, CDCl$_3$): δ 21.4, 29.6, 34.6, 38.0, 43.2, 54.0, 114.3, 118.7, 119.3, 121.8, 126.2, 129.5, 132.3, 136.5, 146.1, 149.0, 153.4;

C$_{43}$H$_{52}$N$_4$OS (calculated): C, 76.74; H, 7.79; N, 8.33; O, 2.38; S, 4.76. (measured): C, 76.69; H, 7.73; N, 8.45; O, 2.32; S, 4.71.

Example II-14

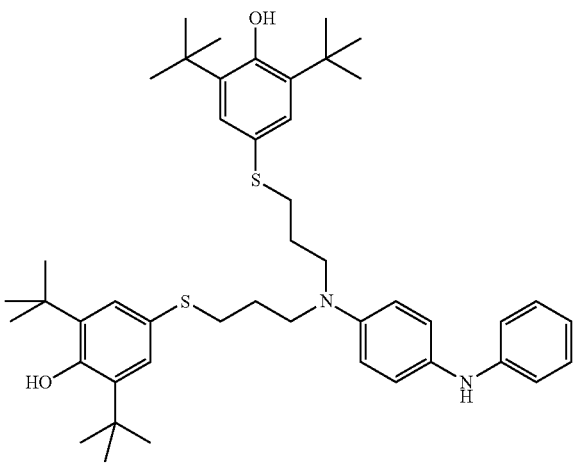 [SMILES: CC(C)(C)c1cc(SCCCN(CCCSc2cc(C(C)(C)C)c(O)c(C(C)(C)C)c2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 17.98 g (89 mmol) 1,2-dibromopropane, 6.62 g (36 mmol) N-phenyl p-phenylene diamine, 0.62 g (5.12 mmol) potassium carbonate and 150 mL isopropanol, rapidly stirred, reacted at 80 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (36H), 1.95 (4H), 3.04 (4H), 3.12 (4H), 5.32 (2H), 6.80-7.26 (13H), 7.55 (1H);

$^{13}$C NMR (75 MHz, CDCl$_3$): δ 28.5, 29.6, 34.6, 48.4, 101.3, 116.6, 117.1, 119.3, 121.8, 126.2, 129.5, 136.5, 142.8, 146.1, 149.1, 153.4;

C$_{46}$H$_{64}$N$_2$O$_2$S$_2$ (calculated): C, 74.55; H, 8.70; N, 3.78; O, 4.32; S, 8.65. (measured): C, 74.59; H, 8.73; N, 3.67; O, 4.35; S, 8.64.

Example II-15

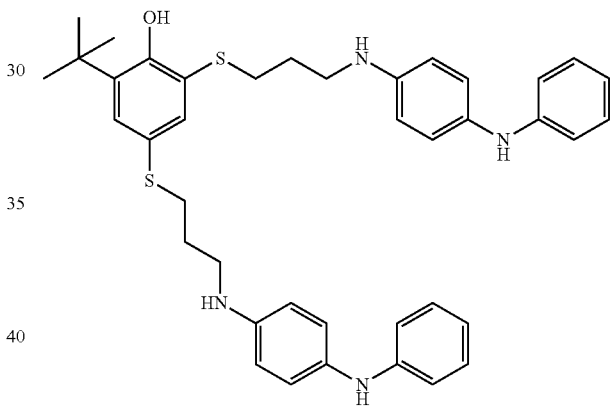

Under the protective atmosphere of nitrogen gas, to a 250 ml four-necked flask equipped with a stirrer, a thermometer, a condensing tube and a dropping funnel, there were added 7.70 g (36 mmol) 2-tert-butyl-4,6-dimercaptophenol, 10.40 g (92 mmol) 1,2-dichloropropane, 13.06 g (71 mmol) N-phenyl p-phenylene diamine, 0.43 g (3.15 mmol) potassium carbonate and 150 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (9H), 1.88 (4H), 2.85 (4H), 3.17 (4H), 3.55 (2H), 6.97-7.26 (19H), 7.28 (1H), 7.55 (2H), 8.30 (1H);

$^{13}$C NMR (75 MHz, CDCl$_3$): δ 28.8, 29.2, 30.0, 31.4, 34.5, 44.8, 45.4, 113.5, 114.3, 118.9, 121.8, 122.7, 125.3, 126.2, 129.5, 132.3, 146.4, 149.0, 154.9;

C$_{40}$H$_{46}$N$_4$OS$_2$ (calculated): C, 72.47; H, 6.99; N, 8.45; O, 2.41; S, 9.67. (measured): C, 72.52; H, 7.03; N, 8.37; O, 2.43; S, 9.64.

Example II-16

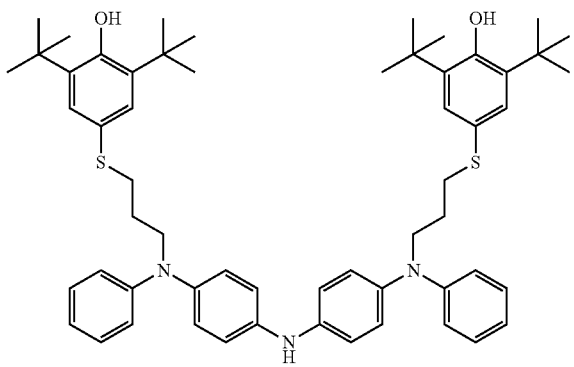 [SMILES: CC(C)(C)c1cc(SCCCN(c2ccccc2)c2ccc(Nc3ccc(N(CCCSc4cc(C(C)(C)C)c(O)c(C(C)(C)C)c4)c4ccccc4)cc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 18.56 g (78 mmol) 2-tert-butyl-4-mercaptophenol, 10.74 g (95 mmol) 1,2-dichloropropane, 11.23 g (32 mmol) N-phenyl-N'[4-(phenylamino)phenyl]-1,4-phenylene diamine, 0.79 g (5.71 mmol) potassium carbonate and 150 mL toluene, rapidly stirred, reacted at 100 degrees Celsius for 3 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 1.36 (36H), 2.02 (4H), 3.03 (4H), 3.50 (4H), 5.32 (2H), 6.80-7.17 (18H), 7.20 (1H), 7.27 (4H);
$^{13}$C NMR (75 MHz, CDCl$_3$): δ 28.5, 29.6, 30.1, 31.8, 34.6, 49.9, 92.4, 114.0, 116.6, 117.1, 122.0, 126.2, 129.2, 136.5, 142.8, 148.7, 153.4;
C$_{58}$H$_{73}$N$_3$O$_2$S$_2$ (calculated): C, 76.69; H, 8.10; N, 4.63; O, 3.52; S, 7.06. (measured): C, 76.61; H, 8.05; N, 4.71; O, 3.49; S, 7.03.

Example II-17

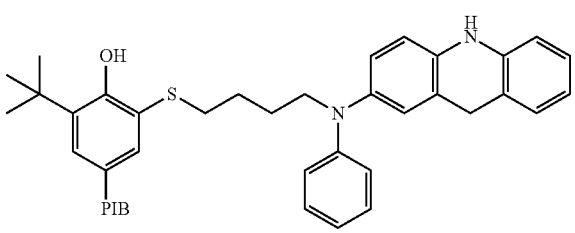

Under the protective atmosphere of nitrogen gas, to a 250 ml four-necked flask equipped with a stirrer, a thermometer, a condensing tube and a dropping funnel, there were added 47.16 g (45 mmol) polyisobutenyl thiophenol produced by Example II-1, 6.48 g (51 mmol) 1,4-dichlorobutane, 13.78 g (53 mmol) N,N'-diphenyl-1,4-phenylene diamine, 0.86 g (8.15 mmol) sodium carbonate and 150 mL benzene, rapidly stirred, reacted at 80 degrees Celsius for 2.5 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 0.88, 0.98, 1.33, 1.40, 1.59, 1.64, 1.73, 1.82, 1.93, 3.25, 3.38, 3.71, 4.86, 6.97, 7.02, 7.19, 7.26, 7.55;
$^{13}$C NMR (75 MHz, CDCl$_3$): δ 27.1, 28.9, 30.1, 31.6, 32.3, 34.5, 37.9, 43.9, 57.1, 114.0, 117.7, 119.4, 121.8, 129.5, 131.6, 144.5, 146.1, 148.7, 155.0.

Example II-18

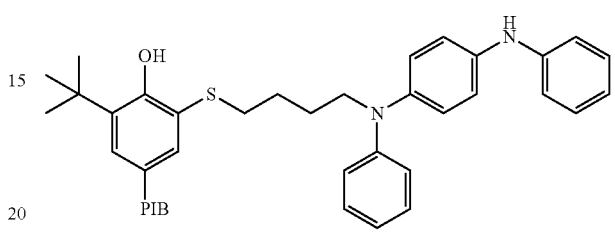

Under the protective atmosphere of nitrogen gas, to a 250 ml four-necked flask equipped with a stirrer, a thermometer, a condensing tube and a dropping funnel, there were added 29.34 g (28 mmol) polyisobutenyl thiophenol produced by Example II-1, 2.91 g (35 mmol) formaldehyde, 6.24 g (24 mmol) N,N'-diphenyl-1,4-phenylene diamine, 0.34 g (3.2 mmol) sodium carbonate and 150 mL toluene, rapidly stirred, reacted at 90 degrees Celsius for 2 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 0.86, 0.98, 1.02, 1.40, 1.60, 1.83, 2.59, 3.25, 3.72, 4.86, 6.80, 6.97, 7.02, 7.17, 7.26, 7.55;
$^{13}$C NMR (75 MHz, CDCl$_3$): δ 28.2, 30.1, 32.3, 33.1, 34.5, 38.1, 49.8, 59.1, 114.3, 119.4, 121.8, 125.2, 122.0, 127.3, 129.5, 132.3, 143.3, 146.1, 151.3.

Comparative Example II-1

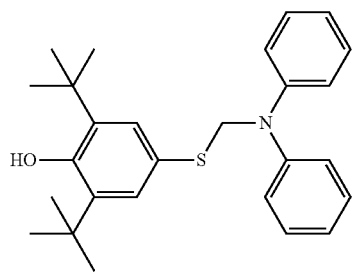 [SMILES: CC(C)(C)c1cc(SCN(c2ccccc2)c2ccccc2)cc(C(C)(C)C)c1O]

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 7.22 g (87 mmol) formaldehyde, 14.37 g (85 mmol) diphenyl amine and 150 mL methanol, rapidly stirred, reacted at 60 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 5.21 (2H), 5.32 (1H), 6.99 (6H), 7.17 (2H), 7.27 (4H);

$^{13}$C NMR (75 MHz, CDCl$_3$): δ 29.6, 34.6, 55.2, 120.4, 123.3, 125.9, 126.2, 129.2, 136.6, 150.0, 153.5;

C$_{27}$H$_{33}$NOS (calculated): C, 77.28; H, 7.93; N, 3.34; O, 3.81; S, 7.64. (measured): C, 77.22; H, 7.89; N, 3.31; O, 3.83; S, 7.67.

Comparative Example II-2

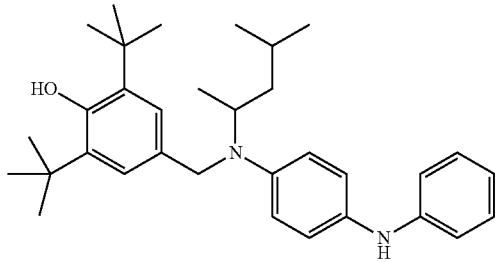 [SMILES: CC(C)CC(C)N(Cc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 10.71 g (52 mmol) 2,6-di-tert-butyl-4-mercaptophenol, 1.89 g (63 mmol) formaldehyde, 17.42 g (65 mmol) N-(1,3-dimethyl butyl)-N'-phenyl p-phenylene diamine and 150 mL methanol, rapidly stirred, reacted at 70 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11 (3H), 1.29 (1H), 1.36 (18H), 3.45 (1H), 4.53 (2H), 5.32 (2H), 6.97-7.07 (9H), 7.26 (2H), 7.55 (1H);

$^{13}$C NMR (75 MHz, CDCl$_3$): δ17.9, 22.40, 24.6, 30.4, 34.3, 45.7, 54.5, 56.7, 116.6, 120.4, 121.8, 125.9, 128.9, 129.5, 135.6, 146.1, 153.5, 154.8;

C$_{33}$H$_{46}$N$_2$O (calculated): C, 81.43; H, 9.53; N, 5.76; O, 3.29. (measured): C, 81.38; H, 9.51; N, 5.79; O, 3.31.

Comparative Example II-3

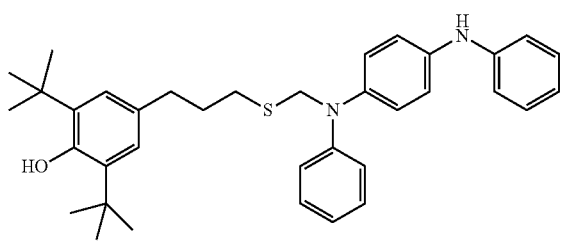 [SMILES: CC(C)(C)c1cc(CCCSCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 9.24 g (33 mmol) 2,6-ditert-butyl-4-(3-mercaptopropyl) phenol, 3.07 g (37 mmol) formaldehyde, 11.71 g (45 mmol) N,N'-diphenyl-1,4-phenylene diamine and 150 mL benzene, rapidly stirred, reacted at 80 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.40 (18H), 1.99 (1H), 2.61-2.80 (6H), 4.63 (2H), 5.32 (1H), 6.97-7.02 (12H), 7.26 (4H), 7.55 (1H);

$^{13}$C NMR (75 MHz, CDCl$_3$): δ 28.7, 31.1, 34.3, 35.7, 54.1, 117.1, 119.4, 123.3, 124.8, 129.2, 131.8, 136.0, 142.8, 144.9, 146.1, 151.9;

C$_{36}$H$_{44}$N$_2$OS (calculated): C, 78.22; H, 8.02; N, 5.07; O, 2.89; S, 5.80. (measured): C, 78.27; H, 7.96; N, 4.98; O, 2.92; S, 5.83.

Example II-19 to Example II-35 and Comparative Example II-4 to Comparative Example II-8

Each of the hindered phenol compounds of Example II-2 to Example II-18 and Comparative Example II-1 to Comparative Example II-3 was respectively mixed with a lubricant base oil in line with the composition and ratio specified in Table II-1 at 40 degrees Celsius for 2 h, to obtain the lubricant oil compositions of Example II-19 to Example II-35 and the lubricant oil compositions of Comparative Example II-4 to Comparative Example II-6. Further, in line with the composition and ratio specified in Table II-2, the antioxidant was respectively mixed with a lubricant base oil at 40 degrees Celsius for 2 h, to obtain the lubricant oil compositions of Comparative Example II-7 to Comparative Example II-10. Herein, based on the total weight of each lubricant oil composition, the amount of the antioxidant to be used in each case was 0.5 wt %, the lubricant base oil used was a Group II hydrogenated base oil (produced by Sinopec Group, Gaoqiao Shanghai Branch). Further, the base oil without the antioxidant was taken as Control.

TABLE II-1

| lubricant oil composition | antioxidant | lubricant base oil | antioxidant amount |
|---|---|---|---|
| Example II-19 | Example II-2 | II | 0.50% |
| Example II-20 | Example II-3 | II | 0.50% |
| Example II-21 | Example II-4 | II | 0.50% |
| Example II-22 | Example II-5 | II | 0.50% |
| Example II-23 | Example II-6 | II | 0.50% |
| Example II-24 | Example II-7 | II | 0.50% |
| Example II-25 | Example II-8 | II | 0.50% |
| Example II-26 | Example II-9 | II | 0.50% |
| Example II-27 | Example II-10 | II | 0.50% |
| Example II-28 | Example II-11 | II | 0.50% |
| Example II-29 | Example II-12 | II | 0.50% |
| Example II-30 | Example II-13 | II | 0.50% |
| Example II-31 | Example II-14 | II | 0.50% |
| Example II-32 | Example II-15 | II | 0.50% |
| Example II-33 | Example II-16 | II | 0.50% |
| Example II-34 | Example II-17 | II | 0.50% |
| Example II-35 | Example II-18 | II | 0.50% |
| Comparative Example II-4 | Comparative Example II-1 | II | 0.50% |
| Comparative Example II-5 | Comparative Example II-2 | II | 0.50% |
| Comparative Example II-6 | Comparative Example II-3 | II | 0.50% |
| Control | — | II | — |

TABLE II-2

| lubricant oil composition | hindered phenol compound | aromatic amine | hindered phenol compound amount | aromatic amine amount | lubricant base oil |
|---|---|---|---|---|---|
| Comparative Example II-7 | 2,2'-thiobis[3-(3,5-ditert-butyl-4-hydroxyl phenyl)propionic acid ethyl ester] | — | 0.50% | — | II |
| Comparative Example II-8 | — | N-(4-tert-octyl phenyl)-1-naphthylamine | — | 0.50% | II |
| Comparative Example II-9 | 2,6-ditert-butyl-4-amylthiophenol | 4,4'-ditert-octyl diphenyl amine | 0.25% | 0.25% | II |
| Comparative Example II-10 | 4,4'-[thiobismethylene]bis[2,6-ditert-butyl phenol] | 3,7-ditert-octyl phenothiazine | 0.30% | 0.20% | II |

The lubricant oil compositions of Example II-19 to Example II-35, the lubricant oil compositions of Comparative Example II-4 to Comparative Example II-10 and the Control were taken as test samples, to evaluate the oxidation resistance at elevated temperatures, with a PDSC temperature of 210 degrees Celsius, the results of were shown in Table II-3.

TABLE II-3

| lubricant oil composition | PDSC oxidative induction period (min) |
|---|---|
| Example II-19 | 17.5 |
| Example II-20 | 21.3 |
| Example II-21 | 19.7 |
| Example II-22 | 20.1 |
| Example II-23 | 22.6 |
| Example II-24 | 18.7 |
| Example II-25 | 17.6 |
| Example II-26 | 26.1 |
| Example II-27 | 21.3 |
| Example II-28 | 22.6 |
| Example II-29 | 23.7 |
| Example II-30 | 22.5 |
| Example II-31 | 20.3 |
| Example II-32 | 18.9 |
| Example II-33 | 22.4 |
| Example II-34 | 16.3 |
| Example II-35 | 17.1 |
| Comparative Example II-4 | 4.9 |
| Comparative Example II-5 | 7.5 |
| Comparative Example II-6 | 16.1 |
| Comparative Example II-7 | 8.6 |
| Comparative Example II-8 | 15.2 |
| Comparative Example II-9 | 5.3 |
| Comparative Example II-10 | 7.1 |
| Control | 0.2 |

The lubricant oil compositions of Example II-19 to Example II-35, the lubricant oil compositions of Comparative Example II-4 to Comparative Example II-10 and the Control were taken as test samples, to evaluate the deposite formation inhibition performance, the results were shown in Table II-4.

TABLE II-4

| lubricant oil composition | deposit amount (mg) |
|---|---|
| Example II-22 | 16.9 |
| Example II-25 | 15.1 |
| Example II-29 | 10.8 |
| Example II-31 | 13.5 |
| Example II-34 | 6.8 |
| Example II-35 | 7.1 |
| Comparative Example II-4 | 19.5 |
| Comparative Example II-5 | 23.4 |
| Comparative Example II-6 | 20.8 |
| Comparative Example II-7 | 21.6 |
| Comparative Example II-8 | 25.6 |
| Comparative Example II-9 | 19.2 |
| Comparative Example II-10 | 18.5 |
| Control | 32.8 |

The lubricant oil compositions of Example II-19 to Example II-35, the lubricant oil compositions of Comparative Example II-4 to Comparative Example II-10 and the Control were taken as test samples, to evaluate the anticorrosion performance. The results of BRT (ball rust test) were shown in Table II-5.

TABLE II-5

| lubricant oil composition | corrosion degree |
|---|---|
| Example II-22 | slight |
| Example II-25 | slight |
| Example II-29 | slight |
| Example II-31 | moderate |
| Example II-34 | slight |
| Example II-35 | slight |
| Comparative Example II-4 | moderate |
| Comparative Example II-5 | moderate |
| Comparative Example II-6 | moderate |
| Comparative Example II-7 | moderate |
| Comparative Example II-8 | moderate |
| Comparative Example II-9 | moderate |
| Comparative Example II-10 | moderate |
| Control | severe |

The lubricant oil compositions of Example II-19 to Example II-35, the lubricant oil compositions of Comparative Example II-4 to Comparative Example II-10 and the Control were taken as test samples, to evaluate the performances of inhibiting increase in viscosity and inhibiting increase in acid value, the results of were shown in Table II-6.

TABLE II-6

| lubricant oil composition | increase in viscosity (%) | increase in acid value (mgKOH·g$^{-1}$) |
|---|---|---|
| Example II-19 | 25.7 | 2.523 |
| Example II-20 | 21.3 | 1.967 |
| Example II-21 | 20.9 | 2.031 |
| Example II-22 | 23.4 | 1.834 |
| Example II-23 | 21.6 | 2.007 |
| Example II-24 | 19.9 | 1.679 |
| Example II-25 | 21.5 | 1.372 |
| Example II-26 | 18.7 | 2.021 |
| Example II-27 | 19.3 | 2.318 |
| Example II-28 | 21.7 | 1.936 |
| Example II-29 | 20.6 | 2.217 |
| Example II-30 | 22.3 | 1.894 |
| Example II-31 | 19.3 | 2.334 |
| Example II-32 | 21.5 | 2.119 |
| Example II-33 | 24.3 | 1.793 |
| Example II-34 | 23.8 | 2.106 |
| Example II-35 | 21.5 | 1.984 |
| Comparative Example II-4 | 33.5 | 4.621 |
| Comparative Example II-5 | 27.5 | 3.482 |
| Comparative Example II-6 | 25.8 | 5.168 |
| Comparative Example II-7 | 27.6 | 2.953 |
| Comparative Example II-8 | 30.5 | 3.846 |
| Comparative Example II-9 | 28.1 | 5.429 |
| Comparative Example II-10 | 24.7 | 6.517 |
| Control | 67.2 | 24.525 |

Example III-1

To a 500 ml four-necked flask equipped with a stirrer, a thermometer, a condensing tube and a dropping funnel, there were added 58.79 g (0.323 mol) 2-tert-butyl-6-mercapto-phenol, 6.88 g (0.048 mol) boron trifluoride.diethyl ether (an alkylation catalyst), 100 ml n-hexane (as the solvent) and 161.61 g (0.162 mol) polyisobutene (Mn=1000, from Jilin Chemical Group Fine Chemicals Co., Ltd.), reacted at 80 degrees Celsius for 2 h. Upon completion of the reaction, the reaction mixture was washed once with a 5 wt % KOH aqueous solution, and then washed with hot water till neutral to remove any catalyst, and then vacuum distillated to remove any solvent and unreacted phenols, to obtain a polyisobutenyl thiophenol, having a hydroxyl value of 53.49 mgKOH/g. The hydroxyl value was determined by referring to the acetic anhydride method in GB/T7383-2007.

The reaction procedure can be illustrated as follows.

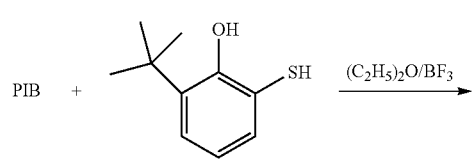

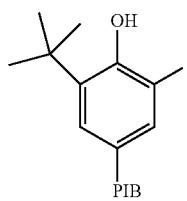

On the $^1$H-NMR spectra of the produced polyisobutenyl thiophenol, the peak at the chemical shift of 1.40 was identified as the characteristic peak of the hydrogen of the tert-butyl on the benzene ring; the single peak at the chemical shift of 3.58 was identified as the characteristic peak of the hydrogen of the mercapto on the benzene ring; the single peak at the chemical shift of 4.84 was identified as the characteristic peak of the hydrogen of the hydroxyl on the benzene ring; the single peak at the chemical shift of 7.12 and that at 7.20 were respectively identified as the characteristic peak of the two hydrogens on the benzene ring. If the integral of the hydrogen of the hydroxyl on the benzene ring is defined as 1, the value of the integral ratio between the hydrogen on the benzene ring, the hydrogen of the mercapto and the hydrogen of the hydroxyl were calculated as 0.95: 0.97:1.05:0.94, approximating to the theoretical value of 1:1:1:1. As can be seen from this NMR spectra analysis, the polyisobutenyl thiophenol was obtained as anticipated.

Example III-2

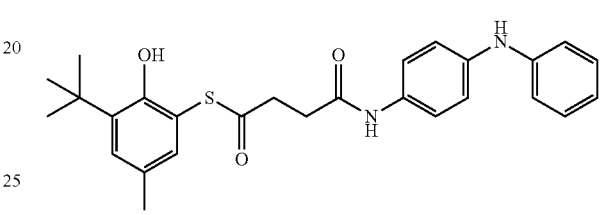

Under the protective atmosphere of nitrogen gas, to a 250 ml four-necked flask equipped with a stirrer, a thermometer, a condensing tube and a dropping funnel, there were added 30.58 g (156 mmol) 2-mercapto-4-methyl-6-methyl phenol, 11.21 g (112 mmol) succinic anhydride, 32.38 g (176 mmol) N-phenyl p-phenylene diamine, 3.45 g (25 mmol) potassium carbonate and 100 mL acetone, rapidly stirred, reacted at the room temperature for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.40 (9H), 2.37 (3H), 2.86 (2H), 3.01 (2H), 4.84 (1H), 6.95-7.26 (11H), 7.45 (1H), 7.55 (1H);

$^{13}$C NMR (75 MHz, CDCl$_3$): δ 21.2, 30.1, 34.5, 36.4, 39.3, 114.3, 119.4, 121.8, 125.8, 129.5, 132.3, 133.5, 137.5, 146.1, 153.5, 174.0, 196.9;

C$_{27}$H$_{30}$N$_2$O$_3$S (calculated): C, 70.10; H, 6.54; N, 6.06; O, 10.38; S, 6.93. (measured): C, 70.03; H, 6.54; N, 6.01; O, 10.47; S, 6.85.

Example III-3

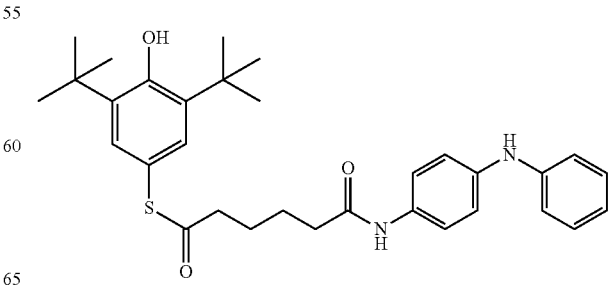

Under the protective atmosphere of nitrogen gas, to a 250 ml four-necked flask equipped with a stirrer, a thermometer, a condensing tube and a dropping funnel, there were added 31.65 g (133 mmol) 2,6-di-tert-butyl-4-mercaptophenol, 7.94 g (62 mmol) adipic anhydride, 28.15 g (153 mmol) N-phenyl p-phenylene diamine, 0.79 g (7.5 mmol) sodium carbonate and 100 mL isopropanol, rapidly stirred, reacted at the room temperature for 24 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 1.57 (2H), 1.72 (2H), 2.23 (2H), 2.66 (2H), 5.32 (2H), 6.97-7.26 (9H), 7.45 (1H), 7.48 (2H), 7.55 (1H);

$^{13}$C NMR (75 MHz, CDCl$_3$): δ 24.9, 25.4, 29.6, 34.6, 37.8, 43.5, 114.3, 119.3, 121.8, 123.8, 126.2, 132.3, 136.5, 137.5, 146.1, 153.4, 171.6, 196.9;

C$_{32}$H$_{40}$N$_2$O$_3$S (calculated): C, 72.14; H, 7.57; N, 5.26; O, 9.01; S, 6.02. (measured): C, 72.24; H, 7.59; N, 5.18; O, 9.05; S, 5.95.

Example III-4

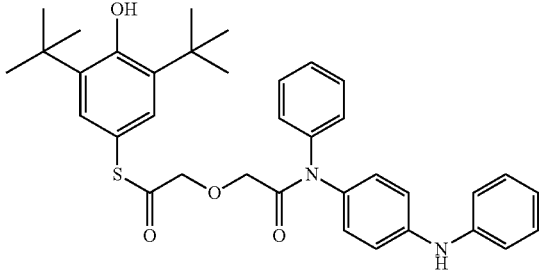 [SMILES: CC(C)(C)c1cc(SC(=O)COCC(=O)N(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 8.57 g (36 mmol) 2,6-di-tert-butyl-4-mercaptophenol, 2.56 g (15 mmol) 2,2'-oxydiacetyl chloride, 10.14 g (39 mmol) N,N'-diphenyl-1,4-phenylene diamine and 100 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 4.11 (2H), 4.33 (2H), 5.32 (1H), 6.97-7.48 (16H), 7.55 (1H);

$^{13}$C NMR (75 MHz, CDCl$_3$): δ 29.6, 34.6, 69.2, 71.9, 116.6, 119.3, 121.8, 126.2, 127.3, 127.7, 129.1, 129.5, 136.5, 141.9, 142.8, 146.1, 153.5, 165.1, 189.9;

C$_{36}$H$_{40}$N$_2$O$_4$S (calculated): C, 72.45; H, 6.76; N, 4.69; O, 10.72; S, 5.37. (measured): C, 72.40; H, 6.71; N, 4.72; O, 10.78; S, 5.35.

Example III-5

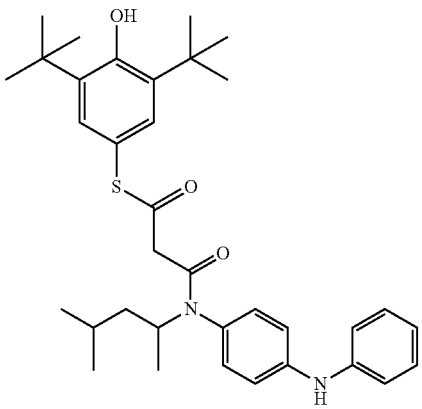 [SMILES: CC(C)CC(C)N(C(=O)CC(=O)Sc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 16.22 g (115 mmol) malonyl dichloride, 18.49 g (69 mmol) N-(1,3-dimethylbutyl)-N'-phenyl p-phenylene diamine, 0.76 g (7.2 mmol) sodium carbonate and 150 mL acetonitrile, rapidly stirred, reacted at the room temperature for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11 (3H), 1.36 (15H), 1.54-1.72 (6H), 3.67-3.91 (3H), 5.32 (1H), 6.80-7.17 (11H), 7.55 (1H);

$^{13}$C NMR (75 MHz, CDCl$_3$): δ 17.92, 22.4, 24.6, 29.6, 31.9, 34.6, 44.6, 52.7, 53.1, 115.4, 116.6, 119.4, 121.8, 126.2, 129.5, 131.4, 136.6, 142.8, 146.1, 153.5, 161.7, 187.6;

C$_{35}$H$_{46}$N$_2$O$_3$S (calculated): C, 73.13; H, 8.07; N, 4.87; O, 8.35; S, 5.58. (measured): C, 73.08; H, 8.01; N, 4.84; O, 8.42; S, 5.63.

Example III-6

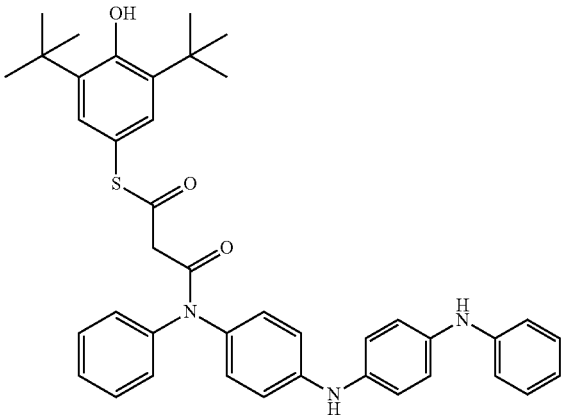 [SMILES: CC(C)(C)c1cc(SC(=O)CC(=O)N(c2ccccc2)c2ccc(Nc3ccc(Nc4ccccc4)cc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 3.57 g (15 mmol) 2,6-di-tert-butyl-4-mercaptophenol, 8.74 g (62 mmol) malonyl dichloride, 21.76 g (103 mmol) N-phenyl-N'[4-(phenylamino)phenyl]-1,4-phenylene diamine and 100 mL toluene, rapidly stirred, reacted at 110 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 3.79 (2H), 5.32 (1H), 6.97-7.17 (14H), 7.20 (1H), 7.22-7.35 (6H), 7.55 (1H);

$^{13}$C NMR (75 MHz, CDCl$_3$): δ 29.6, 34.6, 52.8, 114.3, 116.3, 117.7, 119.3, 121.8, 126.2, 126.7, 127.3, 129.3, 132.4, 136.5, 141.9, 142.8, 143.3, 146.1, 153.5, 162.1, 186.2;

$C_{41}H_{43}N_3O_3S$ (calculated): C, 74.85; H, 6.59; N, 6.39; O, 7.30; S, 4.87. (measured): C, 74.81; H, 6.51; N, 6.45; O, 7.24; S, 4.85.

Example III-7

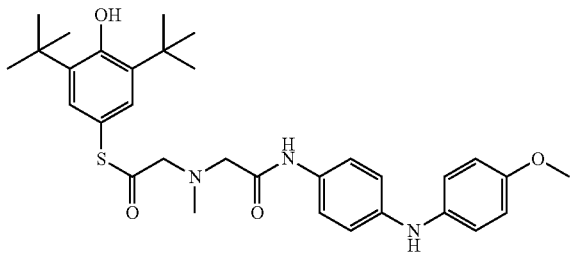 [SMILES: COc1ccc(Nc2ccc(NC(=O)CN(C)CC(=O)Sc3cc(C(C)(C)C)c(O)c(C(C)(C)C)c3)cc2)cc1]

Under the protective atmosphere of nitrogen gas, to a 250 ml four-necked flask equipped with a stirrer, a thermometer, a condensing tube and a dropping funnel, there were added 34.51 g (145 mmol) 2,6-di-tert-butyl-4-mercaptophenol, 5.11 g (35 mmol) N-methyl iminodiacetic acid, 4.49 g (21 mmol) 4-amino-4'-methoxy diphenyl amine, 0.28 g (2.6 mmol) sodium carbonate and 100 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 2.27 (3H), 3.73 (2H), 3.76 (3H), 4.06 (2H), 5.23 (1H), 6.97-7.17 (8H), 7.20 (1H), 7.48 (2H), 8.24 (1H);

$^{13}$C NMR (75 MHz, CDCl$_3$): δ 29.6, 34.6, 45.2, 55.0, 55.5, 114.3, 119.3, 120.6, 121.5, 126.2, 132.3, 136.5, 137.5, 153.4, 154.5, 163.1, 192.6;

$C_{32}H_{41}N_3O_4S$ (calculated): C, 68.18; H, 7.33; N, 7.45; O, 11.35; S, 5.69. (measured): C, 68.11; H, 7.29; N, 7.52; O, 11.38; S, 5.57.

Example III-8

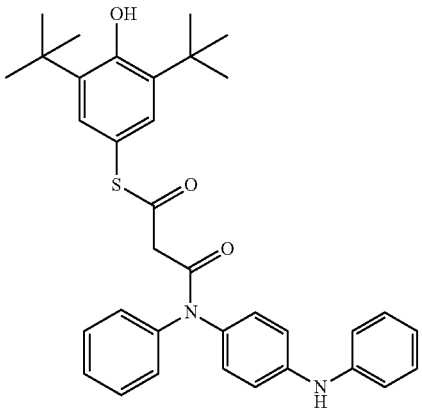 [SMILES: CC(C)(C)c1cc(SC(=O)CC(=O)N(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 0.99 g (9.51 mmol) malonic acid, 6.51 g (25 mmol) N,N'-diphenyl-1,4-phenylene diamine, 0.65 g (6.5 mmol) potassium hydrogen carbonate and 150 mL toluene, rapidly stirred, reacted at 150 degrees Celsius for 6 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 3.85 (2H), 5.32 (1H), 6.80-7.17 (10H), 7.27 (4H), 7.35 (2H), 7.55 (1H);
$^{13}$C NMR (75 MHz, CDCl$_3$): δ 29.6, 34.6, 52.6, 116.6, 119.4, 121.8, 122.6, 126.2, 127.7, 129.5, 136.6, 142.8, 146.1, 153.4, 161.8, 186.3; $C_{35}H_{38}N_2O_3S$ (calculated): C, 74.17; H, 6.76; N, 4.94; O, 8.47; S, 5.66. (measured): C, 74.25; H, 6.81; N, 4.83; O, 8.41; S, 5.59.

Example III-9

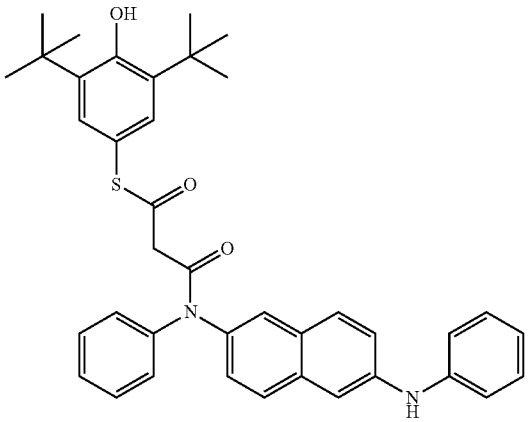 [SMILES: CC(C)(C)c1cc(SC(=O)CC(=O)N(c2ccccc2)c2ccc3cc(Nc4ccccc4)ccc3c2)cc(C(C)(C)C)c1O]

Under the protective atmosphere of nitrogen gas, to a 250 ml four-necked flask equipped with a stirrer, a thermometer, a condensing tube and a dropping funnel, there were added 8.33 g (35 mmol) 2,6-di-tert-butyl-4-mercaptophenol, 7.19 g (51 mmol) malonyl dichloride, 9.61 g (31 mmol) N,N'-diphenyl-2,6-naphthalene diamine, 0.68 g (4.9 mmol) potassium hydrogen carbonate and 150 mL toluene, rapidly stirred, reacted at 110 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 3.84 (2H), 5.32 (1H), 5.80 (1H), 7.00-7.84 (18H);

$^{13}$C NMR (75 MHz, CDCl$_3$): δ 29.6, 34.6, 52.8, 106.9, 111.0, 116.5, 119.9, 120.7, 121.8, 126.2, 127.7, 128.9, 129.1, 136.5, 140.8, 142.8, 153.5, 160.5, 186.2;

C$_{39}$H$_{40}$N$_2$O$_3$S (calculated): C, 75.94; H, 6.54; N, 4.54; O, 7.78; S, 5.20. (measured): C, 75.85; H, 6.51; N, 4.63; O, 7.72; S, 5.23.

Example III-10

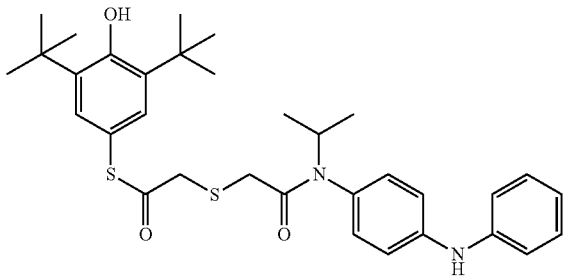 [SMILES: CC(C)N(C(=O)CSCC(=O)Sc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 6.19 g (26 mmol) 2,6-di-tert-butyl-4-mercaptophenol, 16.38 g (92 mmol) thiodipropionic acid, 3.84 g (17 mmol) N-isopropyl-N'-phenyl p-phenylene diamine and 150 mL toluene, rapidly stirred, reacted at 80 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.19 (6H), 1.36 (18H), 3.74 (1H), 3.94 (2H), 3.96 (2H), 5.32 (1H), 6.80-7.26 (11H), 7.55 (1H);

$^{13}$C NMR (75 MHz, CDCl$_3$): δ 20.6, 29.6, 34.6, 34.7, 41.9, 48.2, 116.6, 119.3, 121.8, 126.2, 129.5, 136.5, 139.6, 142.8, 146.1, 153.5, 166.2, 189.8;

C$_{33}$H$_{42}$N$_2$O$_3$S$_2$ (calculated): C, 68.48; H, 7.31; N, 4.84; O, 8.29; S, 11.08. (measured): C, 68.41; H, 7.28; N, 4.91; O, 8.30; S, 11.11.

Example III-11

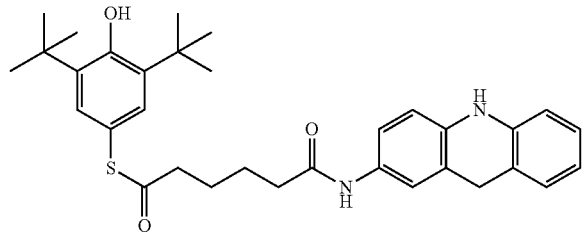 [SMILES: CC(C)(C)c1cc(SC(=O)CCCCC(=O)Nc2ccc3c(c2)Cc2ccccc2N3)cc(C(C)(C)C)c1O]

Under the protective atmosphere of nitrogen gas, to a 250 ml four-necked flask equipped with a stirrer, a thermometer, a condensing tube and a dropping funnel, there were added 4.99 g (21 mmol) 2,6-di-tert-butyl-4-mercaptophenol, 6.78 g (53 mmol) adipic anhydride, 5.70 g (31 mmol) N-phenyl p-phenylene diamine and 150 mL ethanol, rapidly stirred, reacted at 60 degrees Celsius for 2 h, cooled to the room temperature, there were added 7.05 g (85 mmol) formaldehyde, heated to 85 degrees Celsius and reacted for 2.5 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 1.57-2.66 (8H), 4.15 (2H), 5.32 (1H), 6.80-7.24 (9H), 8.73 (1H);

$^{13}$C NMR (75 MHz, CDCl$_3$): δ 24.9, 25.3, 29.6, 32.6, 34.6, 37.8, 43.6, 113.0, 116.3, 118.9, 119.2, 123.3, 123.9, 124.6, 126.2, 127.9, 136.5, 139.5, 140.5, 153.4, 174.0, 196.9;

C$_{33}$H$_{40}$N$_2$O$_3$S (calculated): C, 72.76; H, 7.40; N, 5.14; O, 8.81; S, 5.89. (measured): C, 72.69; H, 7.35; N, 5.23; O, 8.78; S, 5.83.

Example III-12

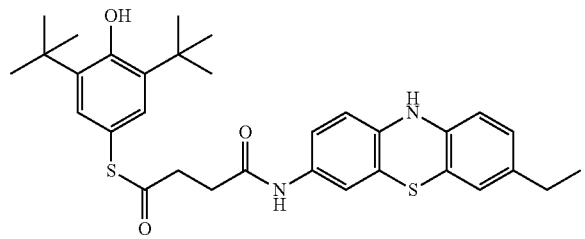 [SMILES: CCc1ccc2c(c1)Sc1cc(NC(=O)CCC(=O)Sc3cc(C(C)(C)C)c(O)c(C(C)(C)C)c3)ccc1N2]

Under the protective atmosphere of nitrogen gas, to a 250 ml four-necked flask equipped with a stirrer, a thermometer, a condensing tube and a dropping funnel, there were added 19.52 g (82 mmol) 2,6-di-tert-butyl-4-mercaptophenol, 17.06 g (121 mmol) succinyl chloride, 19.93 g (94 mmol) 4-amino-4'-ethyl diphenyl amine, 2.22 g (16.1 mmol) potassium carbonate and 150 mL toluene, rapidly stirred, after reacted at the room temperature for 1 h, to the toluene layer, there were added 10.11 g (316 mmol) sulfur and 0.04 g (0.35 mmol) iodine, heated to 150 degrees Celsius and reacted for 8 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.23 (3H), 1.36 (18H), 2.61 (2H), 2.94 (2H), 3.09 (2H), 5.32 (1H), 5.70 (1H), 6.98-7.17 (7H), 7.93 (1H);

$^{13}$C NMR (75 MHz, CDCl$_3$): δ 15.60, 29.0, 29.6, 34.6, 36.1, 115.9, 116.1, 118.9, 124.9, 126.2, 127.9, 129.7, 136.6, 141.2, 146.2, 153.4, 174.0;

C$_{32}$H$_{38}$N$_2$O$_3$S (calculated): C, 68.29; H, 6.81; N, 4.98; O, 8.53; S, 11.40. (measured): C, 68.11; H, 6.75; N, 4.86; O, 8.59; S, 11.61.

Example III-13

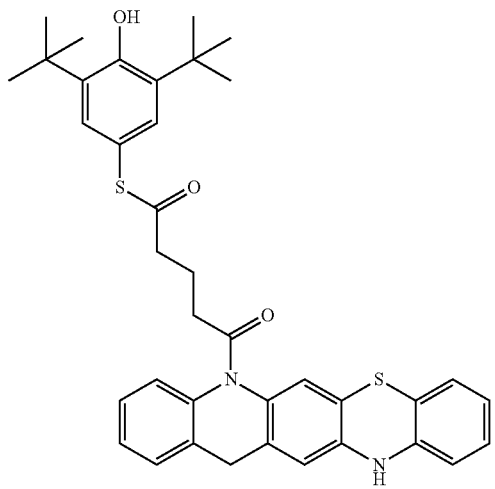 [SMILES: CC(C)(C)c1cc(SC(=O)CCCC(=O)N2c3ccccc3Cc3cc4c(cc32)Sc2ccccc2N4)cc(C(C)(C)C)c1O]

Under the protective atmosphere of nitrogen gas, to a 250 ml four-necked flask equipped with a stirrer, a thermometer, a condensing tube and a dropping funnel, there were added 10.95 g (46 mmol) 2,6-di-tert-butyl-4-mercaptophenol, 8.11 g (48 mmol) glutaryl chloride, 13.78 g (53 mmol) N,N'-diphenyl-1,4-phenylene diamine and 150 mL trimethylbenzene, rapidly stirred, after reacted at 85 degrees Celsius for 1 h, there were added 3.82 g (46 mmol) formaldehyde, after reacted at 85 degrees Celsius for 1 h, cooled to the room temperature, there were added 10.11 g (316 mmol) sulfur and 0.27 g (2.11 mmol) iodine, heated to 180 degrees Celsius and reacted for 1 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 2.11-2.81 (6H), 4.21 (2H), 5.32 (1H), 6.44 (1H), 6.50-7.37 (12H);

$^{13}$C NMR (75 MHz, CDCl$_3$): δ 21.2, 29.6, 32.2, 34.6, 35.4, 43.0, 114.4, 116.0, 119.1, 120.6, 121.6, 124.3, 126.6, 127.0, 130.2, 133.8, 136.5, 141.1, 153.5, 166.3, 196.9;

C$_{38}$H$_{40}$N$_2$O$_3$S$_2$ (calculated): C, 71.66; H, 6.33; N, 4.40; O, 7.54; S, 10.07. (measured): C, 71.59; H, 6.28; N, 4.49; O, 7.51; S, 10.10.

Example III-14

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 12.55 g (89 mmol) malonyl dichloride, 6.62 g (36 mmol) N-phenyl p-phenylene diamine, 0.62 g (4.51 mmol) potassium carbonate and 150 mL isopropanol, rapidly stirred, reacted at 80 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (36H), 3.98 (4H), 5.32 (1H), 6.80-7.26 (13H), 7.55 (1H)

$^{13}$C NMR (75 MHz, CDCl$_3$): δ 29.6, 34.6, 52.1, 104.6, 116.6, 117.7, 119.3, 121.8, 124.6, 126.2, 129.45, 136.5, 142.8, 146.1, 153.5, 156.9, 186.8;

C$_{46}$H$_{56}$N$_2$O$_6$S$_2$ (calculated): C, 69.31; H, 7.08; N, 3.51; O, 12.04; S, 8.05. (measured): C, 69.25; H, 7.01; N, 3.57; O, 12.01; S, 7.99.

Example III-15

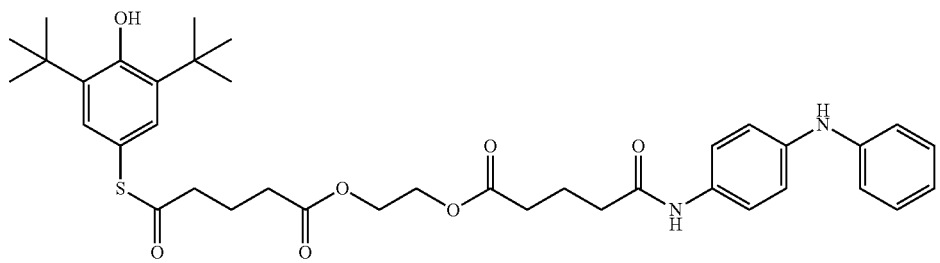 [SMILES: CC(C)(C)c1cc(SC(=O)CCCC(=O)OCCOC(=O)CCCC(=O)Nc2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 8.57 g (36 mmol) 2,6-di-tert-butyl-4-mercaptophenol, 26.68 g (92 mmol) glutaric acid 1,2-ethylene glycol ester, 13.06 g (71 mmol) N-phenyl p-phenylene diamine and 150 mL toluene, rapidly stirred, reacted at 90 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (12H), 1.54 (6H), 2.04 (4H), 2.29-2.67 (8H), 4.23 (4H), 5.32 (1H), 6.97-7.26 (9H), 7.45 (1H), 7.48 (2H), 7.55 (1H);

$^{13}$C NMR (75 MHz, CDCl$_3$): δ 20.9, 21.3, 29.6, 31.98, 33.9, 34.6, 34.9, 43.0, 62.0, 114.3, 115.9, 119.3, 121.8, 126.2, 129.5, 132.3, 136.5, 137.5, 146.1, 153.5, 171.6, 173.5, 196.9;

C$_{38}$H$_{48}$N$_2$O$_7$S (calculated): C, 67.43; H, 7.15; N, 4.14; O, 16.55; S, 4.74. (measured): C, 67.53; H, 7.19; N, 4.08; O, 16.47; S, 4.76.

Example III-16

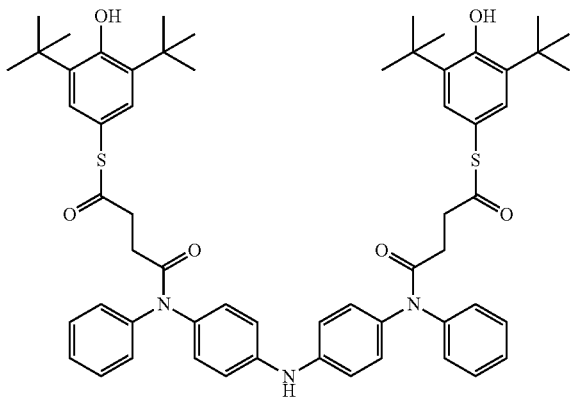 [SMILES: CC(C)(C)c1cc(SC(=O)CCC(=O)N(c2ccccc2)c2ccc(Nc3ccc(N(C(=O)CCC(=O)Sc4cc(C(C)(C)C)c(O)c(C(C)(C)C)c4)c4ccccc4)cc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 18.56 g (78 mmol) 2,6-di-tert-butyl-4-mercaptophenol, 11.21 g (92 mmol) succinic acid, 11.23 g (32 mmol) N-phenyl-N'-[4-(phenylamino)phenyl]-1,4-phenylene diamine and 150 mL toluene, rapidly stirred, reacted at 100 degrees Celsius for 3 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36-1.54 (36H), 2.89-3.19 (8H), 5.32 (2H), 6.80-7.35 (22H), 7.55 (1H);

$^{13}$C NMR (75 MHz, CDCl$_3$): δ 29.6, 34.4, 35.5, 37.8, 93.8, 116.6, 122.5, 126.2, 127.6, 129.2, 141.9, 142.8, 143.3, 15.7, 173.2, 196.9;

C$_{60}$H$_{69}$N$_3$O$_6$S$_2$ (calculated): C, 72.62; H, 7.01; N, 4.23; O, 9.67; S, 6.46. (measured): C, 72.65; H, 7.07; N, 4.26; O, 9.61; S, 6.42.

Example III-17

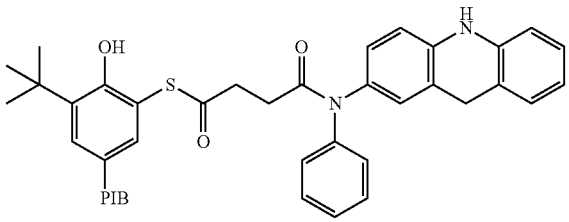

Under the protective atmosphere of nitrogen gas, to a 250 ml four-necked flask equipped with a stirrer, a thermometer, a condensing tube and a dropping funnel, there were added 47.16 g (45 mmol) polyisobutenyl thiophenol produced by Example III-1, 5.11 g (51 mmol) succinic anhydride, 9.75 g (53 mmol) N-phenyl p-phenylene diamine, 0.86 g (8.15 mmol) sodium carbonate and 150 mL benzene, rapidly stirred, reacted at 80 degrees Celsius for 2.5 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.88, 0.99, 1.02, 1.40, 1.41, 1.46, 1.52, 1.64, 1.68, 1.92, 2.21-2.29, 2.57, 2.74, 4.86, 6.97, 7.00, 7.02, 7.26, 7.35, 7.55;

$^{13}$C NMR (75 MHz, CDCl$_3$): δ 23.9, 24.9, 25.4, 28.2, 30.1, 34.5, 34.5, 35.4, 38.4, 43.6, 51.1, 116.0, 117.7, 119.4, 121.8, 126.7, 129.5, 133.6, 142.8, 146.1, 154.5, 173.3.

Example III-18

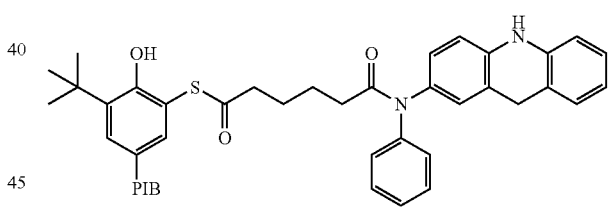

Under the protective atmosphere of nitrogen gas, to a 250 ml four-necked flask equipped with a stirrer, a thermometer, a condensing tube and a dropping funnel, there were added 29.34 g (28 mmol) polyisobutenyl thiophenol produced by Example III-1, 2.91 g (35 mmol) adipoyl dichloride, 6.24 g (24 mmol) N,N'-diphenyl-1,4-phenylene diamine, 0.34 g (3.2 mmol) sodium carbonate and 150 mL benzene, rapidly stirred, reacted at 60 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.82, 0.99, 1.02, 1.40, 1.46, 1.52, 1.60, 1.68, 1.92, 2.21-2.29, 2.59, 2.74, 4.86, 6.80, 6.97, 7.02, 7.17, 7.26, 7.55;

$^{13}$C NMR (75 MHz, CDCl$_3$): δ 23.9, 25.0, 25.4, 28.2, 30.1, 34.5, 35.3, 38.4, 43.6, 48.6, 51.1, 116.6, 119.4, 121.8, 125.2, 126.8, 127.3, 129.5, 133.6, 142.8, 143.3, 146.1, 154.5, 173.3.

Example III-19

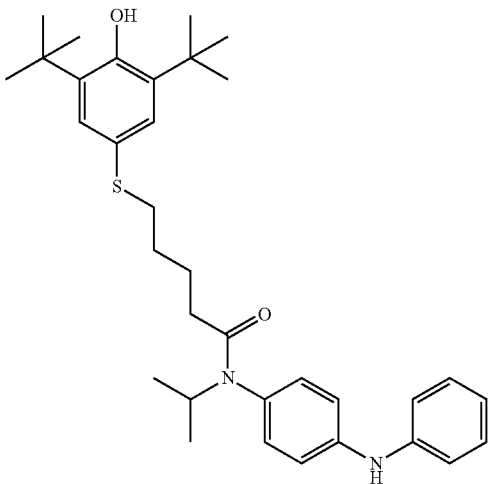 [SMILES: CC(C)N(C(=O)CCCCSc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 6.19 g (26 mmol) 2,6-di-tert-butyl-4-mercaptophenol, 13.64 g (88 mmol) 5-chloro-valeryl chloride, 3.84 g (17 mmol) N-isopropyl-N'-phenyl p-phenylene diamine, 1.23 g (12.3 mmol) potassium hydrogen carbonate and 150 mL toluene, rapidly stirred, reacted at 80 degrees Celsius for 2 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 1.19 (6H), 1.36 (18H), 1.55-1.97 (4H), 2.03 (2H), 2.86 (2H), 3.74 (1H), 5.32 (1H), 6.80-7.26 (11H), 7.55 (1H);
$^{13}$C NMR (75 MHz, CDCl$_3$): δ 20.6, 25.0, 28.3, 29.6, 34.6, 35.5, 48.2, 116.6, 119.3, 121.8, 126.2, 129.5, 136.5, 139.6, 142.8, 146.1, 153.5, 169.9;
C$_{34}$H$_{46}$N$_2$O$_2$S (calculated): C, 74.68; H, 8.48; N, 5.12; O, 5.85; S, 5.86. (measured): C, 74.61; H, 8.42; N, 5.19; O, 5.83; S, 5.91.

Example III-20

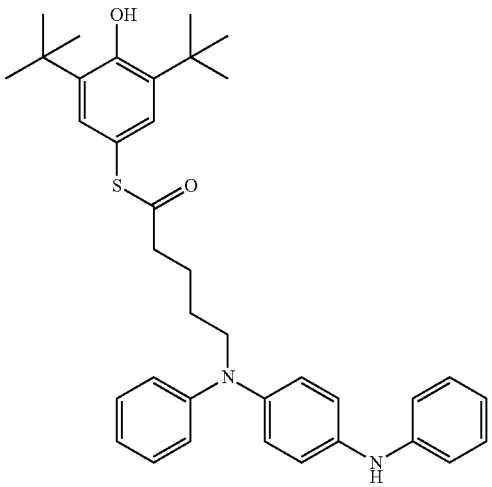 [SMILES: CC(C)(C)c1cc(SC(=O)CCCCN(c2ccccc2)c2ccc(Nc3ccccc3)cc2)cc(C(C)(C)C)c1O]

Under the protective atmosphere of nitrogen gas, to a 250 ml four-necked flask equipped with a stirrer, a thermometer, a condensing tube and a dropping funnel, there were added 21.66 g (91 mmol) 2,6-di-tert-butyl-4-mercaptophenol, 1.47 g (9.51 mmol) 5-chloro-valeryl chloride, 6.51 g (25 mmol) N,N'-diphenyl-1,4-phenylene diamine, 0.65 g (6.5 mmol) potassium hydrogen carbonate and 150 mL benzene, rapidly stirred, reacted at 75 degrees Celsius for 6 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 1.36 (18H), 1.70-1.97 (4H), 2.54 (2H), 3.47 (2H), 5.32 (1H), 6.80-7.26 (16H), 7.55 (1H);
$^{13}$C NMR (75 MHz, CDCl$_3$): δ 24.7, 27.3, 29.6, 34.6, 43.3, 46.8, 117.7, 119.3, 121.8, 126.2, 129.5, 136.5, 142.8, 146.1, 148.7, 153.5, 169.9;
C$_{37}$H$_{44}$N$_2$O$_2$S (calculated): C, 76.51; H, 7.64; N, 4.82; O, 5.51; S, 5.52. (measured): C, 76.61; H, 7.66; N, 4.71; O, 5.57; S, 5.58.

Example III-21

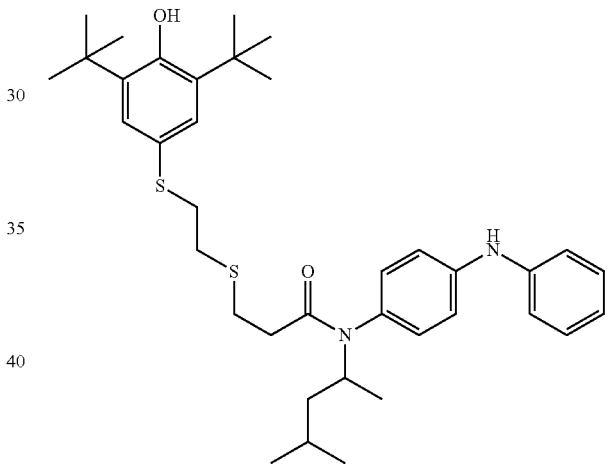

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 16.22 g (115 mmol) malonyl dichloride, 18.49 g (69 mmol) N-(1,3-dimethyl butyl)-N'-phenyl p-phenylene diamine, 0.76 g (7.2 mmol) sodium carbonate and 150 mL acetonitrile, rapidly stirred, reacted at the room temperature for 3 h. Upon completion of the reaction, the solvent and water (generated during the reaction) were removed by vacuum distillation, the titled hindered phenol compound was obtained by using column chromatography.

The compound was characterized as follows:
$^1$H NMR (300 MHz, CDCl$_3$): δ 0.80 (6H), 1.11 (3H), 1.36 (18H), 1.54-1.73 (3H), 2.54-3.28 (8H), 3.65 (1H), 5.32 (1H), 6.80-7.26 (11H), 7.55 (1H);
$^{13}$C NMR (75 MHz, CDCl$_3$): δ 17.9, 22.4, 24.6, 29.6, 31.85, 34.6, 40.1, 44.9, 52.8, 111.8, 119.3, 121.8, 126.2, 129.5, 131.1, 136.5, 142.8, 146.1, 148.7, 153.5, 168.4;
C$_{37}$H$_{52}$N$_2$O$_2$S$_2$ (calculated): C, 71.57; H, 8.44; N, 4.51; O, 5.15; S, 10.33. (measured): C, 71.51; H, 8.55; N, 4.66; O, 5.05; S, 10.25.

Comparative Example III-1

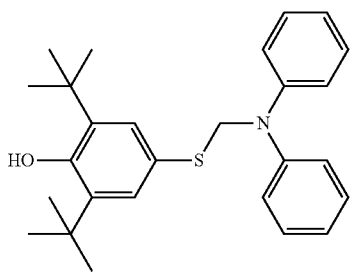 [SMILES: CC(C)(C)c1cc(SCN(c2ccccc2)c2ccccc2)cc(C(C)(C)C)c1O]

Under the protective atmosphere of nitrogen gas, to a 250 ml four-necked flask equipped with a stirrer, a thermometer, a condensing tube and a dropping funnel, there were added 20.23 g (85 mmol) 2,6-di-tert-butyl-4-mercaptophenol, 7.22 g (87 mmol) formaldehyde, 14.37 g (85 mmol) diphenyl amine and 150 mL methanol, rapidly stirred, reacted at 60 degrees Celsius for 2 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.36 (18H), 5.21 (2H), 5.32 (1H), 6.99 (6H), 7.17 (2H), 7.27 (4H);

$^{13}$C NMR (75 MHz, CDCl$_3$): δ 29.6, 34.6, 55.2, 120.4, 123.3, 125.9, 126.2, 129.2, 136.6, 150.0, 153.5;

C$_{27}$H$_{33}$NOS (calculated): C, 77.28; H, 7.93; N, 3.34; O, 3.81; S, 7.64. (measured): C, 77.22; H, 7.89; N, 3.31; O, 3.83; S, 7.67.

Comparative Example III-2

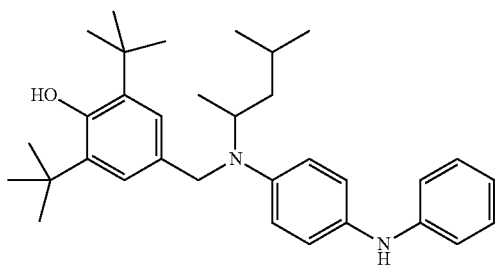 [SMILES: CC(C)CC(C)N(Cc1cc(C(C)(C)C)c(O)c(C(C)(C)C)c1)c1ccc(Nc2ccccc2)cc1]

Under the protective atmosphere of nitrogen gas, to a 250 ml four-necked flask equipped with a stirrer, a thermometer, a condensing tube and a dropping funnel, there were added 10.71 g (52 mmol) 2,6-di-tert-butyl-4-mercaptophenol, 1.89 g (63 mmol) formaldehyde, 17.42 g (65 mmol) N-(1,3-dimethyl butyl)-N'-phenyl p-phenylene diamine and 150 mL methanol, rapidly stirred, reacted at 70 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 0.80 (6H), 1.11 (3H), 1.29 (1H), 1.36 (18H), 3.45 (1H), 4.53 (2H), 5.32 (2H), 6.97-7.07 (9H), 7.26 (2H), 7.55 (1H);

$^{13}$C NMR (75 MHz, CDCl$_3$): δ 17.9, 22.40, 24.6, 30.4, 34.3, 45.7, 54.5, 56.7, 116.6, 120.4, 121.8, 125.9, 128.9, 129.5, 135.6, 146.1, 153.5, 154.8;

C$_{33}$H$_{46}$N$_2$O (calculated): C, 81.43; H, 9.53; N, 5.76; O, 3.29. (measured): C, 81.38; H, 9.51; N, 5.79; O, 3.31.

Comparative Example III-3

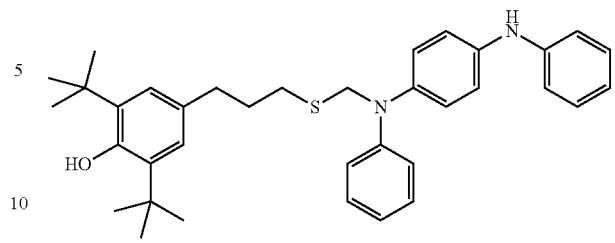

Under the protective atmosphere of nitrogen gas, to a 250 ml four-necked flask equipped with a stirrer, a thermometer, a condensing tube and a dropping funnel, there were added 9.24 g (33 mmol) 2,6-ditert-butyl-4-(3-mercaptopropyl) phenol, 3.07 g (37 mmol) formaldehyde, 11.71 g (45 mmol) N,N'-diphenyl-1,4-phenylene diamine and 150 mL benzene, rapidly stirred, reacted at 80 degrees Celsius for 4 h. Upon completion of the reaction, the solvent and water (generated during the reaction) were removed by vacuum distillation, the titled hindered phenol compound was obtained by using column chromatography.

The compound was characterized as follows:

$^1$H NMR (300 MHz, CDCl$_3$): δ 1.40 (18H), 1.99 (1H), 2.61-2.80 (6H), 4.63 (2H), 5.32 (1H), 6.97-7.02 (12H), 7.26 (4H), 7.55 (1H);

$^{13}$C NMR (75 MHz, CDCl$_3$): δ 28.7, 31.1, 34.3, 35.7, 54.1, 117.1, 119.4, 123.3, 124.8, 129.2, 131.8, 136.0, 142.8, 144.9, 146.1, 151.9;

C$_{36}$H$_{44}$N$_2$OS (calculated): C, 78.22; H, 8.02; N, 5.07; O, 2.89; S, 5.80. (measured): C, 78.27; H, 7.96; N, 4.98; O, 2.92; S, 5.83.

Example III-19 to Example III-35 and Comparative Example III-4 to Comparative Example III-8

Each of the hindered phenol compounds of Example III-2 to Example III-21 and Comparative Example III-1 to Comparative Example III-3 was respectively mixed with a lubricant base oil in line with the composition and ratio specified in Table III-1 at 40 degrees Celsius for 2 h, to obtain the lubricant oil compositions of Example III-22 to Example III-41 and the lubricant oil compositions of Comparative Example III-4 to Comparative Example III-6. Further, in line with the composition and ratio specified in Table III-2, the antioxidant was respectively mixed with a lubricant base oil at 40 degrees Celsius for 2 h, to obtain the lubricant oil compositions of Comparative Example III-7 to Comparative Example III-10. Herein, based on the total weight of each lubricant oil composition, the amount of the antioxidant to be used in each case was 0.5 wt %, the lubricant base oil used was a Group II hydrogenated base oil (produced by Sinopec Group, Gaoqiao Shanghai Branch). Further, the base oil without the antioxidant was taken as Control.

TABLE III-1

| lubricant oil composition | antioxidant | lubricant base oil | antioxidant amount |
|---|---|---|---|
| Example III-22 | Example III-2 | II | 0.50% |
| Example III-23 | Example III-3 | II | 0.50% |
| Example III-24 | Example III-4 | II | 0.50% |
| Example III-25 | Example III-5 | II | 0.50% |
| Example III-26 | Example III-6 | II | 0.50% |
| Example III-27 | Example III-7 | II | 0.50% |

TABLE III-1-continued

| lubricant oil composition | antioxidant | lubricant base oil | antioxidant amount |
|---|---|---|---|
| Example III-28 | Example III-8 | II | 0.50% |
| Example III-29 | Example III-9 | II | 0.50% |
| Example III-30 | Example III-10 | II | 0.50% |
| Example III-31 | Example III-11 | II | 0.50% |
| Example III-32 | Example III-12 | II | 0.50% |
| Example III-33 | Example III-13 | II | 0.50% |
| Example III-34 | Example III-14 | II | 0.50% |
| Example III-35 | Example III-15 | II | 0.50% |
| Example III-36 | Example III-16 | II | 0.50% |
| Example III-37 | Example III-17 | II | 0.50% |
| Example III-38 | Example III-18 | II | 0.50% |
| Example III-39 | Example III-19 | II | 0.50% |
| Example III-40 | Example III-20 | II | 0.50% |
| Example III-41 | Example III-21 | II | 0.50% |
| Comparative Example III-4 | Comparative Example III-1 | II | 0.50% |
| Comparative Example III-5 | Comparative Example III-2 | II | 0.50% |
| Comparative Example III-6 | Comparative Example III-3 | II | 0.50% |
| Control | — | II | — |

TABLE III-2

| lubricant oil composition | hindered phenol compound | aromatic amine | hindered phenol compound amount | aromatic amine amount | lubricant base oil |
|---|---|---|---|---|---|
| Comparative Example III-7 | 2,2'-thiobis[3-(3,5-ditert-butyl-4-hydroxyl phenyl)propionic acid ethyl ester] | — | 0.50% | — | II |
| Comparative Example III-8 | — | N-(4-tert-octyl phenyl)-1-naphthylamine | — | 0.50% | II |
| Comparative Example III-9 | 2,6-ditert-butyl-4-amylthiophenol | 4,4'-ditert-octyl diphenyl amine | 0.25% | 0.25% | II |
| Comparative Example III-10 | 4,4'-[thiobismethylene]bis[2,6-ditert-butyl phenol] | 3,7-ditert-octyl phenothiazine | 0.30% | 0.20% | II |

The lubricant oil compositions of Example III-22 to Example III-41, the lubricant oil compositions of Comparative Example III-4 to Comparative Example III-10 and the Control were taken as test samples, to evaluate the oxidation resistance at elevated temperatures, with a PDSC temperature of 210 degrees Celsius, the results of were shown in Table III-3.

TABLE III-3

| lubricant oil composition | PDSC oxidative induction period (min) |
|---|---|
| Example III-22 | 16.7 |
| Example III-23 | 18.9 |
| Example III-24 | 19.7 |
| Example III-25 | 21.3 |
| Example III-26 | 18.9 |
| Example III-27 | 22.3 |
| Example III-28 | 20.7 |
| Example III-29 | 26.3 |
| Example III-30 | 21.5 |
| Example III-31 | 19.3 |
| Example III-32 | 22.4 |
| Example III-33 | 20.7 |
| Example III-34 | 20.3 |
| Example III-35 | 19.6 |
| Example III-36 | 22.5 |
| Example III-37 | 16.7 |
| Example III-38 | 17.6 |
| Example III-39 | 17.3 |
| Example III-40 | 18.9 |
| Example III-41 | 20.1 |
| Comparative Example III-4 | 4.9 |
| Comparative Example III-5 | 7.5 |
| Comparative Example III-6 | 16.1 |
| Comparative Example III-7 | 8.6 |
| Comparative Example III-8 | 15.2 |
| Comparative Example III-9 | 5.3 |
| Comparative Example III-10 | 7.1 |
| Control | 0.2 |

The lubricant oil compositions of Example III-22 to Example III-41, the lubricant oil compositions of Comparative Example III-4 to Comparative Example III-10 and the Control were taken as test samples, to evaluate the deposite formation inhibition performance, the results were shown in Table III-4.

TABLE III-4

| lubricant oil composition | deposit amount (mg) |
|---|---|
| Example III-25 | 13.6 |
| Example III-28 | 12.1 |
| Example III-32 | 11.2 |
| Example III-34 | 15.7 |
| Example III-37 | 6.3 |
| Example III-38 | 4.8 |
| Example III-39 | 10.7 |
| Example III-41 | 12.5 |

TABLE III-4-continued

| lubricant oil composition | deposit amount (mg) |
|---|---|
| Comparative Example III-4 | 19.5 |
| Comparative Example III-5 | 23.4 |
| Comparative Example III-6 | 20.8 |
| Comparative Example III-7 | 21.6 |
| Comparative Example III-8 | 25.6 |
| Comparative Example III-9 | 19.2 |
| Comparative Example III-10 | 18.5 |
| Control | 32.8 |

The lubricant oil compositions of Example III-22 to Example III-41, the lubricant oil compositions of Comparative Example III-4 to Comparative Example III-10 and the Control were taken as test samples, to evaluate the anticorrosion performance. The results of BRT (ball rust test) were shown in Table III-5.

TABLE III-5

| lubricant oil composition | corrosion degree |
|---|---|
| Example III-25 | slight |
| Example III-28 | slight |
| Example III-32 | slight |
| Example III-34 | moderate |
| Example III-37 | slight |
| Example III-38 | slight |
| Example III-39 | slight |
| Example III-41 | slight |
| Comparative Example III-4 | moderate |
| Comparative Example III-5 | moderate |
| Comparative Example III-6 | moderate |
| Comparative Example III-7 | moderate |
| Comparative Example III-8 | moderate |
| Comparative Example III-9 | moderate |
| Comparative Example III-10 | moderate |
| Control | severe |

The lubricant oil compositions of Example III-22 to Example III-41, the lubricant oil compositions of Comparative Example III-4 to Comparative Example III-10 and the Control were taken as test samples, to evaluate the performances of inhibiting increase in viscosity and inhibiting increase in acid value, the results of were shown in Table III-6.

TABLE III-6

| lubricant oil composition | increase in viscosity (%) | increase in acid value (mgKOH · g$^{-1}$) |
|---|---|---|
| Example III-22 | 25.6 | 2.631 |
| Example III-23 | 22.1 | 2.035 |
| Example III-24 | 20.4 | 1.967 |
| Example III-25 | 23.6 | 1.639 |
| Example III-26 | 18.4 | 2.004 |
| Example III-27 | 19.1 | 1.569 |
| Example III-28 | 24.7 | 1.812 |
| Example III-29 | 20.6 | 1.645 |
| Example III-30 | 19.3 | 1.996 |
| Example III-31 | 20.9 | 2.733 |
| Example III-32 | 25.2 | 2.317 |
| Example III-33 | 23.3 | 1.962 |
| Example III-34 | 20.8 | 2.775 |
| Example III-35 | 19.9 | 2.284 |
| Example III-36 | 24.1 | 1.965 |
| Example III-37 | 22.5 | 1.882 |
| Example III-38 | 20.7 | 2.337 |
| Example III-39 | 22.5 | 2.023 |
| Example III-40 | 21.9 | 1.864 |
| Example III-41 | 21.2 | 2.067 |
| Comparative Example III-4 | 33.5 | 4.621 |

TABLE III-6-continued

| lubricant oil composition | increase in viscosity (%) | increase in acid value (mgKOH · g$^{-1}$) |
|---|---|---|
| Comparative Example III-5 | 27.5 | 3.482 |
| Comparative Example III-6 | 25.8 | 5.168 |
| Comparative Example III-7 | 27.6 | 2.953 |
| Comparative Example III-8 | 30.5 | 3.846 |
| Comparative Example III-9 | 28.1 | 5.429 |
| Comparative Example III-10 | 24.7 | 6.517 |
| Control | 67.2 | 24.525 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:
1. A hindered phenol compound of Formula (I)

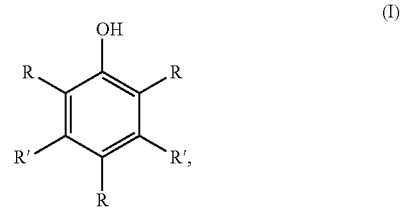

wherein each of the plural Rs independently selected from the group consisting of a $C_{1-300}$ linear or branched alkyl, a $C_{1-10}$ linear or branched alkyl, a polyolefin group having a number-average molecular weight (Mn) of from 300 to 3000, a functional group of Formula (II)

and a functional group of Formula (III)

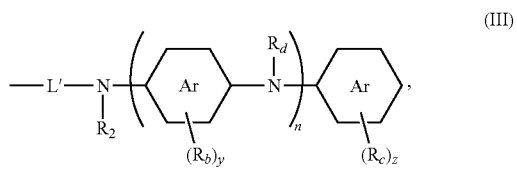

with the proviso that at least one R in Formula (I) is a functional group of Formula (II),
wherein each of the plural R's is independently selected from the group consisting of hydrogen, a $C_{1-20}$ linear or branched alkyl, and a $C_{1-4}$ linear or branched alkyl,
wherein L is a m+1 valent $C_{1-20}$ linear or branched alkyl optionally substituted by one or more substituent selected from the group consisting of oxo, a $C_{1-20}$ hydrocarbyl, a $C_{1-20}$ linear or branched alkyl, a $C_{6-20}$ aryl, and a $C_{3-20}$ linear or branched hetero-alkyl, or a m+1 valent $C_{3-20}$ linear or branched hetero-alkyl optionally substituted by one or more substituent selected from the group consisting of oxo, a $C_{1-20}$ hydrocarbyl, a $C_{1-20}$ linear or branched alkyl, a $C_{6-20}$ aryl, and a $C_{3-20}$ linear or branched hetero-alkyl;

L' is a functional group represented by

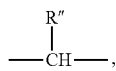, wherein R'' is selected from the group consisting of hydrogen, a $C_{1-20}$ hydrocarbyl, a $C_{1-20}$ linear or branched alkyl, a $C_{3-20}$ linear or branched hetero-alkyl, a $C_{1-10}$ linear or branched alkyl, and a $C_{3-10}$ linear or branched hetero-alkyl;

wherein each of the plural As is independently

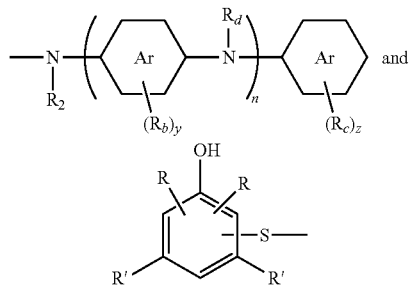

wherein at least one A in Formula (II) is

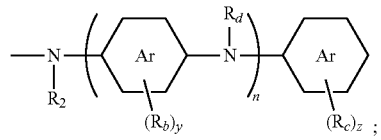;

wherein m is 1, 2, 3, or 4,
wherein each of the plural $R_2$s is independently selected from the group consisting of hydrogen, a $C_{1-20}$ linear or branched alkyl, a functional group of Formula (IV)

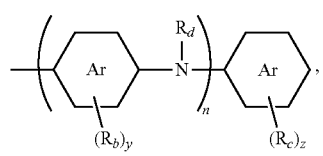 (IV)

a functional group of Formula (V)

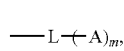 (V)

and a $C_{1-10}$ linear or branched alkyl;
wherein each of the plural $R_b$s is independently selected from the group consisting of hydrogen, a $C_{1-20}$ linear or branched alkyl, and a $C_{1-10}$ linear or branched alkyl;

wherein each of the plural $R_c$s may be identical to or different from each other, each is independently selected from the group consisting of hydrogen, a $C_{1-20}$ linear or branched alkyl, and a $C_{1-20}$ linear or branched alkyloxy a $C_{1-10}$ linear or branched alkyl, and a $C_{1-10}$ linear or branched alkyloxy;

y is 0, 1, 2, or 3;
z is 0, 1, 2, or 3;
n is an integer in the range of from 1 to 8;
n' is an integer in the range of from 0 to 7, with the proviso that n'+n≤8;
wherein each of the plural $R_d$s is independently hydrogen or a functional group of Formula (V);
wherein each of the plural

rings is independently a benzene ring or a naphthalene ring, wherein two

rings optionally form a phenothiazine ring with a N atom and a S atom bridging the two

rings or optionally form a 9,10-dihydroacridine ring or derivatives thereof with a N atom and

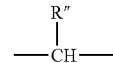

bridging the two

rings,
wherein the linear or branched hetero-alkyl is a functional group obtained by directly replacing one or more —$CH_2$— located inside a linear or branched alkyl with a corresponding number of replacement functional group selected from —O—, —S—, and —NR'''— R''' being H or a $C_{1-4}$ linear or branched alkyl), or a functional group obtained by directly replacing one or more —CH< located inside a linear or branched alkyl by a corresponding number of replacement functional group —N<, and
wherein in the hindered phenol compound of Formula (I), at least one $R_d$ is hydrogen.

2. The hindered phenol compound according to claim 1, wherein m=1, wherein L is

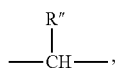

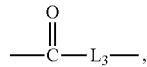

a m+1 valent $C_{2-20}$ linear or branched alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, or a m+1 valent $C_{3-20}$ linear or branched hetero-alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, and wherein $L_3$ is a m+1 valent $C_{2-19}$ linear or branched alkyl optionally substituted by one or more substituent selected from the group consisting of oxo, a $C_{1-20}$ hydrocarbyl, $C_{1-20}$ linear or branched alkyl, a $C_{6-20}$ aryl, and a $C_{3-20}$ linear or branched hetero-alkyl, or a m+1 valent $C_{3-19}$ linear or branched hetero-alkyl optionally substituted by one or more substituent selected from the group consisting of oxo, a $C_{1-20}$ hydrocarbyl, a $C_{1-20}$ linear or branched alkyl, a $C_{6-20}$ aryl, and a $C_{3-20}$ linear or branched hetero-alkyl.

3. The hindered phenol compound according to claim 1, wherein the functional group of Formula (II) has Formula ($II_X$), Formula ($II_{XX}$), or Formula ($II_{XXX}$), in Formula ($II_X$)

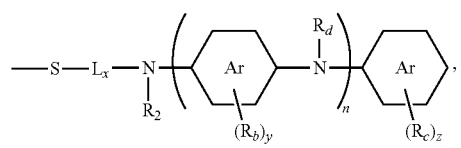

(II_x)

$L_X$ is

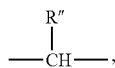

wherein R" is selected from the group consisting of hydrogen, a $C_{1-20}$ hydrocarbyl, a $C_{1-20}$ linear or branched alkyl, a $C_{3-20}$ linear or branched hetero-alkyl, a $C_{1-10}$ linear or branched alkyl, and a $C_{3-10}$ linear or branched hetero-alkyl, in Formula ($II_{XX}$)

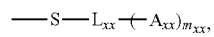

(II_xx)

$L_{XX}$ is a $m_{XX}+1$ valent $C_{2-20}$ linear or branched alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, or a $m_{XX}+1$ valent $C_{3-20}$ linear or branched hetero-alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl;

wherein each of the plural $A_{XX}$s is independently

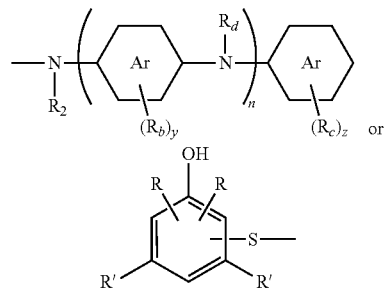

wherein each of the plural Rs is independently selected from the group consisting of hydrogen, a $C_{1-300}$ linear or branched alkyl, a $C_{1-10}$ linear or branched alkyl, a polyolefin group having a number-average molecular weight (Mn) of from 300 to 3000, a functional group of Formula ($II_{XX}$), and a functional group of Formula (III);

wherein each of the plural R's is independently selected from the group consisting of hydrogen, a $C_{1-20}$ linear or branched alkyl, and a $C_{1-4}$ linear or branched alkyl, wherein at least one $A_{XX}$ is

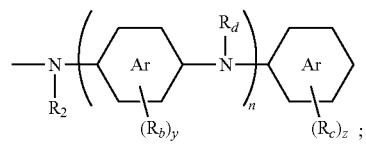

$m_{XX}$ is 1, 2, 3, or 4,
in Formula ($II_{XXX}$)

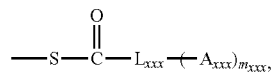

(II_xxx)

$L_{XXX}$ is a $m_{XXX}+1$ valent $C_2$ to $C19-m_{XXX}$ linear or branched alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, or a $m_{XXX}+1$ valent $C_3$ to $C19-m_{XXX}$ linear or branched hetero-alkyl optionally substituted by one or more substituent selected from the group consisting of a $C_{1-20}$ hydrocarbyl, a $C_{1-20}$ linear or branched alkyl, a C6-20 aryl, a $C_{3-20}$ linear or branched hetero-alkyl, and a functional group of

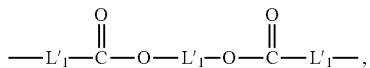

wherein each of the plural L'₁s is independently a $C_{1-10}$ linear or branched alkyl or a $C_{3-10}$ linear or branched hetero-alkyl, with the proviso that (1) each of the plural L'₁s independently represents a 2 valent to $m_{XXX}+1$ valent group so as to make

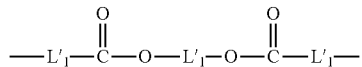

$m_{XXX}+1$ valent as a whole, and (2) a total atom number of all L'₁ groups is no more than 14, wherein each of the plural L'₁s is independently and optionally further substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl; wherein each of the plural $A_{XXX}$s is independently

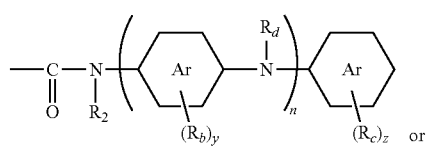

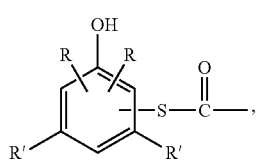 or

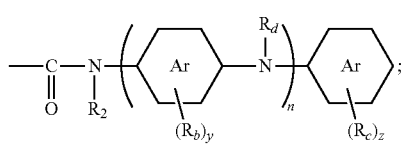

wherein at least one $A_{XXX}$ is
wherein $m_{XXX}$ is 1, 2, 3, and 4,
and/or,
wherein a functional group of Formula (V) has Formula ($V_X$)

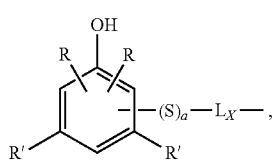

Formula ($V_{XX}$)

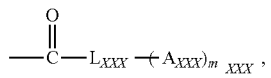

or
Formula ($V_{XXX}$)

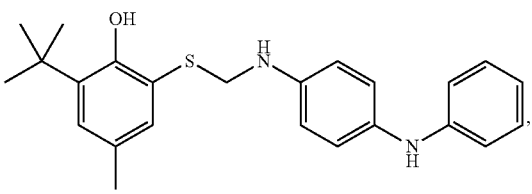

and wherein a=1 in Formula (Vx).

4. A hindered phenol compound selected from the group consisting of

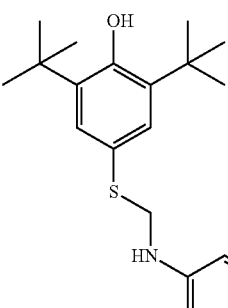

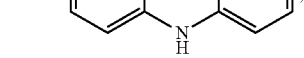

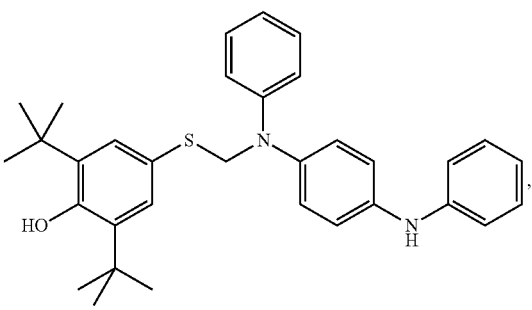

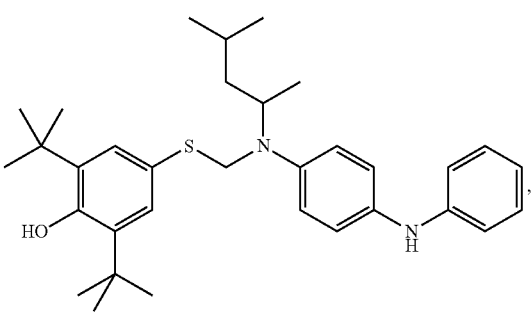

175
-continued
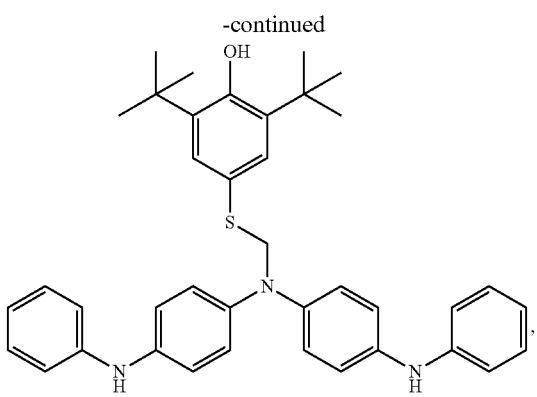
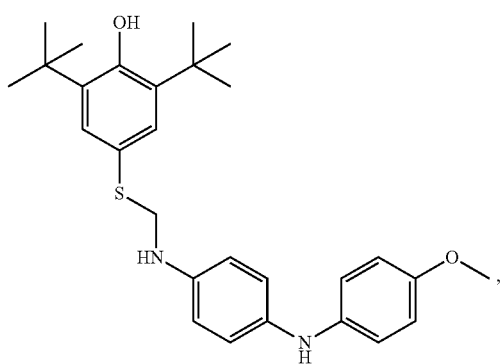
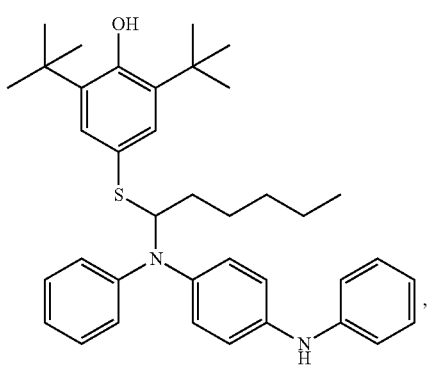
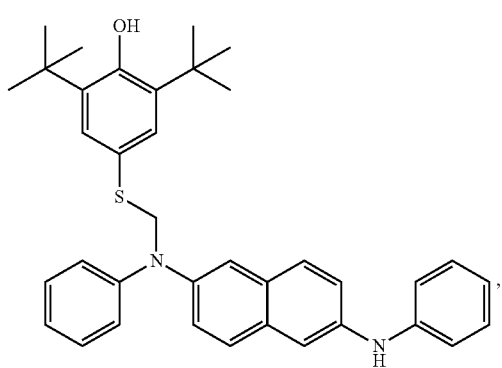
176
-continued
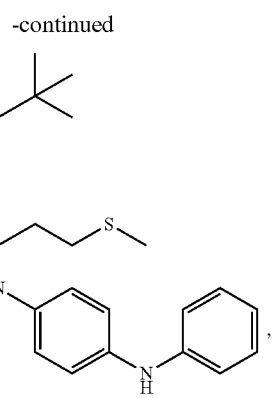
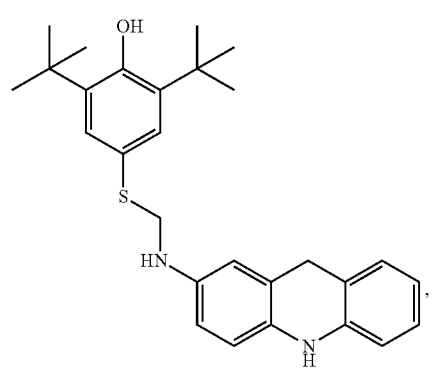
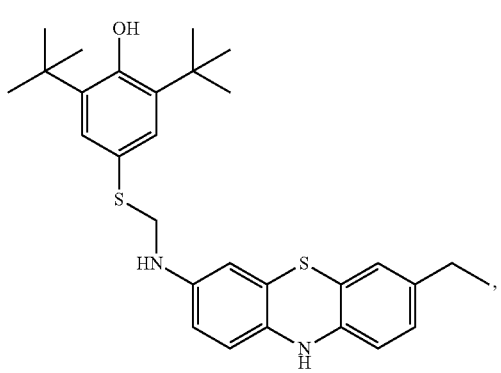
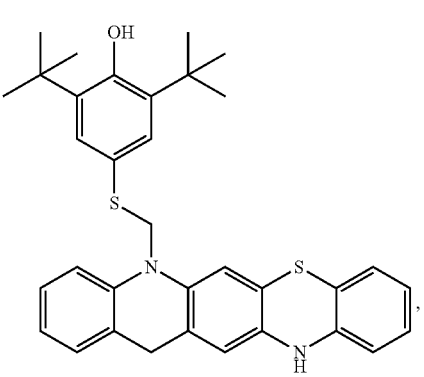

177
-continued
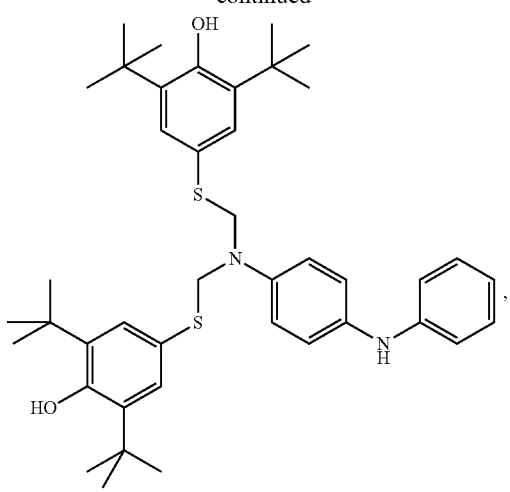
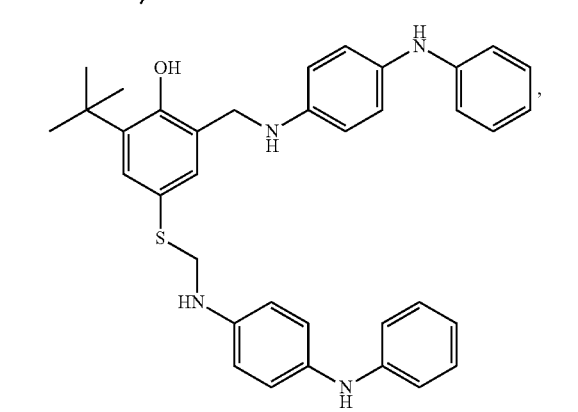
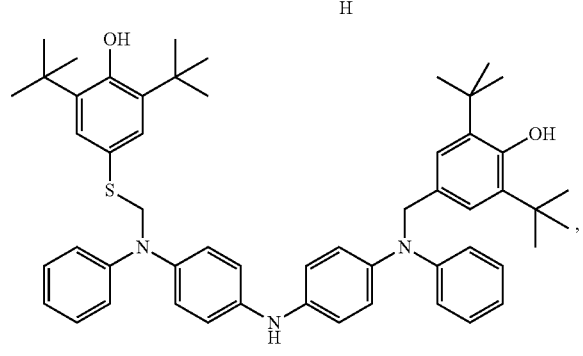
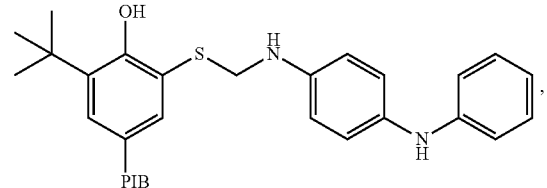
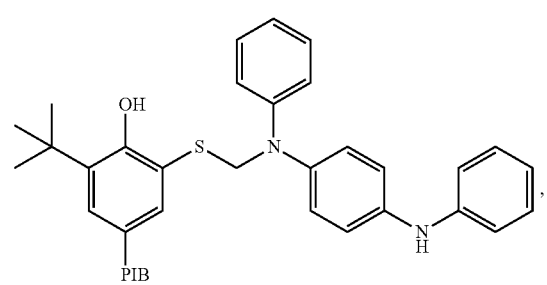
178
-continued
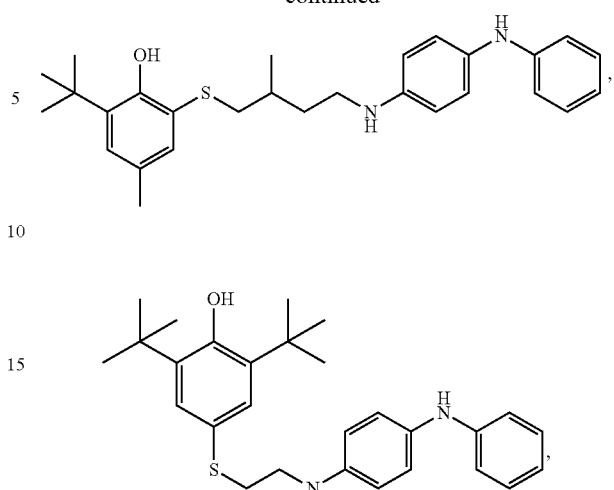
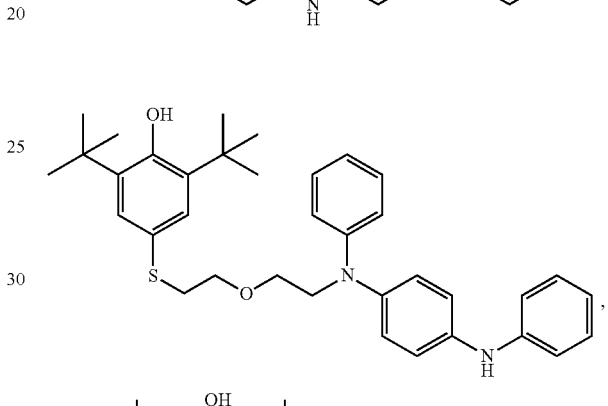
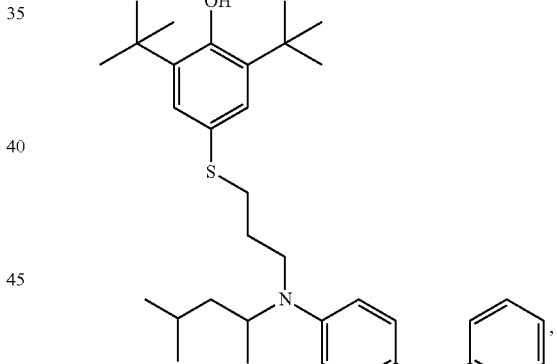
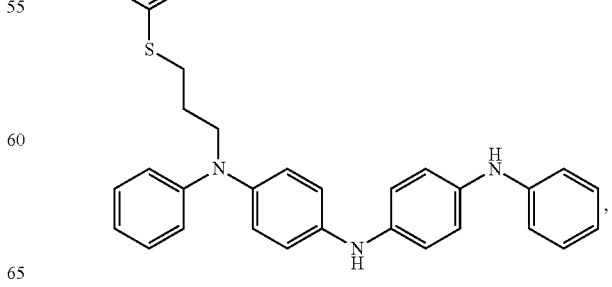

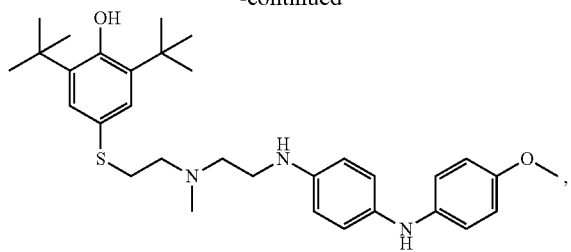
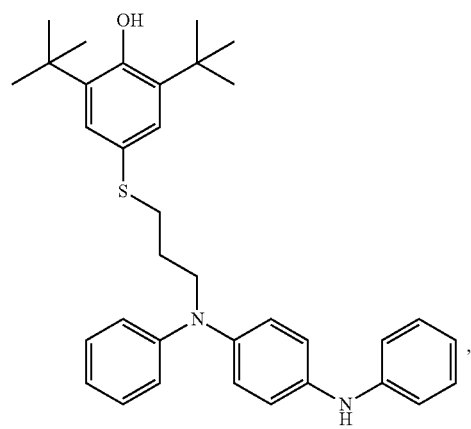
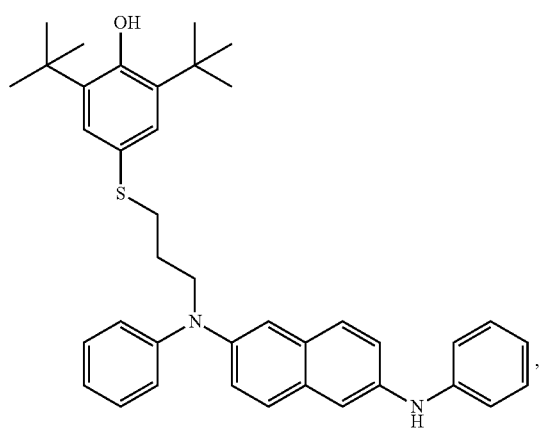
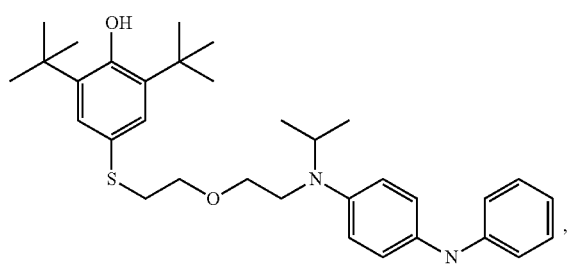
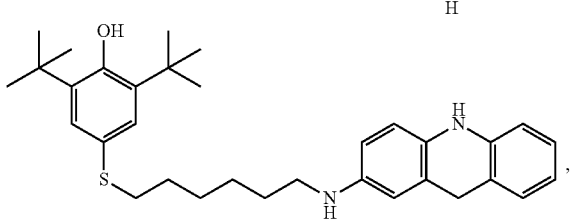
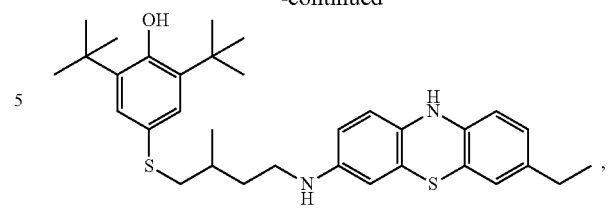
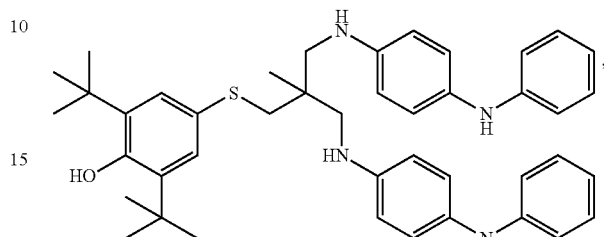
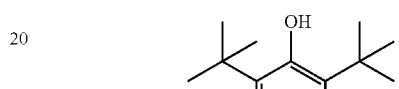
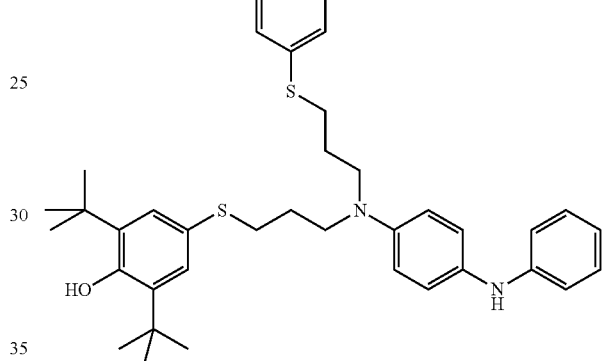
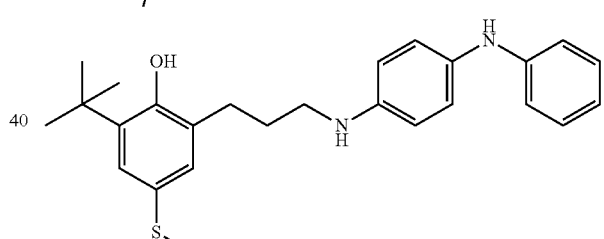
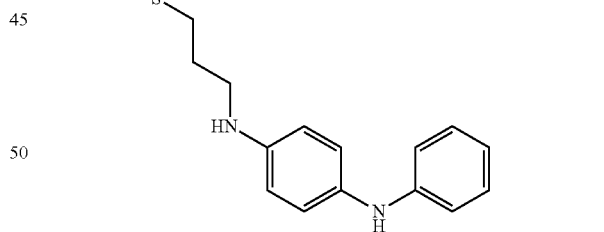
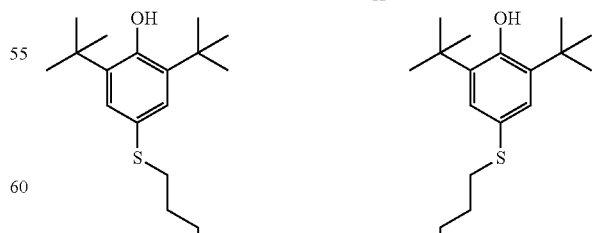
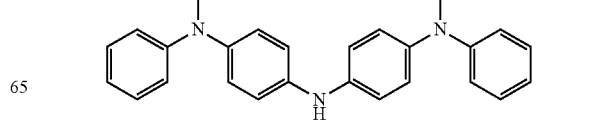

181
-continued
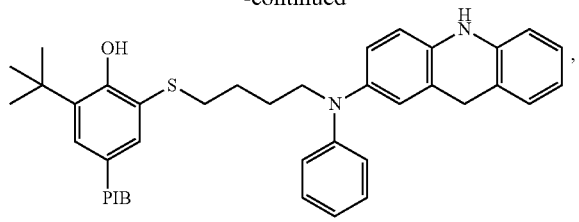
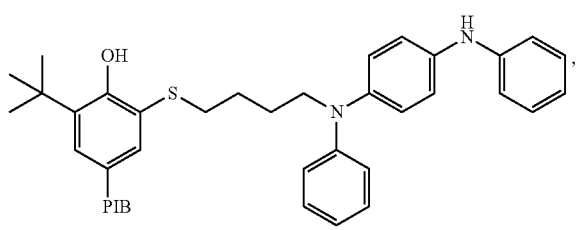
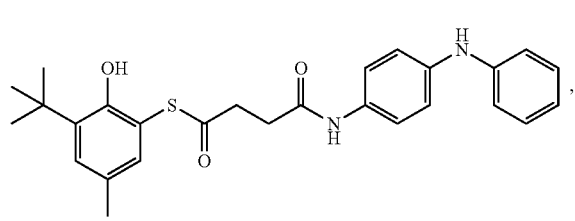
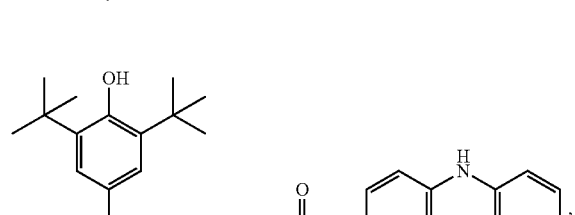
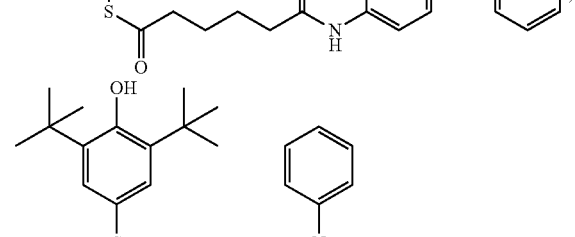
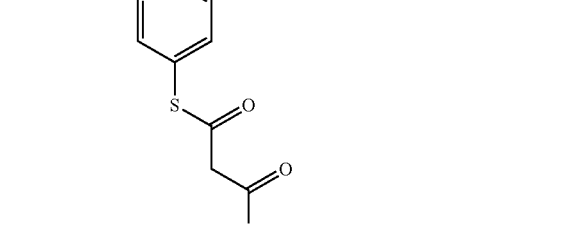
182
-continued
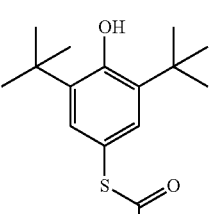
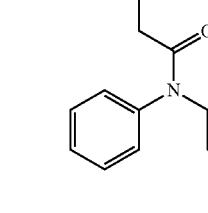
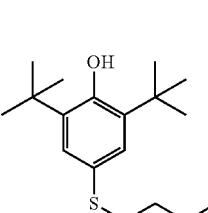
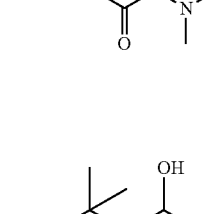
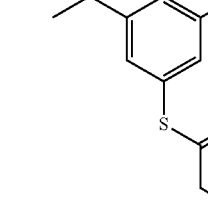
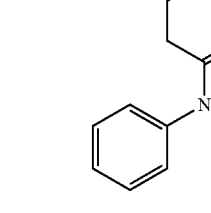

-continued
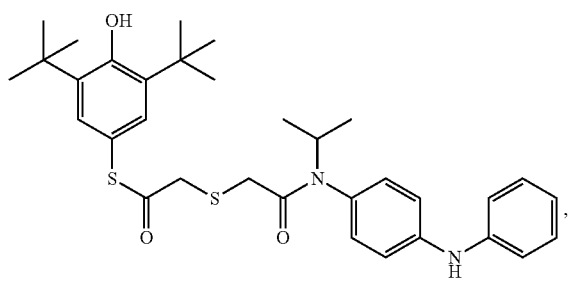
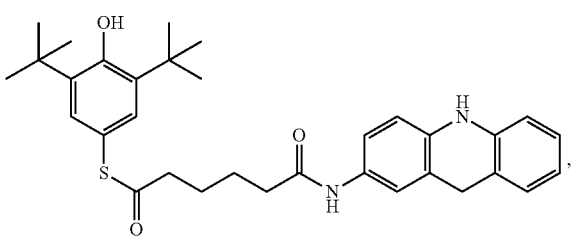
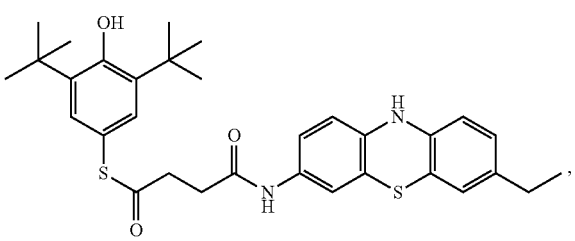
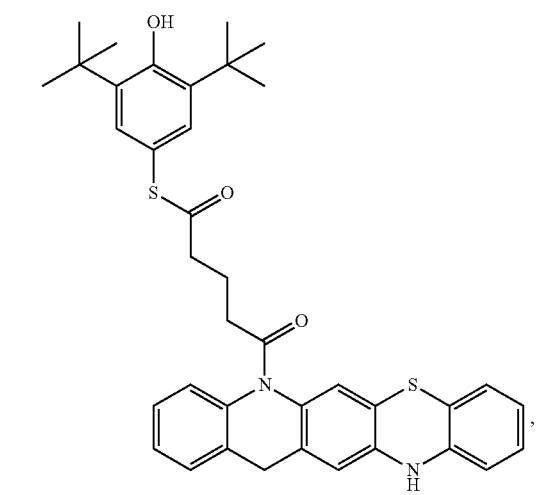
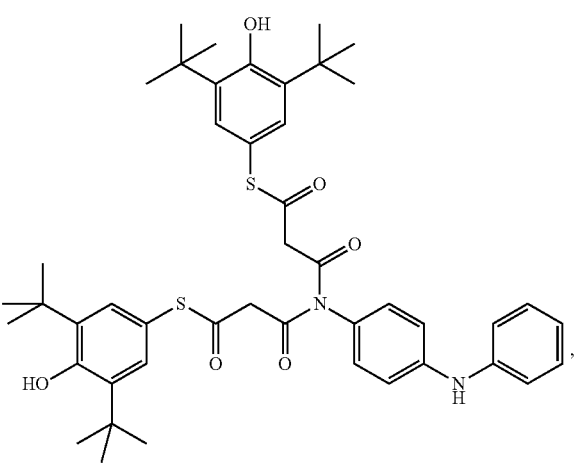
-continued
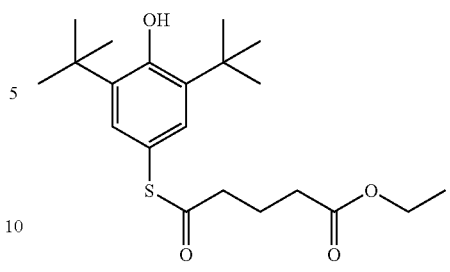
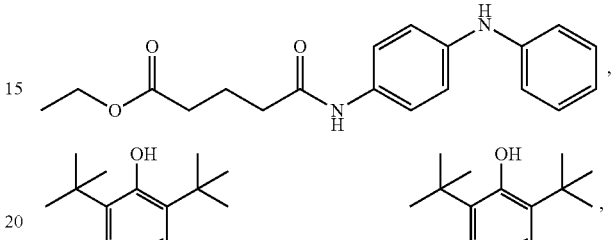
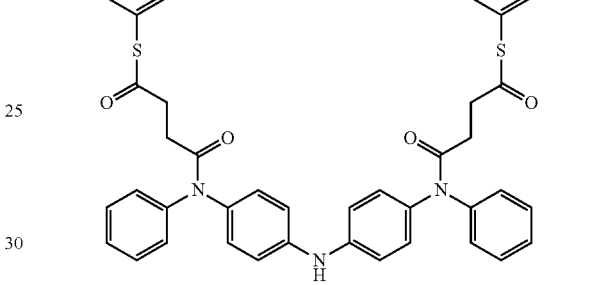
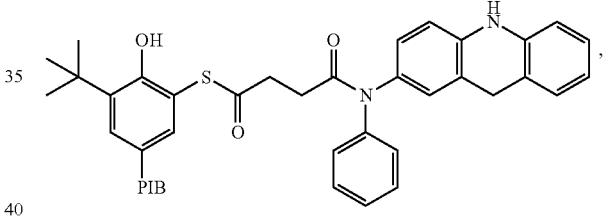
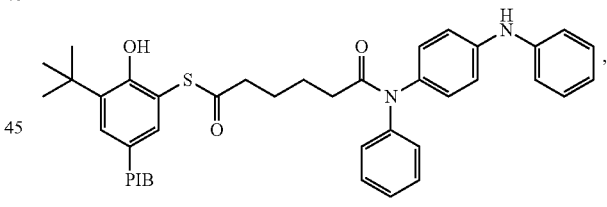
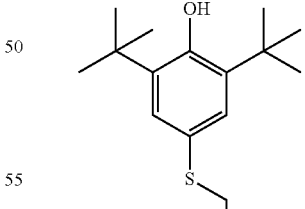
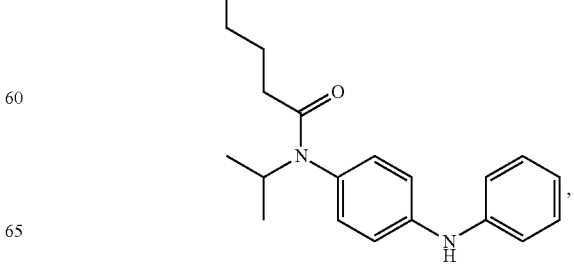

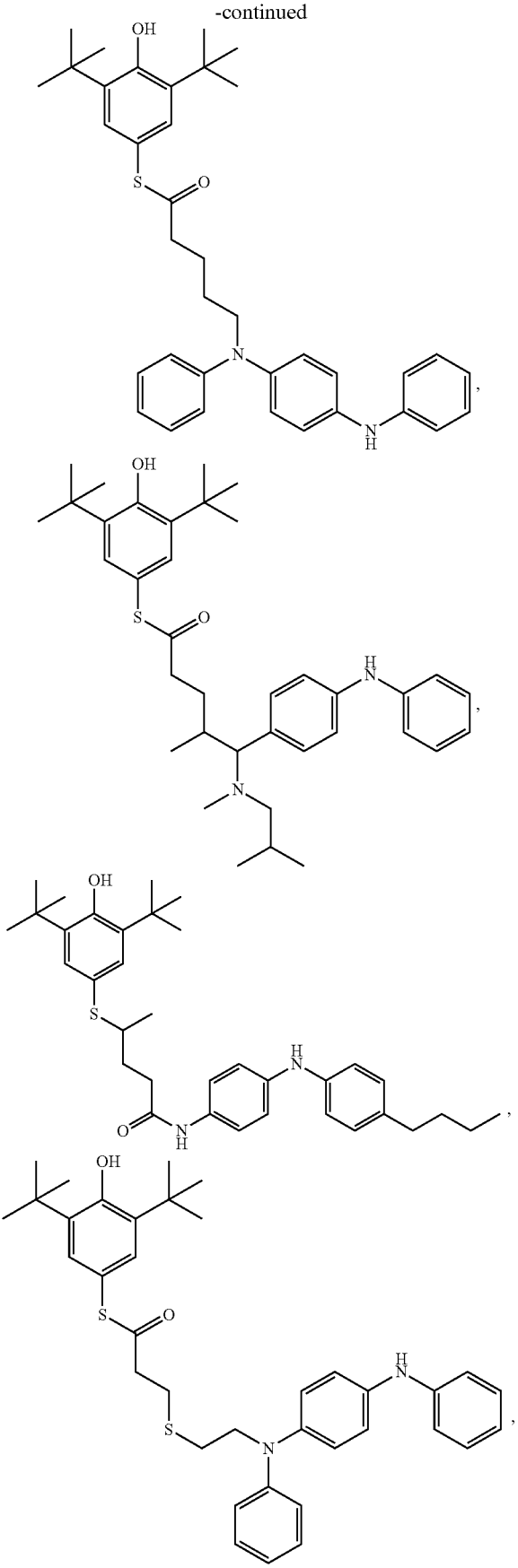

5. A process for producing a hindered phenol compound, comprising:
   Step (A): reacting a phenol compound of Formula (X) with an amine compound of Formula (Y) in the presence of at least one bridging compound selected from the group consisting of a compound of Formula (A) and formaldehyde; and optionally
   Step (B): reacting a product of Step (A) with a sulfuring agent and/or an aldehyde compound of Formula (Z), wherein in Formula (X)

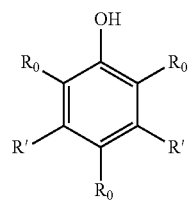

each of the plural $R_0$s is independently selected from the group consisting of hydrogen, —SH, and a $C_{1-300}$ linear or branched alkyl, a $C_{1-10}$ linear or branched alkyl, and a polyolefin group having a number-average molecular weight (Mn) of from 300 to 3000, with the proviso that at least one $R_0$ in Formula (X) is —SH;

each of the plural R's is independently selected from the group consisting of hydrogen, a $C_{1-20}$ linear or branched alkyl and a $C_{1-4}$ linear or branched alkyl, wherein in Formula (Y)

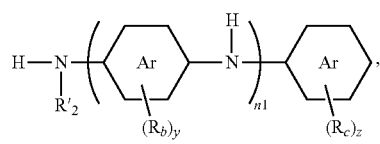

$R'_2$ is hydrogen, a $C_{1-20}$ linear or branched alkyl, or

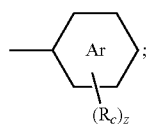

each of the plural $R_b$s is-independently selected from the group consisting of hydrogen, a $C_{1-20}$ linear or branched alkyl, and a $C_{1-10}$ linear or branched alkyl;

each of the plural $R_c$s is-independently selected from the group consisting of hydrogen, a $C_{1-20}$ linear or branched alkyl, and a $C_{1-20}$ linear or branched alkyloxy, a $C_{1-10}$ linear or branched alkyl, and a $C_{1-10}$ linear or branched alkyloxy, y is 0, 1, 2, and 3;
z is 0, 1, 2, and 3;
n1 is an integer in the range of from 1 to 8;
each of the plural

rings is a benzene ring or a naphthalene ring, wherein in Formula (A)

$$R_f\text{---}(\text{Fun})_{m1}, \quad (A)$$

$R_f$ is a m1 valent $C_{1-20}$ hydrocarbyl optionally substituted by one or more substituent selected from the group consisting of oxo, a $C_{1-20}$ hydrocarbyl, a $C_{1-20}$ linear or branched alkyl, a $C_{6-20}$ aryl, and a $C_{3-20}$ linear or branched hetero-alkyl or a m1 valent $C_{3-20}$ linear or branched hetero-alkyl optionally substituted by one or more substituent selected from the group consisting of oxo, a $C_{1-20}$ hydrocarbyl, a $C_{1-20}$ linear or branched alkyl, a $C_{6-20}$ aryl, and a $C_{3-20}$ linear or branched hetero-alkyl;

m1 is 2, 3, 4, or 5, each of the plural Funs is independently a halogen atom, a carboxylic acid residue group, an anhydride residue group, or an aldehyde residue group, wherein when m1 is 1, the group Fun is an aldehyde residue group, wherein the carboxylic acid residue group is obtained by removing one carbonyl group

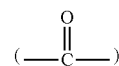

from a carboxyl group (—COOH), with the proviso the carbon atom in $R_f$ directly bonding to the carboxylic acid residue group is in a carbonyl group, wherein the anhydride residue group is obtained by removing two carbonyl groups from an anhydride group

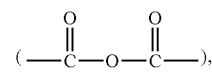

with the proviso that it is necessary for the two carbon atoms in $R_f$ directly bonding to the anhydride residue group are in two carbonyl groups, respectively, wherein the aldehyde residue group is obtained by removing one carbonyl group from a formyl group

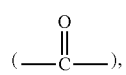

with the proviso that the carbon atom in $R_f$ directly bonding to the aldehyde residue is in a carbonyl group; and wherein in Formula (Z)

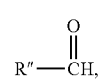

R" is selected from the group consisting of hydrogen, a $C_{1-20}$ hydrocarbyl, a $C_{1-20}$ linear or branched alkyl, a $C_{3-20}$ linear or branched hetero-alkyl, a $C_{1-10}$ linear or branched alkyl, and a $C_{3-10}$ linear or branched hetero-alkyl.

6. The process according to claim 5, wherein the bridging compound is one or more selected from the group consisting of an aldehyde compound represented by Formula ($A_Y$), a polyhalo-compound represented by Formula ($A_{YY}$), a polybasic carboxylic acid represented by Formula ($A_{YYY}$) or derivatives thereof, and an anhydride of the polybasic carboxylic acid, and an acyl halide of the polybasic carboxylic acid, wherein in Formula ($A_Y$)

($A_Y$)

$R_Y$ is selected from the group consisting of hydrogen, a $C_{1-20}$ hydrocarbyl, a $C_{1-20}$ linear or branched alkyl, a $C_{3-20}$ linear or branched hetero-alkyl, a $C_{1-10}$ linear or branched alkyl, and a $C_{3-10}$ linear or branched hetero-alkyl, wherein in Formula ($A_{YY}$)

($A_{YY}$)

$R_{halo}$ is a $m_{YY}$ valent $C_{2-20}$ linear or branched alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl or a $m_{YY}$ valent $C_{3-20}$ linear or branched hetero-alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, wherein the group Halo is a halogen atom, $m_{YY}$ is 2, 3, 4, or 5, wherein in Formula ($A_{YYY}$)

($A_{YYY}$)

$R_L$ is a $m_{YYY}$ valent $C_2$ to $C20$-$m_{YYY}$ linear or branched alkyl optionally substituted by one or more substituent selected from the group consisting of a $C_{1-20}$ hydrocarbyl, a $C_{1-20}$ linear or branched alkyl, a $C_{6-20}$ aryl, and a $C_{3-20}$ linear or branched hetero-alkyl, a $m_{YYY}$ valent $C3$ to $C20$-$m_{YYY}$ linear or branched hetero-alkyl optionally substituted by one or more substituent selected from the group consisting of a $C_{1-20}$ hydrocarbyl, a $C_{1-20}$ linear or branched alkyl, a $C_{6-20}$ aryl, a $C_{3-20}$ linear or branched hetero-alkyl, and a functional group represented by

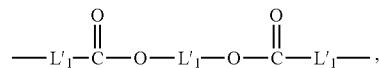

wherein each of the plural $L'_1$s is independently a $C_{1-10}$ linear or branched alkyl or a $C_{3-10}$ linear or branched hetero-alkyl, with the proviso that (1) each of the plural $L'_1$s independently represents a 2 valent to $m_{YYY}$ valent group, so as to make

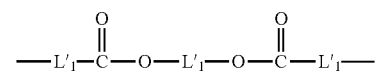

$m_{YYY}$ valent as a whole, and (2) a total atom number of all $L'_1$ groups is no more than 14, wherein each of the plural $L'_1$s is independently and optionally further substituted by one or more substituent selected from the group consisting of a $C_{1-20}$ hydrocarbyl, a $C_{1-20}$ linear or branched alkyl, a C6-20 aryl, and a $C_{3-20}$ linear or branched hetero-alkyl, and $m_{YYY}$ is 2, 3, 4, or 5.

7. The process of claim 5, wherein in Step(A), a molar ratio of the phenol compound of Formula (X) to the amine compound of Formula (Y) is 1:0.1-10, a molar ratio of the phenol compound of Formula (X) to the bridging compound is 1:0.1-10, and wherein in the optional Step (B), a molar ratio of the amine compound of Formula (Y) to the sulfuring agent is 1:1-10, a molar ratio of the amine compound of Formula (Y) to the aldehyde compound of Formula (Z) is 1:0.1-10.

8. A process of using the hindered phenol compound of claim 1, comprising mixing the hindered phenol compound with a lubricant base oil.

9. A lubricant oil composition, comprising a lubricant base oil and a hindered phenol compound according to claim 1 or a hindered phenol compound produced according to the process of claim 5 as an antioxidant, wherein the antioxidant is 0.001-30 wt % of a total weight of the lubricant oil composition.

10. The lubricant oil composition according to claim 9, wherein the antioxidant is 0.1-10 wt % of the total weight of the lubricant oil composition, and the lubricant base oil is a mineral base oil, an animal oil, a vegetable oil, a synthetic oil, or mixtures thereof.

11. The process of claim 8, wherein the lubricant base oil is a mineral base oil, an animal oil, a vegetable oil, a synthetic oil, or mixtures thereof.

12. The lubricant oil composition of claim 9, wherein the mineral base oil has a viscosity index of above 80, or has a saturated hydrocarbon content of above 90 wt % and a sulfur content of less than 0.03 wt %, wherein the synthetic base oil comprises one or more selected from polyolefins, synthetic esters, silicone oils, and polyethers.

13. The lubricant oil composition of claim 9, comprising one or more hindered phenol compound selected from 191
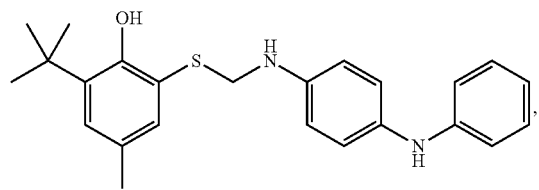
192
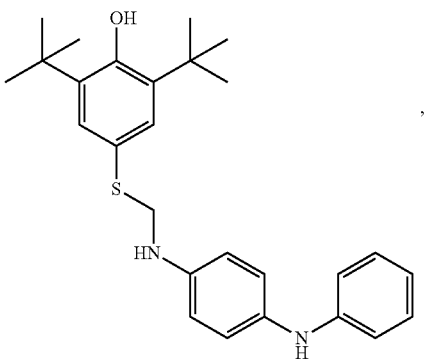
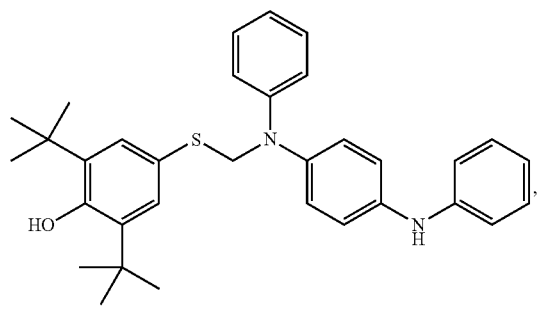
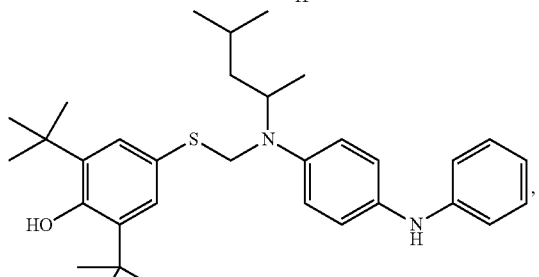
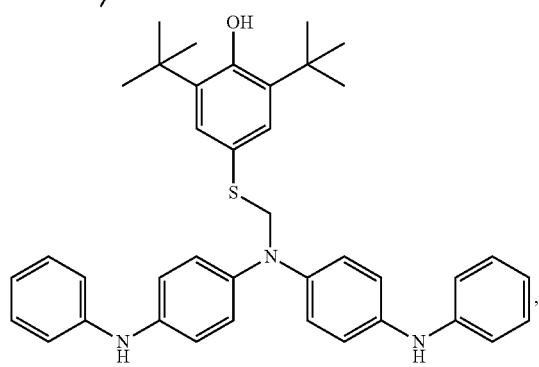
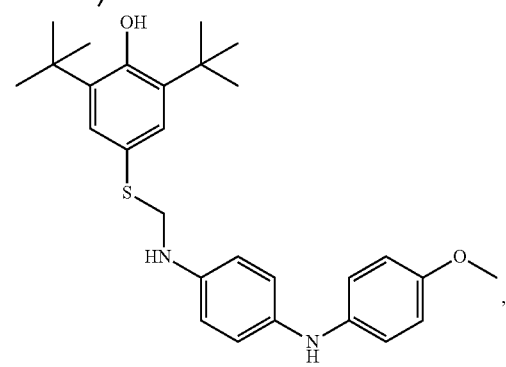
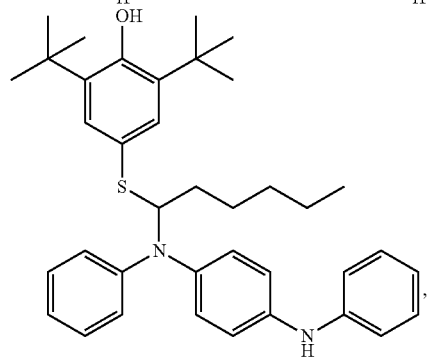
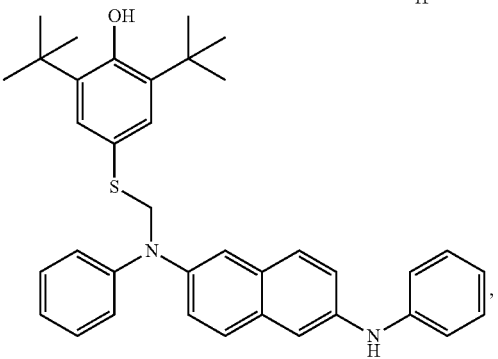
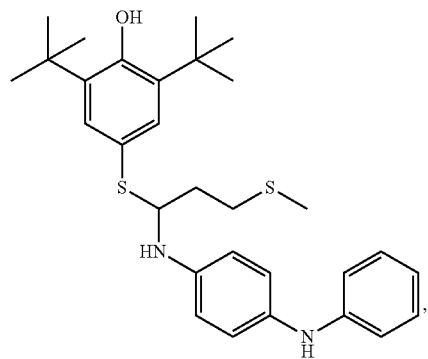
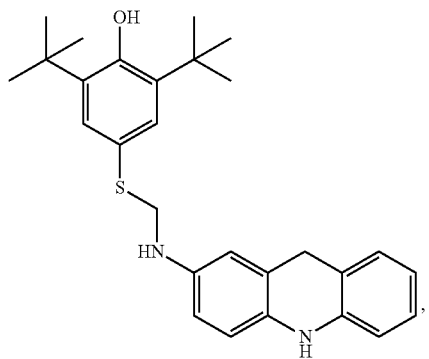

193
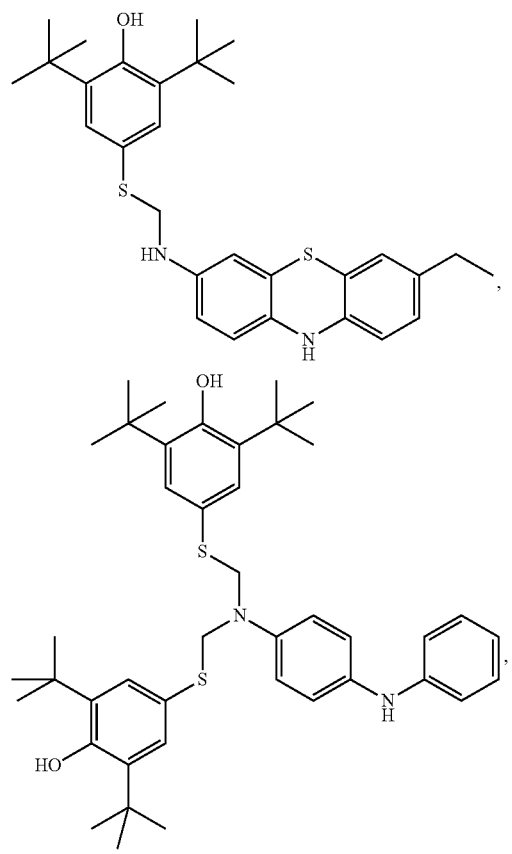
-continued
194
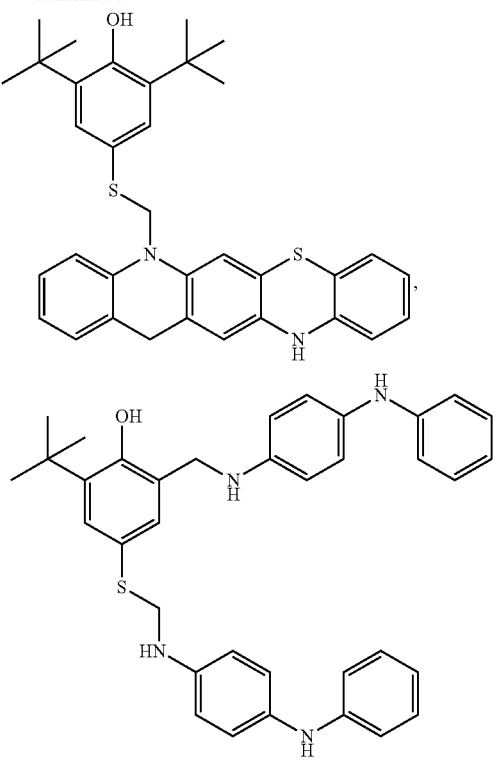
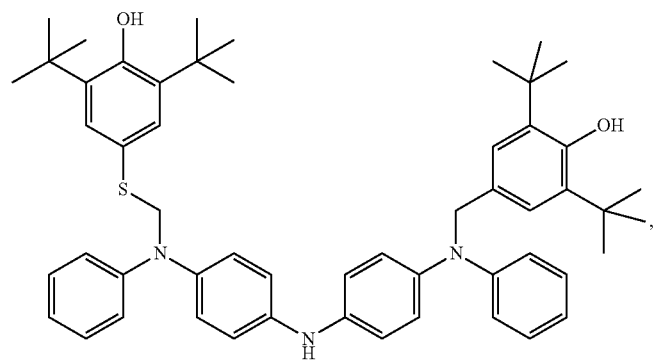
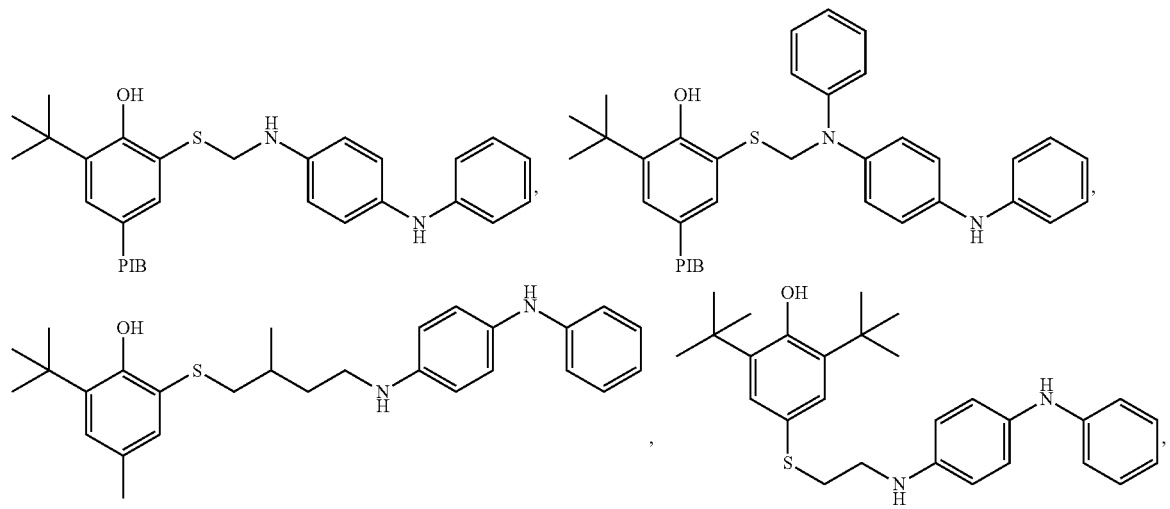

195
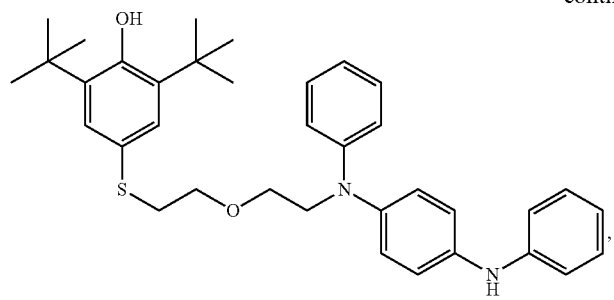
196
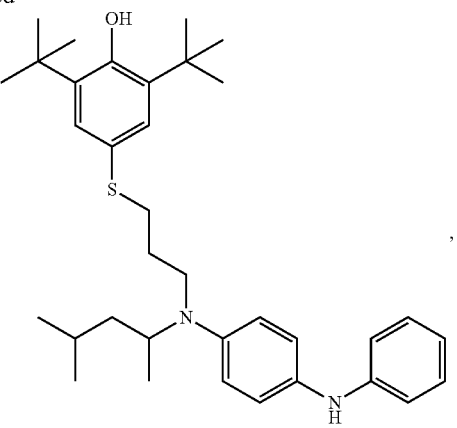
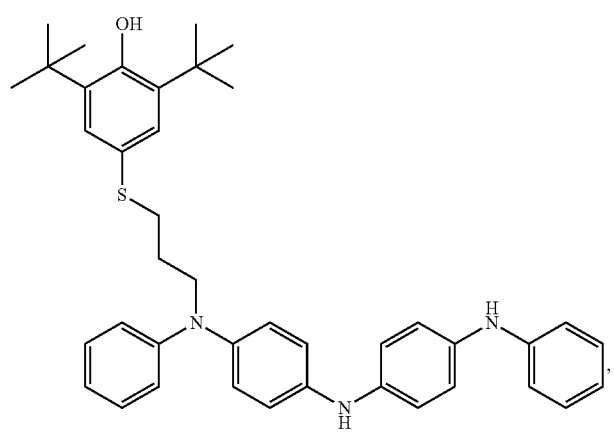
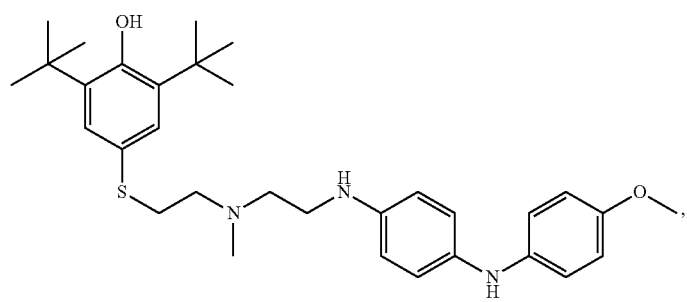
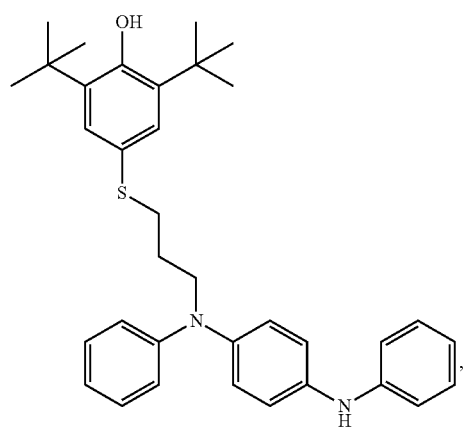
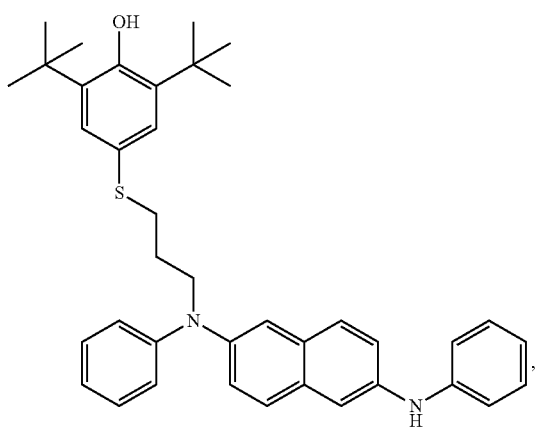

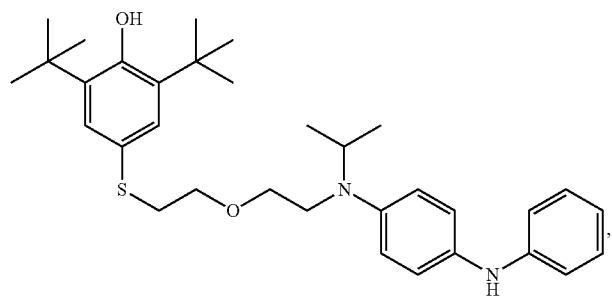
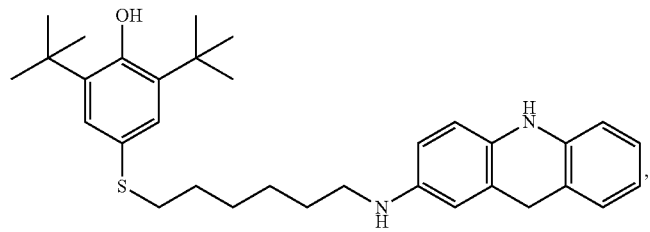
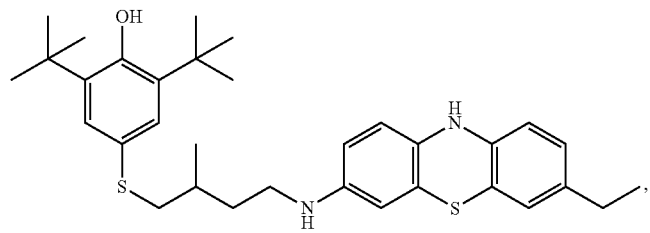
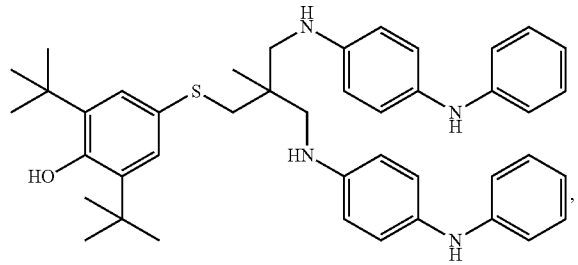
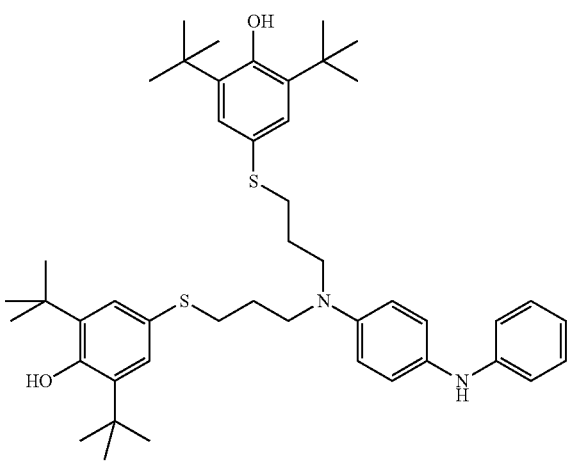
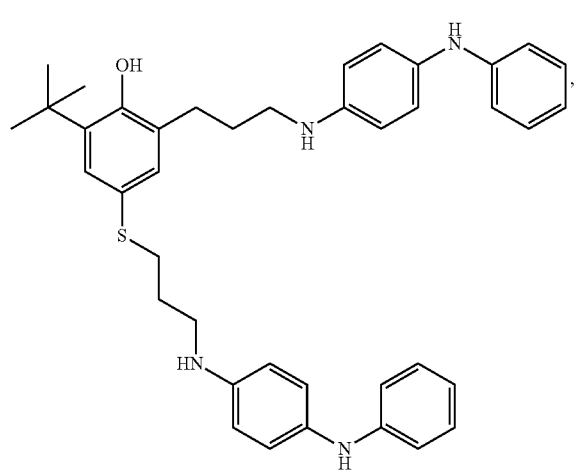

-continued
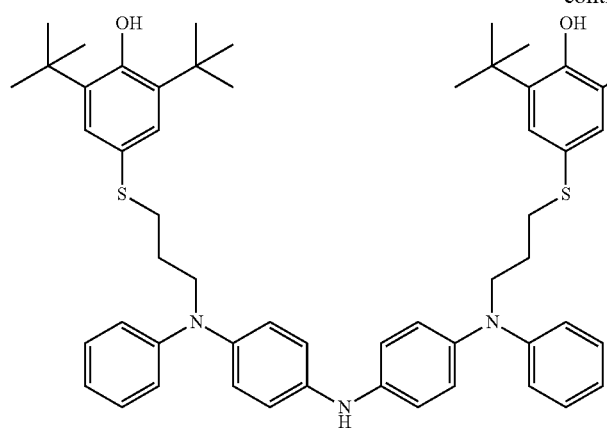
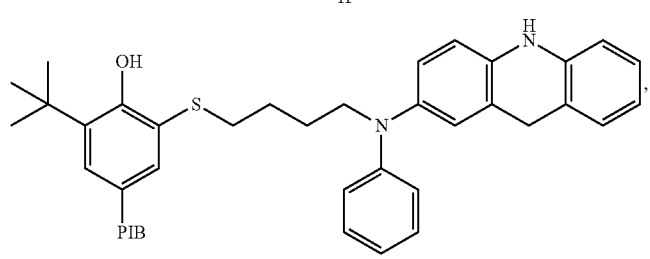
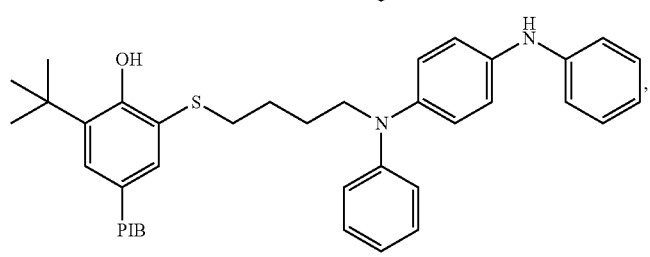
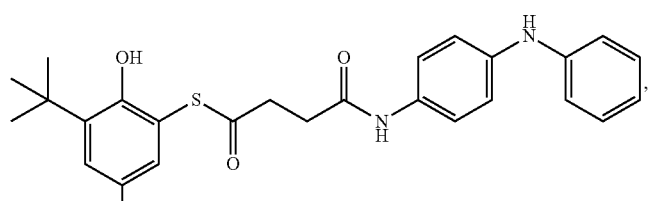
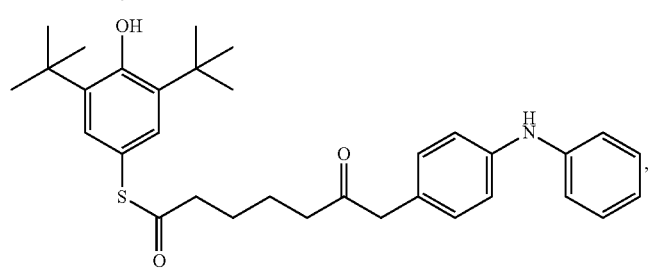
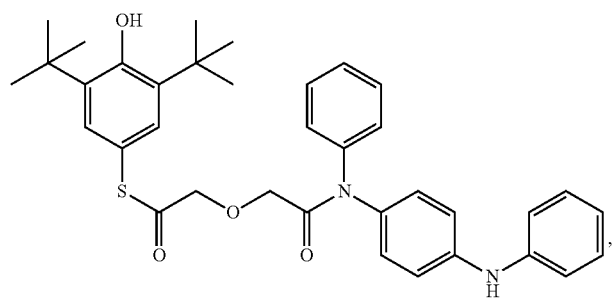

-continued
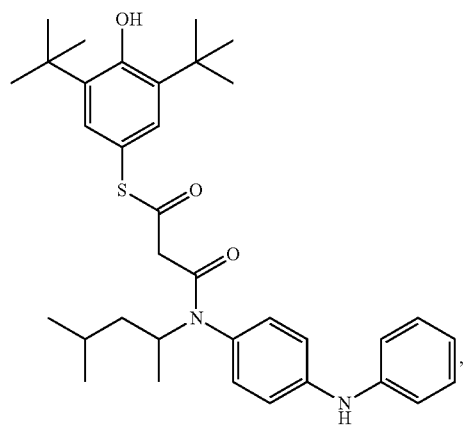
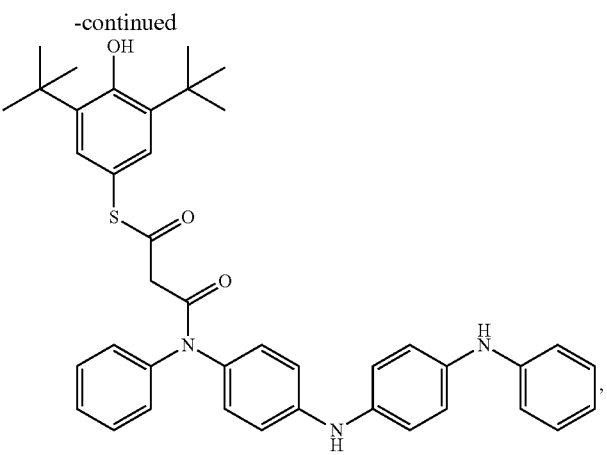
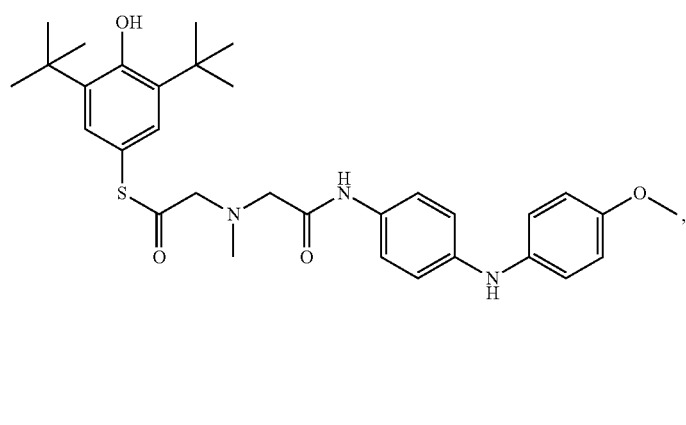
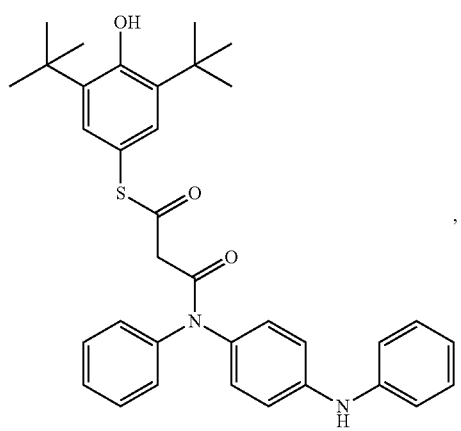
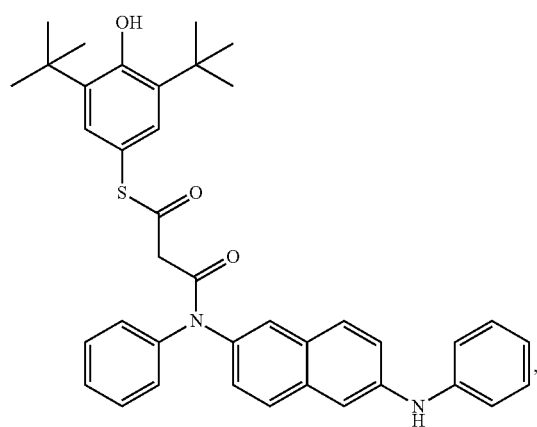
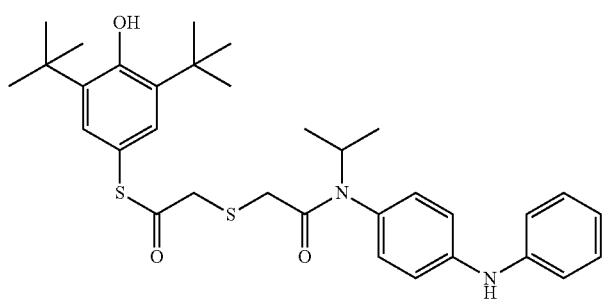
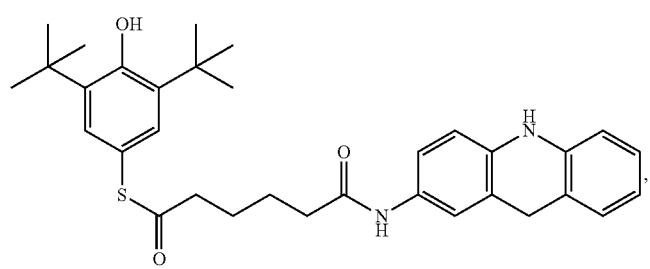

-continued
203
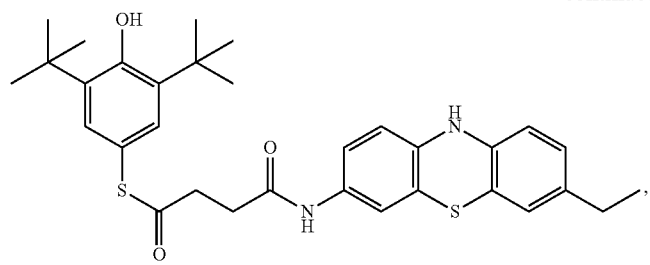
204
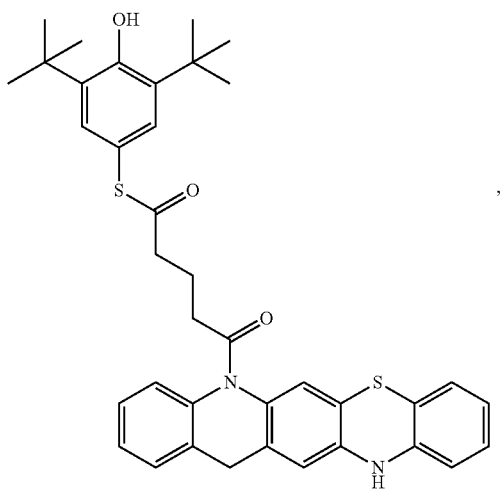
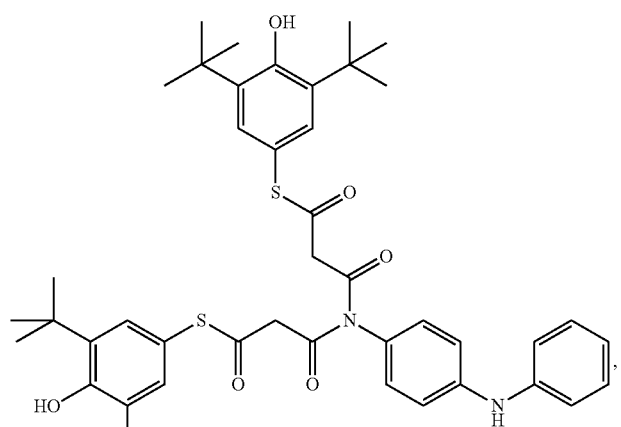
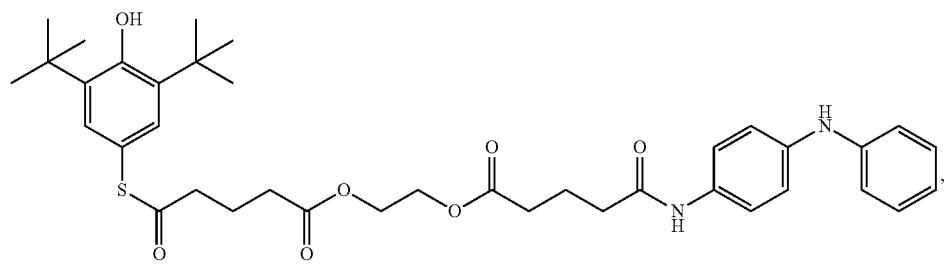
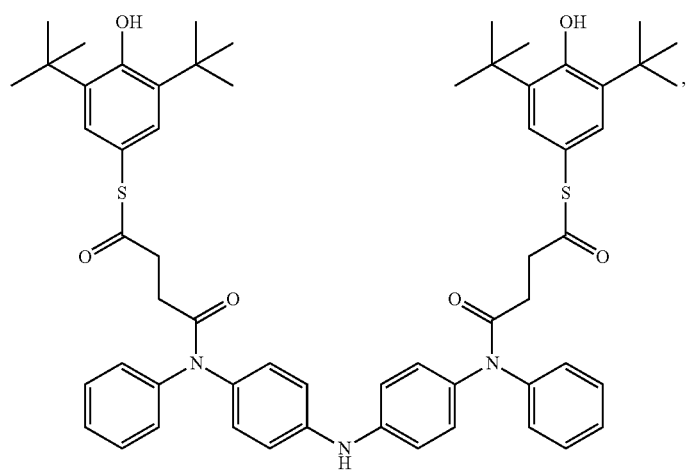

-continued
205
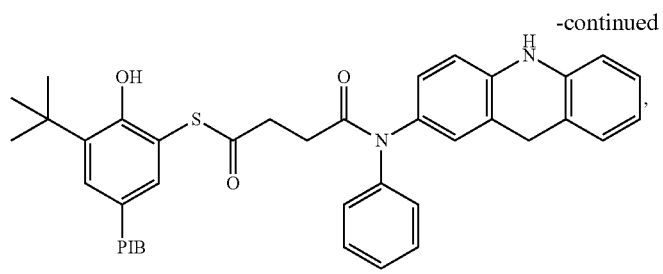
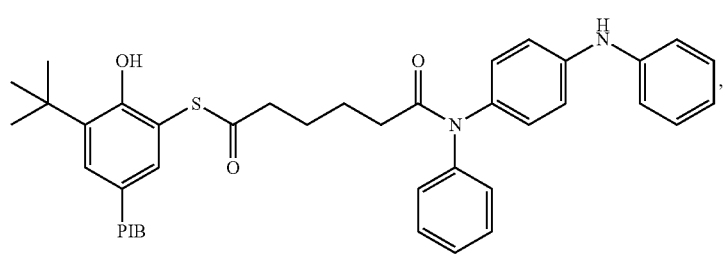
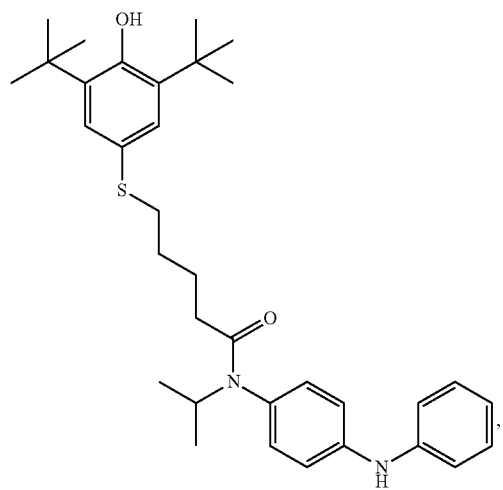
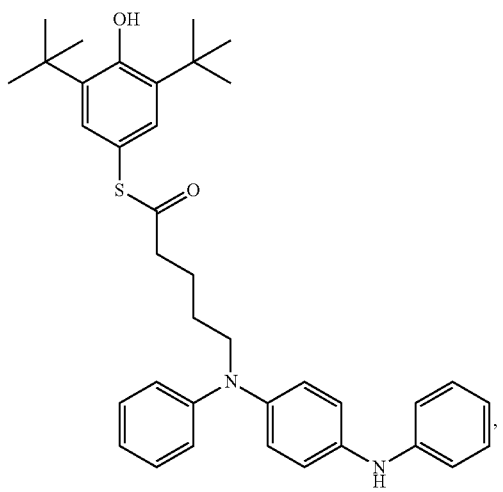
206
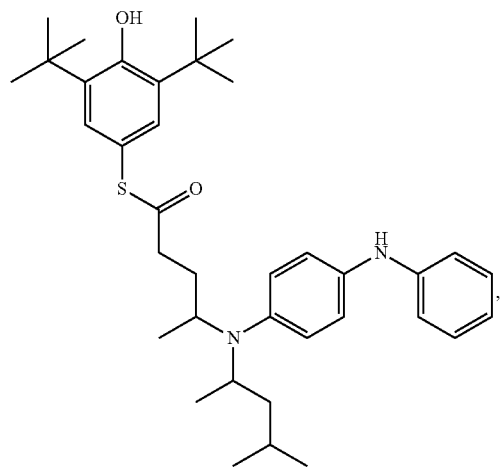
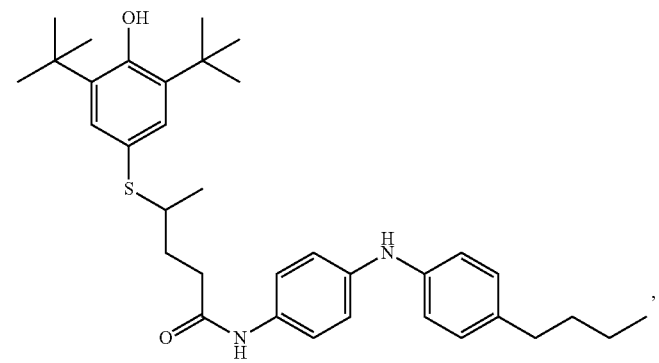

-continued

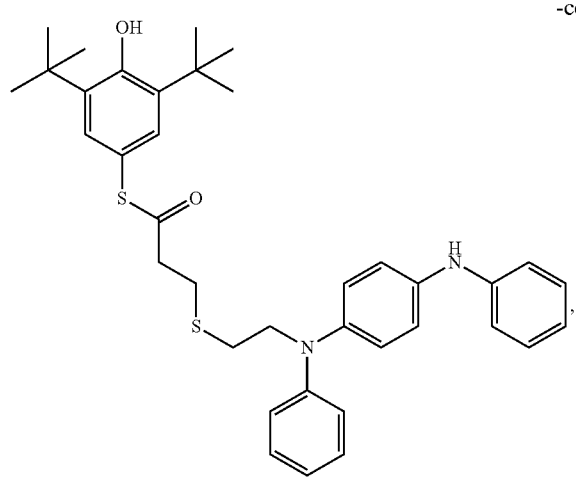

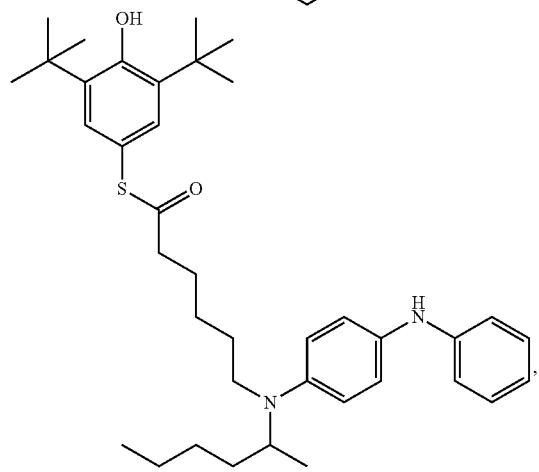

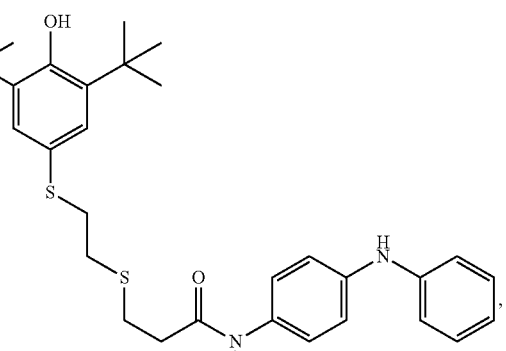

and

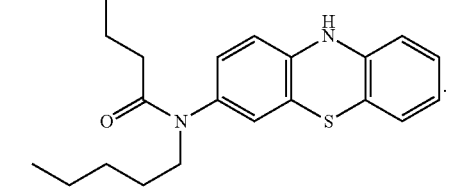

14. The hindered phenol compound of claim 1, wherein at least one of the plural As is

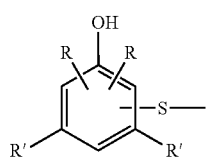

wherein each of the plural Rs is independently selected from the group consisting of hydrogen, a $C_{1-10}$ linear or branched alkyl, a polyolefin group having a number-average molecular weight (Mn) of from 300 to 3000, and each of the plural R's is independently selected from the group consisting of hydrogen and a $C_{1-4}$ linear or branched alkyl.

15. The hindered phenol compound of claim 1, wherein at least one of the plural $R_c$s is situated at a position opposite to a N atom on the

ring.

16. The process of claim 5, wherein Step (B) is performed, the sulfuring agent is sulfur, and the aldehyde compound of Formula (Z) is formaldehyde.

17. The process of claim 5, wherein in Step(A), the molar ratio of the phenol compound of Formula (X) to the amine compound is 1:0.8-2.0, the molar ratio of the phenol compound of Formula (X) to the bridging compound is 1:0.3-3.0.

18. The process of claim 5, wherein in the optional Step (B), the molar ratio of the amine compound of Formula (Y) to the sulfuring agent is 1:1.5-3.0, the molar ratio of the amine compound of Formula (Y) to the aldehyde compound of Formula (Z) is 1:1:0.8-2.0.

* * * * *